United States Patent

Kay et al.

Patent Number: 5,856,273
Date of Patent: Jan. 5, 1999

[54] HERBICIDALLY ACTIVE PHENYLSUBSTITUTED 5-AND 6-MEMBERED HETEROCYCLIC COMPOUNDS

[75] Inventors: Ian Trevor Kay, Penzance; John Edward Duncan Barton, North Stoke; David John Collins, Crowthorne; Bogdan Kowalczyk, Wokingham; Glynn Mitchell, Cookham, all of United Kingdom; John Martin Shribbs, Petaluma, Calif.; John Micheal Cox, Wokingham; Nigel John Barnes, Maidenhead, both of United Kingdom; Stephen Christopher Smith, Bracknell, United Kingdom

[73] Assignee: Zeneca Limited, United Kingdom

[21] Appl. No.: 446,778

[22] PCT Filed: Nov. 16, 1993

[86] PCT No.: PCT/GB93/02350

§ 371 Date: Oct. 6, 1995

§ 102(e) Date: Oct. 6, 1995

[87] PCT Pub. No.: WO94/13652

PCT Pub. Date: Jun. 23, 1994

[30] Foreign Application Priority Data

Dec. 4, 1992 [GB] United Kingdom .................. 9225377

[51] Int. Cl.$^6$ .................. A01N 43/78; A01N 43/36; C07D 207/273; C07D 403/06

[52] U.S. Cl. .................. 504/266; 504/270; 504/272; 504/221; 504/222; 504/223; 504/225; 504/236; 504/238; 504/239; 504/248; 504/244; 504/251; 504/262; 504/166; 504/167; 504/168; 504/169; 504/176; 504/177; 504/178; 504/179; 504/180; 548/126; 548/131; 548/300.1; 548/311.1; 548/215; 548/225; 548/314.7; 548/262.2; 548/263.2; 548/543; 548/544; 546/63; 546/255; 546/268.1; 544/111; 544/106; 544/98; 544/224; 544/239; 544/242; 544/298; 544/238; 544/58.2

[58] Field of Search .................. 504/266, 270, 504/272, 221, 222, 223, 225, 236, 238, 239, 248, 244, 251, 262; 548/182, 183, 126, 131, 300.1, 311.1, 215, 225, 314.7, 262.2, 263.2, 543, 544, 63, 255, 268.1; 546/63, 255, 268.1; 544/111, 106, 98, 224, 239, 242, 298, 238

[56] References Cited

FOREIGN PATENT DOCUMENTS

| | | |
|---|---|---|
| 0200415 | 10/1986 | European Pat. Off. |
| 1 343 368 | 1/1974 | United Kingdom . |
| 1 414 213 | 11/1975 | United Kingdom . |
| 2 080 289 | 2/1982 | United Kingdom . |

*Primary Examiner*—Mukund J. Shah
*Assistant Examiner*—Pavanaram K. Sripada
*Attorney, Agent, or Firm*—Marian T. Thomson

[57] ABSTRACT

A compound of formula (I):

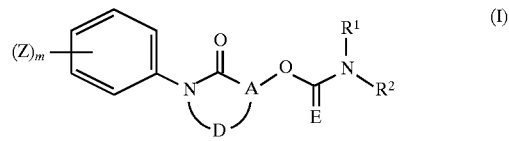

where E is oxygen or sulphur; A is $CR^3$ or N where $R^3$ is hydrogen or hydrocarbyl; D completes a 5 or 6-membered non-aromatic heterocyclic ring which optionally contains additional heteroatoms selected from oxygen, nitrogen or sulphur and which is optionally substituted by an optionally substituted lower hydrocarbyl group, or an optionally substituted heteroaryl group; $R^1$ and $R^2$ are each independently hydrogen; optionally substituted lower hydrocarbyl, or optionally substituted heteroaryl, or $R^1$ and $R^2$ together with the nitrogen atom to which they are attached, form a heterocyclic ring; Z represents halogen optionally substituted lower hydrocarbyl, optionally substituted lower hydocarbyloxy, optionally substituted lower hydrocarbylthio, hydrocarbylsulphinyl or hydrocarbylsulphonyl, cyano, nitro, CHO, NHOH, $ONR^{7'}R^{7''}$, $SF_5$; CO (optionally substituted lower hydrocarbyl), acylamino, $COOR^7$, $SO_2NR^8R^9$, $CONR^{10}R^{11}$, $OR^{12}$ or $NR^{13}R^{14}$ where $R^7$, $R^{7'}$, $R^{7''}$, $R^8$, $R^9$, $R^{10}$ and $R^{11}$ are independently hydrogen or lower hydrocarbyl; $R^{12}$ is hydrogen; $SO_2$ lower hydrocarbyl or $COR^{15}$; $R^{13}$ and $R^{14}$ are independently lower hydrocarbyl, lower hydrocarbyloxy or a group $R^{12}$; $R^{15}$ is $OR^{16}$, $NR^{17}R^{18}$, hydrogen or lower hydrocarbyl; $R^{16}$ is lower hydrocarbyl; $R^{17}$ and $R^{18}$ are independently hydrogen or lower hydrocarbyl; provided that when there are two or more substituents Z, they may be the same or different; and m is 0 or an integer from 1 to 5.

16 Claims, No Drawings

HERBICIDALLY ACTIVE PHENYLSUBSTITUTED 5-AND 6-MEMBERED HETEROCYCLIC COMPOUNDS

This invention relates to chemical compounds useful as herbicides, to processes for preparing them, and to herbicidal compositions and processes utilising them.

Herbicidal compounds based upon carbonyl substituted nitrogen containing heterocyclic rings are known for example from British Patent No. 1345159 and DE OS 2212558.

The applicants have found a group of compounds which have a particular substituent pattern and which are active as herbicides.

According to the present invention there is provided a compound of formula (I):

where E is oxygen or sulphur; A is $CR^3$ or N where $R^3$ is hydrogen or hydrocarbyl; D completes a 5 or 6-membered non-aromatic heterocyclic ring which optionally contains additional heteroatoms selected from oxygen nitrogen or sulphur and which is optionally substituted by an optionally substituted lower hydrocarbyl group, or an optionally substituted heteroaryl group; $R^1$ and $R^2$ are each independently hydrogen, optionally substituted lower hydrocarbyl, or optionally substituted heteroaryl, or $R^1$ and $R^2$ together with the nitrogen atom to which they are attached, form a heterocyclic ring;

Z represents halogen, optionally substituted lower hydrocarbyl, optionally substituted lower hydrocarbyloxy, optionally substituted lower hydrocarbylthio, hydrocarbylsulphinyl, or hydrocarbylsulphonyl, cyano, nitro, CHO, NHOH, $ONR7'R7''$, $SF_5$, CO(optionally substituted lower hydrocarbyl), acylamino, $COOR^7$, $SO_2NR^8R^9$, $CONR^{10}R^{11}$, $OR^{12}$ or $NR^{13}R^{14}$ where $R^7$, $R^{7'}$, $R^{7''}$, $R^8$, $R^9$, $R^{10}$ and $R^{11}$ are independently H or lower hydrocarbyl; $R^{12}$ is hydrogen, $SO_2$ lower hydrocarbyl or $COR^{15}$; $R^{13}$ and $R^{14}$ are independently lower hydrocarbyl, lower hydrocarbyloxy or a group $R^{12}$; $R^{15}$ is $OR^{16}$, $NR^{17}R^{18}$, hydrogen or lower hydrocarbyl; $R^{16}$ is lower hydrocarbyl, $R^{17}$ and $R^{18}$ are independently hydrogen or lower hydrocarbyl provided that when there are two or more substituents Z, they may be the same or different; and m is 0 or an integer from 1 to 5.

D completes a saturated or unsaturated heterocyclic moiety. Preferably D completes a saturated heterocylic ring.

Particular examples of compounds of formula (I) are compounds of formula (II); wherein A, E, $R^1$, $R^2$, Z and m are as defined in relation to formula (I), and W, X and Y are independently selected from $CR^4R^5$, $NR^6$, O and S(O)p where p is 0, 1 or 2, $R^4$, $R^5$ and $R^6$ are independently selected from hydrogen, optionally substituted lower hydrocarbyl, or optionally substituted heteroaryl, or $R^4$ and $R^5$ together with the carbon atom to which they are attached may form a carbocyclic ring; and n is 0 or 1 provided that no more than two of A, W, X and Y comprise heteroatoms in the ring; and when more than one of W, X or Y is $CR^4R^5$, $R^4$ and $R^5$ may each be the same or different; and when more than one of W, X or Y is $NR^6$, $R^6$ may each be the same or different.

The expression lower hydrocarbyl in the foregoing definitions, whether the expression is used on its own or as part of a larger radical such as for example lower hydrocarbyloxy, is intended to include hydrocarbyl radicals of, for example, up to ten carbon atoms. Subclasses of such hydrocarbyl radicals include radicals with up to four, or up to six carbon atoms. The expression hydrocarbyl is intended to include within its scope aliphatic, alicyclic, and aromatic hydrocarbyl groups and combinations thereof. It thus includes, for example, alkyl, alkenyl, and alkynyl radicals, cyclopropyl, cyclopropylmethyl, cyclobutyl, cyclopentyl, and cyclohexyl radicals, the adamantyl radical and the phenyl radical.

When the lower hydrocarbyl group is substituted, the substituents may include, for example, halogen (i.e. chlorine, bromine, fluorine or iodine), cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, carboxy, carboxyamide in which the groups attached to the N atom may be hydrogen or optionally substituted lower hydrocarbyl; alkoxy carbonyl wherein the alkoxy group may have from 1 to 6 or more carbon atoms, and aryl such as phenyl.

The expression heteroaryl in the foregoing definitions is intended to include such radicals as pyridyl, pyrimidyl, triazinyl, thienyl, furyl, and thiazolyl. When the heteroaryl radical is substituted, the substituents may include those recited above for substituted lower hydrocarbyl.

Particular examples of values for $R^4$ and $R^5$ include hydrogen, methyl, ethyl, propyl, and butyl. When $R^4$ and $R^5$ together with the carbon atom to which they are attached form a carbocyclic ring, the ring may be for example a cyclobutyl, cyclopentyl, or cyclohexyl ring.

Particular examples of values for $R^1$ and $R^2$ include hydrogen, methyl, ethyl, propyl, iso-propyl, n-butyl, iso-butyl, sec-butyl, t-butyl, n-pentyl and its isomers, n-hexyl and its isomers, n-heptyl and its isomers, $C(CH_3)_2C\equiv CH$, $C(CH_3)_2CH=CH_2$, $C(CH_3)_2CN$, alpha-methyl benzyl, cyclohexyl, cyclopentyl, cyclobutyl, cyclopropyl, 1-methyl cyclohexyl, 1-methyl-cyclopentyl, 1-methyl-cyclobutyl, 1-methyl-cyclopropyl, 1-cyano-cyclohexyl, 1-cyano-cyclopentyl, 1-cyano-cyclobutyl, 1-cyano-cyclopropyl, 1-ethynyl-cyclohexyl, 1-ethynyl-cyclopentyl, 1-ethynyl-cyclobutyl, 1-ethynyl-cycloypropyl, phenyl, p-chlorophenyl and benzyl. When $R^1$ and $R^2$, together with the nitrogen atom to which they are attached, form a heterocyclic ring, the ring may be for example a pyrrolidino, piperidino, thiomorpholino or morpholino ring, each of which may be substituted, e.g. with one or more methyl groups.

Examples of particular values for Z include methyl, ethyl, n-propyl, iso-propyl, trifluoromethyl, difluoromethyl, pentafluoroethyl, trichloromethyl, ethoxyvinyl, fluorine, chlorine, bromine, iodine, methoxy, ethoxy, n-propoxy, iso-propoxy, trifluoromethoxy, tetrafluoroethoxy, cyano, nitro, amino, mono- or dialkylamino in which each alkyl group may have from 1 to 6 or more carbon atoms, hydroxylamino, acyl (e.g. acetyl or trifluoroacetyl), methylthio, methylsulphinyl, methylsulphonyl, trifluoromethylthio, trifluoromethylsulphinyl, trifluoromethylsulphonyl, sulphonamido, carboxy, alkoxycarbonyl in which the alkoxy group may have from 1 to 6 or more carbon atoms, carboxyamide in which the groups attached to the N atom may be hydrogen or optionally substituted lower hydrocarbyl; or acylamino (e.g. acetamido). When there is more than one substituent Z, the substituents may be the same or different.

Examples of the heterocyclic ring containing W, X and Y are rings of sub-formula (i), including groups of sub-formulae (a)–(o) where $R^3$, $R^4$, $R^5$ and $R^6$ are as defined above and $R^{4'}$ and $R^{4''}$ and $R^{5'}$ and $R^{5''}$ are as defined above for $R^4$ and $R^5$ respectively.

Particular examples of compounds of formula (I) are compounds wherein D completes a thiazolidine ring of sub-formula (a), E is 0, R3 is a group CH; m, p, $R^1$, $R^2$, $R^4$ and $R^5$ are as defined above and Z is halogen, optionally substituted lower hydrocarbyl, optionally substituted lower hydrocarbyloxy, optionally substituted lower hydrocarbyl-thio, -sulphinyl, or -sulphonyl, cyano, nitro, acyl, amino, or acylamino provided that when there are two or more substituents Z, they may be the same or different.

A is preferably $CR^3$, especially CH.

Preferably the group of sub-formula (i) is a thiazolidinone group of sub-formula (a) on a pyrrolidinone group of sub-formula (b).

E is preferably oxygen.

Preferred values for Z are $CF_3$, $OCF_3$, $OCHF_2$, $CHF_2$, OMe, F, Cl, Br, I, $NH_2$, $NO_2$, CN, $C_{1-4}$alkyl, $C_{1-4}$alkoxy, $COC_{1-4}$alkyl, $NHCOC_{1-4}$alkyl, $SO_2C_{1-4}$ alkyl, $OCF_2CHF_2$, $CF_2CF_3$, $OCF_2CHF_2$ and $SO_2NR^8R^9$.

Especially preferred values for Z are $CF_3$, $OCF_3$, $OCH_3$, F, Cl, Br and I.

m is preferably 1, 2 or 3.

The preferred substitution pattern for the Z groups is for a single Z group at the 3-position; or two Z groups at the 3,4- and 3,5-positions; or three Z groups at the 3, 4 and 5 positions, the Z group at the 4-position being halo, especially fluoro.

$R^1$ is preferably iso-propyl, sec-butyl, t-butyl, $C(CH_3)_2C\equiv CH$ or a 3–6 membered cyloalkyl, optionally substituted by $CH_3$ or $C\equiv CH$ at the α position of the cycloalkyl ring.

$R^2$ is preferably preferably hydrogen or $C_{1-4}$ alkyl, especially hydrogen.

A preferred value for $R^3$ is hydrogen.

$R^4$, $R^{4'}$ and $R^{4''}$ are preferably hydrogen or $C_{1-4}$ alkyl.

$R^5$, $R^{5'}$ and $R^{5''}$ are preferably hydrogen or $C_{1-4}$ alkyl.

$R^6$ is preferably $C_{1-4}$ alkyl, especially methyl.

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molelcular or inter-molecular hydrogen bonding, or otherwise.

Some of the compounds of the invention can exist in enantiomeric or diastereomeric forms. The invention includes all individual forms and mixtures thereof in all proportions.

Particular examples of compounds of the invention one listed in Tables I to XV.

TABLE I

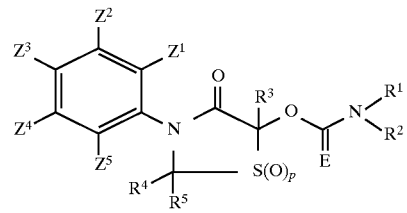

(Table I)

| Comp No | $Z^1$ | $Z^2$ | $Z^3$ | $Z^4$ | $Z^5$ | p | $R^4$ | $R^5$ | $R^3$ | E | $R^1$ | $R^2$ |
|---|---|---|---|---|---|---|---|---|---|---|---|---|
| 1 | H | Cl | Cl | H | H | 0 | H | H | H | O | C(Me)3 | H |
| 2 | H | CF3 | F | H | H | 0 | H | H | H | O | CH(Et)Ph | H |
| 3 | H | Cl | H | H | H | 0 | H | H | H | O | 1-Me-cyclopropyl | H |
| 4 | H | CF3 | H | F | H | 0 | H | H | H | O | C(Me)3 | H |
| 5 | H | CF3 | H | H | H | 0 | H | H | H | O | CH(Me)2 | H |
| 6 | H | $CF^3$ | F | H | H | 0 | H | H | H | O | CH(Me)Ph | H |
| 7 | H | CF3 | H | CF3 | H | 0 | H | H | H | O | 1-Me-cyclopropyl | H |
| 8 | H | OCF3 | F | H | H | 0 | H | H | H | O | 1-Me-cyclopropyl | H |
| 9 | H | CF3 | H | H | H | 0 | H | H | H | O | Me | H |
| 10 | H | Cl | F | H | H | 0 | H | H | H | O | C(Et)2Me | H |
| 11 | H | OCF3 | H | H | H | 0 | H | H | H | O | C(Et)2CCH | H |
| 12 | H | CF3 | F | H | H | 0 | H | H | H | O | 1-Me-cyclopropyl | H |
| 13 | H | Cl | F | H | H | 0 | H | H | H | O | cyclopentyl | H |
| 14 | H | I | H | H | H | 0 | H | H | H | O | C(Me)2CCH | H |
| 15 | H | Cl | Cl | H | H | 0 | H | H | H | O | cyclohexyl | H |
| 16 | H | CF3 | H | H | H | 0 | H | H | H | O | Et | H |
| 17 | H | CF3 | H | H | H | 0 | H | H | H | O | CH2Ph | H |
| 18 | H | SO2N(Me)2 | H | H | H | 0 | H | H | H | O | C(Me)2CCH | H |
| 19 | H | Cl | H | CF3 | H | 0 | H | H | H | O | CH(Me)2 | H |
| 20 | H | CF3 | H | H | H | 0 | H | H | H | O | Ph | H |
| 21 | H | Cl | H | Cl | H | 0 | H | H | H | O | C(Me)2CCH | H |
| 22 | H | Cl | Cl | H | H | 0 | H | H | H | O | C(Me)2CCH | H |
| 23 | H | I | H | H | H | 0 | H | H | H | O | cyclohexyl | H |
| 24 | H | Cl | H | H | H | 0 | H | H | H | O | CMeEtCCH | H |
| 25 | H | Cl | H | Cl | H | 0 | H | H | H | O | 1-(CCH)cyclopropyl | H |
| 26 | H | CF3 | H | H | H | 0 | H | H | H | O | C(Me)3 | H |
| 27 | H | CF3 | H | CF3 | H | 0 | H | H | H | O | C(Me)2CCH | H |
| 28 | H | Cl | F | H | H | 0 | H | H | H | O | C(Me)2CN | H |
| 29 | H | CF3 | F | H | H | 0 | H | H | H | O | cyclohexyl | H |
| 30 | H | CF3 | H | CF3 | H | 0 | H | H | H | O | CH(Me)2 | H |
| 31 | H | OCF3 | H | H | H | 0 | H | H | H | O | Me | Me |
| 32 | H | OCF3 | H | H | H | 0 | H | H | H | O | 1-Me-cyclohexyl | H |
| 33 | H | H | CF3 | H | H | 0 | H | H | H | O | CH(Me)2 | H |
| 34 | H | CF3 | H | H | H | 0 | H | H | H | O | CMeEtCCH | H |
| 35 | H | Cl | H | H | H | 0 | H | H | H | O | C(Me)3 | H |

TABLE I-continued (Table I)

| Comp No | Z¹ | Z² | Z³ | Z⁴ | Z⁵ | p | R⁴ | R⁵ | R³ | E | R¹ | R² |
|---|---|---|---|---|---|---|---|---|---|---|---|---|
| 36 | H | CF3 | H | H | H | 0 | H | H | H | O | C(Et)2Me | H |
| 37 | H | CF3 | H | H | H | 0 | H | H | H | O | 1-Me-cyclopentyl | H |
| 38 | H | CF3 | H | H | H | 0 | H | H | H | O | —(CH2)4— | |
| 39 | H | OCF3 | H | H | H | 0 | H | H | H | O | C(Et)3 | H |
| 40 | H | Cl | H | Cl | H | 0 | H | H | H | O | C(Me)3 | H |
| 41 | H | CF3 | F | H | H | 0 | H | H | H | O | C(Et)3 | H |
| 42 | H | Cl | F | H | H | 0 | H | H | H | O | 1-(CCH)-cyclopropyl | H |
| 43 | H | CF3 | H | CF3 | H | 0 | H | H | H | O | cyclohexyl | H |
| 44 | H | Cl | F | H | H | 0 | H | H | H | O | CH(Me)2 | H |
| 45 | H | Cl | F | H | H | 0 | H | H | H | O | C(Me)3 | H |
| 46 | H | Cl | H | H | H | 0 | H | H | H | O | cyclohexyl | H |
| 47 | H | Br | H | H | H | 0 | H | H | H | O | 1-Me-cyclopropyl | H |
| 48 | Cl | H | H | H | H | 0 | H | H | H | O | C(Me)3 | H |
| 49 | H | OCF2CHF2 | H | H | H | 0 | H | H | H | O | CH(Me)2 | H |
| 50 | H | OCF3 | F | H | H | 0 | H | H | H | O | CH(Me)2 | H |
| 51 | H | CF3 | H | F | H | 0 | H | H | H | O | CH(Me)2 | H |
| 52 | H | H | OMe | H | H | 0 | H | H | H | O | C(Me)3 | H |
| 53 | H | OCF3 | H | H | H | 0 | H | H | H | O | C(Me)2Pr | H |
| 54 | H | OCF3 | H | H | H | 0 | H | H | H | O | cyclohexyl | H |
| 55 | H | Cl | H | H | H | 0 | H | H | H | O | C(Me)2CCH | H |
| 56 | Cl | Cl | H | H | H | 0 | H | H | H | O | C(Me)3 | H |
| 57 | H | Cl | H | Cl | H | 0 | H | H | H | O | cyclopentyl | H |
| 58 | H | Br | H | H | H | 0 | H | H | H | O | CH(Me)Ph | H |
| 59 | H | Cl | H | Cl | H | 0 | H | H | H | O | CH(Me)2 | H |
| 60 | H | OCF2CHF2 | H | H | H | 0 | H | H | H | O | C(Me)2CCH | H |
| 61 | Cl | H | H | H | H | 0 | H | H | H | O | CH(Me)2 | H |
| 62 | H | CF3 | H | H | H | 0 | H | H | H | O | cyclohexyl | H |
| 63 | H | CF3 | H | H | H | 0 | H | H | H | O | 1-Me-cyclopropyl | H |
| 64 | H | OCHF2 | H | H | H | 0 | H | H | H | O | CH(Me)2 | H |
| 65 | H | Me | H | H | H | 0 | H | H | H | O | cyclohexyl | H |
| 66 | H | CF3 | H | H | H | 0 | H | H | H | O | 1-Me-cyclopropyl | H |
| 67 | H | SO2NH2 | H | H | H | 0 | H | H | H | O | C(Me)3 | H |
| 68 | H | Cl | F | Cl | H | 0 | H | H | H | O | C(Me)2CCH | H |
| 69 | H | CF3 | H | H | H | 0 | H | H | H | O | C(Me)2Ph | H |
| 70 | H | CF3 | F | H | H | 0 | H | H | Me | O | C(Me)2CCH | H |
| 71 | H | CF3 | H | H | H | 0 | H | H | H | S | C(Me)3 | H |
| 72 | H | Cl | H | Cl | H | 0 | H | H | H | S | cyclopentyl | H |
| 73 | H | CF3 | H | Me | H | 0 | H | H | H | O | C(Me)2CCH | H |
| 74 | H | SO2CF3 | H | H | H | 0 | H | H | H | O | C(Me)2CCH | H |
| 75 | H | Cl | H | H | H | 0 | H | H | H | O | CH(Me)Ph | H |
| 76 | H | OCF3 | H | H | H | 0 | H | H | H | O | C(Me)2CH=CH2 | H |
| 77 | H | H | Me | H | H | 0 | H | H | H | O | C(Me)3 | H |
| 78 | H | OCF3 | H | H | H | 0 | H | H | H | O | 1-(CN)-cyclopropyl | H |
| 79 | H | CF3 | F | H | H | 0 | H | H | H | O | C(Me)2Pr | H |
| 80 | H | CF3 | H | H | H | 0 | H | H | H | O | C(Me)2Pr | H |
| 81 | H | CF3 | H | H | H | 0 | H | H | H | O | C(Et)2CCH | H |
| 82 | H | OCF3 | H | H | H | 0 | H | H | H | O | CH(Me)2 | H |
| 83 | H | OCF3 | H | H | H | 0 | H | H | H | O | 1-(CCH)-cyclopentyl | H |
| 84 | H | H | Cl | H | H | 0 | H | H | H | O | C(Me)3 | H |
| 85 | H | OCF3 | H | H | H | 0 | H | H | H | O | —(CH2)4— | |
| 86 | H | CF3 | F | H | H | 0 | H | H | H | O | 1-Me-cyclohexyl | H |
| 87 | H | Cl | F | H | H | 0 | H | H | H | O | 1-Me-cyclohexyl | H |
| 88 | H | CF3 | H | CF3 | H | 0 | H | H | H | O | CH(Me)Ph | H |
| 89 | H | Cl | H | Cl | H | 0 | H | H | H | O | —(CH2)2O(CH2)2— | |
| 90 | H | OCF2CHF2 | H | H | H | 0 | H | H | H | O | cyclopentyl | H |
| 91 | Cl | H | H | Cl | H | 0 | H | H | H | O | C(Me)3 | H |
| 92 | H | OCF3 | F | H | H | 0 | H | H | H | O | CH(Me)Ph | H |
| 93 | H | OCF3 | F | H | H | 0 | H | H | H | O | cyclohexyl | H |
| 94 | H | CF3 | H | H | H | 0 | —(CH2)5— | | H | O | C(Me)3 | H |
| 95 | H | Cl | H | CF3 | H | 0 | H | H | H | O | CH(Et)Ph | H |
| 96 | H | SO2CF3 | H | H | H | 0 | H | H | H | O | 1-Me-cyclopropyl | H |
| 97 | H | SCF3 | H | H | H | 0 | H | H | H | O | C(Me)3 | H |
| 98 | H | CF3 | H | Me | H | 0 | H | H | H | O | C(Me)3 | H |
| 99 | H | CF3 | H | CF3 | H | 0 | H | H | H | S | C(Me)2CCH | H |
| 100 | F | H | H | CF3 | H | 0 | H | H | H | O | C(Me)3 | H |
| 101 | H | CF3 | H | H | H | 0 | Me | H | H | O | C(Me)3 | H |

TABLE I-continued (Table I)

| Comp No | Z¹ | Z² | Z³ | Z⁴ | Z⁵ | p | R⁴ | R⁵ | R³ | E | R¹ | R² |
|---|---|---|---|---|---|---|---|---|---|---|---|---|
| 102 | H | OCF3 | H | H | H | 0 | H | H | H | S | C(Me)3 | H |
| 103 | H | OCF3 | H | F | H | 0 | H | H | H | O | CH(Me)Ph | H |
| 104 | H | OCHF2 | H | H | H | 0 | H | H | H | O | 1-Me-cyclopropyl | H |
| 105 | H | Cl | H | CF3 | H | 0 | H | H | H | O | C(Me)2CCH | H |
| 106 | H | OCF2CHF2 | H | H | H | 0 | H | H | H | O | CMeEtCCH | H |
| 107 | H | CF3 | H | H | H | 2 | H | H | H | O | C(Me)3 | H |
| 108 | H | CF3 | H | H | H | 1 | H | H | H | O | C(Me)3 | H |
| 109 | H | Cl | H | H | H | 0 | H | H | H | O | 1-Me-cyclohexyl | H |
| 110 | H | Cl | H | Cl | H | 0 | H | H | H | O | C(Me)2Et | H |
| 111 | H | Cl | F | H | H | 0 | H | H | H | O | cyclohexyl | H |
| 112 | H | Cl | Me | H | H | 0 | H | H | H | O | C(Me)3 | H |
| 113 | H | CF3 | F | H | H | 0 | H | H | H | O | 1-Me-cyclobutyl | H |
| 114 | H | OCF3 | H | H | H | 0 | H | H | H | O | 1-(CCH)-cyclohexyl | H |
| 115 | H | CF3 | H | H | H | 0 | H | H | H | O | 1-Me-cyclobutyl | H |
| 116 | H | CF3 | H | H | H | 0 | H | H | H | O | C(Et)3 | H |
| 117 | H | OCF3 | H | H | H | 0 | H | H | H | O | CH(Me)Ph | H |
| 118 | H | Cl | H | Cl | H | 0 | H | H | H | O | 1-Me-cyclopropyl | H |
| 119 | H | CF3 | H | H | H | 0 | H | H | H | O | C(Me)2Et | H |
| 120 | H | OCF2CHF2 | H | H | H | 0 | H | H | H | O | cyclohexyl | H |
| 121 | H | CF3 | H | F | H | 0 | H | H | H | O | C(Me)2CCH | H |
| 122 | H | CF3 | H | H | H | 0 | H | H | H | O | Et | Et |
| 123 | H | CON(Me)2 | H | H | H | 0 | H | H | H | O | C(Me)2CCH | H |
| 124 | H | OCF3 | H | H | H | 0 | H | H | Me | O | C(Me)3 | H |
| 125 | H | OCF2CHF2 | H | H | H | 0 | H | H | H | O | 1-Me-cyclopropyl | H |
| 126 | H | OCF3 | H | H | H | 0 | H | H | H | O | C(Me)2Ph | H |
| 127 | H | CF3 | H | H | H | 0 | H | H | H | O | 1-(CCH)-cyclopentyl | H |
| 128 | H | OCF3 | H | H | H | 0 | H | H | H | O | C(Me)2Et | H |
| 129 | H | CF3 | F | H | H | 0 | H | H | H | O | C(Me)2CCH | H |
| 130 | H | Cl | F | H | H | 0 | H | H | H | S | CH(Et)Ph | H |
| 131 | H | CF3 | H | CF3 | H | 0 | H | H | H | O | 1-(CCH)-cyclopropyl | H |
| 132 | H | I | H | H | H | 0 | H | H | H | O | 1-Me-cyclopropyl | H |
| 133 | H | CF3 | H | H | H | 2 | H | H | H | S | CH(Me)2 | H |
| 134 | H | CF3 | H | H | H | 1 | H | H | H | O | CH(Me)2 | H |
| 135 | H | Cl | H | CF3 | H | 0 | H | H | H | O | CH(Me)2 | Me |
| 136 | H | Cl | Cl | H | H | 0 | H | H | H | O | CH(Me)Ph | H |
| 137 | H | SO2NHMe | H | H | H | 0 | H | H | H | O | C(Me)3 | H |
| 138 | H | CF3 | H | CF3 | H | 0 | H | H | H | O | C(Me)3 | H |
| 139 | H | I | F | H | H | 0 | H | H | H | O | C(Me)2CCH | H |
| 140 | H | OMe | H | H | H | 0 | H | H | H | O | cyclohexyl | H |
| 141 | H | OCHF2 | H | H | H | 0 | H | H | H | O | C(Me)2CCH | H |
| 142 | H | Cl | H | CF3 | H | 0 | H | H | H | O | CH(Me)Ph | H |
| 143 | H | OCF2CHF2 | H | H | H | 0 | H | H | H | O | 1-(CCH)-cyclopropyl | H |
| 144 | H | Br | H | H | H | 0 | H | H | H | O | cyclohexyl | H |
| 145 | H | Cl | H | Cl | H | 0 | H | H | H | O | CH(Me)2 | Me |
| 146 | H | CF3 | H | CF3 | H | 0 | H | H | H | O | Me | Me |
| 147 | H | CF3 | H | H | H | 0 | H | H | H | O | 1-(CN)-cyclopentyl | H |
| 148 | H | OCF3 | H | H | H | 0 | H | H | H | O | 1-Me-cyclobutyl | H |
| 149 | H | CF3 | H | H | H | 0 | H | H | H | O | CH(Me)2 | Me |
| 150 | H | CF3 | H | H | H | 0 | H | H | H | O | CH(Et)Ph | H |
| 151 | H | Br | H | H | H | 0 | H | H | H | O | CH(Me)2 | H |
| 152 | H | OCF2CHF2 | H | H | H | 0 | H | H | H | O | CH(Me)Ph | H |
| 153 | H | CF3 | H | F | H | 0 | H | H | H | O | C(Me)2Et | H |
| 154 | H | SF5 | H | H | H | 0 | H | H | H | O | CH(Me)Ph | H |
| 155 | H | Cl | Cl | H | H | 0 | H | H | H | O | 1-Me-cyclopropyl | H |
| 156 | H | COMe | H | H | H | 0 | H | H | H | O | C(Me)3 | H |
| 157 | H | CF3 | H | F | H | 0 | H | H | H | O | C(Me)2CCH | H |
| 158 | H | CF3 | H | CF3 | H | 0 | H | H | H | S | C(Me)3 | H |
| 159 | H | CF3 | H | H | H | 0 | H | H | H | O | Me | Me |
| 160 | H | CF3 | H | H | H | 0 | H | H | Et | S | C(Me)3 | H |
| 161 | H | CF3 | F | H | H | 0 | H | H | H | S | cyclohexyl | H |
| 162 | H | CF3 | F | H | H | 0 | H | H | H | O | CH(Me)2 | Me |
| 163 | H | OCF3 | H | H | H | 0 | H | H | H | O | 1-Me-cyclopentyl | H |
| 164 | H | CF3 | H | H | H | 0 | H | H | H | O | cyclopentyl | H |
| 165 | H | Cl | F | H | H | 0 | H | H | H | O | C(Me)2Et | H |
| 166 | H | H | H | H | H | 0 | H | H | H | O | CH(Me)2 | H |
| 167 | H | Cl | F | H | H | 0 | H | H | H | O | CMeEtCCH | H |

TABLE I-continued (Table I)

| Comp No | Z¹ | Z² | Z³ | Z⁴ | Z⁵ | p | R⁴ | R⁵ | R³ | E | R¹ | R² |
|---|---|---|---|---|---|---|---|---|---|---|---|---|
| 168 | H | Cl | H | Cl | H | 0 | H | H | H | O | CH(Me)Ph | H |
| 169 | H | Cl | H | H | H | 0 | H | H | H | O | cyclopentyl | H |
| 170 | H | Br | H | H | H | 0 | H | H | H | O | cyclopentyl | H |
| 171 | H | CF3 | H | H | H | 0 | H | H | H | O | C(Me)2CCH | H |
| 172 | H | OCF2CHF2 | H | H | H | 0 | H | H | H | O | CH(Et)Ph | H |
| 173 | H | OCF3 | F | H | H | 0 | H | H | H | O | CMeEtCCH | H |
| 174 | H | CF3 | H | H | H | 0 | H | H | H | O | C(Me)2CN | H |
| 175 | H | CF3 | H | F | H | 0 | H | H | H | O | cyclopentyl | H |
| 176 | H | COOH | H | H | H | 0 | H | H | H | O | C(Me)2CCH | H |
| 177 | H | OME | H | CF3 | H | 0 | H | H | H | O | C(Me)2CCH | H |
| 178 | H | CF3 | H | H | H | 0 | H | H | H | O | 1-(CN)-cyclopentyl | H |
| 179 | H | CF3 | F | H | H | 0 | Ph | H | H | O | C(Me)3 | H |
| 180 | H | CF3 | H | H | H | 0 | Me | Me | H | O | C(Me)3 | H |
| 181 | H | Cl | H | H | H | 0 | H | H | H | S | C(Me)3 | H |
| 182 | H | I | H | H | H | 0 | H | H | H | O | CH(Me)Ph | H |
| 183 | H | CF3 | H | CF3 | H | 0 | H | H | H | O | CMeEtCCH | H |
| 184 | H | CF3 | H | H | H | 0 | H | H | H | O | 1-Me-cyclohexyl | H |
| 185 | H | Cl | F | H | H | 0 | H | H | H | O | 1-(CN)-cyclopentyl | H |
| 186 | H | Cl | H | Cl | H | 0 | H | H | H | O | CH(Et)Ph | H |
| 187 | H | Cl | H | H | H | 0 | H | H | H | I | C(Me)2CCH | H |
| 188 | H | I | H | H | H | 0 | H | H | H | O | CMeEtCCH | H |
| 189 | H | OCF3 | F | H | H | 0 | H | H | H | O | C(Me)3 | H |
| 190 | H | CF3 | H | F | H | 0 | H | H | H | O | CH(Me)Ph | H |
| 191 | H | Cl | H | CF3 | H | 0 | H | H | H | O | C(Me)3 | H |
| 192 | H | SF5 | H | H | H | 0 | H | H | H | O | 1-Me-cyclopropyl | H |
| 193 | H | OCF3 | F | H | H | 0 | H | H | H | O | cyclohexyl | H |
| 194 | H | CONH2 | H | H | H | 0 | H | H | H | O | C(Me)3 | H |
| 195 | H | OCF3 | H | H | H | 0 | —(CH2)5— | | H | O | C(Me)3 | H |
| 196 | H | CF3 | H | H | H | 0 | H | H | H | S | C(Me)2CCH | H |
| 197 | H | CF3 | F | H | H | 0 | H | H | H | O | CH(Me)2 | H |
| 198 | H | CONHMe | H | H | H | 0 | H | H | H | O | C(Me)3 | H |
| 199 | H | COCF3 | H | H | H | 0 | H | H | H | O | C(Me)3 | H |
| 200 | H | OCF3 | H | F | H | 0 | H | H | H | O | C(Me)2CCH | H |
| 201 | H | SF5 | H | H | H | 0 | H | H | H | O | C(Me)2CCH | H |
| 202 | H | CF3 | H | F | H | 0 | H | H | H | O | cyclohexyl | H |
| 203 | H | Cl | H | H | H | 0 | H | H | H | O | —(CH2)2O(CH2)2— | |
| 204 | H | Cl | H | Cl | H | 0 | H | H | H | O | cyclohexyl | H |
| 205 | H | Cl | F | H | H | 0 | H | H | H | O | 1-(CCH)-cyclohexyl | H |
| 206 | H | CF3 | F | H | H | 0 | H | H | H | O | C(Me)3 | H |
| 207 | H | OCF3 | H | H | H | 0 | H | H | H | O | Et | Et |
| 208 | H | CF3 | F | H | H | 0 | H | H | H | O | cyclopentyl | H |
| 209 | H | CF3 | H | H | H | 0 | H | H | H | O | 1-(CCH)-cyclopropyl | H |
| 210 | H | OCF3 | H | H | H | 0 | H | H | H | O | CH2Ph | H |
| 211 | H | SF5 | H | H | H | 0 | H | H | H | O | CH(Me)2 | H |
| 212 | H | CF3 | F | H | H | 0 | H | H | H | O | CMeEtCCH | H |
| 213 | H | Cl | F | H | H | 0 | H | H | H | O | CH(Me)2 | Me |
| 214 | H | Cl | H | Cl | H | 0 | H | H | H | O | CMeEtCCH | H |
| 215 | H | Br | H | H | H | 0 | H | H | H | O | C(Me)2Et | H |
| 216 | H | SF5 | H | H | H | 0 | H | H | H | O | C(Me)3 | H |
| 217 | H | OCF3 | F | H | H | 0 | H | H | H | O | C(Me)2Et | H |
| 218 | H | Cl | H | CF3 | H | 0 | H | H | H | O | cyclohexyl | H |
| 219 | H | CF3 | H | F | H | 0 | H | H | H | O | CMeEtCCH | H |
| 220 | H | CF3 | H | H | H | 0 | H | H | H | O | C(Me)2CCHMe | H |
| 221 | H | CF3 | H | H | H | 0 | H | H | H | O | C(Me)3 | H |
| 222 | H | OCHF2 | H | H | H | 0 | H | H | H | O | CH(Me)Ph | H |
| 223 | H | Cl | Cl | H | H | 0 | H | H | H | O | CH(Me)2 | H |
| 224 | H | OCF3 | H | F | H | 0 | H | H | H | O | C(Me)3 | H |
| 225 | H | OMe | H | H | H | 0 | H | H | H | O | C(Me)2CCH | H |
| 226 | H | SCF3 | H | H | H | 0 | H | H | H | O | C(Me)2CCH | H |
| 227 | H | CF3 | H | H | H | 0 | Ph | H | H | O | C(Me)3 | H |
| 228 | H | Cl | F | Cl | H | 0 | H | H | H | O | C(Me)3 | H |
| 229 | H | Cl | F | H | H | 0 | H | H | H | S | C(Me)3 | H |
| 230 | H | CF3 | F | F | H | 0 | H | H | H | O | C(Me)3 | H |
| 231 | H | CF3 | Cl | H | H | 0 | H | H | H | O | C(Me)3 | H |
| 232 | H | CN | H | H | H | 0 | H | H | H | O | C(Me)2CCH | H |
| 233 | H | CF3 | H | H | H | 0 | H | H | Me | O | CH(Me)2 | H |

TABLE I-continued (Table I)

| Comp No | Z¹ | Z² | Z³ | Z⁴ | Z⁵ | p | R⁴ | R⁵ | R³ | E | R¹ | R² |
|---|---|---|---|---|---|---|---|---|---|---|---|---|
| 234 | H | SO2CF3 | H | H | H | 0 | H | H | H | O | CH(Me)Ph | H |
| 235 | H | Cl | H | CF3 | H | 0 | H | H | H | O | cyclopentyl | H |
| 236 | H | OCF3 | F | H | H | 0 | H | H | H | O | C(Me)2CCH | H |
| 237 | H | Br | H | H | H | 0 | H | H | H | O | CMeEtCCH | H |
| 238 | H | Cl | H | H | H | 0 | H | H | H | O | CH(Me)2 | H |
| 239 | H | CF3 | H | CF3 | H | 0 | H | H | H | O | CH(Et)Ph | H |
| 240 | H | Cl | F | H | H | 0 | H | H | H | O | C(Et)3 | H |
| 241 | OMe | H | H | H | H | 0 | H | H | H | O | C(Me)3 | H |
| 242 | H | CF3 | F | H | H | 0 | H | H | H | O | C(Et)2Me | H |
| 243 | H | OCF3 | H | H | H | 0 | H | H | H | O | C(Me)2CCH | H |
| 244 | H | CF3 | H | H | H | 0 | H | H | H | O | —(CH2)5— | |
| 245 | H | OCF3 | H | H | H | 0 | H | H | H | O | Et | H |
| 246 | H | CF3 | F | H | H | 0 | H | H | H | O | C(Me)2Et | H |
| 247 | H | Cl | F | H | H | 0 | H | H | H | O | CH(Me)Ph | H |
| 248 | H | CF3 | H | H | H | 0 | H | H | H | O | (S)—CH(Me)Ph | H |
| 249 | H | CF3 | H | H | H | 0 | H | H | H | O | (S)—CH(Me)Ph | H |
| 250 | H | Cl | H | Cl | H | 0 | H | H | H | O | 1-(CN)-cyclopentyl | H |
| 251 | H | Cl | H | H | H | 0 | H | H | H | O | 1-(CCH)-cyclopropyl | H |
| 252 | H | OCF2CHF2 | H | H | H | 0 | H | H | H | O | C(Me)2Et | H |
| 253 | H | CF3 | H | F | H | 0 | H | H | H | O | CH(Et)Ph | H |
| 254 | H | Cl | H | CF3 | H | 0 | H | H | H | O | 1-(CCH)-cyclopropyl | H |
| 255 | H | CF3 | H | H | H | 0 | H | H | H | O | (R)—CH(Me)Ph | H |
| 256 | H | CF3 | H | H | H | 0 | H | H | H | O | (R)—CH(Me)Ph | H |
| 257 | H | OCF3 | H | H | H | 0 | H | H | H | O | —(CH2)5— | |
| 258 | H | Me | H | H | H | 0 | H | H | H | O | C(Me)2CCH | H |
| 259 | H | SO2NH2 | H | H | H | 0 | H | H | H | O | C(Me)2CCH | H |
| 260 | H | CF3 | H | H | H | 0 | H | H | H | O | —(CH2)2O(CH2)2— | |
| 261 | H | OCF3 | H | H | H | 0 | Ph | H | H | O | C(Me)3 | H |
| 262 | H | CF3 | H | H | H | 0 | H | H | H | O | (CH2)2Cl | H |
| 263 | H | OCF3 | H | H | H | 0 | H | H | H | S | C(Me)2CCH | H |
| 264 | H | COMe | H | H | H | 0 | H | H | H | O | C(Me)2CCH | H |
| 265 | H | SO2CF3 | H | H | H | 0 | H | H | H | O | cyclohexyl | H |
| 266 | H | Cl | H | CF3 | H | 0 | H | H | H | O | C(Me)2Et | H |
| 267 | H | Br | H | H | H | 0 | H | H | H | O | 1-(CCH)-cyclopropyl | H |
| 268 | H | Cl | H | H | H | 0 | H | H | H | O | C(Me)2Et | H |
| 269 | H | CF3 | H | H | H | 0 | H | H | H | O | —CH2)2S(CH2)2— | |
| 270 | H | CF3 | H | H | H | 0 | H | H | H | O | 4-(2,6-dichloropyridyl) | H |
| 271 | H | OCF3 | H | H | H | 0 | H | H | H | O | C(Me)2CCMe | H |
| 272 | H | CF3 | F | H | H | 0 | H | H | H | O | 1-Me-cyclopentyl | H |
| 273 | H | Cl | F | H | H | 0 | H | H | H | O | —CH2)4— | |
| 274 | H | CF3 | H | H | H | 0 | H | H | H | O | C(Me)2CH=CH2 | H |
| 275 | H | CF3 | H | CF3 | H | 0 | H | H | H | O | cyclopentyl | H |
| 276 | H | Cl | H | H | H | 0 | H | H | H | O | CH(Et)Ph | H |
| 277 | H | Br | H | H | H | 0 | H | H | H | O | CH(Et)Ph | H |
| 278 | H | CF3 | H | H | H | 0 | H | H | H | O | CH(Ph)2 | H |
| 279 | H | I | H | H | H | 0 | H | H | H | O | cyclopentyl | H |
| 280 | H | CF3 | H | F | H | 0 | H | H | H | O | 1-(CCH)-cyclopropyl | H |
| 281 | H | NO2 | H | H | H | 0 | H | H | H | O | C(Me)3 | H |
| 282 | H | CN | H | H | H | 0 | H | H | H | O | C(Me)3 | H |
| 283 | H | Cl | H | CF3 | H | 0 | H | H | H | O | CMeEtCCH | H |
| 284 | H | Me | H | H | H | 0 | H | H | H | O | CH(Me)Ph | H |
| 285 | H | F | H | H | H | 0 | H | H | H | O | C(Me)3 | H |
| 286 | H | COOH | H | H | H | 0 | H | H | H | O | C(Me)3 | H |
| 287 | H | CF3 | H | H | H | 0 | H | H | Me | O | C(Me)3 | H |
| 288 | H | CF3 | F | H | H | 0 | H | H | H | S | C(Me)3 | H |
| 289 | H | Br | F | H | H | 0 | H | H | H | O | C(Me)3 | H |
| 290 | H | OMe | H | H | H | 0 | H | H | H | O | 1-Me-cyclopropyl | H |
| 291 | H | OCHF2 | H | H | H | 0 | H | H | H | O | cyclohexyl | H |
| 292 | H | Cl | H | CF3 | H | 0 | H | H | H | O | 1-Me-cyclopropyl | H |
| 293 | H | Br | H | H | H | 0 | H | H | H | O | C(Me)2CCH | H |
| 294 | H | CF3 | H | CF3 | H | 0 | H | H | H | O | C(Me)2Et | H |
| 295 | H | CF3 | F | H | H | 0 | H | H | H | O | C(Me)2CN | H |
| 296 | H | OCF3 | H | H | H | 0 | H | H | H | O | —(CH2)2O(CH2)2— | |
| 297 | H | CF3 | H | H | H | 0 | H | H | H | O | 1-(CN)-cyclopropyl | H |
| 298 | H | OCF3 | H | H | H | 0 | H | H | H | O | 1-Me-cyclopropyl | H |
| 299 | H | CF3 | F | H | H | 0 | H | H | H | O | 1-(CN)-cyclopropyl | H |

TABLE I-continued

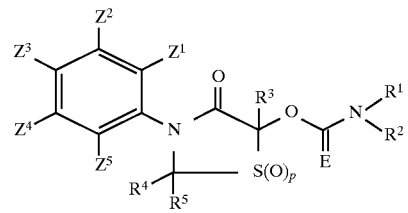

(Table I)

| Comp No | Z¹ | Z² | Z³ | Z⁴ | Z⁵ | p | R⁴ | R⁵ | R³ | E | R¹ | R² |
|---|---|---|---|---|---|---|---|---|---|---|---|---|
| 300 | H | SF5 | H | H | H | 0 | H | H | H | O | C(Me)2Et | H |
| 301 | H | OCF2CHF2 | H | H | H | 0 | H | H | H | O | C(Me)3 | H |
| 302 | H | SO2CF3 | H | H | H | 0 | H | H | H | O | CH(Me)2 | H |
| 303 | H | N(Me)2 | H | H | H | 0 | H | H | H | O | C(Me)3 | H |
| 304 | H | CF3 | H | H | H | 0 | H | H | Me | O | CH(Me)2 | CH3 |
| 305 | H | SF5 | H | H | H | 0 | H | H | H | O | cyclohexyl | H |
| 306 | H | CF3 | H | H | H | 0 | H | H | H | S | cyclohexyl | H |
| 307 | H | NH2 | H | H | H | 0 | H | H | H | O | C(Me)3 | H |
| 308 | H | OCF3 | H | H | H | 0 | H | H | H | O | 1-(CN)-cyclopentyl | H |
| 309 | H | Cl | H | Cl | H | 0 | H | H | H | O | —(CH2)5— | |
| 310 | H | CF3 | F | H | H | 0 | H | H | H | O | —(CH2)4— | |
| 311 | H | OCF3 | H | H | H | 0 | H | H | H | O | —CH2)2S(CH2)2— | |
| 312 | H | CF3 | H | H | H | 0 | H | H | H | O | 1-(CCH)-cyclobutyl | H |
| 313 | H | OCF3 | H | H | H | 0 | H | H | H | O | CMeEtCCH | |
| 314 | H | CF3 | F | H | H | 0 | H | H | H | O | 1-(CCH)-cyclopropyl | H |
| 315 | H | OCHF2 | H | H | H | 0 | H | H | H | O | C(Me)3 | H |
| 316 | H | Me | H | H | H | 0 | H | H | H | O | C(Me)3 | H |
| 317 | H | CF3 | H | H | H | 0 | H | H | Et | O | CH(Me)2 | H |
| 318 | H | N(SO2Me)2 | H | H | H | 0 | H | H | H | O | C(Me)3 | H |
| 319 | H | CF3 | H | H | H | 0 | H | H | H | O | 1-(CCH)-cyclohexyl | H |
| 320 | H | OCF3 | H | H | H | 0 | H | H | H | O | Me | H |
| 321 | H | OMe | H | H | H | 0 | H | H | H | O | C(Me)3 | H |
| 322 | H | CF3 | F | H | H | 0 | H | H | H | O | C(Et)2CCH | H |
| 323 | H | OCF3 | H | H | H | 0 | H | H | H | O | C(Et)2Me | H |
| 324 | H | CF3 | F | H | H | 0 | H | H | H | O | C(Me)2CH=CH2 | H |
| 325 | H | OCF3 | H | H | H | 0 | H | H | H | O | CH(Et)Ph | H |
| 326 | H | COOMe | H | H | H | 0 | H | H | H | O | C(Me)3 | H |
| 327 | H | CF3 | F | H | H | 0 | H | H | H | O | 1-(CCH)-cyclohexyl | H |
| 328 | H | Br | H | H | H | 0 | H | H | H | O | C(Me)3 | H |
| 329 | H | OCF3 | H | H | H | 0 | H | H | H | O | cyclopentyl | H |
| 330 | H | CF3 | F | H | H | 0 | H | H | Et | O | C(CH3)2CCH | H |
| 331 | H | I | H | H | H | 0 | H | H | H | O | C(Me)3 | H |
| 332 | H | OCF3 | H | H | H | 0 | H | H | H | O | 1-(CCH)-cyclobutyl | H |
| 333 | H | CF3 | H | H | H | 0 | H | H | Pr | O | C(Me)3 | H |
| 334 | H | OCF3 | H | H | H | 0 | H | H | H | O | C(Me)2CN | H |
| 335 | H | OCF3 | H | H | H | 0 | H | H | H | O | 1-(CCH-cyclopropyl | H |
| 336 | H | OPh | H | H | H | 0 | H | H | H | O | C(Me)3 | H |
| 337 | H | H | H | H | H | 0 | H | H | H | O | C(Me)3 | H |
| 338 | H | OCF3 | H | H | H | 0 | H | H | H | O | CH(Me)2 | Me |
| 339 | H | NHCOMe | H | H | H | 0 | H | H | H | O | C(Me)3 | H |
| 340 | H | SO2Me | H | H | H | 0 | H | H | H | O | C(Me)3 | H |
| 341 | H | Cl | Cl | Cl | H | 0 | H | H | H | O | C(Me)3 | H |
| 342 | H | SMe | H | H | H | 0 | H | H | H | O | C(Me)3 | H |
| 343 | H | OCF3 | H | H | H | 1 | H | H | H | O | C(Me)3 | H |
| 344 | H | OCF3 | H | H | H | 0 | H | H | H | O | C(Me)3 | H |
| 345 | H | CF3 | H | H | H | 2 | H | H | H | O | cyclohexyl | H |
| 346 | H | OMe | H | CF3 | H | 0 | H | H | H | O | C(Me)3 | H |
| 347 | H | CF3 | H | H | H | 1 | H | H | H | O | cyclohexyl | H |
| 348 | H | NO2 | H | CF3 | H | 0 | H | H | H | O | C(Me)3 | H |
| 349 | H | OCF3 | H | H | H | 2 | H | H | H | O | C(Me)3 | H |
| 350 | H | SO2CF3 | H | H | H | 0 | H | H | H | O | C(Me)3 | H |
| 351 | H | CF3 | H | H | H | 0 | H | H | H | O | C(Me)2CH2OMe | H |
| 352 | H | CF3 | H | H | H | 0 | H | H | H | O | C(Me)2CH2Cl | H |
| 353 | H | C(OEt)=CH2 | H | H | H | 0 | H | H | H | O | C(Me)3 | H |
| 354 | H | CF3 | H | H | H | 0 | H | H | H | O | 1-adamantyl | H |
| 355 | H | (PhCH2)2NSO2 | H | H | H | 0 | H | H | H | O | C(Me)3 | H |
| 356 | H | NHOH | H | CF3 | H | 0 | H | H | H | O | C(Me)3 | H |
| 357 | H | NH2 | H | CF3 | H | 0 | H | H | H | O | C(Me)3 | H |
| 358 | H | CF3 | H | H | H | 0 | H | H | H | S | CH(Me)2 | H |
| 359 (+form) | H | CF3 | H | H | H | 0 | H | H | H | O | C(Me)3 | H |
| 360 (−form) | H | CF3 | H | H | H | 0 | H | H | H | O | C(Me)3 | H |

TABLE II (Table II)

[Chemical structure diagram showing a substituted phenyl group with Z1-Z5 substituents connected via N to a carbonyl group, with R3, R4, R5, R4', R5' substituents and an O-C(=E)-N(R1)(R2) carbamate group]

| Comp No | Z¹ | Z² | Z³ | Z⁴ | Z⁵ | R¹ | R² | R³ | R⁴ | R⁵ | R⁴' | R⁵' | E |
|---|---|---|---|---|---|---|---|---|---|---|---|---|---|
| 361 | H | CF3 | H | H | H | C(Me)3 | H | H | H | H | H | H | O |
| 362 | H | CF3 | H | H | H | CH(Et)Ph | H | H | H | H | H | H | O |
| 363 | H | OCF3 | H | H | H | cyclopentyl | H | H | H | H | H | H | O |
| 364 | H | CF3 | H | CF3 | H | C(Me)2CCH | H | H | H | H | H | H | O |
| 365 | H | CF3 | H | H | H | C(Me)3 | H | H | H | H | Me | H | O |
| 366 | H | OCHF2 | H | H | H | C(Me)2CCH | H | H | H | H | H | H | O |
| 367 | H | OCF3 | H | H | H | CH(Me)Ph | H | H | H | H | H | H | O |
| 368 | H | CF3 | H | H | H | 1-Me-cyclobutyl | H | H | H | H | H | H | O |
| 369 | H | CF3 | H | H | H | CH(Me)2 | H | H | H | H | H | H | O |
| 370 | H | CF3 | H | H | H | 1-(CCH)-cyclohexyl | H | H | H | H | H | H | O |
| 371 | H | CF3 | F | H | H | C(Me)3 | H | H | H | H | H | H | O |
| 372 | H | OCHF2 | H | H | H | C(Me)3 | H | H | H | H | H | H | O |
| 373 | H | I | H | H | H | C(Me)3 | H | H | H | H | H | H | O |
| 374 | H | OCF3 | H | H | H | C(Me)3 | H | H | H | H | H | H | S |
| 375 | H | CF3 | F | H | H | CH(Me)Phe | H | H | H | H | H | H | O |
| 376 | H | CF3 | H | H | H | C(Me)2Ph | H | H | H | H | H | H | O |
| 377 | H | CF3 | H | H | H | C(Me)2Et | H | H | H | H | H | H | O |
| 378 | H | CF3 | H | H | H | cyclohexyl | H | H | H | H | H | H | O |
| 379 | H | CF3 | H | H | H | Et | Et | H | H | H | H | H | O |
| 380 | H | OCF3 | H | H | H | C(Me)2Et | H | H | H | H | H | H | O |
| 381 | H | Cl | H | H | H | C(Me)3 | H | H | H | H | H | H | O |
| 382 | H | Cl | Cl | H | H | C(Me)3 | H | H | H | H | H | H | O |
| 383 | F | H | CF3 | H | Cl | CH(Me)2 | H | H | H | H | H | H | O |
| 384 | H | CF3 | H | H | H | C(Me)2CCH | H | H | H | H | H | H | O |
| 385 | H | CF3 | H | H | H | CMeEtCCH | H | H | H | H | H | H | O |
| 386 | H | CF3 | H | H | H | C(Me)2CH=CH2 | H | H | H | H | H | H | O |
| 387 | H | OCF3 | H | H | H | 1-Me-cyclopropyl | H | H | H | H | H | H | O |
| 388 | H | CF3 | F | H | H | CH(Me)2 | H | H | H | H | H | H | O |
| 389 | H | Cl | F | H | H | C(Me)3 | H | H | H | H | H | H | O |
| 390 | F | H | CF3 | H | Cl | C(Me)3 | H | H | H | H | H | H | O |
| 391 | H | CF3 | H | H | H | 1-Me-cyclopropyl | H | H | H | H | H | H | O |
| 392 | H | CF3 | H | H | H | CH(Me)Ph | H | H | H | H | H | H | O |
| 393 | H | OCF3 | H | H | H | CH(Et)Ph | H | H | H | H | H | H | O |
| 394 | H | CF3 | H | H | H | C(Me)3 | H | Me | H | H | H | H | O |
| 395 | H | Cl | F | H | H | C(Me)2CCH | H | H | H | H | H | H | O |
| 396 | H | OCF3 | H | H | H | 1-(CCH)-cyclopropyl | H | H | H | H | H | H | O |
| 397 | H | OCF3 | H | H | H | C(Me)3 | H | H | H | H | H | H | O |
| 398 | H | CF3 | H | H | H | —(CH2)4— | | H | H | H | H | H | O |
| 399 | H | CF3 | H | H | H | CH(Me)2 | Me | H | H | H | H | H | O |
| 400 | H | CF3 | H | H | H | cyclopentyl | H | H | H | H | H | H | O |
| 401 | H | OCF3 | H | H | H | CH(Me)2 | H | H | H | H | H | H | O |
| 402 | H | CF3 | F | H | H | cyclohexyl | H | H | H | H | H | H | O |
| 403 | H | OCHF2 | H | H | H | 1-Me-cyclopropyl | H | H | H | H | H | H | O |
| 404 | H | CF3 | H | H | H | Me | Me | H | H | H | H | H | O |
| 405 | H | CF3 | H | H | H | —(CH2)2O(CH2)2— | | H | H | H | H | H | O |
| 406 | H | CF3 | H | H | H | 1-(CCH)-cyclopropyl | H | H | H | H | H | H | O |
| 407 | H | CF3 | H | H | H | 1-Me-cyclohexyl | H | H | H | H | H | H | O |
| 408 | H | OCF3 | H | H | H | CMeEtCCH | H | H | H | H | H | H | O |
| 409 | F | H | CF3 | H | Cl | Me | Me | H | H | H | H | H | O |
| 410 | H | CF3 | H | CF3 | H | C(Me)3 | H | H | H | H | H | H | O |
| 411 | H | CF3 | H | H | H | —(CH2)5— | | H | H | H | H | H | O |
| 412 | H | CF3 | H | H | H | C(Me)3 | H | H | Me | H | H | H | O |
| 413 | H | OCF3 | H | H | H | C(Me)2CCH | H | H | H | H | H | H | S |
| 414 | H | CF3 | F | H | H | C(Me)2CCH | H | H | H | H | H | H | O |
| 415 | H | CF3 | H | H | H | C(Me)2Pr | H | H | H | H | H | H | O |
| 416 | H | Br | H | H | H | C(Me)2CCH | H | H | H | H | H | H | O |
| 417 | H | Cl | H | Cl | H | C(Me)2CCH | H | H | H | H | H | H | O |
| 418 | H | CF3 | F | H | H | 1-Me-cyclopropyl | H | H | H | H | H | H | O |
| 419 | H | CF3 | H | H | H | C(Me)2CCH | H | H | H | H | H | H | S |
| 420 | H | OCF3 | H | H | H | C(Me)2CCH | H | H | H | H | H | H | O |
| 421 | H | CF3 | H | H | H | C(Me)2CCMe | H | H | H | H | H | H | O |
| 422 | H | SF5 | H | H | H | C(Me)2CCH | H | H | H | H | H | H | O |
| 423 | H | Cl | H | Cl | H | C(Me)3 | H | H | H | H | H | H | O |
| 424 | H | OCF3 | H | H | H | cyclohexyl | H | H | H | H | H | H | O |
| 425 | H | Cl | H | H | H | C(Me)2CCH | H | H | H | H | H | H | O |

TABLE II-continued

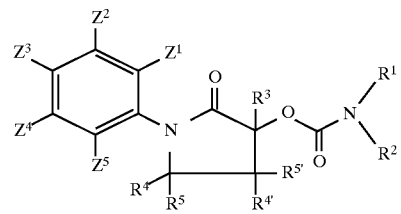

(Table II)

| Comp No | $Z^1$ | $Z^2$ | $Z^3$ | $Z^4$ | $Z^5$ | $R^1$ | $R^2$ | $R^3$ | $R^4$ | $R^5$ | $R^{4'}$ | $R^{5'}$ | E |
|---|---|---|---|---|---|---|---|---|---|---|---|---|---|
| 426 | H | CF3 | H | H | H | C(Me)3 | H | H | H | H | H | H | S |
| 427 | H | CF3 | F | H | H | C(Me)2Et | H | H | H | H | H | H | O |
| 428 | H | CF3 | H | H | H | C(Me)2CN | H | H | H | H | H | H | O |
| 429 | H | CF3 | H | H | H | 1-Me-cyclopentyl | H | H | H | H | H | H | O |
| 430 | H | CF3 | H | H | H | 1-(CN)-cyclopentyl | H | H | H | H | H | H | O |
| 431 | H | OCF2CHF2 | H | H | H | C(Me)3 | H | H | H | H | H | H | O |
| 432 | H | OMe | H | CF3 | H | C(Me)3 | H | H | H | H | H | H | O |

TABLE III (Table III)

| Comp No | $Z^1$ | $Z^2$ | $Z^3$ | $Z^4$ | $Z^5$ | $R^1$ | $R^2$ | $R^3$ | $R^4$ | $R^5$ | $R^{4'}$ | $R^{5'}$ | E |
|---|---|---|---|---|---|---|---|---|---|---|---|---|---|
| 433 | H | CF3 | H | H | H | cyclopentyl | H | H | H | H | H | H | O |
| 434 | H | CF3 | H | H | H | —(CH2)4— | | H | H | H | H | H | O |
| 435 | H | OCF3 | H | H | H | cyclohexyl | H | H | H | H | H | H | O |
| 436 | H | CF3 | H | H | H | C(Me)2CH=CH2 | H | H | H | H | H | H | O |
| 437 | H | CF3 | H | H | H | Me | Me | H | H | H | H | H | O |
| 438 | H | OCF3 | H | H | H | C(Me)3 | H | H | H | H | H | H | O |
| 439 | H | CF3 | H | H | H | Et | Et | H | H | H | H | H | O |
| 440 | H | CF3 | H | H | H | 1-Me-cyclobutyl | H | H | H | H | H | H | O |
| 441 | H | OCF3 | H | H | H | C(Me)3 | H | H | H | H | H | H | S |
| 442 | H | OCHF2 | H | H | H | C(Me)2CCH | H | H | H | H | H | H | O |
| 443 | H | CF3 | F | H | H | 1-Me-cyclopropyl | H | H | H | H | H | H | O |
| 444 | H | CF3 | H | H | H | C(Me)2CCH | H | H | H | H | H | H | O |
| 445 | H | OCHF2 | H | H | H | C(Me)3 | H | H | H | H | H | H | O |
| 446 | H | CF3 | H | H | H | C(Me)2Et | H | H | H | H | H | H | O |
| 447 | H | CF3 | F | H | H | cyclohexyl | H | H | H | H | H | H | O |
| 448 | H | CF3 | H | H | H | C(Me)3 | H | H | H | H | H | H | O |
| 449 | H | OCF2CHF2 | H | H | H | C(Me)3 | H | H | H | H | H | H | O |
| 450 | H | CF3 | H | H | H | —(CH2)5— | | H | H | H | H | H | O |
| 451 | H | OCF3 | H | H | H | 1-Me-cyclopropyl | H | H | H | H | H | H | O |
| 452 | H | CF3 | F | H | H | C(Me)3 | H | H | H | H | H | H | O |
| 453 | H | CF3 | H | H | H | C(Me)3 | H | H | H | H | H | H | S |
| 454 | H | Cl | H | Cl | H | C(Me)2CCH | H | H | H | H | H | H | O |
| 455 | H | CF3 | H | H | H | 1-Me-cyclopentyl | H | H | H | H | H | H | O |
| 456 | H | I | H | H | H | C(Me)3 | H | H | H | H | H | H | O |
| 457 | H | CF3 | H | H | H | C(Me)2CCMe | H | H | H | H | H | H | O |
| 458 | H | CF3 | H | H | H | —(CH2)2O(CH2)2— | | H | H | H | H | H | O |
| 459 | H | CF3 | H | CF3 | H | C(Me2CCH | H | H | H | H | H | H | O |
| 460 | H | OCF3 | H | H | H | C(Me)2CCH | H | H | H | H | H | H | O |
| 461 | H | CF3 | H | H | H | 1-Me-cyclopropyl | H | H | H | H | H | H | O |
| 462 | H | CF3 | H | H | H | C(Me)2CN | H | H | H | H | H | H | O |
| 463 | H | CF3 | H | H | H | 1-(CCH)-cyclohexyl | H | H | H | H | H | H | O |
| 464 | H | CF3 | H | H | H | C(Me)2CCH | H | H | H | H | H | H | S |
| 465 | H | CF3 | H | H | H | C(Me)3 | H | H | H | H | Me | H | O |
| 466 | H | OCHF2 | H | H | H | 1-Me-cyclopropyl | H | H | H | H | H | H | O |
| 467 | H | CF3 | H | H | H | CH(Me)2 | Me | H | H | H | H | H | O |
| 468 | H | OCF3 | H | H | H | 1-(CCH)-cyclopropyl | H | H | H | H | H | H | O |
| 469 | H | OCF3 | H | H | H | C(Me)2CCH | H | H | H | H | H | H | S |
| 470 | H | CF3 | H | H | H | 1-(CCH)-cyclopropyl | H | H | H | H | H | H | O |
| 471 | H | SF5 | H | H | H | C(Me)2CCH | H | H | H | H | H | H | O |

TABLE III-continued (Table III)

| Comp No | Z¹ | Z² | Z³ | Z⁴ | Z⁵ | R¹ | R² | R³ | R⁴ | R⁵ | R⁴' | R⁵' | E |
|---|---|---|---|---|---|---|---|---|---|---|---|---|---|
| 472 | H | Cl | H | Cl | H | C(Me)3 | H | H | H | H | H | H | O |
| 473 | H | CF3 | H | CF3 | H | C(Me)3 | H | H | H | H | H | H | O |
| 474 | H | Cl | H | H | H | C(Me)2CCH | H | H | H | H | H | H | O |
| 475 | H | OCF3 | H | H | H | CH(Me)2 | H | H | H | H | H | H | O |
| 476 | H | Cl | Cl | H | H | C(Me)3 | H | H | H | H | H | H | O |
| 477 | H | CF3 | H | H | H | C(Me)3 | H | H | Me | H | H | H | O |
| 478 | H | Cl | F | H | H | C(Me)3 | H | H | H | H | H | H | O |
| 479 | H | CF3 | F | H | H | CH(Me)2 | H | H | H | H | H | H | O |
| 480 | H | Cl | F | H | H | C(Me)2CCH | H | H | H | H | H | H | O |
| 481 | H | CF3 | H | H | H | CH(Et)Ph | H | H | H | H | H | H | O |
| 482 | H | CF3 | H | H | H | C(Me)2Pr | H | H | H | H | H | H | O |
| 483 | H | CF3 | H | H | H | CH(Me)Ph | H | H | H | H | H | H | O |
| 484 | H | CF3 | H | H | H | 1-(CN)-cyclopentyl | H | H | H | H | H | H | O |
| 485 | H | CF3 | F | H | H | C(Me)2CCH | H | H | H | H | H | H | O |
| 486 | H | CF3 | H | H | H | cyclohexyl | H | H | H | H | H | H | O |
| 487 | H | Cl | H | H | H | C(Me)3 | H | H | H | H | H | H | O |
| 488 | H | CF3 | H | H | H | CH(Me)2 | H | H | H | H | H | H | O |
| 489 | H | CF3 | H | H | H | 1-Me-cyclohexyl | H | H | H | H | H | H | O |
| 490 | H | Br | H | H | H | C(Me)2CCH | H | H | H | H | H | H | O |
| 491 | H | CF3 | H | H | H | C(Me)3 | H | Me | H | H | H | H | O |
| 492 | H | OMe | H | CF3 | H | C(Me)3 | H | H | H | H | H | H | O |

TABLE IV (Table IV)

| Comp No | Z¹ | Z² | Z³ | Z⁴ | Z⁵ | R¹ | R² | R³ | R⁴ | R⁵ | R⁴' | R⁵' | E | p |
|---|---|---|---|---|---|---|---|---|---|---|---|---|---|---|
| 493 | H | CF3 | H | H | H | cyclopentyl | H | H | H | H | H | H | O | 0 |
| 494 | H | CF3 | H | H | H | —(CH2)4— | | H | H | H | H | H | O | 0 |
| 495 | H | OCF3 | H | H | H | cyclohexyl | H | H | H | H | H | H | O | 0 |
| 496 | H | CF3 | H | H | H | C(Me)2CH=CH2 | H | H | H | H | H | H | O | 0 |
| 497 | H | CF3 | H | H | H | Me | Me | H | H | H | H | H | O | 0 |
| 498 | H | OCF3 | H | H | H | C(Me)3 | H | H | H | H | H | H | O | 0 |
| 499 | H | CF3 | H | H | H | Et | Et | H | H | H | H | H | O | 0 |
| 500 | H | CF3 | H | H | H | 1-Me-cyclobutyl | H | H | H | H | H | H | O | 0 |
| 501 | H | OCF3 | H | H | H | C(Me)3 | H | H | H | H | H | H | S | 0 |
| 502 | H | OCHF2 | H | H | H | C(Me)2CCH | H | H | H | H | H | H | O | 0 |
| 503 | H | CF3 | F | H | H | 1-Me-cyclopropyl | H | H | H | H | H | H | O | 0 |
| 504 | H | CF3 | H | H | H | C(Me)2CCH | H | H | H | H | H | H | O | 0 |
| 505 | H | OCHF2 | H | H | H | C(Me)3 | H | H | H | H | H | H | O | 0 |
| 506 | H | CF3 | H | H | H | C(Me)2Et | H | H | H | H | H | H | O | 0 |
| 507 | H | CF3 | F | H | H | cyclohexyl | H | H | H | H | H | H | O | 0 |
| 508 | H | CF3 | H | H | H | C(Me)3 | H | H | H | H | H | H | O | 0 |
| 509 | H | OCF2CHF2 | H | H | H | C(Me)3 | H | H | H | H | H | H | O | 0 |
| 510 | H | CF3 | H | H | H | —(CH2)5— | | H | H | H | H | H | O | 0 |
| 511 | H | OCF3 | H | H | H | 1-Me-cyclopropyl | H | H | H | H | H | H | O | 0 |
| 512 | H | CF3 | F | H | H | C(Me)3 | H | H | H | H | H | H | O | 0 |
| 513 | H | CF3 | H | H | H | C(Me)3 | H | H | H | H | H | H | S | 0 |
| 514 | H | Cl | H | Cl | H | C(Me)2CCH | H | H | H | H | H | H | O | 0 |
| 515 | H | CF3 | H | H | H | 1-Me-cyclopentyl | H | H | H | H | H | H | O | 0 |
| 516 | H | I | H | H | H | C(Me)3 | H | H | H | H | H | H | O | 0 |

TABLE IV-continued (Table IV)

| Comp No | Z¹ | Z² | Z³ | Z⁴ | Z⁵ | R¹ | R² | R³ | R⁴ | R⁵ | R⁴' | R⁵' | E | p |
|---|---|---|---|---|---|---|---|---|---|---|---|---|---|---|
| 517 | H | CF3 | H | H | H | C(Me)2CCMe | H | H | H | H | H | H | O | 0 |
| 518 | H | CF3 | H | H | H | —(CH2)2O(CH2)2— | | H | H | H | H | H | O | 0 |
| 519 | H | CF3 | H | CF3 | H | C(Me)2CCH | H | H | H | H | H | H | O | 0 |
| 520 | H | OCF3 | H | H | H | C(Me)2CCH | H | H | H | H | H | H | O | 0 |
| 521 | H | CF3 | H | H | H | 1-Me-cyclopropyl | H | H | H | H | H | H | O | 0 |
| 522 | H | CF3 | H | H | H | C(Me)2CN | H | H | H | H | H | H | O | 0 |
| 523 | H | CF3 | H | H | H | 1-(CCH)-cyclohexyl | H | H | H | H | H | H | O | 0 |
| 524 | H | CF3 | H | H | H | C(Me)2CCH | H | H | H | H | H | H | S | 0 |
| 525 | H | CF3 | H | H | H | C(Me)3 | H | H | H | H | Me | H | O | 0 |
| 526 | H | OCHF2 | H | H | H | 1-Me-cyclopropyl | H | H | H | H | H | H | O | 0 |
| 527 | H | CF3 | H | H | H | CH(Me)2 | Me | H | H | H | H | H | O | 0 |
| 528 | H | OCF3 | H | H | H | 1-(CCH)-cyclopropyl | H | H | H | H | H | H | O | 0 |
| 529 | H | OCF3 | H | H | H | C(Me)2CCH | H | H | H | H | H | H | S | 0 |
| 530 | H | CF3 | H | H | H | 1-(CCH)-cyclopropyl | H | H | H | H | H | H | O | 0 |
| 531 | H | SF5 | H | H | H | C(Me)2CCH | H | H | H | H | H | H | O | 0 |
| 532 | H | Cl | H | Cl | H | C(Me)3 | H | H | H | H | H | H | O | 0 |
| 533 | H | CF3 | H | CF3 | H | C(Me)3 | H | H | H | H | H | H | O | 0 |
| 534 | H | Cl | H | H | H | C(Me)2CCH | H | H | H | H | H | H | O | 0 |
| 535 | H | OCF3 | H | H | H | CH(Me)2 | H | H | H | H | H | H | O | 0 |
| 536 | H | Cl | CL | H | H | C(Me)3 | H | H | H | H | H | H | O | 0 |
| 537 | H | CF3 | H | H | H | C(Me)3 | H | H | Me | H | H | H | O | 0 |
| 538 | H | Cl | F | H | H | C(Me)3 | H | H | H | H | H | H | O | 0 |
| 539 | H | CF3 | F | H | H | CH(Me)2 | H | H | H | H | H | H | O | 0 |
| 540 | H | Cl | F | H | H | C(Me)2CCH | H | H | H | H | H | H | O | 0 |
| 541 | H | CF3 | H | H | H | CH(Et)Ph | H | H | H | H | H | H | O | 0 |
| 542 | H | CF3 | H | H | H | C(Me)2Pr | H | H | H | H | H | H | O | 0 |
| 543 | H | CF3 | H | H | H | CH(Me)Ph | H | H | H | H | H | H | O | 0 |
| 544 | H | CF3 | H | H | H | 1-(CN)-cyclopentyl | H | H | H | H | H | H | O | 0 |
| 545 | H | CF3 | F | H | H | C(Me)2CCH | H | H | H | H | H | H | O | 0 |
| 546 | H | CF3 | H | H | H | cyclohexyl | H | H | H | H | H | H | O | 0 |
| 547 | H | Cl | H | H | H | C(Me)3 | H | H | H | H | H | H | O | 0 |
| 548 | H | CF3 | H | H | H | CH(Me)2 | H | H | H | H | H | H | O | 0 |
| 549 | H | CF3 | H | H | H | 1-Me-cyclohexyl | H | H | H | H | H | H | O | 0 |
| 550 | H | Br | H | H | H | C(Me)2CCH | H | H | H | H | H | H | O | 0 |
| 551 | H | CF3 | H | H | H | C(Me)3 | H | Me | H | H | H | H | O | 0 |
| 552 | H | OMe | H | CF3 | H | C(Me)3 | H | H | H | H | H | H | O | 0 |

TABLE V (Table V)

| Comp No | Z¹ | Z² | Z³ | Z⁴ | Z⁵ | R¹ | R² | R⁴ | R⁵ | R⁴' | R⁵' | E |
|---|---|---|---|---|---|---|---|---|---|---|---|---|
| 553 | H | CF3 | H | H | H | Et | Et | H | H | H | H | O |
| 554 | H | CF3 | H | H | H | 1-Me-cyclobutyl | H | H | H | H | H | O |
| 555 | H | OCHF2 | H | H | H | (CMe)2CCH | H | H | H | H | H | O |
| 556 | H | CF3 | F | H | H | 1-Me-cyclopropyl | H | H | H | H | H | O |
| 557 | H | CF3 | H | H | H | C(Me)2CCH | H | H | H | H | H | O |
| 558 | H | OCHF2 | H | H | H | C(Me)3 | H | H | H | H | H | O |
| 559 | H | CF3 | H | H | H | C(Me)2Et | H | H | H | H | H | O |
| 560 | H | CF3 | F | H | H | cyclohexyl | H | H | H | H | H | O |
| 561 | H | CF3 | H | H | H | C(Me)3 | H | H | H | H | H | O |
| 562 | H | CF3 | H | H | H | —(CH2)5— | | H | H | H | H | O |

TABLE V-continued

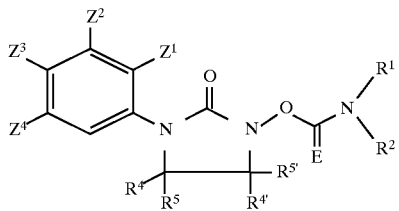

(Table V)

| Comp No | $Z^1$ | $Z^2$ | $Z^3$ | $Z^4$ | $Z^5$ | $R^1$ | $R^2$ | $R^4$ | $R^5$ | $R^{4'}$ | $R^{5'}$ | E |
|---|---|---|---|---|---|---|---|---|---|---|---|---|
| 563 | H | OCF3 | H | H | H | 1-Me-cyclopropyl | H | H | H | H | H | O |
| 564 | H | CF3 | H | H | H | cyclopentyl | H | H | H | H | H | O |
| 565 | H | CF3 | H | H | H | —(CH2)4— | | H | H | H | H | O |
| 566 | H | OCF3 | H | H | H | cyclohexyl | H | H | H | H | H | O |
| 567 | H | CF3 | H | H | H | Me | Me | H | H | H | H | O |
| 568 | H | OCF3 | H | H | H | C(Me)3 | H | H | H | H | H | O |
| 569 | H | CF3 | F | H | H | C(Me)3 | H | H | H | H | H | O |
| 570 | H | Cl | H | Cl | H | C(Me)2CCH | H | H | H | H | H | O |
| 571 | H | CF3 | H | H | H | 1-Me-cyclopentyl | H | H | H | H | H | O |
| 572 | H | CF3 | H | H | H | —(CH2)2O(CH2)2— | | H | H | H | H | O |
| 573 | H | OCF3 | H | H | H | C(Me)2CCH | H | H | H | H | H | O |
| 574 | H | CF3 | H | H | H | 1-Me-cyclopropyl | H | H | H | H | H | O |
| 575 | H | CF3 | H | H | H | 1-(CCH)-cyclohexyl | H | H | H | H | H | O |
| 576 | H | CF3 | H | H | H | C(Me)3 | H | H | H | Me | H | O |
| 577 | H | OCHF2 | H | H | H | 1-Me-cyclopropyl | H | H | H | H | H | O |
| 578 | H | CF3 | H | H | H | CH(Me)2 | Me | H | H | H | H | O |
| 579 | H | OCF3 | H | H | H | C(Me)2CCH | H | H | H | H | H | S |
| 580 | H | SF5 | H | H | H | C(Me)2CCH | H | H | H | H | H | O |
| 581 | H | Cl | H | Cl | H | C(Me)3 | H | H | H | H | H | O |
| 582 | H | CF3 | H | CF3 | H | C(Me)3 | H | H | H | H | H | O |
| 583 | H | OCF3 | H | H | H | CH(Me)2 | H | H | H | H | H | O |
| 584 | H | Cl | F | H | H | C(Me)3 | H | H | H | H | H | O |
| 585 | H | CF3 | F | H | H | CH(Me)2 | H | H | H | H | H | O |
| 586 | H | CF3 | H | H | H | C(Me)2Pr | H | H | H | H | H | O |
| 587 | H | CF3 | H | H | H | 1-(CN)-cyclopentyl | H | H | H | H | H | O |
| 588 | H | CF3 | H | H | H | C(Me)2CCH | H | H | H | H | H | O |
| 589 | H | Cl | H | H | H | C(Me)3 | H | H | H | H | H | O |
| 590 | H | CF3 | H | H | H | CH(Me)2 | H | H | H | H | H | O |
| 591 | H | Br | H | H | H | C(Me)2CCH | H | H | H | H | H | O |
| 592 | H | CF3 | H | H | H | C(Me)2CH2OMe | H | H | H | H | H | O |
| 593 | H | CF3 | H | H | H | C(Me)3 | H | H | H | H | H | S |
| 594 | H | CF3 | H | H | H | C(Me)2CCMe | H | H | H | H | H | O |
| 595 | H | CF3 | H | CF3 | H | C(Me)2CCH | H | H | H | H | H | O |
| 596 | H | CF3 | H | H | H | C(Me)2CCH | H | H | H | H | H | S |
| 597 | H | OCF3 | H | H | H | 1-(CCH)-cyclopropyl | H | H | H | H | H | O |
| 598 | H | Cl | CL | H | H | C(Me)3 | H | H | H | H | H | O |
| 599 | H | CF3 | H | H | H | CH(Et)Ph | H | H | H | H | H | O |
| 600 | H | CF3 | H | H | H | CH(Me)Ph | H | H | H | H | H | O |
| 601 | H | CF3 | H | H | H | 1-Me-cyclohexyl | H | H | H | H | H | O |
| 602 | H | CF3 | H | H | H | C(Me)2CH=CH2 | H | H | H | H | H | O |
| 603 | H | OCF3 | H | H | H | C(Me)3 | H | H | H | H | H | S |
| 604 | H | OCF2CHF2 | H | H | H | C(Me)3 | H | H | H | H | H | O |
| 605 | H | I | H | H | H | C(Me)3 | H | H | H | H | H | O |
| 606 | H | CF3 | H | H | H | C(Me)2CN | H | H | H | H | H | O |
| 607 | H | CF3 | H | H | H | 1-(CCH)-cyclopropyl | H | H | H | H | H | O |
| 608 | H | Cl | H | H | H | C(Me)2CCH | H | H | H | H | H | O |
| 609 | H | CF3 | H | H | H | C(Me)3 | H | Me | H | H | H | O |
| 610 | H | Cl | F | H | H | C(Me)2CCH | H | H | H | H | H | O |
| 611 | H | CF3 | H | H | H | cyclohexyl | H | H | H | H | H | O |
| 612 | H | OMe | H | CF3 | H | C(Me)3 | H | H | H | H | H | O |

TABLE VI

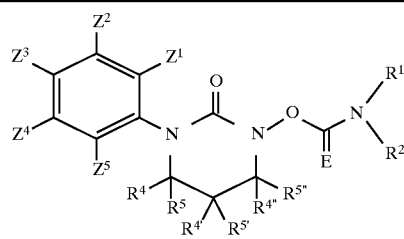

(Table Vi)

| Comp No | Z¹ | Z² | Z³ | Z⁴ | Z⁵ | R¹ | R² | R⁴ | R⁵ | R⁴' | R⁵' | R⁴" | R⁵" | E |
|---|---|---|---|---|---|---|---|---|---|---|---|---|---|---|
| 613 | H | CF3 | H | H | H | CH(Et)Ph | H | H | H | H | H | H | H | O |
| 614 | H | CF3 | H | H | H | 1-Me-cyclobutyl | H | H | H | H | H | H | H | O |
| 615 | H | CF3 | H | H | H | CH(Me)2 | Me | H | H | H | H | H | H | O |
| 616 | H | CF3 | H | H | H | 1-(CCH)-cyclohexyl | H | H | H | H | H | H | H | O |
| 617 | H | CF3 | H | H | H | —(CH2)2O(CH2)2— | | H | H | H | H | H | H | O |
| 618 | H | OCF3 | H | H | H | cyclohexyl | H | H | H | H | H | H | H | O |
| 619 | H | CF3 | F | H | H | C(Me)2CCH | H | H | H | H | H | H | H | O |
| 620 | H | CF3 | F | H | H | cyclohexyl | H | H | H | H | H | H | H | O |
| 621 | H | OCHF2 | H | H | H | C(Me)3 | H | H | H | H | H | H | H | O |
| 622 | H | CF3 | H | CF3 | H | C(Me)2CCH | H | H | H | H | H | H | H | O |
| 623 | H | Cl | H | H | H | C(Me)3 | H | H | H | H | H | H | H | O |
| 624 | H | Cl | H | H | H | C(Me)2CCH | H | H | H | H | H | H | H | O |
| 625 | H | Br | H | H | H | C(Me)2CCH | H | H | H | H | H | H | H | O |
| 626 | H | OCF2CHF2 | H | H | H | C(Me)3 | H | H | H | H | H | H | H | O |
| 627 | H | CF3 | H | H | H | C(Me)3 | H | H | H | H | H | Me | H | O |
| 628 | H | CF3 | H | H | H | C(Me)3 | H | H | H | H | H | H | H | S |
| 629 | H | OCF3 | H | H | H | C(Me)2CCH | H | H | H | H | H | H | H | S |
| 630 | H | CF3 | H | H | H | cyclohexyl | H | H | H | H | H | H | H | O |
| 631 | H | Cl | F | H | H | C(Me)2CCH | H | H | H | H | H | H | H | O |
| 632 | H | CF3 | H | H | H | C(Me)3 | H | Me | H | H | H | H | H | O |
| 633 | H | CF3 | H | H | H | 1-(CCH)-cyclopropyl | H | H | H | H | H | H | H | O |
| 634 | H | CF3 | H | H | H | C(Me)2CN | H | H | H | H | H | H | H | O |
| 635 | H | I | H | H | H | C(Me)3 | H | H | H | H | H | H | H | O |
| 636 | H | OCF3 | H | H | H | C(Me)3 | H | H | H | H | H | H | H | S |
| 637 | H | CF3 | H | H | H | C(Me)2CH=CH2 | H | H | H | H | H | H | H | O |
| 638 | H | CF3 | H | H | H | 1-Me-cyclohexyl | H | H | H | H | H | H | H | O |
| 639 | H | CF3 | H | H | H | CH(Me)Ph | H | H | H | H | H | H | H | O |
| 640 | H | Cl | H | Cl | H | C(Me)3 | H | H | H | H | H | H | H | O |
| 641 | H | OCF3 | H | H | H | 1-(CCH)-cyclopropyl | H | H | H | H | H | H | H | O |
| 642 | H | CF3 | H | H | H | C(Me)2CCH | H | H | H | H | H | H | H | S |
| 643 | H | CF3 | H | H | H | C(Me)2CCMe | H | H | H | H | H | H | H | O |
| 644 | H | CF3 | H | H | H | C(Me)2CH2OMe | H | H | H | H | H | H | H | O |
| 645 | H | CF3 | H | H | H | CH(Me)2 | H | H | H | H | H | H | H | O |
| 646 | H | CF3 | H | H | H | 1-(CN)-cyclopentyl | H | H | H | H | H | H | H | O |
| 647 | H | CF3 | H | H | H | C(Me)2Pr | H | H | H | H | H | H | H | O |
| 648 | H | CF3 | F | H | H | CH(Me)2 | H | H | H | H | H | H | H | O |
| 649 | H | Cl | F | H | H | C(Me)3 | H | H | H | H | H | H | H | O |
| 650 | H | OCF3 | H | H | H | CH(Me)2 | H | H | H | H | H | H | H | O |
| 651 | H | CF3 | H | CF3 | H | C(Me)3 | H | H | H | H | H | H | H | O |
| 652 | H | Cl | H | Cl | H | C(Me)3 | H | H | H | H | H | H | H | O |
| 653 | H | SF5 | H | H | H | C(Me)2CCH | H | H | H | H | H | H | H | O |
| 654 | H | OCHF2 | H | H | H | 1-Me-cyclopropyl | H | H | H | H | H | H | H | O |
| 655 | H | CF3 | H | H | H | C(Me)3 | H | H | H | Me | H | H | H | O |
| 656 | H | CF3 | H | H | H | 1-Me-cyclopropyl | H | H | H | H | H | H | H | O |
| 657 | H | OCF3 | H | H | H | C(Me)2CCH | H | H | H | H | H | H | H | O |
| 658 | H | CF3 | H | H | H | 1-Me-cyclopentyl | H | H | H | H | H | H | H | O |
| 659 | H | Cl | H | Cl | H | C(Me)2CCH | H | H | H | H | H | H | H | O |
| 660 | H | CF3 | F | H | H | C(Me)3 | H | H | H | H | H | H | H | O |
| 661 | H | OCF3 | H | H | H | C(Me)3 | H | H | H | H | H | H | H | O |
| 662 | H | CF3 | H | H | H | Me | Me | H | H | H | H | H | H | O |
| 663 | H | CF3 | H | H | H | —(CH2)4— | | H | H | H | H | H | H | O |
| 664 | H | CF3 | H | H | H | cyclopentyl | H | H | H | H | H | H | H | O |
| 665 | H | OCF3 | H | H | H | 1-Me-cyclopropyl | H | H | H | H | H | H | H | O |
| 666 | H | CF3 | H | H | H | —(CH2)5— | | H | H | H | H | H | H | O |
| 667 | H | CF3 | H | H | H | C(Me)3 | H | H | H | H | H | H | H | O |
| 668 | H | CF3 | H | H | H | C(Me)2Et | H | H | H | H | H | H | H | O |
| 669 | H | CF3 | H | H | H | C(Me)2CCH | H | H | H | H | H | H | H | O |
| 670 | H | CF3 | F | H | H | 1-Me-cyclopropyl | H | H | H | H | H | H | H | O |
| 671 | H | OCHF2 | H | H | H | C(Me)2CCH | H | H | H | H | H | H | H | O |
| 672 | H | OMe | H | CF3 | H | C(Me)₂CCH | H | H | H | H | H | H | H | O |

TABLE VII (Table VII)

[Structure diagram showing a benzene ring with substituents Z¹, Z², Z³, Z⁴, Z⁵ connected via N to a piperidine ring with R³, R⁴, R⁵, R⁴', R⁵', R⁴", R⁵" substituents, and an O-C(=E)-N(R¹)(R²) carbamate group]

| Comp No | Z¹ | Z² | Z³ | Z⁴ | Z⁵ | R¹ | R² | R³ | R⁴ | R⁵ | R⁴' | R⁵' | R⁴" | R⁵" | E |
|---|---|---|---|---|---|---|---|---|---|---|---|---|---|---|---|
| 673 | H | CF3 | H | H | H | CH(Et)Ph | H | H | H | H | H | H | H | H | O |
| 674 | H | CF3 | H | H | H | 1-Me-cyclobutyl | H | H | H | H | H | H | H | H | O |
| 675 | H | CF3 | H | H | H | CH(Me)2 | Me | H | H | H | H | H | H | H | O |
| 676 | H | CF3 | H | H | H | 1-(CCH)-cyclohexyl | H | H | H | H | H | H | H | H | O |
| 677 | H | CF3 | H | H | H | —(CH2)2O(CH2)2— | | H | H | H | H | H | H | H | O |
| 678 | H | CF3 | F | H | H | C(Me)2CCH | H | H | H | H | H | H | H | H | O |
| 679 | H | CF3 | F | H | H | cyclohexyl | H | H | H | H | H | H | H | H | O |
| 680 | H | OCHF2 | H | H | H | C(Me)3 | H | H | H | H | H | H | H | H | O |
| 681 | H | CF3 | H | CF3 | H | C(Me)2CCH | H | H | H | H | H | H | H | H | O |
| 682 | H | Cl | H | H | H | C(Me)3 | H | H | H | H | H | H | H | H | O |
| 683 | H | Cl | H | H | H | C(Me)2CCH | H | H | H | H | H | H | H | H | O |
| 684 | H | Br | H | H | H | C(Me)2CCH | H | H | H | H | H | H | H | H | O |
| 685 | H | OCF2CHF2 | H | H | H | C(Me)3 | H | H | H | H | H | H | H | H | O |
| 686 | H | CF3 | H | H | H | C(Me)3 | H | H | H | H | H | H | H | H | S |
| 687 | H | CF3 | H | H | H | cyclohexyl | H | H | H | H | H | H | H | H | O |
| 688 | H | Cl | F | H | H | C(Me)2CCH | H | H | H | H | H | H | H | H | O |
| 689 | H | CF3 | H | H | H | 1-(CCH)-cyclopropyl | H | H | H | H | H | H | H | H | O |
| 690 | H | CF3 | H | H | H | C(Me)2CN | H | H | H | H | H | H | H | H | O |
| 691 | H | CF3 | H | H | H | C(Me)2CH=CH2 | H | H | H | H | H | H | H | H | O |
| 692 | H | CF3 | H | H | H | 1-Me-cyclohexyl | H | H | H | H | H | H | H | H | O |
| 693 | H | Cl | Cl | H | H | C(Me)3 | H | H | H | H | H | H | Me | H | O |
| 694 | H | OCF3 | H | H | H | 1-(CCH)-cyclopropyl | H | H | H | H | H | H | H | H | O |
| 695 | H | CF3 | H | H | H | C(Me)2CCH | H | H | H | H | H | H | H | H | S |
| 696 | H | CF3 | H | H | H | C(Me)3 | H | H | H | H | H | H | H | H | O |
| 697 | H | CF3 | H | H | H | CH(Me)2 | H | H | H | H | H | H | H | H | O |
| 698 | H | CF3 | H | H | H | C(Me)2Pr | H | H | H | H | H | H | H | H | O |
| 699 | H | CF3 | F | H | H | CH(Me)2 | H | H | H | H | H | H | H | H | O |
| 700 | H | CF3 | H | H | H | C(Me)3 | H | H | H | H | H | H | H | H | O |
| 701 | H | CF3 | H | H | H | C(Me)3 | H | Me | H | H | H | H | H | H | O |
| 702 | H | CF3 | H | H | H | C(Me)2Et | H | H | H | H | H | H | H | H | O |
| 703 | H | CF3 | H | H | H | C(Me)2CCH | H | H | H | H | H | H | H | H | O |
| 704 | H | CF3 | F | H | H | 1-Me-cyclopropyl | H | H | H | H | H | H | H | H | O |
| 705 | H | OCHF2 | H | H | H | C(Me)2CCH | H | H | H | H | H | H | H | H | O |
| 706 | H | OCF3 | H | H | H | cyclohexyl | H | H | H | H | H | H | H | H | O |
| 707 | H | CF3 | H | H | H | C(Me)3 | H | H | H | H | H | H | H | H | O |
| 708 | H | OCF3 | H | H | H | C(Me)2CCH | H | H | H | H | H | H | H | H | S |
| 709 | H | CF3 | H | H | H | C(Me)3 | H | H | Me | H | H | H | H | H | O |
| 710 | H | OCF3 | H | H | H | C(Me)3 | H | H | H | H | H | H | H | H | S |
| 711 | H | CF3 | H | H | H | CH(Me)Ph | H | H | H | H | H | H | H | H | O |
| 712 | H | CF3 | H | H | H | C(Me)2CCMe | H | H | H | H | H | H | H | H | O |
| 713 | H | CF3 | H | H | H | 1-(CN)-cyclopentyl | H | H | H | H | H | H | H | H | O |
| 714 | H | SF5 | H | H | H | C(Me)2CCH | H | H | H | H | H | H | H | H | O |
| 715 | H | CF3 | H | H | H | 1-Me-cyclopropyl | H | H | H | H | H | H | H | H | O |
| 716 | H | CF3 | F | H | H | C(Me)3 | H | H | H | H | H | H | H | H | O |
| 717 | H | CF3 | H | H | H | Me | Me | H | H | H | H | H | H | H | O |
| 718 | H | Cl | F | H | H | C(Me)3 | H | H | H | H | H | H | H | H | O |
| 719 | H | OCF3 | H | H | H | CH(Me)2 | H | H | H | H | H | H | H | H | O |
| 720 | H | CF3 | H | CF3 | H | C(Me)3 | H | H | H | H | H | H | H | H | O |
| 721 | H | Cl | H | Cl | H | C(Me)3 | H | H | H | H | H | H | H | H | O |
| 722 | H | OCHF2 | H | H | H | 1-Me-cyclopropyl | H | H | H | H | H | H | H | H | O |
| 723 | H | CF3 | H | H | H | C(Me)3 | H | H | H | H | H | Me | H | H | O |
| 724 | H | OCF3 | H | H | H | C(Me)2CCH | H | H | H | H | H | H | H | H | O |
| 725 | H | CF3 | H | H | H | 1-Me-cyclopentyl | H | H | H | H | H | H | H | H | O |
| 726 | H | Cl | H | Cl | H | C(Me)2CCH | H | H | H | H | H | H | H | H | O |
| 727 | H | OCF3 | H | H | H | C(Me)3 | H | H | H | H | H | H | H | H | O |
| 728 | H | CF3 | H | H | H | —(CH2)4— | | H | H | H | H | H | H | H | O |
| 729 | H | CF3 | H | H | H | cyclopentyl | H | H | H | H | H | H | H | H | O |
| 730 | H | OCF3 | H | H | H | 1-Me-cyclopropyl | H | H | H | H | H | H | H | H | O |
| 731 | H | CF3 | H | H | H | —(CH2)5— | | H | H | H | H | H | H | H | O |
| 732 | H | OMe | H | CF3 | H | C(Me)3 | H | H | H | H | H | H | H | H | O |

TABLE VIII

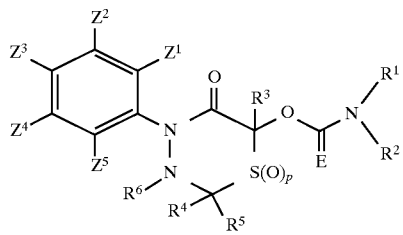

| Comp No | $Z^1$ | $Z^2$ | $Z^3$ | $Z^4$ | $Z^5$ | $R^1$ | $R^2$ | $R^3$ | $R^6$ | $R^4$ | $R^5$ | E | p |
|---|---|---|---|---|---|---|---|---|---|---|---|---|---|
| 733 | H | CF3 | H | H | H | C(Me)3 | H | Me | Me | H | H | O | 0 |
| 734 | H | OCF3 | H | H | H | C(Me)2CCH | H | H | Me | H | H | S | 0 |
| 735 | H | OCF3 | H | H | H | C(Me)3 | H | H | Me | H | H | S | 0 |
| 736 | H | CF3 | H | H | H | C(Me2CCH | H | H | Me | H | H | S | 0 |
| 737 | H | CF3 | H | H | H | C(Me)3 | H | H | Me | H | H | S | 0 |
| 738 | H | CF3 | H | H | H | C(Me)3 | H | H | Me | —(CH2)5 | | O | 0 |
| 739 | H | CF3 | H | H | H | C(Me)3 | H | H | Me | Me | Me | O | 0 |
| 740 | H | Cl | Cl | H | H | C(Me)3 | H | H | Me | H | H | O | 0 |
| 741 | H | SF5 | H | H | H | C(Me)2CCH | H | H | Me | H | H | O | 0 |
| 742 | H | OCF2CHF2 | H | H | H | C(Me)3 | H | H | Me | H | H | O | 0 |
| 743 | H | I | H | H | H | C(Me)3 | H | H | Me | H | H | O | 0 |
| 744 | H | Br | H | H | H | C(Me)2CCH | H | H | Me | H | H | O | 0 |
| 745 | H | Cl | F | H | H | C(Me)2CCH | H | H | Me | H | H | O | 0 |
| 746 | H | Cl | F | H | H | C(Me)3 | H | H | Me | H | H | O | 0 |
| 747 | H | Cl | H | H | H | C(Me)2CCH | H | H | Me | H | H | O | 0 |
| 748 | H | Cl | H | H | H | C(Me)3 | H | H | Me | H | H | O | 0 |
| 749 | H | Cl | H | Cl | H | C(Me)2CCH | H | H | Pr | H | H | O | 0 |
| 750 | H | Cl | H | Cl | H | C(Me)3 | H | H | Me | H | H | O | 0 |
| 751 | H | CF3 | H | CF3 | H | C(Me)2CCH | H | H | Et | H | H | O | 0 |
| 752 | H | CF3 | H | H | H | C(Me)3 | H | H | Me | H | H | O | 0 |
| 753 | H | OCHF2 | H | H | H | 1-Me-cyclopropyl | H | H | Me | H | H | O | 0 |
| 754 | H | OCHF2 | H | H | H | C(Me)2CCH | H | H | Et | H | H | O | 0 |
| 755 | H | OCHF2 | H | H | H | C(Me)3 | H | H | Me | H | H | O | 0 |
| 756 | H | CF3 | F | H | H | C(Me)2Et | H | H | Me | H | H | O | 0 |
| 757 | H | CF3 | F | H | H | 1-Me-cyclopropyl | H | H | Me | H | H | O | 0 |
| 758 | H | CF3 | F | H | H | cyclohexyl | H | H | Me | H | H | O | 0 |
| 759 | H | CF3 | F | H | H | CH(Me)Ph | H | H | Pr | H | H | O | 0 |
| 760 | H | CF3 | F | H | H | C(Me)2CCH | H | H | Et | H | H | O | 0 |
| 761 | H | CF3 | F | H | H | C(Me)3 | H | H | Et | H | H | O | 0 |
| 762 | H | OCF3 | H | H | H | 1-(CCH)-cyclopropyl | H | H | Me | H | H | O | 0 |
| 763 | H | OCF3 | H | H | H | CMeEtCCH | H | H | Me | H | H | O | 0 |
| 764 | H | OCF3 | H | H | H | CH(Me)2 | H | H | Me | H | H | O | 0 |
| 765 | H | OCF3 | H | H | H | 1-Me-cyclopropyl | H | H | Me | H | H | O | 0 |
| 766 | H | OCF3 | H | H | H | cyclohexyl | H | H | Me | H | H | O | 0 |
| 767 | H | OCF3 | H | H | H | CH(Me)Ph | H | H | Me | H | H | O | 0 |
| 768 | H | OCF3 | H | H | H | C(Me)2CCH | H | H | Me | H | H | O | 0 |
| 769 | H | OCF3 | H | H | H | C(Me)3 | H | H | Me | H | H | O | 0 |
| 770 | H | CF3 | H | H | H | Et | ET | H | Me | H | H | O | 0 |
| 771 | H | CF3 | H | H | H | Me | Me | H | Me | H | H | O | 0 |
| 772 | H | CF3 | H | H | H | C(Me)2CCMe | H | H | Me | H | H | O | 0 |
| 773 | H | CF3 | H | H | H | C(Me)2Ph | H | H | Me | H | H | O | 0 |
| 774 | H | CF3 | H | H | H | —(CH2)2O(CH2)2— | | H | Et | H | H | O | 0 |
| 775 | H | CF3 | H | H | H | —(CH2)5— | | H | Me | H | H | O | 0 |
| 776 | H | CF3 | H | H | H | —(CH2)4— | | H | Me | H | H | O | 0 |
| 777 | H | CF3 | H | H | H | 1-(CCH)-cyclohexyl | H | H | Et | H | H | O | 0 |
| 778 | H | CF3 | H | H | H | C(Me)2CH=CH2 | H | H | Et | H | H | O | 0 |
| 779 | H | CF3 | H | H | H | 1-Me-cyclohexyl | H | H | Et | H | H | O | 0 |
| 780 | H | CF3 | H | H | H | 1-Me-cyclopentyl | H | H | Et | H | H | O | 0 |
| 781 | H | CF3 | H | H | H | C(Me)2Pr | H | H | Me | H | H | O | 0 |
| 782 | H | CF3 | H | H | H | CH(Me)2 | Me | H | Me | H | H | O | 0 |
| 783 | H | CF3 | H | H | H | 1-(CN)-cyclopentyl | H | H | Me | H | H | O | 0 |
| 784 | H | CF3 | H | H | H | C(Me)2CN | H | H | Me | H | H | O | 0 |
| 785 | H | CF3 | H | H | H | 1-Me-cyclobutyl | H | H | Me | H | H | O | 0 |
| 786 | H | CF3 | H | H | H | 1-(CCH)-cyclopropyl | H | H | Me | H | H | O | 0 |
| 787 | H | CF3 | H | H | H | CMeEtCCH | H | H | Me | H | H | O | 0 |
| 788 | H | CF3 | H | H | H | cyclopentyl | H | H | Me | H | H | O | 0 |
| 789 | H | CF3 | H | H | H | CH(Et)Ph | H | H | Me | H | H | O | 0 |
| 790 | H | CF3 | H | H | H | C(Me)2Et | H | H | Me | H | H | O | 0 |
| 791 | H | CF3 | H | H | H | CH(Me)2 | H | H | Me | H | H | O | 0 |
| 792 | H | CF3 | H | H | H | 1-Me-cyclopropyl | H | H | Me | H | H | O | 0 |
| 793 | H | CF3 | H | H | H | cyclohexyl | H | H | Me | H | H | O | 0 |
| 794 | H | CF3 | H | H | H | CH(Me)Ph | H | H | Me | H | H | O | 0 |
| 795 | H | CF3 | H | H | H | C(Me)2CCH | H | H | Me | H | H | O | 0 |
| 796 | H | CF3 | H | CF3 | H | C(Me)3 | H | H | Me | H | H | O | 0 |

TABLE VIII-continued (Table VIII)

| Comp No | Z¹ | Z² | Z³ | Z⁴ | Z⁵ | R¹ | R² | R³ | R⁶ | R⁴ | R⁵ | E | p |
|---|---|---|---|---|---|---|---|---|---|---|---|---|---|
| 797 | H | CF3 | H | H | H | C(Me)3 | H | H | Et | H | H | O | 0 |
| 798 | H | OMe | H | CF3 | H | C(Me)2CCH | H | H | Me | H | H | O | 0 |

TABLE IX (Table IX)

| Comp No | Z¹ | Z² | Z³ | Z⁴ | Z⁵ | R¹ | R² | R³ | R⁴ | R⁵ | R⁴' | R⁵' | E |
|---|---|---|---|---|---|---|---|---|---|---|---|---|---|
| 799 | H | CF3 | H | H | H | cyclopentyl | H | H | H | H | H | H | O |
| 800 | H | CF3 | H | H | H | —(CH2)4— | | H | H | H | H | H | O |
| 801 | H | OCF3 | H | H | H | cyclohexyl | H | H | H | H | H | H | O |
| 802 | H | CF3 | H | H | H | C(Me)2CH=CH2 | H | H | H | H | H | H | O |
| 803 | H | CF3 | H | H | H | Me | Me | H | H | H | H | H | O |
| 804 | H | OCF3 | H | H | H | C(Me)3 | H | H | H | H | H | H | O |
| 805 | H | CF3 | H | H | H | Et | Et | H | H | H | H | H | O |
| 806 | H | CF3 | H | H | H | 1-Me-cyclobutyl | H | H | H | H | H | H | O |
| 807 | H | OCF3 | H | H | H | C(Me)3 | H | H | H | H | H | H | S |
| 808 | H | CF3 | F | H | H | 1-Me-cyclopropyl | H | H | H | H | H | H | O |
| 809 | H | CF3 | H | H | H | C(Me)2CCH | H | H | H | H | H | H | O |
| 810 | H | OCHF2 | H | H | H | C(Me)3 | H | H | H | H | H | H | O |
| 811 | H | CF3 | H | H | H | C(Me)2Et | H | H | H | H | H | H | O |
| 812 | H | CF3 | F | H | H | cyclohexyl | H | H | H | H | H | H | O |
| 813 | H | CF3 | H | H | H | C(Me)3 | H | H | H | H | H | H | O |
| 814 | H | CF3 | H | H | H | —(CH2)5— | | H | H | H | H | H | O |
| 815 | H | CF3 | F | H | H | C(Me)3 | H | H | H | H | H | H | O |
| 816 | H | CF3 | H | H | H | C(Me)3 | H | H | H | H | H | H | O |
| 817 | H | Cl | H | Cl | H | C(Me)2CCH | H | H | H | H | H | H | O |
| 818 | H | CF3 | H | H | H | 1-Me-cyclopentyl | H | H | H | H | H | H | O |
| 819 | H | I | H | H | H | C(Me)3 | H | H | H | H | H | H | O |
| 820 | H | CF3 | H | H | H | C(Me)2CCMe | H | H | H | H | H | H | O |
| 821 | H | CF3 | H | H | H | —(CH2)2O(CH2)2— | | H | H | H | H | H | O |
| 822 | H | OCF3 | H | H | H | C(Me)2CCH | H | H | H | H | H | H | O |
| 823 | H | CF3 | H | H | H | 1-Me-cyclopropyl | H | H | H | H | H | H | O |
| 824 | H | CF3 | H | H | H | C(Me)2CN | H | H | H | H | H | H | O |
| 825 | H | CF3 | H | H | H | C(Me)2CCH | H | H | H | H | H | H | S |
| 826 | H | OCHF2 | H | H | H | 1-Me-cyclopropyl | H | H | H | H | H | H | O |
| 827 | H | OCF3 | H | H | H | 1-(CCH)-cyclopropyl | H | H | H | H | H | H | O |
| 828 | H | OCF3 | H | H | H | C(Me)2CCH | H | H | H | H | H | H | S |
| 829 | H | SF5 | H | H | H | C(Me)2CCH | H | H | H | H | H | H | O |
| 830 | H | Cl | H | Cl | H | C(Me)3 | H | H | H | H | H | H | O |
| 831 | H | CF3 | H | CF3 | H | C(Me)3 | H | H | H | H | H | H | O |
| 832 | H | Cl | H | H | H | C(Me)2CCH | H | H | H | H | H | H | O |
| 833 | H | Cl | CL | H | H | C(Me)3 | H | H | H | H | H | H | O |
| 834 | H | CF3 | F | H | H | CH(Me)2 | H | H | H | H | H | H | O |
| 835 | H | Cl | F | H | H | C(Me)2CCH | H | H | H | H | H | H | O |
| 836 | H | CF3 | H | H | H | CH(Et)Ph | H | H | H | H | H | H | O |
| 837 | H | CF3 | H | H | H | C(Me)2Pr | H | H | H | H | H | H | O |
| 838 | H | CF3 | H | H | H | CH(Me)Ph | H | H | H | H | H | H | O |
| 839 | H | CF3 | H | H | H | 1-(CN)-cyclopentyl | H | H | H | H | H | H | O |
| 840 | H | CF3 | H | H | H | cyclohexyl | H | H | H | H | H | H | O |

TABLE IX-continued

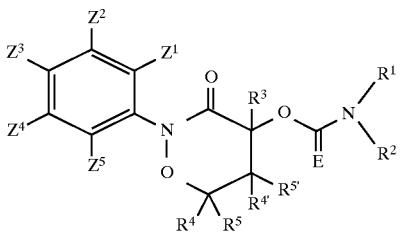
(Table IX)

| Comp No | $Z^1$ | $Z^2$ | $Z^3$ | $Z^4$ | $Z^5$ | $R^1$ | $R^2$ | $R^3$ | $R^4$ | $R^5$ | $R^{4'}$ | $R^{5'}$ | E |
|---|---|---|---|---|---|---|---|---|---|---|---|---|---|
| 841 | H | Cl | H | H | H | C(Me)3 | H | H | H | H | H | H | O |
| 842 | H | CF3 | H | H | H | 1-Me-cyclohexyl | H | H | H | H | H | H | O |
| 843 | H | Br | H | H | H | C(Me)2CCH | H | H | H | H | H | H | O |
| 844 | H | CF3 | H | H | H | CH(Me)2 | H | H | H | H | H | H | O |
| 845 | H | CF3 | H | H | H | 1-(CCH)-cyclopropyl | H | H | H | H | H | H | O |
| 846 | H | CF3 | H | H | H | CH(Me)2 | Me | H | H | H | H | H | O |
| 847 | H | CF3 | H | H | H | 1-(CCH)-cyclohexyl | H | H | H | H | H | H | O |
| 848 | H | OCF3 | H | H | H | 1-Me-cyclopropyl | H | H | H | H | H | H | O |
| 849 | H | OCF3 | H | H | H | CH(Me)2 | H | H | H | H | H | H | O |
| 850 | H | CF3 | F | H | H | C(Me)2CCH | H | H | H | H | H | H | O |
| 851 | H | OCHF2 | H | H | H | C(Me)2CCH | H | H | H | H | H | H | O |
| 852 | H | CF3 | H | CF3 | H | C(Me)2CCH | H | H | H | H | H | H | O |
| 853 | H | Cl | F | H | H | C(Me)3 | H | H | H | H | H | H | O |
| 854 | H | OCF2CHF2 | H | H | H | C(Me)3 | H | H | H | H | H | H | O |
| 855 | H | OMe | H | CF3 | H | C(Me)3 | H | H | H | H | H | H | O |

TABLE X

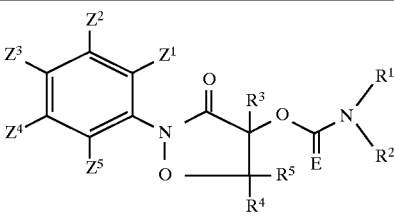
(Table X)

| Comp No | $Z^1$ | $Z^2$ | $Z^3$ | $Z^4$ | $Z^5$ | $R^1$ | $R^2$ | $R^3$ | $R^4$ | $R^5$ | E |
|---|---|---|---|---|---|---|---|---|---|---|---|
| 856 | H | CF3 | H | H | H | 1-Me-cyclopropyl | H | H | H | H | O |
| 857 | H | OCHF2 | H | H | H | 1-Me-cyclopropyl | H | H | H | H | O |
| 858 | H | CF3 | F | H | H | 1-Me-cyclopropyl | H | H | H | H | O |
| 859 | H | CF3 | H | H | H | C(Me)2CCH | H | H | H | H | S |
| 860 | H | CF3 | H | H | H | cyclopentyl | H | H | H | H | O |
| 861 | H | OCF3 | H | H | H | 1-(CCH)-cyclopropyl | H | H | H | H | O |
| 862 | H | I | H | H | H | C(Me)3 | H | H | H | H | O |
| 863 | H | OCF3 | H | H | H | 1-Me-cyclopropyl | H | H | H | H | O |
| 864 | H | CF3 | F | H | H | C(Me)3 | H | H | H | H | O |
| 865 | H | CF3 | H | H | H | C(Me)2CCH | H | H | H | H | O |
| 866 | H | OCF3 | H | H | H | CH(Me)2 | H | H | H | H | O |
| 867 | H | CF3 | H | CF3 | H | C(Me)2CCH | H | H | H | H | O |
| 868 | H | CF3 | H | CF3 | H | C(Me)3 | H | H | H | H | O |
| 869 | H | CF3 | H | H | H | C(Me)2Et | H | H | H | H | O |
| 870 | H | CF3 | H | H | H | C(Me)2CH=CH2 | H | H | H | H | O |
| 871 | H | OCF3 | H | H | H | C(Me)3 | H | H | H | H | O |
| 872 | H | CF3 | H | H | H | C(Me)3 | H | Me | H | H | O |
| 873 | H | Cl | H | Cl | H | C(Me)3 | H | H | H | H | O |
| 874 | H | Cl | F | H | H | C(Me)3 | H | H | H | H | O |
| 875 | H | CF3 | H | H | H | Et | Et | H | H | H | O |
| 876 | H | Cl | Cl | H | H | C(Me)3 | H | H | H | H | O |
| 877 | H | CF3 | H | H | H | C(Me)3 | H | H | H | H | S |
| 878 | H | OCF3 | H | H | H | C(Me)2CCH | H | H | H | H | S |
| 879 | H | Cl | H | H | H | C(Me)3 | H | H | H | H | O |
| 880 | H | CF3 | H | H | H | cyclohexyl | H | H | H | H | O |
| 881 | H | CF3 | H | H | H | 1-Me-cyclopentyl | H | H | H | H | O |
| 882 | H | CF3 | H | H | H | Me | Me | H | H | H | O |
| 883 | H | OCF3 | H | H | H | C(Me)3 | H | H | H | H | O |
| 884 | H | OCF3 | H | H | H | C(Me)2CCH | H | H | H | H | O |
| 885 | H | CF3 | H | H | H | —(CH2)—O—(CH2) | H | H | H | O |

TABLE X-continued

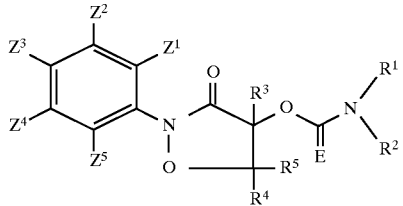
(Table X)

| Comp No | $Z^1$ | $Z^2$ | $Z^3$ | $Z^4$ | $Z^5$ | $R^1$ | $R^2$ | $R^3$ | $R^4$ | $R^5$ | E |
|---|---|---|---|---|---|---|---|---|---|---|---|
| 886 | H | CF3 | H | H | H | CH(Et)Ph | H | H | H | H | O |
| 887 | H | CF3 | H | H | H | C(Me)2CN | H | H | H | H | O |
| 888 | H | CF3 | H | H | H | CH(Me)2 | Me | H | H | H | O |
| 889 | H | CF3 | H | H | H | —(CH2)4— | | H | H | H | O |
| 890 | H | CF3 | H | H | H | C(Me)3 | H | H | H | H | O |
| 891 | H | CF3 | H | H | H | 1-Me-cyclohexyl | H | H | H | H | O |
| 892 | H | CF3 | H | H | H | 1-Me-cycobutyl | H | H | H | H | O |
| 893 | H | CF3 | F | H | H | CH(Me)2 | H | H | H | H | O |
| 894 | H | Cl | F | H | H | C(Me)2CCH | H | H | H | H | O |
| 895 | H | OCF2CHF2 | H | H | H | C(Me)3 | H | H | H | H | O |
| 896 | H | OCF3 | H | H | H | cyclohexyl | H | H | H | H | O |
| 897 | H | CF3 | F | H | H | C(Me)2CCH | H | H | H | H | O |
| 898 | H | CF3 | H | H | H | CH(Me)Ph | H | H | H | H | O |
| 899 | H | CF3 | H | H | H | CH(Me)2 | H | H | H | H | O |
| 900 | H | CF3 | H | H | H | 1-(CCH)-cyclopropyl | H | H | H | H | O |
| 901 | H | CF3 | H | H | H | 1-(CN-cyclopentyl | H | H | H | H | O |
| 902 | H | CF3 | H | H | H | C(Me)2Pr | H | H | H | H | O |
| 903 | H | CF3 | H | H | H | 1-(CCH)-cyclohexyl | H | H | H | H | O |
| 904 | H | CF3 | H | H | H | —(CH2)5— | | H | H | H | O |
| 905 | H | CF3 | H | H | H | C(Me)2CCMe | H | H | H | H | O |
| 906 | H | CF3 | F | H | H | cyclohexyl | H | H | H | H | O |
| 907 | H | OCHF2 | H | H | H | C(Me)3 | H | H | H | H | O |
| 908 | H | OCHF2 | H | H | H | C(Me)2CCH | H | H | H | H | O |
| 909 | H | Cl | H | Cl | H | C(Me)2CCH | H | H | H | H | O |
| 910 | H | Cl | H | H | H | C(Me)2CCH | H | H | H | H | O |
| 911 | H | Br | H | H | H | C(Me)2CCH | H | H | H | H | O |
| 912 | H | SF5 | H | H | H | C(Me)2CCH | H | H | H | H | O |
| 913 | H | CF3 | H | H | H | C(Me)3 | H | H | Me | H | O |
| 914 | H | CF3 | H | H | H | C(Me)3 | H | H | Me | Me | O |
| 915 | H | OMe | H | CF3 | H | C(Me)3 | H | H | H | H | O |

TABLE XI

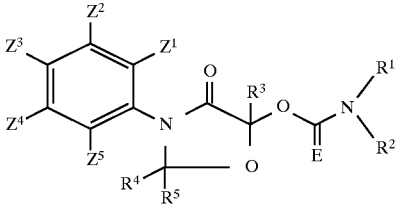
(Table XI)

| Comp No | $Z^1$ | $Z^2$ | $Z^3$ | $Z^4$ | $Z^5$ | $R^1$ | $R^2$ | $R^3$ | $R^4$ | $R^5$ | E |
|---|---|---|---|---|---|---|---|---|---|---|---|
| 916 | H | Cl | F | H | H | C(Me)2CCH | H | H | H | H | O |
| 917 | H | CF3 | H | H | H | —(CH2)2O(CH2)2— | | H | H | H | O |
| 918 | H | CF3 | H | H | H | C(Me)2CN | H | H | H | H | O |
| 919 | H | CF3 | H | H | H | 1-Me-cyclopentyl | H | H | H | H | O |
| 920 | H | CF3 | H | H | H | CH(Me)2 | H | H | H | H | O |
| 921 | H | CF3 | H | H | H | C(Me)2CCH | H | H | H | H | O |
| 922 | H | CF3 | H | CF3 | H | C(Me)3 | H | H | H | H | O |
| 923 | H | CF3 | H | H | H | cyclohexyl | H | H | H | H | O |
| 924 | H | CF3 | H | H | H | C(Me)2CH=CH2 | H | H | H | H | O |
| 925 | H | CF3 | H | H | H | C(Me)3 | H | H | H | H | S |
| 926 | H | Br | H | H | H | C(Me)2CCH | H | H | H | H | O |
| 927 | H | CF3 | H | H | H | C(Me)3 | H | H | Me | H | O |
| 928 | H | CF3 | H | H | H | 1-(CN)-cyclopentyl | H | H | H | H | O |
| 929 | H | CF3 | H | H | H | C(Me)2Pr | H | H | H | H | O |
| 930 | H | OCHF2 | H | H | H | C(Me)2CCH | H | H | H | H | O |
| 931 | H | CF3 | H | H | H | 1-Me-cyclopropyl | H | H | H | H | O |

TABLE XI-continued

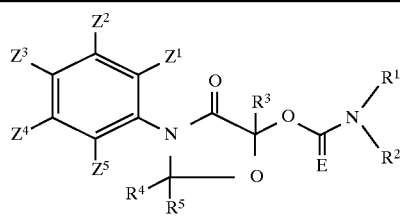

(Table XI)

| Comp No | $Z^1$ | $Z^2$ | $Z^3$ | $Z^4$ | $Z^5$ | $R^1$ | $R^2$ | $R^3$ | $R^4$ | $R^5$ | E |
|---|---|---|---|---|---|---|---|---|---|---|---|
| 932 | H | CF3 | H | H | H | C(Me)2CCH | H | H | H | H | S |
| 933 | H | OCF3 | H | H | H | 1-(CCH)-cyclopropyl | H | H | H | H | O |
| 934 | H | Cl | F | H | H | C(Me)3 | H | H | H | H | O |
| 935 | H | OCHF2 | H | H | H | 1-Me-cyclopropyl | H | H | H | H | O |
| 936 | H | CF3 | F | H | H | 1-Me-cyclopropyl | H | H | H | H | O |
| 937 | H | CF3 | H | H | H | cyclopentyl | H | H | H | H | O |
| 938 | H | I | H | H | H | C(Me)3 | H | H | H | H | O |
| 939 | H | OCF3 | H | H | H | 1-Me-cyclopropyl | H | H | H | H | O |
| 940 | H | CF3 | F | H | H | C(Me)3 | H | H | H | H | O |
| 941 | H | OCF3 | H | H | H | CH(Me)2 | H | H | H | H | O |
| 942 | H | CF3 | H | CF3 | H | C(Me)2CCH | H | H | H | H | O |
| 943 | H | CF3 | H | H | H | C(Me)2Et | H | H | H | H | O |
| 944 | H | OCF3 | H | H | H | C(Me)3 | H | H | H | H | S |
| 945 | H | CF3 | H | H | H | C(Me)3 | H | Me | H | H | O |
| 946 | H | CF3 | H | H | H | Et | Et | H | H | H | O |
| 947 | H | Cl | Cl | H | H | C(Me)3 | H | H | H | H | O |
| 948 | H | OCF3 | H | H | H | C(Me)2CCH | H | H | H | H | S |
| 949 | H | Cl | H | H | H | C(Me)3 | H | H | H | H | O |
| 950 | H | CF3 | H | H | H | Me | Me | H | H | H | O |
| 951 | H | CF3 | H | H | H | CH(Et)Ph | H | H | H | H | O |
| 952 | H | CF3 | H | H | H | —(CH2)4— | | H | H | H | O |
| 953 | H | OCF3 | H | H | H | C(Me)3 | H | H | H | H | O |
| 954 | H | CF3 | H | H | H | C(Me)3 | H | H | H | H | O |
| 955 | H | CF3 | H | H | H | 1-Me-cyclohexyl | H | H | H | H | O |
| 956 | H | CF3 | H | H | H | 1-Me-cyclobutyl | H | H | H | H | O |
| 957 | H | CF3 | F | H | H | CH(Me)2 | H | H | H | H | O |
| 958 | H | OCF2CHF2 | H | H | H | C(Me)3 | H | H | H | H | O |
| 959 | H | OCF3 | H | H | H | cyclohexyl | H | H | H | H | O |
| 960 | H | CF3 | F | H | H | C(Me)2CCH | H | H | H | H | O |
| 961 | H | CF3 | H | H | H | 1-(CCH)-cyclopropyl | H | H | H | H | O |
| 962 | H | CF3 | H | H | H | 1-(CCH)-cyclohexyl | H | H | H | H | O |
| 963 | H | CF3 | H | H | H | —(CH2)5— | | H | H | H | O |
| 964 | H | CF3 | H | H | H | C(Me)2CCMe | H | H | H | H | O |
| 965 | H | CF3 | F | H | H | cyclohexyl | H | H | H | H | O |
| 966 | H | OCHF2 | H | H | H | C(Me)3 | H | H | H | H | O |
| 967 | H | Cl | H | Cl | H | C(Me)2CCH | H | H | H | H | O |
| 968 | H | Cl | H | H | H | C(Me)2CCH | H | H | H | H | O |
| 969 | H | SF5 | H | H | H | C(Me)2CCH | H | H | H | H | O |
| 970 | H | CF3 | H | H | H | C(Me)3 | H | H | Me | Me | O |
| 971 | H | OCF3 | H | H | H | C(Me)2CCH | H | H | H | H | O |
| 972 | H | Cl | H | Cl | H | C(Me)3 | H | H | H | H | O |
| 973 | H | CF3 | H | H | H | CH(Me)2 | Me | H | H | H | O |
| 974 | H | CF3 | H | H | H | CH(Me)Ph | H | H | H | H | O |
| 975 | H | OMe | H | CF3 | H | C(Me)2CCH | H | H | H | H | O |

TABLE XII

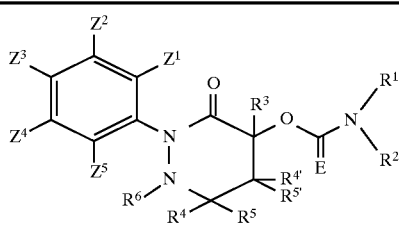

(Table XII)

| Comp No | $Z^1$ | $Z^2$ | $Z^3$ | $Z^4$ | $Z^5$ | $R^1$ | $R^2$ | $R^3$ | $R^4$ | $R^5$ | $R^{4'}$ | $R^{5'}$ | $R^6$ | E |
|---|---|---|---|---|---|---|---|---|---|---|---|---|---|---|
| 976 | H | Cl | H | Cl | H | C(Me)3 | H | H | H | H | H | H | Me | O |
| 977 | H | OCF3 | H | H | H | C(Me)2CCH | H | H | H | H | H | H | Me | O |

TABLE XII-continued (Table XII)

| Comp No | Z¹ | Z² | Z³ | Z⁴ | Z⁵ | R¹ | R² | R³ | R⁴ | R⁵ | R⁴' | R⁵' | R⁶ | E |
|---|---|---|---|---|---|---|---|---|---|---|---|---|---|---|
| 978 | H | SF5 | H | H | H | C(Me)2CCH | H | H | H | H | H | H | Me | O |
| 979 | H | OCHF2 | H | H | H | C(Me)3 | H | H | H | H | H | H | Et | O |
| 980 | H | CF3 | H | H | H | C(Me)2CCMe | H | H | H | H | H | H | Me | O |
| 981 | H | CF3 | H | H | H | —(CH2)5— | | H | H | H | H | H | Et | O |
| 982 | H | CF3 | H | H | H | 1-(CCH)-cyclohexyl | H | H | H | H | H | H | Et | O |
| 983 | H | CF3 | H | H | H | 1-(CCH)-cyclopropyl | H | H | H | H | H | H | Et | O |
| 984 | H | OCF3 | H | H | H | cyclohexyl | H | H | H | H | H | H | Et | O |
| 985 | H | OCF2CHF2 | H | H | H | C(Me)3 | H | H | H | H | H | H | Et | O |
| 986 | H | CF3 | F | H | H | CH(Me)2 | H | H | H | H | H | H | Me | O |
| 987 | H | CF3 | H | H | H | 1-Me-cyclobutyl | H | H | H | H | H | H | Pr | O |
| 988 | H | CF3 | H | H | H | 1-Me-cyclohexyl | H | H | H | H | H | H | Et | O |
| 989 | H | CF3 | H | H | H | C(Me)3 | H | H | H | H | H | H | Me | O |
| 990 | H | OCF3 | H | H | H | C(Me)3 | H | H | H | H | H | H | Et | O |
| 991 | H | CF3 | H | H | H | CH(Et)Ph | H | H | H | H | H | H | Et | O |
| 992 | H | CF3 | H | H | H | Me | Me | H | H | H | H | H | Et | O |
| 993 | H | Cl | H | H | H | C(Me)3 | H | H | H | H | H | H | Pr | O |
| 994 | H | OCF3 | H | H | H | C(Me)2CCH | H | H | H | H | H | H | Me | S |
| 995 | H | CF3 | H | H | H | C(Me)3 | H | Me | H | H | H | H | Et | O |
| 996 | H | CF3 | H | CF3 | H | C(Me)2CCH | H | H | H | H | H | H | Et | O |
| 997 | H | CF3 | F | H | H | C(Me)3 | H | H | H | H | H | H | Et | O |
| 998 | H | OCF3 | H | H | H | 1-Me-cyclopropyl | H | H | H | H | H | H | Me | O |
| 999 | H | I | H | H | H | C(Me)3 | H | H | H | H | H | H | Me | O |
| 1000 | H | CF3 | H | H | H | cyclopentyl | H | H | H | H | H | H | Me | O |
| 1001 | H | CF3 | F | H | H | 1-Me-cyclopropyl | H | H | H | H | H | H | Et | O |
| 1002 | H | Cl | F | H | H | C(Me)3 | H | H | H | H | H | H | Et | O |
| 1003 | H | OCF3 | H | H | H | 1-(CCH)-cyclopropyl | H | H | H | H | H | H | Me | O |
| 1004 | H | CF3 | H | H | H | C(Me)2CCH | H | H | H | H | H | H | Me | S |
| 1005 | H | CF3 | H | H | H | 1-Me-cyclopropyl | H | H | H | H | H | H | Me | O |
| 1006 | H | OCHF2 | H | H | H | C(Me)2CCH | H | H | H | H | H | H | Me | O |
| 1007 | H | CF3 | H | H | H | C(Me)2Pr | H | H | H | H | H | H | Et | O |
| 1008 | H | CF3 | H | H | H | 1-(CN)-cyclopentyl | H | H | H | H | H | H | Et | O |
| 1009 | H | CF3 | H | H | H | C(Me)3 | H | H | Me | H | H | H | Me | O |
| 1010 | H | CF3 | H | H | H | C(Me)3 | H | H | H | H | H | H | Pr | S |
| 1011 | H | CF3 | H | H | H | C(Me)2CH=CH2 | H | H | H | H | H | H | Me | O |
| 1012 | H | CF3 | H | H | H | cyclohexyl | H | H | H | H | H | H | Et | O |
| 1013 | H | CF3 | H | CF3 | H | C(Me)3 | H | H | H | H | H | H | Me | O |
| 1014 | H | CF3 | H | H | H | C(Me)2CCH | H | H | H | H | H | H | Et | O |
| 1015 | H | CF3 | H | H | H | CH(Me)2 | H | H | H | H | H | H | Et | O |
| 1016 | H | CF3 | H | H | H | 1-Me-cyclopentyl | H | H | H | H | H | H | Me | O |
| 1017 | H | CF3 | H | H | H | C(Me)2CN | H | H | H | H | H | H | Me | O |
| 1018 | H | CF3 | H | H | H | —(CH2)2O(CH2)2— | | H | H | H | H | H | Pr | O |
| 1019 | H | OCF3 | H | H | H | CH(Me)2 | H | H | H | H | H | H | Et | O |
| 1020 | H | CF3 | H | H | H | Et | Et | H | H | H | H | H | Me | O |
| 1021 | H | CF3 | H | H | H | —(CH2)4— | | H | H | H | H | H | Me | O |
| 1022 | H | CF3 | H | H | H | CH(Me)2 | Me | H | H | H | H | H | Me | O |
| 1023 | H | CF3 | F | H | H | cyclohexyl | H | H | H | H | H | H | Me | O |
| 1024 | H | CF3 | H | H | H | C(Me)2Et | H | H | H | H | H | H | Me | O |
| 1025 | H | CF3 | F | H | H | C(Me)2CCH | H | H | H | H | H | H | Pr | O |
| 1026 | H | OCHF2 | H | H | H | 1-Me-cyclopropyl | H | H | H | H | H | H | Et | O |
| 1027 | H | Cl | H | Cl | H | C(Me)2CCH | H | H | H | H | H | H | Et | O |
| 1028 | H | Cl | F | H | H | C(Me)2CCH | H | H | H | H | H | H | Me | O |
| 1029 | H | OCF3 | H | H | H | C(Me)3 | H | H | H | H | H | H | Et | S |
| 1030 | H | CF3 | H | H | H | CH(Me)Ph | H | H | H | H | H | H | Me | O |
| 1031 | H | Cl | Cl | H | H | C(Me)3 | H | H | H | H | H | H | Et | O |
| 1032 | H | CF3 | H | H | H | C(Me)3 | H | H | Me | Me | H | H | Et | O |
| 1033 | H | Cl | H | H | H | C(Me)2CCH | H | H | H | H | H | H | Me | O |
| 1034 | H | Br | H | H | H | C(Me)2CCH | H | H | H | H | H | H | Et | O |
| 1035 | H | CF3 | H | H | H | C(Me)3 | H | H | H | H | Me | H | Me | O |
| 1036 | H | CF3 | H | H | H | C(Me)2CCH | H | H | H | H | Me | Me | Et | O |
| 1037 | H | OMe | H | CF3 | H | C(Me)3 | H | H | H | H | H | H | Me | O |

TABLE XIII

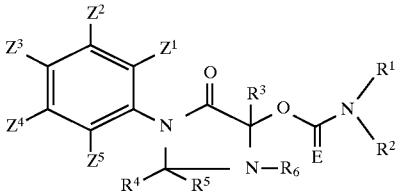

(Table XIII)

| Comp No | Z¹ | Z² | Z³ | Z⁴ | Z⁵ | R¹ | R² | R³ | R⁴ | R⁵ | R⁶ | E |
|---|---|---|---|---|---|---|---|---|---|---|---|---|
| 1038 | H | Cl | F | H | H | C(Me)2CCH | H | H | H | H | Me | O |
| 1039 | H | CF3 | H | H | H | —(CH2)2O(CH2)2— | | H | H | H | Me | O |
| 1040 | H | CF3 | H | H | H | C(Me)2CN | H | H | H | H | Me | O |
| 1041 | H | CF3 | H | H | H | 1-Me-cyclopentyl | H | H | H | H | Me | O |
| 1042 | H | CF3 | H | H | H | CH(Me)2 | H | H | H | H | Me | O |
| 1043 | H | CF3 | H | H | H | C(Me)2CCH | H | H | H | H | Me | O |
| 1044 | H | CF3 | H | CF3 | H | C(Me)3 | H | H | H | H | Me | O |
| 1045 | H | CF3 | H | H | H | cyclohexyl | H | H | H | H | Me | O |
| 1046 | H | CF3 | H | H | H | C(Me)2CH=CH2 | H | H | H | H | Me | O |
| 1047 | H | CF3 | H | H | H | C(Me)3 | H | H | H | H | Me | S |
| 1048 | H | Br | H | H | H | C(Me)2CCH | H | H | H | H | Me | O |
| 1049 | H | CF3 | H | H | H | C(Me)3 | H | H | Me | H | Et | O |
| 1050 | H | CF3 | H | H | H | 1-(CN)-cyclopentyl | H | H | H | H | Et | O |
| 1051 | H | CF3 | H | H | H | C(Me)2Pr | H | H | H | H | Et | O |
| 1052 | H | OCHF2 | H | H | H | C(Me)2CCH | H | H | H | H | Et | O |
| 1053 | H | CF3 | H | H | H | 1-Me-cyclopropyl | H | H | H | H | Me | O |
| 1054 | H | CF3 | H | H | H | C(Me)2CCH | H | H | H | H | Me | S |
| 1055 | H | OCF3 | H | H | H | 1-(CCH)-cyclopropyl | H | H | H | H | Me | O |
| 1056 | H | Cl | F | H | H | C(Me)3 | H | H | H | H | Me | O |
| 1057 | H | OCHF2 | H | H | H | 1-Me-cyclopropyl | H | H | H | H | Me | O |
| 1058 | H | CF3 | F | H | H | 1-Me-cyclopropyl | H | H | H | H | Me | O |
| 1059 | H | CF3 | H | H | H | cyclopentyl | H | H | H | H | Me | O |
| 1060 | H | I | H | H | H | C(Me)3 | H | H | H | H | Me | O |
| 1061 | H | OCF3 | H | H | H | 1-Me-cyclopropyl | H | H | H | H | Me | O |
| 1062 | H | CF3 | F | H | H | C(Me)3 | H | H | H | H | Me | O |
| 1063 | H | OCF3 | H | H | H | CH(Me)2 | H | H | H | H | Me | O |
| 1064 | H | CF3 | H | CF3 | H | C(Me)2CCH | H | H | H | H | Et | O |
| 1065 | H | CF3 | H | H | H | C(Me)2Et | H | H | H | H | Et | O |
| 1066 | H | OCF3 | H | H | H | C(Me)3 | H | H | H | H | Me | S |
| 1067 | H | CF3 | H | H | H | C(Me)3 | H | Me | H | H | Me | O |
| 1068 | H | CF3 | H | H | H | Et | Et | H | H | H | Me | O |
| 1069 | H | Cl | Cl | H | H | C(Me)3 | H | H | H | H | Me | O |
| 1070 | H | OCF3 | H | H | H | C(Me)2CCH | H | H | H | H | Me | S |
| 1071 | H | Cl | H | H | H | C(Me)3 | H | H | H | H | Me | O |
| 1072 | H | CF3 | H | H | H | Me | Me | H | H | H | Me | O |
| 1073 | H | CF3 | H | H | H | CH(Et)Ph | H | H | H | H | Me | O |
| 1074 | H | CF3 | H | H | H | —(CH2)4— | | H | H | H | Me | O |
| 1075 | H | OCF3 | H | H | H | C(Me)3 | H | H | H | H | Me | O |
| 1076 | H | CF3 | H | H | H | C(Me)3 | H | H | H | H | Me | O |
| 1077 | H | CF3 | H | H | H | 1-Me-cyclohexyl | H | H | H | H | Et | O |
| 1078 | H | CF3 | H | H | H | 1-Me-cyclobutyl | H | H | H | H | Et | O |
| 1079 | H | CF3 | F | H | H | CH(Me)2 | H | H | H | H | Pr | O |
| 1080 | H | OCF2CHF2 | H | H | H | C(Me)3 | H | H | H | H | Pr | O |
| 1081 | H | OCF3 | H | H | H | cyclohexyl | H | H | H | H | Pr | O |
| 1082 | H | CF3 | F | H | H | C(Me)2CCH | H | H | H | H | Pr | O |
| 1083 | H | CF3 | H | H | H | 1-(CCH)-cyclopropyl | H | H | H | H | Me | O |
| 1084 | H | CF3 | H | H | H | 1-(CCH)-cyclohexyl | H | H | H | H | Me | O |
| 1085 | H | CF3 | H | H | H | —(CH2)5— | | H | H | H | Me | O |
| 1086 | H | CF3 | H | H | H | C(Me)2CCMe | H | H | H | H | Me | O |
| 1087 | H | CF3 | F | H | H | cyclohexyl | H | H | H | H | Me | O |
| 1088 | H | OCHF2 | H | H | H | C(Me)3 | H | H | H | H | Me | O |
| 1089 | H | Cl | H | Cl | H | C(Me)2CCH | H | H | H | H | Me | O |
| 1090 | H | Cl | H | H | H | C(Me)2CCH | H | H | H | H | Me | O |
| 1091 | H | SF5 | H | H | H | C(Me)2CCH | H | H | H | H | Me | O |
| 1092 | H | CF3 | H | H | H | C(Me)3 | H | H | Me | Me | Me | O |
| 1093 | H | OCF3 | H | H | H | C(Me)2CCH | H | H | H | H | H | O |
| 1094 | H | Cl | H | Cl | H | C(Me)3 | H | H | H | H | Et | O |
| 1095 | H | CF3 | H | H | H | CH(Me)2 | Me | H | H | H | Et | O |
| 1096 | H | CF3 | H | H | H | CH(Me)Ph | H | H | H | H | Pr | O |
| 1097 | H | OMe | H | CF3 | H | C(Me)3 | H | H | H | H | Me | O |

TABLE XIV (Table XIV)

| Comp No | $Z^1$ | $Z^2$ | $Z^3$ | $Z^4$ | $Z^5$ | $R^1$ | $R^2$ | $R^3$ | $R^4$ | $R^5$ | $R^6$ | E |
|---|---|---|---|---|---|---|---|---|---|---|---|---|
| 1098 | H | CF3 | H | H | H | CH(Me)2 | Me | H | H | H | Et | O |
| 1099 | H | CF3 | F | H | H | 1-Me-cyclopropyl | H | H | H | H | Me | O |
| 1100 | H | Cl | H | H | H | C(Me)3 | H | H | H | H | Me | O |
| 1101 | H | CF3 | H | H | H | CH(Me)Ph | H | H | H | H | Pr | O |
| 1102 | H | Cl | H | Cl | H | C(Me)3 | H | H | H | H | Et | O |
| 1103 | H | CF3 | H | H | H | C(Me)3 | H | H | Me | Me | Me | O |
| 1104 | H | SF5 | H | H | H | C(Me)2CCH | H | H | H | H | Me | O |
| 1105 | H | Cl | H | H | H | C(Me)2CCH | H | H | H | H | Me | O |
| 1106 | H | Cl | H | Cl | H | C(Me)2CCH | H | H | H | H | Me | O |
| 1107 | H | OCHF2 | H | H | H | C(Me)3 | H | H | H | H | Me | O |
| 1108 | H | CF3 | F | H | H | cyclohexyl | H | H | H | H | Me | O |
| 1109 | H | CF3 | H | H | H | C(Me)2CCMe | H | H | H | H | Me | O |
| 1110 | H | CF3 | H | H | H | 1-(CCH)-cyclohexyl | H | H | H | H | Me | O |
| 1111 | H | CF3 | H | H | H | 1-(CCH)-cyclopropyl | H | H | H | H | Me | O |
| 1112 | H | OCF3 | H | H | H | cyclohexyl | H | H | H | H | Pr | O |
| 1113 | H | OCF2CHF2 | H | H | H | C(Me)3 | H | H | H | H | Pr | O |
| 1114 | H | CF3 | F | H | H | CH(Me)2 | H | H | H | H | Pr | O |
| 1115 | H | CF3 | H | H | H | 1-Me-cyclobutyl | H | H | H | H | Et | O |
| 1116 | H | CF3 | H | H | H | C(Me)3 | H | H | H | H | Me | O |
| 1117 | H | OCF3 | H | H | H | C(Me)3 | H | H | H | H | Me | O |
| 1118 | H | CF3 | H | H | H | —(CH2)4— | | H | H | H | Me | O |
| 1119 | H | CF3 | H | H | H | CH(Et)Ph | H | H | H | H | Me | O |
| 1120 | H | CF3 | H | H | H | Me | Me | H | H | H | Me | O |
| 1121 | H | OCF3 | H | H | H | C(Me)2CCH | H | H | H | H | Me | S |
| 1122 | H | Cl | Cl | H | H | C(Me)3 | H | H | H | H | Me | O |
| 1123 | H | CF3 | H | H | H | C(Me)3 | H | Me | H | H | Me | O |
| 1124 | H | OCF3 | H | H | H | C(Me)3 | H | H | H | H | Me | S |
| 1125 | H | CF3 | H | CF3 | H | C(Me)2CCH | H | H | H | H | Et | O |
| 1126 | H | OCF3 | H | H | H | CH(Me)2 | H | H | H | H | Me | O |
| 1127 | H | OCF3 | H | H | H | 1-Me-cyclopropyl | H | H | H | H | Me | O |
| 1128 | H | I | H | H | H | C(Me)3 | H | H | H | H | Me | O |
| 1129 | H | CF3 | H | H | H | cyclopentyl | H | H | H | H | Me | O |
| 1130 | H | OCHF2 | H | H | H | 1-Me-cyclopropyl | H | H | H | H | Me | O |
| 1131 | H | CF3 | H | H | H | C(Me)2CCH | H | H | H | H | Me | S |
| 1132 | H | CF3 | H | H | H | C(Me)2Pr | H | H | H | H | Et | O |
| 1133 | H | CF3 | H | H | H | 1-(CN)-cyclopentyl | H | H | H | H | Et | O |
| 1134 | H | Br | H | H | H | C(Me)2CCH | H | H | H | H | Me | O |
| 1135 | H | CF3 | H | H | H | C(Me)3 | H | H | H | H | Me | S |
| 1136 | H | CF3 | H | H | H | cyclohexyl | H | H | H | H | Me | O |
| 1137 | H | CF3 | H | CF3 | H | C(Me)3 | H | H | H | H | Me | O |
| 1138 | H | CF3 | H | H | H | CH(Me)2 | H | H | H | H | Me | O |
| 1139 | H | CF3 | H | H | H | C(Me)2CN | H | H | H | H | Me | O |
| 1140 | H | CF3 | H | H | H | —(CH2)2O(CH2)2— | | H | H | H | Me | O |
| 1141 | H | Cl | F | H | H | C(Me)2CCH | H | H | H | H | Me | O |
| 1142 | H | CF3 | H | H | H | Et | Et | H | H | H | Me | O |
| 1143 | H | Cl | F | H | H | C(Me)3 | H | H | H | H | Me | O |
| 1144 | H | CF3 | H | H | H | C(Me)2Et | H | H | H | H | Et | O |
| 1145 | H | CF3 | H | H | H | 1-Me-cyclohexyl | H | H | H | H | Et | O |
| 1146 | H | OCF3 | H | H | H | 1-(CCH)-cyclopropyl | H | H | H | H | Me | O |
| 1147 | H | CF3 | F | H | H | C(Me)2CCH | H | H | H | H | Pr | O |
| 1148 | H | OCHF2 | H | H | H | C(Me)2CCH | H | H | H | H | Et | O |
| 1149 | H | CF3 | H | H | H | —(CH2)5— | | H | H | H | Me | O |
| 1150 | H | CF3 | H | H | H | 1-Me-cyclopentyl | H | H | H | H | Me | O |
| 1151 | H | CF3 | H | H | H | C(Me)3 | H | H | Me | H | Et | O |
| 1152 | H | CF3 | F | H | H | C(Me)3 | H | H | H | H | Me | O |
| 1153 | H | OCF3 | H | H | H | C(Me)2CCH | H | H | H | H | Me | O |
| 1154 | H | CF3 | H | H | H | C(Me)2CCH | H | H | H | H | Me | O |
| 1155 | H | CF3 | H | H | H | C(Me)2CH=CH2 | H | H | H | H | Me | O |
| 1156 | H | CF3 | H | H | H | 1-Me-cyclopropyl | H | H | H | H | Me | O |
| 1157 | H | OMe | H | CF3 | H | C(Me)3 | H | H | H | H | Me | O |

TABLE XV

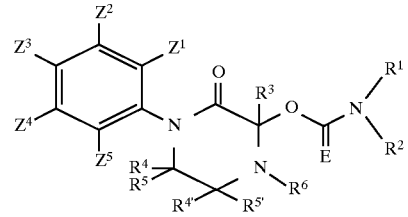

| Comp No | Z¹ | Z² | Z³ | Z⁴ | Z⁵ | R¹ | R² | R³ | R⁴ | R⁵ | R⁴' | R⁵' | R⁶ | E |
|---|---|---|---|---|---|---|---|---|---|---|---|---|---|---|
| 1158 | H | CF3 | H | H | H | 1-Me-cyclopropyl | H | H | H | H | H | H | Me | O |
| 1159 | H | CF3 | H | H | H | C(Me)3 | H | H | H | H | Me | H | Me | O |
| 1160 | H | I | H | H | H | C(Me)3 | H | H | H | H | H | H | Me | O |
| 1161 | H | CF3 | H | H | H | C(Me)3 | H | H | H | H | H | H | Pr | S |
| 1162 | H | CF3 | H | CF3 | H | C(Me)2CCH | H | H | H | H | H | H | Et | O |
| 1163 | H | OCF3 | H | H | H | C(Me)3 | H | H | H | H | H | H | Et | S |
| 1164 | H | SF3 | H | H | H | C(Me)3 | H | H | Me | Me | H | H | Et | O |
| 1165 | H | CF3 | F | H | H | 1-Me-cyclopropyl | H | H | H | H | H | H | Et | O |
| 1166 | H | CF3 | H | H | H | 1-(CN)-cyclopentyl | H | H | H | H | H | H | Et | O |
| 1167 | H | CF3 | H | H | H | C(Me)2CN | H | H | H | H | H | H | Me | O |
| 1168 | H | CF3 | H | H | H | CH(Me)2 | H | H | H | H | H | H | Et | O |
| 1169 | H | Cl | H | H | H | C(Me)2CCH | H | H | H | H | H | H | Me | O |
| 1170 | H | CF3 | H | H | H | CH(Me)Ph | H | H | H | H | H | H | Me | O |
| 1171 | H | Cl | F | H | H | C(Me)2CCH | H | H | H | H | H | H | Me | O |
| 1172 | H | Cl | H | Cl | H | C(Me)2CCH | H | H | H | H | H | H | Et | O |
| 1173 | H | OCHF2 | H | H | H | 1-Me-cyclopropyl | H | H | H | H | H | H | Et | O |
| 1174 | H | CF3 | H | H | H | C(Me)2Et | H | H | H | H | H | H | Me | O |
| 1175 | H | CF3 | F | H | H | cyclohexyl | H | H | H | H | H | H | Me | O |
| 1176 | H | CF3 | H | H | H | —(CH2)4— | | H | H | H | H | H | Me | O |
| 1177 | H | CF3 | H | H | H | Et | Et | H | H | H | H | H | Me | O |
| 1178 | H | CF3 | H | H | H | —(CH2)2O(CH2)2— | | H | H | H | H | H | Pr | O |
| 1179 | H | CF3 | H | H | H | C(Me)2CCH | H | H | H | H | H | H | Et | O |
| 1180 | H | CF3 | H | CF3 | H | C(Me)3 | H | H | H | H | H | H | Me | O |
| 1181 | H | CF3 | H | H | H | cyclohexyl | H | H | H | H | H | H | Et | O |
| 1182 | H | CF3 | H | H | H | C(Me)3 | H | H | Me | H | H | H | Me | O |
| 1183 | H | CF3 | H | H | H | C(Me)2Pr | H | H | H | H | H | H | Et | O |
| 1184 | H | OCHF2 | H | H | H | C(Me)2CCH | H | H | H | H | H | H | Me | O |
| 1185 | H | CF3 | H | H | H | C(Me)2CCH | H | H | H | H | H | H | Me | S |
| 1186 | H | OCF3 | H | H | H | 1-(CCH)-cyclopropyl | H | H | H | H | H | H | Me | O |
| 1187 | H | Cl | F | H | H | C(Me)3 | H | H | H | H | H | H | Et | O |
| 1188 | H | CF3 | H | H | H | cyclopentyl | H | H | H | H | H | H | Me | O |
| 1189 | H | CF3 | F | H | H | C(Me)3 | H | H | H | H | H | H | Et | O |
| 1190 | H | CF3 | H | H | H | C(Me)3 | H | Me | H | H | H | H | Et | O |
| 1191 | H | OCF3 | H | H | H | C(Me)2CCH | H | H | H | H | H | H | Me | S |
| 1192 | H | Cl | H | H | H | C(Me)3 | H | H | H | H | H | H | Pr | O |
| 1193 | H | CF3 | H | H | H | Me | Me | H | H | H | H | H | Et | O |
| 1194 | H | OCF3 | H | H | H | C(Me)3 | H | H | H | H | H | H | Et | O |
| 1195 | H | CF3 | H | H | H | 1-Me-cyclobutyl | H | H | H | H | H | H | Pr | O |
| 1197 | H | CF3 | F | H | H | CH(Me)2 | H | H | H | H | H | H | Me | O |
| 1198 | H | OCF3 | H | H | H | cyclohexyl | H | H | H | H | H | H | Et | O |
| 1199 | H | CF3 | H | H | H | 1-(CCH)-cyclopropyl | H | H | H | H | H | H | Et | O |
| 1200 | H | CF3 | H | H | H | —(CH2)5— | | H | H | H | H | H | Et | O |
| 1201 | H | CF3 | H | H | H | C(Me)2CCMe | H | H | H | H | H | H | Me | O |
| 1202 | H | SF5 | H | H | H | C(Me)2CCH | H | H | H | H | H | H | Me | O |
| 1203 | H | OCF3 | H | H | H | C(Me)2CCH | H | H | H | H | H | H | Me | O |
| 1204 | H | Cl | H | Cl | H | C(Me)3 | H | H | H | H | H | H | Me | O |
| 1205 | H | CF3 | H | H | H | C(Me)2CH=CH2 | H | H | H | H | H | H | Me | O |
| 1206 | H | CF3 | H | H | H | 1-(CCH)-cyclohexyl | H | H | H | H | H | H | Et | O |
| 1207 | H | CF3 | H | H | H | C(Me)3 | H | H | H | H | H | H | Me | O |
| 1208 | H | Cl | Cl | H | H | C(Me)3 | H | H | H | H | H | H | Et | O |
| 1209 | H | CF3 | H | H | H | 1-Me-cyclohexyl | H | H | H | H | H | H | Et | O |
| 1210 | H | OCF3 | H | H | H | 1-Me-cyclopropyl | H | H | H | H | H | H | Me | O |
| 1211 | H | OCHF2 | H | H | H | C(Me)3 | H | H | H | H | H | H | Et | O |
| 1212 | H | OCF2CHF2 | H | H | H | C(Me)3 | H | H | H | H | H | H | Et | O |
| 1213 | H | CF3 | H | H | H | CH(Et)Ph | H | H | H | H | H | H | Et | O |
| 1214 | H | OCF3 | H | H | H | CH(Me)2 | H | H | H | H | H | H | Et | O |
| 1215 | H | CF3 | H | H | H | CH(Me)2 | Me | H | H | H | H | H | Me | O |
| 1216 | H | CF3 | F | H | H | C(Me)2CCH | H | H | H | H | H | H | Pr | O |
| 1217 | H | Br | H | H | H | C(Me)2CCH | H | H | H | H | H | H | Et | O |
| 1218 | H | CF3 | H | H | H | C(Me)2CCH | H | H | H | H | Me | Me | Et | O |
| 1219 | H | CF3 | H | H | H | 1-Me-cyclopentyl | H | H | H | H | H | H | Me | O |
| 1220 | H | OMe | H | CF3 | H | C(Me)3 | H | H | H | H | H | H | Me | O |

Compounds of formula (I) are suitably prepared by a variety of processes.

In particular compounds of formula (I) can be prepared by reacting a compound of formula (III) where A, D, Z and m are as defined in relation to formula (I): with a compound of formula (IV) or, where R is hydrogen, a compound of formula (V) where $R^1$ is as defined in relation to formula (I) and $R^{19}$ is a leaving group in the presence of a base.

Suitable bases include weak bases such as triethylamine, pyridine or N-ethyl-N,N-diisopropyl amine.

Suitable leaving groups $R^{19}$ include halogen such as chloro.

The reaction is suitably effected in an organic solvent such as dichloromethane, trichloromethane, tetrahydrofuran or diethyl ether at temperatures of from 0° to 80° C., preferably at ambient temperature.

Certain compounds of formula (III) are novel and as such form a further aspect of the invention. Compounds of formula (IV) and (V) are known compounds or can be prepared from known compounds by conventional methods. Compounds of formula (V) can be prepared and used in situ using standard techniques.

Using the same reactions, the NCO group of compounds of formula (V) can be replaced by an NCS group. If desired the NCS group can be formed in situ using standard techniques.

An alternative method of preparing compounds of formula (I) from compounds of formula (III) is by reacting the compound of formula (III) with $ClC(O)OCH(Cl)CCl_3$ in the presence of a base to product a compound of formula (XIII) in which Z, D, A and m are as defined in relation to formula (I). The reaction is suitably carried out at from −10° to 10° C. in the presence of a solvent. Suitable bases are heteroarometric nitrogen bases, such as pyridine. Suitable solvents are dichloromethane or chloroform. The compounds of formula (XIII) are then reacted with an amine of formula (VIII) $HNR^1R^2$ where $R^1$ and $R^2$ are as defined in relation to formula (I) to produce a compound of formula (I). The reaction is suitably carried out at from −10° to 30° C. in the presence of a base, and a solvent. Suitable bases are pyridine, and triethylamine. Suitable solvents are dichloromethane or chloroform. The compounds of formula (XIII) need not be isolated, but can be reacted in situ with the compound of formula (VIII).

Instead of $Cl(C(O)OCH(Cl)CCl_3$ the compounds of formula (III) may be reacted with phosgene to produce a compound of formula (XIV) in which Z, A, D and m are as defined in relation to formula (I). The compounds of formula (XIV) are then reacted with amine of formula (VIII) as hereinbefore defined to produce a compound of formula (I). The reaction is suitably carried out at from −20° to 50° C. in the presence of a base and a solvent.

Suitable bases are pyridine or triethylamine. Suitable solvents are chloroform, dichloro methane or tetrahydrofuran. The compound of formula (XIV) need not be isolated and can be reacted in situ with the compound of formula (VIII).

Certain compounds of formula (III) where Y is sulphur and A is $CR^3$ are suitably prepared by reacting a compound of formula (VI); where Z, D and m are as defined in relation to formula (I), and $R^{20}$ is a leaving group such as halo, especially chloro; with water in the presence of a base and a water miscible solvent.

Suitable bases include weak inorganic bases such as sodium bicarbonate.

The reaction is suitably effected in a solvent such as tetrahydrofuran or dioxane at temperatures of from 0° to 50° C.

Certain compounds of formula (III) where A, D, Z and m are as defined in relation to formula (I) by hydrolysis of a compound of formula (VI): where A, D, Z and m are as defined in relation to formula (I) and $R^{20}$ is $OCOR^{21}$. The reaction is conveniently carried out in the presence of an alcohol, such as methanol, and silica gel.

Suitably group $R^{21}$ is trifluoromethyl. The reaction is suitably effected in a solvent such as dichloromethane at temperatures of from 0° to 50° C., preferably ambient temperature.

Certain compounds of formula (VI) where Y is sulphur and A is $CR^3$ and D, Z and m are as defined in relation to formula (I) and $R^{20}$ is halogen can be prepared by halogenation of a compound of formula (X); with a halogenating agent. Suitable halogenating agents include sulphuryl chloride, or chlorine.

The reaction is suitably effected in an organic solvent such as dichloromethane or chloroform, at temperatures of from 0° to 50° C., preferably ambient temperature.

Certain compounds of formula (III) may be prepared by oxygenating a compound of formula (X), where A, D, Z and m are as defined in relationship to formula (I), with a strong base such as $LiN(SiMe_3)_2$ or $LiN(iPr)_2$, followed by reaction with a compound of formula (XVII).

The reaction is suitably effected in a solvent such as tetrahydrofuran at temperatures of from −100° to 30° C., preferably from −80° to 0° C. In compounds of formula (XVII) Ar is suitably a p-tolyl group and Ar' is suitably phenyl.

Certain compounds of formula (III), particularly those where A is N, and where D, Z and m are as defined in relationship to formula (I), are suitably prepared by hydrogenolysis of a compound of formula (VI) where $R^{20}$ is $OCH_2Ph$ and Z, D and m are as defined in relation to formula (I). The reaction is suitably effected in a protic solvent such as an alcohol (e.g. methanol) in the presence of a catalyst. A suitable catalyst is palladium on carbon. The reaction is suitably effected at temperatures of from 0° to 50° C., preferably ambient temperature.

The compounds of formula (X) can be prepared in various ways depending upon the particular nature of the ring completed by the group D.

It is possible where the substituents Z are of a nature and distribution to activate phenyl ring to nucleophilic substitution to couple a compound of formula (XI); where Z and m are as defined and $R^{22}$ is a leaving group, with a compound of formula (XII); where A is $CR^3$ and D is as defined hereinbefore: in the presence of a base.

Suitable leaving groups $R^{22}$ include halogen such as fluoro.

Suitable bases include strong bases such as potassium hydroxide or sodium hydroxide.

The reaction is suitably effected in an organic solvent such as dimethylsulphoxide or dimethylformamide at temperatures of from 0° to 90° C.

Examples of suitable compounds of formula (XI) include 3,4-difluoro-5-chloro-α,α,α-trifluorotoluene and 3,4,5-trifluoro-α,α,α-trifluorotoluene.

An alternative and more generally applicable route to compounds of formula (III), (VI) and (X) will involve introducing an appropriate side chain in a suitably substituted phenyl derivative and cyclising the side chain to form the desired heterocyclic moiety. For example an isoxazolidinone ring, and a dihydro-1,2-oxazinone ring system can be prepared from compounds of formula (XV) in which Z and m are as defined in relation to formula (I).

By reaction with $ClCO(CH_2)_2Br$ compounds of formula (XV) can be converted to compounds of formula (XVI) in which Z and m are as defined in relation to formula (I). The reaction is suitably carried out at from −20° to 40° C., preferably at 0°–25° C., in the presence of a base and a solvent. Suitable bases are triethylamine or pyridine. Suitable solvents are tetrahydrofuran or dichloromethane. Compounds of formula (XVI) may be converted to compounds of formula (III) wherein D completes an isoxazolidinone ring and Z and m are as defined in relation to formula (I) by reaction with a strong base, followed by reaction with a compound of formula (XVII) in which Ar is p-tolyl and Ar' is phenyl. The reaction is suitably carried out at from −80° to 10° C. in the presence of a solvent. Suitable bases are lithium hexamethyldisilazide or lithium diisopropylamide. A suitable solvent is tetrahydrofuran.

By reaction with ClC(O)CH(Br)CH$_2$CH$_2$Br compounds of formula (XV) can be converted to compounds of formula (XVIII) in which Z and m are as defined in relation to formula (I). The reaction is suitably carried out in a solvent in the presence of a base at a temperature of from −20° C. to 40° C. preferably at 0° C. to 25° C. Suitable bases are tertiary amines such as triethylamine and suitable solvents are ethers such as tetrahydrofuran. The chloro and bromo groups can be converted to iodo groups by reaction with sodium iodide at temperatures of from 0° to 80° C. in solvents such as acetone. The iodo group can be further converted to an OCOCF$_3$ group by reaction with [bis(trifluoroacetoxy)iodo]benzene in a solvent. Suitably the reaction is carried out at from 0° to 30° C. preferably at ambient temperature. Suitable solvents are chlorinated hydrocarbons such as methylene dichloride. The OCOCF$_3$ groups can be converted to OH groups i.e. to compounds of formula (III) in which D competes a dihydro-1,2 oxazinone ring and Z and m are as defined in relation to formula (I) by treatment with methanol at from 0° to 80° C., preferably at ambient temperatures, in the presence of silica gel and a solvent. Suitable solvents are chlorinated hydrocarbons such as methylene dichloride.

Compounds of formula (XV) are known compounds or can be prepared from known compounds by conventional methods.

By reaction with ClC(O)CH$_2$Cl compounds of formula (XXX) where Z and m are as defined in relation to formula (I) may be converted to compounds of formula (XIX) where Z and m are as defined in relation to formula (I). The reaction is suitably carried out from 0° to 50° C. preferably in a solvent in the presence of a base. Suitable bases are strong bases such as sodium hydride and a suitable solvent is tetrahydrofuran. Compounds of formula (XIX) may be converted to compounds of formula (III) which completes a dihdro-1,4-oxazine ring where Z and m are as defined in relation to formula (I) by reaction with LiN(SiMe$_3$)$_2$ in a solvent such as tetrahydrofuran at a temperature of from −80° to 20° C., preferably 0° C., followed by treatment with a compound of formula (XVII) (where Ar and Ar' are as defined above) at a temperature of from 0° to 30° C. in a solvent such as tetrahyrofuran.

Compounds of formula (XXX) are known compounds or can be prepared from known compounds by conventional methods.

Compounds of formula (X) in which D completes a dihydro-1,4-1,4 thiaznone ring and where Z and m are as defined in relation to formula (I) may be prepared from compounds of formula (XXVIII) where Z and m are as defined in relation to formula (I) by heating in a solvent such as xylene or toluene at reflux in the presence of p-toluenesulphonic acid. Compounds of formula (XXVIII) may be prepared from compounds of formula (XXIX) where Z and m are as defined in relation to formula (I) by treatment with ethyl thioglycollate in the presence of a strong base such as sodium hydride in a solvent such as dimethylformamide at temperatures of from 0° to 50° C., preferably ambient temperatures. Compounds of formula (XXIX) may be prepared from compounds of formula (XXX) where 2 and m are as defined in relation to formula (I) by reaction with a brominating agent, preferably carbon tetrabromide and triphenyl phosphine at temperatures of from 0° to 50° C. preferably at ambient temperature in a basic solvent such as pyridine.

Compounds of formula (III) where D completes a 2-imidazolidinone ring and where Z and m are as defined in relation to formula (I) may be produced from compounds of formula (XX) by reaction with hydrogen in the presence of a palladium on carbon catalyst in an appropriate solvent such as methanol at temperatures of from 0° to 30° C. preferably ambient temperature.

Compounds of formula (XX) where Z and m are as defined in relation to formula (I) may be produced from compounds of formula (XXI) where Z and m are as defined in relation to formula (I) reaction with Br(CH$_2$)$_2$Br in the presence of a base in a solvent. Suitable bases are strong bases such as sodium hydride, a suitable solvent is dimethylformamide and the reaction is suitably carried out at from 0° to 50° C. preferably ambient temperature. Compounds of formula (XXI) where Z and m are as defined in relation to formula (I) may be produced from compounds of formula (XXII) where Z and m are as defined in relation to formula (I) by reaction with C$_6$H$_5$CH$_2$ONH$_2$ at temperatures of from 0° to 50° C., preferably ambient temperature.

Compounds of formula (XXII) are known compounds or can be prepared from known compounds by conventional methods.

Compounds of formula (III) where D completes a saturated 2-pyrimidinone ring and where Z and m are as defined in relation to formula (I) may be produced from compound of formula (XXI) in an analogous manner using Br(CH$_2$)$_3$Br in place of Br(CH$_2$)$_2$Br.

Compounds of formula (III) in which D completes a 2-piperidinone ring and where Z and m are as defined in relation to formula (I) may be produced from a compound of formula (X) wherein D completes a 2-piperidinone ring and where Z and m are as defined in relation to formula (I) by reaction with a strong base such as LiN(SiMe$_3$)$_2$ followed by reaction with a compound of formula (XVII) (where Ar and Ar' are as defined above) at temperatures of from −100° to +20° C., preferably 0° C. in a solvent. A suitable solvent is tetrahydrofuran.

The piperidinone compounds of formula (X) may be produced from compounds of formula (XXIII) where Z and m are as defined in relation to formula (I) at a temperature of from 0° to 80° C. preferably 25° to 60° C. in a solvent in the presence of a base. Suitable bases are strong bases such as sodium hydride. A suitable solvent is dimethylformamide. Compounds of formula (XXIII) may be prepared from compounds of formula (XXIV) where Z and m are as defined in relation to formula (I) by reaction with ClC(O)(CH$_2$)$_3$Cl at ambient temperatures.

Compounds of formula (XXIV) are known compounds or can be prepared from known compounds by conventional methods.

Compounds of formula (III) where D completes a 2-pyrrolidinone ring and where Z and m are as defined in relation to formula (I) may be prepared from compound of formula (X) where D completes a pyrrolidinone ring and where Z and m are as defined in relation to formula (I) by reaction with a strong base such as LiN(SiMe$_3$)$_2$ followed by reaction with a compound of formula (XVII) (where Ar and Ar' are as defined above) at temperatures of from −100° to +20° C., preferably 0° C. in a solvent. A suitable solvent is tetrahydrofuran. Pyrrolidine compounds of formula (X) may be prepared by heating and decarboxylating a compound of formula (XXV) where Z and m are as defined in relation to formula (I). Compounds of formula (XXV) may be produced by reacting a compound of formula (XXIV) where Z and m are as defined in relation to formula (I) with a compound of formula (XXXI) prepared according to the method described in Organic Syntheses Vol 60 p66–68.

Compounds of formula (X) where D completes a thiazolidinone ring and where Z and m are as defined in relation to formula (I) may be prepared from the anilines of formula (XXIV) where Z and m are as defined in relation to formula (I) by reaction with thioglycollic acid or thiolactic acid, and a carbonyl compound R$^4$R$^5$CO to give a thiazolidinone (XXVI) where Z and m are as defined in relation to formula (I), R$^3$ is H or methyl. The reaction is preferably carried out in a solvent or diluent and is occassionally carried out in the presence of a strong acid such as p-toluene sulphonic acid. Preferably the solvent is one which is immiscible with water. The solvent may conveniently be one which forms an azeotropic mixture with water, and which has a boiling point in the range from 100° to 150° C., for example toluene or xylene. Conveniently the reaction may be carried out by heating the reaction mixture under reflux and collecting the water carried up in the refluxing solvent by means of a suitable apparatus (e.g. a Dean and Stark trap). Heating under reflux may be discontinued when the volume of water collected indicates that the reaction has proceeded to the required extent. The product may be isolated in the usual way, by evaporating the solvent (e.g. under reduced pressure) to leave the crude 4-thiazolidinone as a residue. This may be purified if desired by conventional methods e.g. by recrystallisation or chromatography.

The reaction may be varied by reacting the aniline of formula (XXIV) where Z and m are as defined in relation to formula (I) and thioglycollic acid in a solvent such as toluene or xylene at temperatures of 100°–150° C. to give a compound of formula (XXXVI) where Z and m are as defined in relation to formula (I). The reaction may be carried out in the presence of an acid catalyst, such as p-toluenesulphonic acid.

Thiazolidinones of formula (X) where D completes a 4-thiazolidinone ring and where Z and m are as defined in relation to formula (I) may then be prepared by reaction of a compound of formula (XXXVI) where Z and m are as defined in relation to formula (I) with a carbonyl compound R$^4$R$^5$CO. The reaction is preferably carried out in a solvent such as toluene or xylene at temperatures of 100° to 150° C. The reaction may be catalysed by the addition of a small amount of a strong acid, such as p-toluene sulphonic acid.

Alternatively thiazolidinones of formula (X) where D completes a 4-thiazolidinone ring and where Z and m are as defined in relation to formula (I) may be prepared by reaction of a compound of formula (XXXVI) where Z and m are as defined in relation to formula (I) with a 1,1-diiodo alkane, such as diiodomethane, in the presence of a strong base and a solvent. Suitable bases are inorganic bases such as sodium hydroxide or potassium hydroxide. Suitable solvents are ethers such as tetrahydrofuran, or acetone. The reaction is conducted at temperatures of 30°–100° C., preferably at the reflux temperature of the solvent.

Alternatively an aniline of formula (XXIV) where Z and m are as defined in relation to formula (I) may be converted to a compound of formula (XXVI) where Z and m are as defined in relationship to formula (I), and R$^3$ is H by reaction with thioglycollic acid and a carbonyl compound R$^4$R$^5$CO in solvent such as ethanol at a temperature of from 0° to 50° C., preferably ambient temperature followed by treatment with thionyl chloride in an organic solvent such as methylene dichloride.

The reaction is suitably carried out at from 0° to 50° C. preferably ambient temperature, in the presence of an organic base such as triethylamine.

The 4-thiazolidinone (XXVI) is treated with a chlorinating agent (e.g. sulphuryl chloride) to convert it to the corresponding chloro compound (XXVII) where Z and m, are as defined in relation of formula (I). Conveniently the reaction is carried out in a solvent, for example a chlorinated hydrocarbon solvent (e.g. dichloromethane, chloroform, or carbon tetrachloride) at a reduced temperature (e.g. a temperature in the range from 0° to 10° C.). The reaction is usually exothermic and cooling (e.g. in an ice-bath) is needed to keep the temperature in the preferred range. The product may be recovered by evaporating off the solvent (e.g. under reduced pressure) leaving the crude chloro-compound as a residue. The crude product (XXVII) may be purified if desired by conventional methods (e.g. by recrystallisation), or used directly in the next stage.

The chloro-compound (XXVII) is converted to the corresponding hydroxy compound (III) where D completess a 4-thiazolidinone ring and Z and m are as defined in relation to formula (I) and by hydrolysis under mild conditions (e.g. at ambient temperature, for example 15°–25° C., and at moderate pH, for example pH 8–9). Conveniently the reaction is carried out in a solvent. The solvent may be for example a water-miscible solvent (e.g. tetrahydrofuran) or a mixture of such a solvent with water. The hydrolysis may be carried out for example by treating the chloro-compound in solution with aqueous sodium bicarbonate at ambient temperature and stirring the mixture until reaction is substantially complete; this may take up to several days. The hydroxy-compound (III) may be isolated by conventional procedures, for example by diluting the reaction mixture with water, extracting the mixture with a water-immiscible organic solvent, drying the organic extract, and evaporating it to leave the crude hydroxy-compound as a residue. This may then be purified if required by conventional methods, (e.g. recrystallisation).

Compounds of formula (III) in which D completes a saturated 1,3,4-thiadiazinone ring and Z and m are as defined in relation to formula (I) may also be prepared from a compound of formula (XXXII) where D completes a saturated thiadiazinone ring and Z and m are as defined inrelation to formula (I) by reaction first with sulphuryl chloride in dichloromethane solution at 0° to 25° C. followed by hydrolysis of the intermediate chloro compound using aqueous sodium bicarbonate solution and a water miscible solvent such as tetrahyrofuran.

Compounds of formula (XXXII) may be prepared by reacting a compound of formula (XXXIII) where Z and m are as defined in relation to formula (I) with a strong base such as sodium hydride followed by treatment with a compound of formula (XXXIV) in which R$^{30}$ is a leaving group such as halo. The reaction is performed at 0°–50° C., preferably at ambient temperature in a solvent such as dimethylformamide.

Compounds of formula (XXXIII) may be prepared from compounds of formula (XXXV) where Z and m are as defined in relation to formula (I) with thioglycollic acid or thiolactic acid and a carbonyl compound of formula $COR^4R^5$ in a manner analogous to the preparation of compounds of formula (XXVI).

Compounds of formula (XXV) are known compounds or can be prepared from known compounds by conventional methods.

Compounds of the invention in which p is 1 or 2 may be prepared by treating the corresponding compounds of formula (I), in which p is 0 with an oxidising agent. The oxidising agent may be, for example, m-chloroperbenzoic acid. When this oxidising agent is used, the reaction may conveniently be carried out in a solvent for example a chlorinated hydrocarbon solvent. Examples of such solvents include dichloromethane and chloroform. The reaction may be performed at ambient temperature (e.g. 15°–25° C.). By using one molar proportion of m-chloroperbenzoic acid, a compound of formula (I), wherein p=0 can be converted into a compound of formula (I) wherein p=1. In the same way, a compound of formula (I) wherein p=1 can be converted to a compound of formula (I) in which p=2 by treatment with one molar proportion of m-chloroperbenzoic acid. Alternatively, a compound of formula (I) in which p=0 may be converted directly to the corresponding compound wherein p=2 by treatment with two molar proportions of m-chloroperbenzoic acid.

Compounds of formula (X) where D completes a 4-oxazolidinone ring and Z and m are as defined in relation to formula (I) may be prepared by methods similar to those described for the preparation of compounds of formula (X) where D completes a 4-thiazolidinone ring and Z and m are defined as in relation to formula (I), but using glycollic acid in place of thioglycollic acid and lactic acid in place of thiolactic acid. Compounds of formula (III) where D completes a form a 4-oxazolidinone ring and Z and m are as defined in relation to formula (I) may be prepared from compounds of formula (X) where D completes a 4-oxazolidinone ring and Z and m are as defined in relation to formula (I) by methods analogous to those described above.

Compounds of formula (X) where D completes a 4-imidazolidinone ring and Z and m are as defined in relation to formula (I) may be prepared by methods analogous to those described for the preparation of compounds of formula (X) where D completes a 4-thiazolidinone ring and Z and m are as defined in relation to formula (I) using α-amino acid derivatives instead of thioglycollic acids.

Compounds of formula (III) where D completes a 4-imidazolidinone ring and Z and m are as defined in relation to formula (I) may be prepared from compounds of formula (X) where D completes a 4-imidazolidinone ring and Z and m are as defined in relation to formula (I) by methods analogous to those described above.

Compounds of formula (X) where D completes a saturated pyrazinone ring and Z and m are as defined in relation to formula (I) may be prepared by methods analogous to those described for the preparation of compounds (X) where D completes a dihydro-4-thiazinone ring and Z and m are as described in relation to formula (I), but using an α-amino ester in place of ethyl thioglycollate. Suitably the α-amino ester is the ethyl ester of sarcosine.

Compounds of formula (III) where D completes a saturated pyrazinone ring and Z and m are as defined in relation to formula (I) may be prepared from compounds of formula (X) where D completes a saturated pyrazinone ring and Z and m are as defined in relation to formula (I) by methods described above.

Compounds of formula (X), where D completes a 3-pyrazolidinone ring and Z and m are as defined in relation to formula (I), may be prepared by a combination of methods analogous to those described for the preparation of compounds of formula (XVI) where Z and m are as defined in relation to formula (I), and compounds of formula (X) where D completes a saturated 1,3,4-thiadiazinone ring and 2 and m are as defined in relation to formula (I), but using a compound of formula (XXXV), where Z and m are as defined in relation to formula (I), in place of a compound of formula (XV), where Z and m are as defined in relation to formula (I).

Compounds of formula (III) where D completes a 3-pyrazolidinone ring and Z and m are as defined in relation to formula (I) may be prepared from compounds of formula (X) where D completes a 3-pyrazolidinone ring and Z and m are as defined in relation to formula (I) by methods analogous to those described above.

Compounds of formula (VI) where D completes a 3-pyridazinone ring and Z and m are as defined in relation to formula (I) and $R^{20}$ is iodo may be prepared by a combination of methods similar to those described for the preparation of compounds of formula (XVIII) where Z and m are as defined in relation to formula (I) and compounds of formula (X) where D completes a saturated 1,3,4-thiadiazinone ring and Z and m are as defined in relation to formula (I), but using a compound of formula (XXXV) where Z and m are as defined in relation to formula (I) in place of a compound of formula (XV) where Z and m are as defined in relation to formula (I).

Compounds of formula (III) where D completes a saturated 3-pyridazinone ring and Z and m are as defined in relation to formula (I) may be prepared from compounds of formula (VI) where D completes a saturated pyridazinone ring and Z and m are as defined in relation to formula (I) and $R^{20}$ is iodo by a method analogous to that described for the preparation of compounds of formula (III) where D completes a saturated 1,2-oxazinone ring and Z and m are as defined in relation to formula (I).

Variations of the above procedures will be apparent to the skilled person in the art, as well as alternative processes for preparing the compounds of the invention.

The compounds of formula (I) above are active as herbicides, and the invention therefore provides in a further aspect a process for severely damaging or killing unwanted plants, which process comprises applying to the plants, or to the growth medium of the plants, a herbicidally effective amount of a compound of formula (I) as hereinbefore defined.

The compounds of formula (I) are active against a broad range of weed species including monocotyledonous and dicotyledonous species. They show some selectivity towards certain species; they may be used, for example, as selective herbicides in soya and maize crops. The compounds of formula (I) are applied (directly to unwanted plants (post-emergence application) but they are preferably applied to the soil before the unwanted plants emerge (pre-emergence application).

The compounds of formula (I) may be used on their own to kill or severely damage plants, but are preferably used in the form of a composition comprising a compound of formula (I) in admixture with a carrier comprising a solid or liquid diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium,calcium, and ammonium lignosulphonate, butylnaphthalene sulphonate, and a mixture of the sodium salts of diisopropyl and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octyl-cresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having a complementary action in the particular application.

Examples of useful complementary herbicides include:

A. benzo-2,1,3-thiadiazin-4-one-2,2-dioxides such as bentazone;
B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);
C. 1,3 dimethylpyrazole derivatives such as pyrazoxyfen, pyrazolate and benzofenap;
D. Dinitrophenols and their derivatives (eg. acetates) such as dinoterb, dinoseb and its ester, dinoseb acetate;
E. dinitroaniline herbicides such as dinitramine, trifluralin, ethalflurolin, pendimethalin, oryzalin;
F. arylurea herbicides such as diuron, flumeturon, metoxuron, neburon, isoproturon, chlorotoluron, chloroxuron, linuron, monolinuron, chlorobromuron, daimuron, methabenzthiazuron;
G. phenylcarbamoyloxyphenylcarbamates such as phenmedipham and desmedipham;
H. 2-phenylpyridazin-3-ones such as chloridazon and norflurazon;
I. uracil herbicides such as lenacil, bromacil and terbacil;
J. triazine herbicides such as atrazine, simazine, aziprotryne, cyanazine, prometryn, dimethametryn, simetryne, and terbutryn;
K. phosphorothioate herbicides such as piperophos, bensulide, and butamifos;
L. thiolcarbamate herbicides such as cycloate, vernolate, molinate, thiobencarb, butylate*, EPTC* , tri-allate, di-allate, esprocarb, tiocarbazil, pyridate, and dimepiperate;

* These compounds are preferably employed in combination with a safener such as dichlormid.

M. 1,2,4-triazin-5-one herbicides such as metamitron and metribuzin;

N. benzoic acid herbicides such as 2,3,6-TBA, dicamba and chloramben;
O. anilide herbicides such as pretilachlor, butachlor, alachlor, propachlor, propanil, metazachlor, metolachlor, acetochlor, and dimethachlor;
P. dihalobenzonitrile herbicides such as dichlobenil, bromoxynil and ioxynil;
Q. haloalkanoic herbicides such as dalapon, TCA and salts thereof;
R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;
S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;
T. cyclohexanedione herbicides such as alloxydim and salts thereof, sethoxydim, cycloxydim, tralkoxydim, and clethodim;
U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and pyrazosulfuron;
V. imidazolidinone herbicides such as imazaquin, imazamethabenz, imazapyr and isopropylammonium salts thereof, imazethapyr;
W. arylanilide herbicides such as flamprop and esters thereof, benzoylprop-ethyl, diflufenican;
X. amino acid herbicides such as glyphosate and glufosinate and their salts and esters, sulphosate and bialaphos;
Y. organoarsenical herbicides such as monosodium methanearsonate (MSMA);
Z. herbicidal amide derivative such as napropamide, propyzamide, carbetamide, tebutam, bromobutide, isoxaben, naproanilide and naptalam;
AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac, mefanacet, and triketone herbicides such as sulcotrione;
BB. Examples of useful contact herbicides include: bipyridylium herbicides such as those in which the active entity is paraquat and those in which the active entity is diquat;

The invention is illustrated by the following Examples. (The preparation of intermediates is described in the Preparative Examples). The abbreviations used in the Examples have the following meanings:

NMR spectrum: nuclear magnetic resonance spectrum which were recorded at 270 or 400 MHz. (This refers to the proton magnetic resonance spectrum unless otherwise stated). The following abbreviations are used to indicate the multiplicity of the peaks in the NMR spectrum: s (singlet); d (doublet); t (triplet); q (quartet) quin (quintet) m (multiplet; br (broad).

IR spectrum: infra-red absorption spectrum.
MS: mass spectrum
GC: gas chromatography TLC: thin layer chromatography
m.p.: melting point b.p: boiling point

PREPARATIVE EXAMPLE 1

Preparation of 3-(3,4-dichloro)phenyl-5-hydroxy-4-thiazolidinone

Step 1 Preparation of 3-(3,4-dichloro)phenyl-4-thiazolidinone

A stirred solution of 3,4-dichloroaniline (10.00 g) in toluene (120 ml) was treated with thioglycollic acid (5.68 g). After 10 minutes, the solution was treated dropwise with 37% aqueous formaldehyde (4.75 ml), followed by p-toluenesulphonic acid (10 mg). The mixture was then heated under reflux, and water was collected in a Dean and Stark apparatus. After 4 hours the mixture was cooled, and extracted with saturated aqueous sodium bicarbonate solution (100 ml). A white solid precipitated, which was filtered off, dried, and recrystallised from ethyl acetate/hexane to give the title compound as a white crystalline solid, yield 5.70 g, mp 151°–152° C.

$^1$H nmr (CDCl$_3$): δ3.71 (2H, s), 4.79 (2H, s), 7.37 (1H, dd), 7.47 (1H, d), 7.64 (1H, d)

Step 2 Preparation of 3-(3,4-dichloro)phenyl-5-hydroxy-4-thiazolidinone

A stirred solution of 3-(3,4-dichloro)phenyl-4-thiazolidinone (prepared as in Step 1 above) (4.50 g) in dichloromethane (130 ml) was cooled in an ice bath. A stream of nitrogen was bubbled through the solution, and a solution of sulphuryl chloride (2.47 g) in dichloromethane (5 ml) was added dropwise. After the addition the solution was allowed to warm to room temperature, and was stirred for a further 2 hours whilst maintaining the nitrogen flow. The solution was evaporated under reduced pressure to leave a solid residue, which, after trituration with hexane, was dissolved in tetrahydrofuran (50 ml). This solution was treated with aqueous sodium bicarbonate solution (50 ml), and the mixture was stirred vigorously for 2 hours. The organic layer was separated, diluted with ethyl acetate (50 ml), washed with brine (50 ml), then dried (MgSO$_4$). Evaporation of the solvent under reduced pressure left a gum, which was chromatographed on silica gel, eluting with hexane/ethyl acetate mixtures, to afford the title compound as a gum which solidified on standing, yield 3.40 g.

$^1$H nmr (CDCl$_3$): δ4.78 (1H, d), 5.06 (1H, d), 5.58 (1H, d), 6.98 (1H, d), 7.40–7.50 (2H, m), 7.80 (1H, d)

PREPARATIVE EXAMPLE 2

Preparation of 5-hydroxy-3-(3-trifluoromethyl) phenyl-4-thiazolidinone

Step 1 Preparation of 3-(3-trifluoromethyl)phenyl-4-thiazolidinone

A stirred solution of 3-trifluoromethylaniline (43.50 g) in toluene (275 ml) was treated with thioglycollic acid (24.90 g). After 10 minutes, the solution was treated dropwise with 37% aqueous formaldehyde (20.8 ml), followed by p-toluenesulphonic acid (30 mg). The mixture was then heated under reflux, and water was collected in a Dean and Stark apparatus. After 23.5 ml of water had been collected, the mixture was cooled, extracted with saturated aqueous sodium bicarbonate solution (100 ml) and dried (MgSO$_4$). Evaporation under reduced pressure left a yellow oil, which afforded the title compound as a white solid on trituration with hexane, yield 44.50 g, mp 59°–60° C.

$^1$H nmr (CDCl$_3$): δ3.76 (2H, s), 4.85 (2H, s), 7.47–7.58 (2H, m), 7.68–7.76 (2H, m)

Step 2 Preparation of 5-chloro-3-(3-trifluoromethyl)phenyl-4-thiazolidinone

A stirred solution of 3-(3-trifluoromethyl)phenyl-4-thiazolidinone (prepared as in Step 1 above) (10.00 g) in dichloromethane (150 ml) was cooled in an ice bath. A stream of nitrogen was bubbled through the solution, and a solution of sulphuryl chloride (5.47 g) in dichloromethane (5 ml) was added dropwise. After the addition the solution was allowed to warm to room temperature, and was stirred for a further 1 hour whilst maintaining the nitrogen flow. The solution was evaporated under reduced pressure to leave the product as a solid residue. This product was used directly in subsequent reactions.

$^1$H nmr (CDCl$_3$): δ4.72 (1H, d), 5.24 (1H, d), 5.77 (1H, s), 7.50–7.61 (2H, m), 7.70–7.82 (2H, m)

Step 3 Preparation of 5-hydroxy-3-(3-trifluoromethyl) phenyl-4-thiazolidinone

A stirred solution of 5-chloro-3-(3-trifluoromethyl) phenyl-4-thiazolidinone (prepared as in Step 2 above) in tetrahydrofuran (100 ml) was treated with aqueous sodium bicarbonate solution (100 ml), and the mixture was stirred vigorously for 3 hours. The organic layer was separated, diluted with ethyl acetate (50 ml), washed with brine (50 ml), then dried (MgSO$_4$). Evaporation of the solvent under reduced pressure left a gum. Trituration with hexane afforded a buff solid, which was recrystallised from ethyl acetate/hexane to give the title compound as a white crystalline solid, yield 7.08 g, mp 87°–88° C.

$^1$H nmr (CDCl$_3$): δ4.70 (1H, d), 5.00 (1H, broad s), 5.05 (1H, d), 5.74 (1H, s), 7.48–7.59 (2H, m), 7.64–7.76 (2H, m)

PREPARATIVE EXAMPLE 3

Preparation of 3-(3,5-bis(trifluoromethyl))phenyl-5-hydroxy-4-thiazolidinone

Step 1 Preparation of 3-(3,5-bis(trifluoromethyl))phenyl-4-thiazolidinone

By a procedure similar to that described in Preparative Example 2, Step 1 above, but using 3,5-bis(trifluoromethyl) aniline (10.42 g), thioglycollic acid (4.10 g), 37% aqueous formaldehyde solution (4.1 ml) and toluene (100 ml), this compound was obtained as a white solid, yield 10.80 g, mp 49°–51° C.

$^1$H nmr (CDCl$_3$): δ3.78 (2H, s), 4.90 (2H, s), 7.73 (1H, s), 8.00 (2H, s)

Step 2 Preparation of 5-chloro-3-(3,5-bis(trifluoromethyl)) phenyl-4-thiazolidinone This compound was prepared by a procedure similar to that described in Preparative Example 2, Step 2 above, but using 3-(3,5-bis(trifluoromethyl))phenyl-4-thiazolidinone (prepared as in Step 1 above) (9.00 g), sulphuryl chloride (3.86 g), and dichloromethane (25 ml). This product was used directly in Step 3.

Step 3 Preparation of 5-hydroxy-3-(3,5-bis(trifluoromethyl) )phenyl-4-thiazolidinone By a procedure similar to that described in Preparative Example 2, Step 3 above, but using 5-chloro-3-(3,5-bis (trifluoromethyl))phenyl-4-thiazolidinone (prepared as in Step 2 above), the title compound was obtained as a white solid, yield 7.10 g, mp 138°–139° C.

$^1$H nmr (CDCl$_3$): δ4.41 (1H, d), 5.16 (1H, d), 5.65 (1H, d), 6.42 (1H, d), 7.73 (1H, s), 8.08 (1H, s)

PREPARATIVE EXAMPLE 4

Preparation of 5-hydroxy-3-(4-trifluoromethyl) phenyl-4-thiazolidinone

Step 1 Preparation of 5-chloro-3-(4-trifluoromethyl)phenyl-4-thiazolidinone

This compound was prepared by a procedure similar to that described in Preparative Example 2, Step 2 above, but using 3-(4-trifluoromethyl)phenyl-4-thiazolidinone (0.78 g), sulphuryl chloride (0.25 ml), and dichloromethane (5 ml). This product was used directly in Step 2.

Step 2 Preparation of 5-hydroxy-3-(4-trifluoromethyl) phenyl-4-thiazolidinone

By a procedure similar to that described in Preparative Example 2, Step 3 above, but using 5-chloro-3-(4-trifluoromethyl)phenyl-4-thiazolidinone (prepared as in Step 1 above), and chromatographing the crude produce on silica gel eluting with diethyl ether, the title compound was obtained as a white solid, yield 0.22 g, mp 100°–101° C.

$^1$H nmr (CDCl$_3$): δ4.47 (1H, broad s), 4.73 (1H, d), 5.05 (1H, d), 5.75 (1H, s), 7.62–7.73 (4H, m)

PREPARATIVE EXAMPLE 5

Preparation of 3-(3-chloro)phenyl-5-hydroxy-4-thiazolidinone

Step 1 Preparation of 3-(3-chloro)phenyl-4-thiazolidinone

By a procedure similar to that described in Preparative Example 2, Step 1 above, but using 3-chloroaniline (30.10 g), thioglycollic acid (21.7 g), 37% aqueous formaldehyde solution (18.3 ml), toluene (350 ml) and p-toluenesulphonic acid (30 mg), and recrystallising the crude product from ethyl acetate/hexane, this compound was obtained as a pale yellow solid, yield 36.80 g, mp 79° C.

$^1$H nmr (CDCl$_3$): δ3.72 (2H, s), 4.80 (2H, s), 7.22 (1H, m), 7.28–7.40 (2H, m), 7.50 (1H, m)

Step 2 Preparation of 5-chloro-3-(3-chloro)phenyl-4-thiazolidinone

This compound was prepared by a procedure similar to that described in Preparative Example 2, Step 2 above, but using 3-(3-chloro)phenyl-4-thiazolidinone (prepared as in Step 1 above) (34.70 g), sulphuryl chloride (13.20 ml), and dichloromethane (150 ml). This product was used directly in Step 3.

Step 3 Preparation of 3-(3-chloro)phenyl-5-hydroxy-4-thiazolidinone

By a procedure similar to that described in Preparative Example 2, Step 3 above, but using 5-chloro-3-(3-chloro) phenyl-4-thiazolidinone (prepared as in Step 2 above), tetrahydrofuran (150 ml) and saturated aqueous sodium bicarbonate (150 ml), and purification of the crude product by silica gel gel chromatography eluting with ethyl acetate/ hexane, the title compound was obtained, yield 19.90 g, mp 112°–114° C.

$^1$H nmr (CDCl$_3$): δ4.64 (1H, d), 5.00 (1H, d), 5.39 (1H, broad s), 5.75 (1H, s), 7.20–7.38 (3H, m), 7.50 (1H, s)

PREPARATIVE EXAMPLE 6

Preparation of 3-(3,5-dichloro)phenyl-5-hydroxy-4-thiazolidinone

Step 1 Preparation of 3-(3,5-dichloro)phenyl-4-thiazolidinone

By a procedure similar to that described in Preparative Example 2, Step 1 above, but using 3,5-dichloroaniline (28.70 g), thioglycollic acid (16.30 g), 37% aqueous formaldehyde solution (13.7 ml), toluene (350 ml) and p-toluenesulphonic acid (30 mg), and recrystallising the crude product from ethyl acetate/hexane, this compound was obtained as a pale yellow solid, yield 28.70 g.

$^1$H nmr (CDCl$_3$): δ3.72 (2H, s), 4.78 (2H, s), 7.21 (1H, t), 7.45 (2H, d)

Step 2 Preparation of 5-chloro-3-(3,5-dichloro)phenyl-4-thiazolidinone

This compound was prepared by a procedure similar to that described in Preparative Example 2, Step 2 above, but using 3-(3,5-dichloro)phenyl-4-thiazolidinone (prepared as in Step 1 above) (28.30 g), sulphuryl chloride (9.2 ml), and dichloromethane (100 ml). This product was used directly in Step 3.

Step 3 Preparation of 3-(3,5-dichloro)phenyl-5-hydroxy-4-thiazolidinone

By a procedure similar to that described in Preparative Example 2, Step 3 above, but using 5-chloro-3-(3,5-dichloro)phenyl-4-thiazolidinone (prepared as in Step 2 above), tetrahydrofuran (125 ml) and saturated aqueous sodium bicarbonate (125 ml), and trituration of the crude product with diethyl ether, the title compound was obtained, yield 16.70 g, mp 107°–111° C.

$^1$H nmr (CDCl$_3$): δ4.61 (1H, d), 4.98 (1H, d), 5.19 (1H, broad s), 5.71 (1H, s), 7.21 (1H, m), 7.42 (2H, m)

PREPARATIVE EXAMPLE 7

Preparation of 3-(3-chloro-4-fluoro)phenyl-5-hydroxy-4-thiazolidinone

Step 1 Preparation of 3-(3-chloro-4-fluoro)phenyl-4-thiazolidinone

By a procedure similar to that described in Preparative Example 2, Step 1 above, but using 3-chloro-4-fluoroaniline (19.46 g), thioglycollic acid (12.50 g), 37% aqueous formaldehyde solution (10.5 ml) and toluene (150 ml), and trituration of the crude product with diethyl ether/hexane, this compound was obtained as a pale yellow solid, yield 22.30 g, mp 95°–97° C.

$^1$H nmr (CDCl$_3$): δ3.72 (2H, s), 4.78 (2H, s), 7.18 (1H, m), 7.31 (1H, m), 7.55 (1H, m)

Step 2 Preparation of 5-chloro-3-(3-chloro-4-fluoro)phenyl-4-thiazolidinone

This compound was prepared by a procedure similar to that described in Preparative Example 2, Step 2 above, but using 3-(3-chloro-4-fluoro)phenyl-4-thiazolidinone (prepared as in Step 1 above) (20.00 g), sulphuryl chloride (11.2 ml), and dichloromethane (100 ml). This product was used directly in Step 3.

$^1$H nmr (CDCl$_3$): δ4.63 (1H, d), 5.27 (1H, d), 5.75 (1H, s), 7.21 (1H, m), 7.37 (1H, m), 7.61 (1H, m)

Step 3 Preparation of 3-(3-chloro-4-fluoro)phenyl-5-hydroxy-4-thiazolidinone

By a procedure similar to that described in Preparative Example 2, Step 3 above, but using 5-chloro-3-(3-chloro-4-fluoro)phenyl-4-thiazolidinone (prepared as in Step 2 above), tetrahydrofuran (50 ml) and saturated aqueous sodium bicarbonate (50 ml), and purification of the crude product by chromatography on silica gel eluting with ethyl acetate/hexane followed by trituration with carbon tetrachloride, the title compound was obtained as a white solid, yield 12.50 g, mp 118°–121° C.

$^1$H nmr (CDCl$_3$): δ4.63 (1H, d), 4.85 (1H broad s), 4.95 (1H, d), 5.73 (1H, s), 7.19 (1H, m), 7.33 (1H, m), 7.58 (1H, m)

PREPARATIVE EXAMPLE 8

Preparation of 3-(2-chloro)phenyl-5-hydroxy-4-thiazolidinone

Step 1 Preparation of 3-(2-chloro)phenyl-4-thiazolidinone

By a procedure similar to that described in Preparative Example 2, Step 1 above, but using 2-chloroaniline (12.75 g), thioglycollic acid (9.2 g), 37% aqueous formaldehyde solution (7.8 ml) and toluene (100 ml), and purification of the crude product by silica gel eluting with ethyl acetate/hexane, this compound was obtained as a white solid, yield 5.70 g, mp 62°–63° C.

$^1$H nmr (CDCl$_3$): δ3.72 (2H, s), 4.69 (2H, s), 7.28–7.40 (3H, m), 7.49 (1H, m)

Step 2 Preparation of 5-chloro-3-(2-chloro)phenyl-4-thiazolidinone

This compound was prepared by a procedure similar to that described in Preparative Example 2, Step 2 above, but using 3-(2-chloro)phenyl-4-thiazolidinone (prepared as in Step 1 above) (5.20 g), sulphuryl chloride (2.0 ml), and dichloromethane (50 ml). This product was used directly in Step 3.

Step 3 Preparation of 3-(2-chloro)phenyl-5-hydroxy-4-thiazolidinone

By a procedure similar to that described in Preparative Example 2, Step 3 above, but using 5-chloro-3-(2-chloro)phenyl-4-thiazolidinone (prepared as in Step 2 above), tetrahydrofuran (25 ml) and saturated aqueous sodium bicarbonate (25 ml), and recrystallisation of the crude product from toluene, the title compound was obtained as a white solid, yield 3.80 g, mp 117°–119° C.

$^1$H nmr (CDCl$_3$): δ4.58 (1H, d), 4.83 (1H, d), 5.05 (1H, s), 5.78 (1H, s), 7.30–7.41 (3H, m), 7.52 (1H, m)

PREPARATIVE EXAMPLE 9

Preparation of 5-hydroxy-3-(4-methoxy)phenyl-4thiazolidinone

Step 1 Preparation of 3-(4-methoxy)phenyl-4-thiazolidinone

By a procedure similar to that described in Preparative Example 2, Step 1 above, but using 4-methoxyaniline (8.43 g), thioglycollic acid (6.30 g), 37% aqueous formaldehyde solution (5.3 ml) and toluene (100 ml), and recrystallisation of the crude product from ethyl acetate/hexane, this compound was obtained as a white solid, yield 7.00 g, mp 95°–97° C.

$^1$H nmr (CDCl$_3$): δ3.72 (2H, s), 3.80 (3H, s), 4.77 (2H, s), 6.90–6.96 (2H, m), 7.27–7.33 (2H, m)

Step 2 Preparation of 5-chloro-3-(4-methoxy)phenyl-4-thiazolidinone

This compound was prepared by a procedure similar to that described in Preparative Example 2, Step 2 above, but using 3-(4-methoxy)phenyl-4-thiazolidinone (prepared as in Step 1 above) (6.20 g), sulphuryl chloride (2.4 ml), and dichloromethane (50 ml). This product was used directly in Step 3.

Step 3 Preparation of 5-hydroxy-3-(4-methoxy)phenyl-4-thiazolidinone

By a procedure similar to that described in Preparative Example 2, Step 3 above, but using 5-chloro-3-(4-methoxy)phenyl-4-thiazolidinone (prepared as in Step 2 above), tetrahydrofuran (30 ml) and saturated aqueous sodium bicarbonate (60 ml), and purification of the crude product by chromatography on silica gel eluting with ethyl acetate/hexane followed by recrystallisation from toluene, the title compound was obtained as a buff solid, yield 3.20 g, mp 126°–128° C.

$^1$H nmr (CDCl$_3$): δ3.81 (3H, s), 4.63 (1H, d), 4.87 (1H, d), 4.94 (1H, d), 5.75 (1H, d), 6.89–6.97 (2H, m), 7.28–7.36 (2H, m)

PREPARATIVE EXAMPLE 10

Preparation of 3-(2,3-dichloro)phenyl-5-hydroxy-4-thiazolidinone

Step 1 Preparation of 3-(2,3-dichloro)phenyl-4-thiazolidinone

By a procedure similar to that described in Preparative Example 2, Step 1 above, but using 2,3-dichloroaniline (10.00 g), thioglycollic acid (5.68 g), 37% aqueous formaldehyde solution (4.75 ml), toluene (120 ml) and p-toluenesulphonic acid (10 mg), and trituration of the crude product with diethyl ether/hexane, this compound was obtained as a white solid, yield 1.43 g.

$^1$H nmr (CDCl$_3$): δ3.73 (2H, s), 4.67 (2H, s), 7.15–7.32 (2H, m), 7.51 (1H, m)

Step 2 Preparation of 5-chloro-3-(2,3-dichloro)phenyl-4-thiazolidinone

This compound was prepared by a procedure similar to that described in Preparative Example 2, Step 2 above, but using 3-(2,3-dichloro)phenyl-4-thiazolidinone (prepared as in Step 1 above) (1.20 g), sulphuryl chloride (0.65 g), and dichloromethane (20 ml). This product was used directly in Step 3.

Step 3 Preparation of 3-(2,3-dichloro)phenyl-5-hydroxy-4-thiazolidinone

By a procedure similar to that described in Preparative Example 2, Step 3 above, but using 5-chloro-3-(2,3-dichloro)phenyl-4-thiazolidinone (prepared as in Step 2 above), tetrahydrofuran (30 ml) and saturated aqueous sodium bicarbonate (25 ml), and trituration of the crude product with diethyl ether, the title compound was obtained as a pale yellow solid, yield 0.66 g.

$^1$H nmr (CDCl$_3$): δ4.52 (1H, d), 4.85 (1H, d), 5.60 (1H, d), 6.99 (1H, d), 7.30–7.40 (2H, m), 7.55 (1H, m)

PREPARATIVE EXAMPLE 11

Preparation of 5-hydroxy-3-(4-methyl)phenyl-4-thiazolidinone

Step 1 Preparation of 3-(4-methyl)phenyl-4-thiazolidinone

By a procedure similar to that described in Preparative Example 1, Step 1 above, but using 4-methylaniline (14.30 g), thioglycollic acid (12.30 g), 37% aqueous formaldehyde solution (10.4 ml) and toluene (150 ml), this compound was obtained as a white solid, yield 10.50 g, mp 138°–141° C.

$^1$H nmr (CDCl$_3$): δ2.34 (3H, s), 3.72 (2H, s), 4.79 (2H, s), 7.15–7.32 (4H, m)

Step 2 Preparation of 5-chloro-3-(4-methyl)phenyl-4-thiazolidinone

This compound was prepared by a procedure similar to that described in Preparative Example 2, Step 2 above, but using 3-(4-methyl)phenyl-4-thiazolidinone (prepared as in Step 1 above) (9.00 g), sulphuryl chloride (3.8 ml), and dichloromethane (100 ml). This product was used directly in Step 3.

Step 3 Preparation of 5-hydroxy-3-(4-methyl)phenyl-4-thiazolidinone

By a procedure similar to that described in Preparative Example 2, Step 3 above, but using 5-chloro-3-(4-methyl)phenyl-4-thiazolidinone (prepared as in Step 2 above), tetrahydrofuran (75 ml) and saturated aqueous sodium bicarbonate (100 ml), and recrystallisation of the crude product from toluene, the title compound was obtained as a pale yellow solid, yield 5.00 g, mp 137°–138° C.

$^1$H nmr (CDCl$_3$): δ2.37 (3H, s), 4.60 (1H, d), 4.95 (1H, d), 5.71 (2H, s+broad s), 7.12–7.31 (4H, m)

PREPARATIVE EXAMPLE 12

Preparation of 3-(4-chloro)phenyl-5-hydroxy-4-thiazolidinone

Step 1 Preparation of 3-(4-chloro)phenyl-4-thiazolidinone

By a procedure similar to that described in Preparative Example 2, Step 1 above, but using 4-chloroaniline (14.50 g), thioglycollic acid (10.50 g), 37% aqueous formaldehyde solution (8.9 ml) and toluene (150 ml), and trituration of the crude product with diethyl ether, this compound was obtained as a white solid, yield 17.60 g, mp 96°–98° C.

$^1$H nmr (CDCl): δ3.72 (2H, s), 4.79 (2H, s), 7.32–7.43 (4H, m)

Step 2 Preparation of 5-chloro-3-(4-chloro)phenyl-4-thiazolidinone

This compound was prepared by a procedure similar to that described in Preparative Example 2, Step 2 above, but using 3-(4-chloro)phenyl-4-thiazolidinone (prepared as in Step 1 above) (15.00 g), sulphuryl chloride (5.7 ml), and dichloromethane (150 ml). This product was used directly in Step 3.

Step 3 Preparation of 3-(4-chloro)phenyl-5-hydroxy-4-thiazolidinone

By a procedure similar to that described in Preparative Example 2, Step 3 above, but using 5-chloro-3-(4-chloro)phenyl-4-thiazolidinone (prepared as in Step 2 above), tetrahydrofuran (50 ml) and saturated aqueous sodium bicarbonate (50 ml), and recrystallisation of the crude product from toluene, the title compound was obtained as a white solid, yield 9.80 g, mp 118°–120 ° C.

$^1$H nmr (CDCl): δ4.62 (1H, d), 4.96 (1H, d), 5.05 (1H, broad s), 5.72 (1H, s), 7.33–7.45 (4H, m)

PREPARATIVE EXAMPLE 13

Preparation of 3-(2,5-dichloro)phenyl-5-hydroxy-4-thiazolidinone

Step 1 Preparation of 3-(2,5-dichloro)phenyl-4-thiazolidinone

By a procedure similar to that described in Preparative Example 2, Step 1 above, but using 2,5-dichloroaniline (10.00 g), thioglycollic acid (5.68 g), 37% aqueous formaldehyde solution (4.75 ml), toluene (120 ml) and p-toluenesulphonic acid (10 mg), and trituration of the crude product with diethyl ether/hexane, this compound was obtained as a white solid, yield 0.78 g.

$^1$H nmr (CDCl$_3$): δ3.71 (2H, s), 4.66 (2H, s), 7.29–7.46 (3H, m)

Step 2 Preparation of 5-chloro-3-(2,5-dichloro)phenyl-4-thiazolidinone

This compound was prepared by a procedure similar to that described in Preparative Example 2, Step 2 above, but using 3-(2,5-dichloro)phenyl-4-thiazolidinone (prepared as in Step 1 above) (0.68 g), sulphuryl chloride (0.37 g), and dichloromethane (15 ml). This product was used directly in Step 3.

Step 3 Preparation of 3-(2,5-dichloro)phenyl-5-hydroxy-4-thiazolidinone

By a procedure similar to that described in Preparative Example 2, Step 3 above, but using 5-chloro-3-(2,5-dichloro)phenyl-4-thiazolidinone (prepared as in Step 2 above), tetrahydrofuran (20 ml) and saturated aqueous sodium bicarbonate (30 ml), and trituration of the crude product with diethyl ether, the title compound was obtained as a buff solid, yield 0.36 g.

$^1$H nmr (CDCl$_3$): δ4.55 (1H, d), 4.87 (1H, d), 5.68 (1H, d), 6.31 (1H, d), 7.25–7.46 (3H, m)

PREPARATIVE EXAMPLE 14

Preparation of 4-hydroxy-2-(3-trifluoromethyl)phenyl-3-isoxazolidinone.

Step 1: Preparation of N-(3-trifluoromethyl)phenylhydroxylamine. This is described in Preparative Example 50.

Step 2: Preparation of 4-bromo-2-(3-trifluoromethyl)phenyl-3-isoxazolidinone

A solution of N-(3-trifluoromethyl)phenylhydroxylamine (4.69 g) and triethylamine (2.94 g) in dry tetrahydrofuran (5 ml) was added dropwise over thirty minutes to a vigorously stirred solution of 2,3-dibromopropionyl chloride (6.63 g) in dry tetrahydrofuran (20 ml) cooled to 0° C. The mixture was allowed to warm slowly to room temperature and to stand overnight. It was then filtered through Hyflo Supercel and the filtrate stirred vigorously with aqueous sodium carbonate solution (2 ml, saturated) for two hours. The mixture was allowed to stand overnight, diluted with ethyl acetate, washed with brine, dried over magnesium sulphate and evaporated under reduced pressure. The residue was chromatographed on silica, using dichloromethane-hexane (3:1) then dichloromethane as eluants, to give the title compound (2.84 g) as an oil.

$^1$H NMR (CDCl$_3$): δ 4.6(1H,dd), 4.75(1H,dd), 4.8(1H, dd), 7.4(2H,m), 7.9(2H,m).

M/S: 309, (M+, Br=79).

Step 3: Preparation of 4-iodo-2-(3-trifluoromethyl)phenyl-3-isoxazolidinone.

A mixture of 4-bromo-2-(3-trifluoromethyl)phenyl-3-isoxazolidinone (0.28 g) and sodium iodide (0.36 g) in acetone (10 ml) was stirred, in the absence of light, for twenty hours at room temperature. It was then filtered through Hyflo Supercel and evaporated under reduced pressure. The residue was dissolved in ethyl acetate, washed with water and brine, dried over magnesium sulphate and evaporated under reduced pressure to give the title compound (0.28 g) as a pale yellow oil, essentially pure by GC.

$^1$H NMR (CDCl$_3$): δ 4.6(1H,dd), 4.75(1H,dd), 4.95(1H, dd), 7.5(2H,m), 8.0(2H,m).

M/S: 357 (M+)

Step 4: Preparation of 2-(3-trifluoromethyl)phenyl-3-isoxazolidinone

A solution of 4-iodo-2(3-trifluoromethyl)phenyl-3-isoxazolidinone (0.20 g), tributyltin hydride (0.16 g) and α,α'-azoisobutyronitrile (0.01 g) in toluene (10 ml) was heated under reflux for two hours. A further quantity (0.01 g) of initiator was added and heating continued for a further hour. The mixture was evaporated under reduced pressure and the residue chromatographed on silica, using hexane then ethyl acetate-hexane (1:3) as eluants. The title compound (0.09 g) was obtained as a pale yellow oil.

$^1$H NMR (CDCl$_3$): δ3.05(2H,t), 4.6(2H,t), 7.5(2H,m), 8.0(2H,m).

M/S: 231 (M+)

This material can be obtained more conveniently by coupling the arylhydroxylamine directly with 3-bromopropionyl chloride. Whilst purification is extremely tedious, partially purified material can be used directly in Step 5.

Thus a solution of N-(3-trifluoromethyl) phenylhydroxylamine (0.50 g) and triethylamine (0.59 g) in dry tetrahydrofuran (5 ml) was added dropwise to a stirred solution of 3-bromopropionyl chloride (0.48 g) in dry tetrahydrofuran (20 ml) cooled to 0° C. The mixture was stirred at 0° C. for two hours, allowed to warm to room temperature, diluted with ethyl acetate and washed with aqueous sodium carbonate solution, then brine. The extract was dried over magnesium sulphate, evaporated under reduced pressure, and the residue chromatographed on silica, using ethyl acetate-hexane (1:3 ) as eluant, to give a pale yellow oil (0.22 g). This contained approximately 30% of the title compound by $^1$H NMR, there being several contaminants.

Step 5: Preparation of 4-hydroxy-2-(3-trifluoromethyl) phenyl-3-isoxazolidinone.

Lithium bis(trimethylsilyl)amide (0.29 ml, 1M solution in tetrahydrofuran) was added slowly to a stirred solution of pure 2-(3-trifluoromethyl)phenyl-3-isoxazolidinone (0.06 g) in dry tetrahydrofuran (5 ml), maintaining the temperature below −75° C. The mixture was stirred for ten minutes at −78° C, allowed to warm to −25° C., recooled to −78° C., then treated with N(4-toluenesulphonyl)-3-phenyloxaziridine (0.08 g, prepared as described in J. Org. Chem., 1988, 53, 2087). It was stirred at −78° C. for a further one hour, allowed to warm to room temperature, poured on to saturated aqueous ammonium chloride solution and extracted with ethyl acetate. The extracts were washed with brine, dried over magnesium sulphate and evaporated under reduced pressure. The residue was chromatographed on silica, using hexane-ethyl acetate (3:1) then ethyl acetate as eluants, to give a pale yellow solid (0.05 g) comprising a mixture of the title compound and toluene p-sulphonamide. This material can be used directly for carbamoylation and the t-butylcarbamate readily separated from toluene p-sulphonamide. $^1$H NMR (CDCl$_3$): title compound signals only: δ 4.0(1H,broad s), 4.35(1H,t), 4.8(1H,t), 4.95(1H,t), 7.5(2H,m), 7.95(2H,m).

GC/MS: M+ 247.

PREPARATIVE EXAMPLE 15

Preparation of 3-(2-fluoro-5-trifluoromethyl)phenyl-5-hydroxy-4-thiazolidinone

Step 1 Preparation of 3-(2-fluoro-5-trifluoromethyl)phenyl-4-thiazolidinone

By a procedure similar to that described in Preparative Example 2, Step 1 above, but using 2-fluoro-5-trifluoromethylaniline (10.20 g), thioglycollic acid (5.80 g), 37% aqueous formaldehyde solution (4.8 ml) and toluene (100 ml), and Kugelrohr distillation of the crude product under reduced pressure, this compound was obtained as a colourless oil, which crystallised on standing, yield 2.80 g, mp 40°–43° C.

$^1$H nmr (CDCl$_3$): δ3.71 (2H, s), 4.74 (2H, s), 7.30 (1H, m), 7.58–7.70 (2H, m)

Step 2 Preparation of 5-chloro-3-(2-fluoro-5-trifluoromethyl)phenyl-4-thiazolidinone This compound was prepared by a procedure similar to that described in Preparative Example 2, Step 2 above, but using 3-(2-fluoro-5-trifluoromethyl)phenyl-4-thiazolidinone (prepared as in Step 1 above) (2.80 g), sulphuryl chloride (0.85 ml), and dichloromethane (25 ml). This product was used directly in Step 3.

Step 3 Preparation of 3-(2-fluoro-5-trifluoromethyl)phenyl-5-hydroxy-4-thiazolidinone By a procedure similar to that described in Preparative Example 2, Step 3 above, but using 5-chloro-3-(2-fluoro-5-trifluoromethyl)phenyl-4-thiazolidinone (prepared as in Step 2 above), tetrahydrofuran (30 ml) and saturated aqueous sodium bicarbonate (50 ml), and recrystallisation of the crude product from chloroform, the title compound was obtained as a white solid, yield 2.10 g, mp 145°–147° C.

$^1$H nmr (CDCl$_3$): δ4.69 (1H, d), 4.96 (1H, d), 5.64 (1H, d), 6.85 (1H, d), 7.28–7.38 (1H, m), 7.61 (1H, m), 7.75 (1H, m)

PREPARATIVE EXAMPLE 16

Preparation of 3-(3-chloro-4-methyl)phenyl-5-hydroxy-4-thiazolidinone

Step 1 Preparation of 3-(3-chloro-4-methyl)phenyl-4-thiazolidinone

By a procedure similar to that described in Preparative Example 2, Step 1 above, but using 3-chloro-4-methylphenylaniline (14.15 g), thioglycollic acid (9.20 g), 37% aqueous formaldehyde solution (7.8 ml) and toluene (120 ml), and trituration of the crude product with diethyl ether/hexane followed by recrystallisation from ethyl acetate/hexane, this compound was obtained as a crystalline solid, yield 10.50 g, mp 90°–91° C.

$^1$H nmr (CDCl$_3$): δ2.32 (3H, s), 3.71 (2H, s), 4.76 (2H, s), 7.25 (2H, s), 7.47 (1H, s)

Step 2 Preparation of 5-chloro-3-(3-chloro-4-methyl)phenyl-4-thiazolidinone

This compound was prepared by a procedure similar to that described in Preparative Example 2, Step 2 above, but using 3-(3-chloro-4-methyl)phenyl-4-thiazolidinone (prepared as in Step 1 above) (8.80 g), sulphuryl chloride (3.13 ml), and dichloromethane (50 ml). This product was used directly in Step 3.

Step 3 Preparation of 3-(3-chloro-4-methyl)phenyl-5-hydroxy-4-thiazolidinone

By a procedure similar to that described in Preparative Example 2, Step 3 above, but using 5-chloro-3-(3-chloro-4-methyl)phenyl-4-thiazolidinone (prepared as in Step 2 above), tetrahydrofuran (50 ml) and saturated aqueous sodium bicarbonate (50 ml), and recrystallisation of the crude product from ethyl acetate/hexane, the title compound was obtained as a white solid, yield 6.20 g, mp 91°–93° C.

$^1$H nmr (CDCl$_3$): δ2.33 (3H, s), 4.61 (1H, d), 4.97 (1H, d), 5.39 (1H, s), 5.73 (1H, s), 7.23 (2H, s), 7.46 (1H, s)

PREPARATIVE EXAMPLE 17

Preparation of 5-hydroxy-3-phenyl-4-thiazolidinone
Step 1 Preparation of 3-phenyl-4-thiazolidinone By a procedure similar to that described in Preparative Example 2, Step 1 above, but using aniline (4.65 g), thioglycollic acid (4.60 g), 37% aqueous formaldehyde solution (4.5 ml), toluene (100 ml) and p-toluenesulphonic acid (10 mg), and purification of the crude product by silica gel chromatography (eluting with chloroform) followed by recrystallisation from chloroform/hexane, this compound was obtained as colourless needles, yield 0.38 g.

$^1$H nmr (CDCl$_3$): δ3.73 (2H, m), 4.81 (2H, m), 7.25 (1H, m), 7.37–7.47 (4H, m)

Step 2 Preparation of 5-chloro-3-phenyl-4-thiazolidinone

This compound was prepared by a procedure similar to that described in Preparative Example 2, Step 2 above, but using 3-phenyl-4-thiazolidinone (prepared as in Step 1 above) (0.38 g), sulphuryl chloride (0.29 g), and dichloromethane (5 ml). This product was used directly in Step 3.

Step 3 Preparation of 5-hydroxy-3-phenyl-4-thiazolidinone

By a procedure similar to that described in Preparative Example 2, Step 3 above, but using 5-chloro-3-phenyl-4-thiazolidinone (prepared as in Step 2 above), tetrahydrofuran (10 ml) and saturated aqueous sodium bicarbonate (15 ml), the title compound was obtained as an oily solid, yield 0.24 g.

$^1$H nmr (CDCl$_3$): δ4.52 (1H, d), 4.89 (1H, d), 5.65 (1H, d), 5.76 (1H, broad s), 7.19 (1H, m), 7.25–7.34 (4H, m)

PREPARATIVE EXAMPLE 18

Preparation of 3-(4-fluoro-3-trifluoromethyl)phenyl-5-hydroxy-4-thiazolidinone
Step 1 Preparation of 3-(4-fluoro-3-trifluoromethyl)phenyl-4-thiazolidinone By a procedure similar to that described in Preparative Example 2, Step 1 above, but using 4-fluoro-3-trifluoromethylaniline (17.90 g), thioglycollic acid (9.20 g), 37% aqueous formaldehyde solution (7.7 ml) and toluene (110 ml), and trituration of the crude product with diethyl ether/hexane, this compound was obtained as a white solid, yield 16.00 g, mp 83°–85° C.

$^1$H nmr (CDCl$_3$): δ3.73 (2H, s), 4.80 (2H, s), 7.25 (1H, m), 7.64–7.72 (2H, m)

Step 2 Preparation of 5-chloro-3-(4-fluoro-3-trifluoromethyl)phenyl-4-thiazolidinone This compound was prepared by a procedure similar to that described in Preparative Example 2, Step 2 above, but using 3-(4-fluoro-3-trifluoromethyl)phenyl-4-thiazolidinone (prepared as in Step 1 above) (14.00 g), sulphuryl chloride (4.3 ml), and dichloromethane (100 ml). This product was used directly in Step 3.

$^1$H nmr (CDCl$_3$): δ4.68 (1H, d), 5.21 (1H, d), 5.77 (1H, s), 7.29 (1H, m), 7.69–7.78 (2H, m)

Step 3 Preparation of 3-(4-fluoro-3-trifluoromethyl)phenyl-5-hydroxy-4-thiazolidinone By a procedure similar to that described in Preparative Example 2, Step 3 above, but using 5-chloro-3-(4-fluoro-3-trifluoromethyl)phenyl-4-thiazolidinone (prepared as in Step 2 above), tetrahydrofuran (50 ml) and saturated aqueous sodium bicarbonate (50 ml), and recrystallisation of the crude product from chloroform, the title compound was obtained as a white solid, yield 12.00 g, mp 118°–121° C.

$^1$H nmr (CDCl$_3$): δ4.40 (1H, d), 4.69 (1H, d), 4.99 (1H, d), 5.75 (1H, d), 7.28 (1H, m), 7.67–7.77 (2H, m)

PREPARATIVE EXAMPLE 19

Preparation of 3-(3-pentafluorosulphanyl)phenyl-5-hydroxy-4-thiazolidinone
Step 1 Preparation of 3-Pentafluorosulphanylaniline Reduced iron powder (8.60 g) was added to a stirred solution of 3-pentafluorosulphanylnitrobenzene (2.65 g) in a mixture of isopropanol (27 ml), water (6 ml) and concentrated hydrochloric acid (0.3 ml). The resulting mixture was heated under reflux for 1 hour, and was then allowed to cool slightly before being filtered through Hyflo. The Hyflo was washed with more isopropanol, and the combined filtrates were evaporated under reduced pressure. The residue was dissolved in a little diethyl ether and the solution was treated with solid sodium hydrogen carbonate, then dried over magnesium sulphate. After filtration to remove the inorganics the solution was evaporated under reduced pressure, and the oily residue was distilled in a Kugelrohr apparatus. The title compound was collected as a colourless oil, bp 110° C. (oven temperature) at 12 mmHg, which crystallised on standing, yield 1.90 g, mp 32°–35° C.

Step 2 Preparation of 3-(3-pentafluorosulphanyl)phenyl-4-thiazolidinone

By a procedure similar to that described in Preparative Example 2, Step 1 above, but using pentafluorosulphanylaniline (prepared as in Step 1 above) (1.90 g), thioglycollic acid (0.80 g), 37% aqueous formaldehyde solution (0.7 ml), toluene (20 ml) and p-toluenesulphonic acid (2 mg), and purification of the crude product by silica gel chromatography eluting with ethyl acetate/hexane, this compound was obtained as a white solid, yield 1.45 g, mp 48°–50° C.

$^1$H nmr (CDCl$_3$): δ3.75 (2H, s), 4.84 (2H, s), 7.52 (1H, m), 7.60–7.69 (2H, m), 7.89 (1H, m)

Step 3 Preparation of 5-chloro-3-(3-pentafluorosulphanyl)phenyl-4-thiazolidinone This compound was prepared by a procedure similar to that described in Preparative Example 2, Step 2 above, but using 3-(3-pentafluorosulphanyl)phenyl-4-thiazolidinone (prepared as in Step 2 above) (1.14 g), sulphuryl chloride (0.3 ml), and dichloromethane (10 ml). This product was used directly in Step 4.

Step 4 Preparation of 3-(3-pentafluorosulphanyl)phenyl-5-hydroxy-4-thiazolidinone By a procedure similar to that described in Preparative Example 2, Step 3 above, but using 5-chloro-3-(3- pentafluorosulphanyl)phenyl-4-thiazolidinone (prepared as in Step 3 above), tetrahydrofuran (20 ml) and saturated aqueous sodium bicarbonate (20 ml), and purification of the crude product by silica gel chromatography eluting with ethyl acetate/hexane followed by recrystallisation from carbon tetrachloride/hexane, the title compound was obtained as a white solid, yield 1.19 g, mp 122°–124° C.

$^1$H nmr (CDCl$_3$): δ4.70 (1H, d), 4.92 (1H, s), 5.03 (1H, d), 5,73 (1H, s), 7.51 (1H, m), 7.57–7.68 (2H, m), 7.89 (1H, m)

PREPARATIVE EXAMPLE 20

Preparation of 3-(2-fluoro-3-trifluoromethyl)phenyl-5-hydroxy-4-thiazolidinone

Step 1 Preparation of 3-(2-fluoro-3-trifluoromethyl)phenyl-4-thiazolidinone

By a procedure similar to that described in Preparative Example 2, Step 1 above, but using 2-fluoro-3-trifluoromethylaniline (10.00 g), thioglycollic acid (5.14 g), 37% aqueous formaldehyde solution (4.30 ml), toluene (110 ml) and p-toluenesulphonic acid, and Kugelrohr distillation of the crude product under reduced pressure, the title compound was obtained as a clear solid, yield 10.60 g.

$^1$H nmr (CDCl$_3$): δ3.72 (2H, s), 4.77 (2H, s), 7.32 (1H, m), 7.55–7.63 (2H, m)

Step 2 Preparation of 5-chloro-3-(2-fluoro-3-trifluoromethyl)phenyl-4-thiazolidinone This compound was prepared by a procedure similar to that described in Preparative Example 2, Step 2 above, but using 3-(2-fluoro-3-trifluoromethyl)phenyl-4-thiazolidinone (prepared as in Step 1 above) (9.00 g), sulphuryl chloride (4.59 g), and dichloromethane (120 ml). This product was used directly in Step 3.

Step 3 Preparation of 3-(2-fluoro-3-trifluoromethyl)phenyl-5-hydroxy-4-thiazolidinone By a procedure similar to that described in Preparative Example 2, Step 3 above, but using 5-chloro-3-(2-fluoro-3-trifluoromethyl)phenyl-4-thiazolidinone (prepared as in Step 2 above), tetrahydrofuran (10 ml) and saturated aqueous sodium bicarbonate (50 ml), and recrystallisation of the crude product from ethyl acetate/hexane, the title compound was obtained as a white solid, yield 4.40 g.

$^1$H nmr (CDCl$_3$): δ4.58 (1H, d), 5.00 (1H, d), 5.63 (1H, d), 6.86 (1H, d), 7.32 (1H, m), 7.57–7.70 (2H, m)

PREPARATIVE EXAMPLE 21

Preparation of 5-hydroxy-2-phenyl-3-(3-trifluoromethyl)phenyl-4-thiazolidinone

Step 1 Preparation of 2-phenyl-3-(3-trifluoromethyl)phenyl-4-thiazolidinone

A stirred solution of benzaldehyde (5.0 ml) and 3-trifluoromethylaniline (6.14 ml) in toluene (100 ml) was heated under reflux, and water was collected in a Dean and Stark apparatus. After 1 hour, thioglycollic acid (4.53 g) was added, and heating was continued for a further 1 hour. GC analysis indicated that the reaction had only proceeded to ca 50% completion. Small amounts of thioglycollic acid were added to the reaction mixture in portions, and heating was continued until gc analysis indicated 99% reaction. The solution was cooled, and evaporated under reduced pressure. The oily residue was dissolved in diethyl ether, washed thoroughly with saturated aqueous sodium bicarbonate solution, brine, then dried (MgSO$_4$). Evaporation of the solvent under reduced pressure left a yellow oil, which was purified by silica gel chromatography, eluting with ethyl acetate/hexane, to give a colourless oil which slowly crystallised on standing. Trituration with hexane afforded the product as a white, crystalline solid, yield 6.90 g, mp 53°–55° C.

$^1$H nmr (CDCl$_3$): δ3.86 (1H, d), 3.98 (1H, d), 6.10 (1H, s), 7.20–7.31 (5H, m), 7.32–7.40 (3H, m), 7.48 (1H, m)

Step 2 Preparation of 5-hydroxy-2-phenyl-3-(3-trifluoromethyl)phenyl-4-thiazolidinone By a procedure similar to that described in Preparative Example 1, Step 2, but using 2-phenyl-3-(3-trifluoromethyl)phenyl-4-thiazolidinone (prepared as in Step 1 above) (3.50 g), sulphuryl chloride (0.88 ml), dichloromethane (25 ml), then tetrahydrofuran (50 ml) and saturated aqueous sodium bicarbonate solution (50 ml), and purification by silica gel chromatography, eluting with ethyl acetate/hexane, the crude product was obtained as a mixture of diastereoisomers, yield 0.036 g.

$^1$H nmr (CDCl$_3$): inter alia δ5.91 (1H, s), 5.95 (1H, s), 6.01 (1H, s), 6.32 (1H, s)

PREPARATIVE EXAMPLE 22

Preparation of 3-(4-chloro-3-trifluoromethyl)phenyl-5-hydroxy-4-thiazolidinone

Step 1 Preparation of 3-(4-chloro-3-trifluoromethyl)phenyl-4-thiazolidinone

By a procedure similar to that described in Preparative Example 2, Step 1 above, but using 4-chloro-3-trifluoromethylaniline (19.60 g), thioglycollic acid (9.20 g), 37% aqueous formaldehyde solution (7.80 ml) and toluene (100 ml), and recrystallisation of the crude product from ethyl acetate/hexane, the title compound was obtained as a solid, yield 14.80 g, mp 94°–95° C.

$^1$H nmr (CDCl$_3$): δ3.72 (2H, s), 4.80 (2H, s), 7.51 (1H, d), 7.65 (1H, dd), 7.80 (1H, d)

Step 2 Preparation of 5-chloro-3-(4-chloro-3-trifluoromethyl)phenyl-4-thiazolidinone This compound was prepared by a procedure similar to that described in Preparative Example 2, Step 2 above, but using 3-(4-chloro-3-trifluoromethyl)phenyl-4-thiazolidinone (prepared as in Step 1 above) (12.00 g), sulphuryl chloride (3.50 ml), and dichloromethane (50 ml). This product was used directly in Step 3.

Step 3 Preparation of 3-(4-chloro-3-trifluoromethyl)phenyl-5-hydroxy-4-thiazolidinone By a procedure similar to that described in Preparative Example 2, Step 3 above, but using 5-chloro-3-(4-chloro-3-trifluoromethyl)phenyl-4-thiazolidinone (prepared as in Step 2 above), tetrahydrofuran (250 ml) and saturated aqueous sodium bicarbonate (50 ml), and recrystallisation of the crude product from ethyl acetate/hexane, the title compound was obtained as a solid, yield 8.10 g, mp 148°–151° C.

$^1$H nmr (CDCl$_3$): δ4.63 (1H, d), 5.08 (1H, d), 5.64 (1H, d), 6.62 (1H, d), 7.52 (1H, d), 7.69 (1H, dd), 7.90 (1H, d)

PREPARATIVE EXAMPLE 23

Preparation of 5-hydroxy-5-methyl-3-(3-trifluoromethyl)phenyl-4-thiazolidinone

Step 1 Preparation of 5-methyl-3-(3-trifluoromethyl)phenyl-4-thiazolidinone

By a procedure similar to that described in Preparative Example 2, Step 1 above, but using 3-trifluoromethylaniline (16.10 g), thiolactic acid (10.60 g), 37% aqueous formaldehyde solution (7.50 ml), toluene (150 ml) and p-toluenesulphonic acid (20 mg), and Kugelrohr distillation of the crude product under reduced pressure, the title compound was obtained as a pale yellow oil, yield 20.10 g.

$^1$H nmr (CDCl$_3$): δ1.63 (3H, d), 3.98 (1H, q), 4.70 (1H, d), 4.86 (1H, d), 7.45–7.58 (2H, d), 7.68–7.79 (2H, d)

Step 2 Preparation of 5-hydroxy-5-methyl-3-(3-trifluoromethyl)phenyl-4-thiazolidinone A stirred solution of 5-methyl-3-(3-trifluoromethyl) phenyl-4-thiazolidinone (prepared as in Step 1 above) (2.61 g) in dichloromethane (65 ml) was cooled in an ice bath. A stream of nitrogen was bubbled through the solution, and a solution of sulphuryl chloride (0.89 ml) was added dropwise. After the addition the solution was stirred for a further 1.5 hours whilst maintaining the nitrogen flow. Water (10 ml) was then added, and the mixture was stirred vigorously for 10 minutes. The organic phase was then separated, washed with brine, dried (MgSO$_4$) and evaporated under reduced pressure to leave a yellow oil (3.33 g). Purification of 1.63 g of this oil by silica gel chromatography, eluting with chloroform/methanol mixtures, afforded the title compound as a pale yellow oil, which crystallised on standing, yield 1.18 g, mp 98°–101° C.

$^1$H nmr (CDCl$_3$): δ1.85 (3H, s), 4.10 (1H, broad s), 4.61 (1H, d), 4.95 (1H, d), 7.45–7.55 (2H, m), 7.65–7.79 (2H, m)

PREPARATIVE EXAMPLE 24

Preparation of 5-hydroxy-3-(2-methoxy)phenyl-4-thiazolidinone

Step 1 Preparation of S-(2-methoxyphenylamino)methyl thioglycollic acid

A stirred solution of ortho-anisidine (18.00 g) and thioglycollic acid (13.40 g) in ethanol (50 ml) was treated with 37% aqueous formaldehyde solution (11.4 ml), and the resulting solution was then stirred for a further 5 hours. Water was added, and the mixture was extracted with dichloromethane. The dichloromethane extracts were washed with 2M hydrochloric acid (2×50 ml) and water, dried (MgSO$_4$), and evaporated under reduced pressure to leave a colourless oil (13.70 g). This oil contained the crude product, and was used directly in the next Step.

Step 2 Preparation of 3-(2-methoxy)phenyl-4-thiazolidinone

A stirred solution of triethylamine (8.40 ml) in dichloromethane (50 ml) was cooled to 5° C., and treated dropwise with thionyl chloride (4.40 ml), followed by a solution of crude S-(2-methoxyphenylamino)methyl thioglycollic acid (prepared as in Step 1 above) (13.70 g) in dichloromethane (50 ml). The mixture was stirred for a further 2 hours, and was then left to stand for 18 hours. A further quantity of triethylamine (8.40 ml) was added, and the mixture was stirred for 5 hours. Water was added, and the mixture was filtered through hyflo. The filtrate was collected, and the organic layer was separated, washed with brine and dried (MgSO$_4$). The solution was evaporated under reduced pressure to leave a brown gum, which was purified by silica gel chromatography, eluting with ethyl acetate/hexane mixtures, to afford the product as a gum, yield 0.73 g.

$^1$H nmr (CDCl$_3$): δ3.72 (2H, s), 3.85 (3H, s), 4.67 (2H, s), 6.94–7.02 (2H, m), 7.24 (1H, m), 7.33 (1H, m)

Step 3 Preparation of 5-hydroxy-3-(2-methoxy)phenyl-4-thiazolidinone

A stirred solution of 3-(2-methoxy)phenyl-4-thiazolidinone (prepared as in Step 2 above) (0.73 g) in dichloromethane (20 ml) was cooled in an ice bath under a nitrogen atmosphere, and sulphuryl chloride (0.28 ml) was added dropwise. After the addition the solution was allowed to slowly warm to room temperature. The solution was evaporated under reduced pressure to leave a red oil, which was dissolved in tetrahydrofuran (10 ml), and treated with aqueous sodium bicarbonate solution (20 ml). This mixture was stirred vigorously for 30 minutes, and was then extracted with dichloromethane (2×50 ml). The combined organic extracts were washed with brine, dried (MgSO$_4$) and evaporated under reduced pressure to leave a solid residue. Silica gel chromatography, eluting with hexane/ethyl acetate mixtures, afforded the title compound as a white, crystalline solid, yield 0.29 g.

$^1$H nmr (CDCl$_3$): δ3.82 (3H, s), 4.18 (1H, broad d), 4.60 (1H, d), 4.80 (1H, dd), 5.73 (1H, d), 6.94–7.04 (2H, m), 7.25 (1H, m), 7.34 (1H, m)

PREPARATIVE EXAMPLE 25

Preparation of 5-hydroxy-3-(3-nitro)phenyl-4-thiazolidinone.

Step 1 Preparation of 3-(3-nitro)phenyl-4-thiazolidinone.

A stirred mixture of 3-nitroaniline (6.575 g) in toluene (100 ml) was treated with thioglycollic acid (3.48 ml) under an atmosphere of nitrogen. After 15 minutes, the suspension was treated, dropwise, with 37% aqueous formaldehyde (4.05 ml) resulting in a slight exotherm (the initial temperature rose to 30° C.). The reaction mixture was then heated to reflux, and water was collected in a Dean and Stark apparatus. After 3 hours the mixture was cooled and allowed to stand at room temperature overnight, during which time a few crystals and a dark oil separated from the reaction mixture. The toluene was decanted and the residue dissolved in ethyl acetate. The combined organics were washed with saturated sodium bicarbonate solution (×2), and brine. The organic layer was dried (Na$_2$SO$_4$) and the solvent removed under reduced pressure to give an orange/brown solid (3.781 g). This was recrystallised using toluene to give orange/brown crystals, yield 1.921 g, mp 142° C.

$^1$H nmr (CDCl$_3$): δ3.77 (2H, s), 4.90 (2H, s), 7.60 (1H, t), 7.95 (1H, dd), 8.10 (1H, dd), 8.31 (1H, t)

Step 2 Preparation of 5-chloro-3-(3-nitro)phenyl-4-thiazolidinone.

A stirred solution of 3-(3-nitro)phenyl-4-thiazolidinone (prepared as described in Step 1 above) (2.626 g) in dichloromethane (50 ml) was cooled in an ice bath and then treated with sulphuryl chloride (1.74 g). The reaction mixture went brown in colour, and after 15 minutes t.l.c. revealed no starting material. The reaction mixture was concentrated under reduced pressure and the product used directly in Step 3.

Step 3 Preparation of 5-hydroxyl-3-(3-nitrophenyl)-4-thiazolidinone.

5-Chloro-3-(3-nitro)phenyl-4-thiazolidinone (prepared as described in Step 2 above) was suspended in a (1:1) mixture of tetrahydrofuran and saturated aqueous sodium bicarbonate solution (60 ml) and stirred vigorously at room temperature overnight. The bulk of the tetrahydrofuran was removed under reduced pressure and ethyl acetate and water added. The organic layer was separated and the aqueous layer extracted with ethyl acetate (×2). The combined organics were dried (Na$_2$SO$_4$) and the solvent removed under reduced pressure to give an orange solid (2.265 g). This was purified on silica gel using ethyl acetate-hexane (45–55% ethyl acetate) as eluant to give the title compound as a solid, yield 1.837 g, mp 129°–131° C.

$^1$H nmr (CDCl$_3$/d$_6$ DMSO): δ 4.72 (1H, d), 5.15 (1H, d), 5.65 (1H, d), 6.89 (1H, d), 7.61 (1H, t), 7.96 (1H, dd), 8.10 (1H, dd), 8.45 (1H, t)

PREPARATIVE EXAMPLE 26

Preparation of 5-hydroxy-3-(3-cyano)phenyl-4-thiazolidinone.

Step 1 Preparation of 3-(3-cyano)phenyl-4-thiazolidinone.

3-Aminobenzonitrile (recrystallised from ethyl acetate-hexane) (4.6 g), ethanol (15 ml) and thioglycollic acid (2.71 ml) were stirred together at room temperature for 30 minutes. 37% aqueous formaldehyde solution (3.16 ml) was then added causing a mild exotherm. A solid precipitate formed and stirring was continued overnight. Water was then added forming an emulsion amd this was extracted with ethyl acetate (×3). The combined extracts were dried (MgSO$_4$) and evaporated under reduced pressure to give a residue (9 g) which was taken up in dichloromethane (150 ml). To this solution was added thionyl chloride (2.85 ml) and after 45 minutes triethylamine (5.43 ml) with cooling in an ice bath. Fuming occured and after 1 hour the reaction mixture was poured onto ice and the product extracted with dichloromethane. The organic layer was washed with brine, dried (MgSO$_4$), and evaporated under reduced pressure to give a dark oil (6.4 g), which was chromatographed on silica using ethyl acetate/hexane mixtures. The title compound was obtained as a yellow solid, yield 2.3 g, and had:

$^1$H nmr (CDCl$_3$): δ3.75 (2H, s), 4.84 (2H, s), 7.51 (2H, m), 7.75 (1H, m), 7.84 (1H, s)

MS: m/e 204 (M$^+$)

Step 2 Preparation of 5-chloro-3-(3-cyano)phenyl-4-thiazolidinone 3-(3-cyano)phenyl-4-thiazolidinone (prepared as described in Step 1 above) (1.935 g) was converted to the title compound by a procedure similar to that described in Preparative Example 25, Step 2 using dichmoromethane (21 ml) and sulphuryl chloride (0.762 ml). The title compound was used immediately in Step 3.

$^1$H nmr (CDCl$_3$): δ4.71 (1H, d), 5.23 (1H, d), 5.78 (1H, s), 7.59 (2H, m), 7.82 (1H, m), 7.89 (1H, s)

Step 3 Preparation of 5-hydroxy-3-(3-cyano)phenyl-4-thiazolidinone

5-Chloro-3-(3-cyano)phenyl-4-thiazolidinone (prepared as described in Step 2) was converted to the title compound by a procedure similar to that described in Preparative Example 25, Step 3 using a mixture of tetrahydrofuran (6 ml) and saturated sodium bicarbonate solution (10 ml). The crude product (1.73 g) was purified on silica gel using ethyl acetate-hexane (2:3) as eluant. The title compound (1.627 g) had:

$^1$H nmr (CDCl$_3$/d$_6$ DMSO): δ4.67 (1H, d), 5.12 (1H, d), 5.62 (1H, d), 6.88 (1H, d), 7.54 (2H, m), 7.80 (1H, m), 7.97 (1H, broad s)

MS: m/e 220 (M$^+$)

PREPARATIVE EXAMPLE 27

Preparation of 5-hydroxy-3-(3-fluoro)phenyl-4-thiazolidinone

Step 1 Preparation of 3-(3-Fluoro)phenyl-4-thiazolidinone.

3-Fluoroaniline (9.344 g) was converted to the title compound using toluene (180 ml), thioglycollic acid (5.85 ml) and 37% aqueous formaldehyde solution (6.83 ml) by a procedure similar to that described in Preparative Example 25, Step 1. The clear toluene layer was decanted from the precipitated dark oil and was washed with saturated sodium bicarbonate solution. The organic layer was dried (MgSO$_4$) and evaporated to give the crude product 3.5 g. This material was purified by silica gel chromatography using ethyl acetate-hexane (1:3) as eluant yielding a solid which was recrystallised from hot hexane (containing a few drops of chloroform) to give the title compound as a white solid, yield 0.880 g.

$^1$H nmr (CDCl$_3$): δ3.74 (2H, s), 4.83 (2H, s), 6.94 (1H, td), 7.19–7.42 (3H, m)

Step 2 Preparation of 5-chloro-3-(3-fluoro)phenyl-4-thiazolidinone.

3-(3-Fluoro)phenyl-4-thiazolidinone (prepared as described in Step 1 above (0.88 g) was converted to the title compound by a procedure similar to that described in Preparative Example 25, Step 2 using dichloromethane (10 ml) and sulphuryl chloride (0.36 ml). The title compound was used immediately in Step 3.

$^1$H nmr (CDCl$_3$): δ4.70 (1H, d), 5.22 (1H, d), 5.77 (1H, s), 7.03 (1H, m), 7.25–7.50 (3H, m)

Step 3 Preparation of 5-hydroxy-3-(3-fluoro)phenyl-4-thiazolidinone

5-Chloro-3-(3-fluoro)phenyl-4-thiazolidinone (prepared as described in Step 2 above) was converted to the title compound by a procedure similar to that described in Preparative Example 25, Step 3 using a mixture of tetrahydrofuran (5 ml) and saturated sodium bicarbonate solution (10 ml). The crude product (0.75 g) was purified on silica gel using ethyl acetate-hexane as eluant (35:65 to 40:60). The title compound (0.42 g) had:

$^1$H nmr (CDCl$_3$/d$_6$ DMSO): δ4.65 (1 H, d), 5.09 (1H, d), 5.62 (1H, d), 6.80 (1H, d), 6.95 (1H, td), 7.23–7.48 (3H, m)

PREPARATIVE EXAMPLE 28

Preparation of 5-hydroxy-3-(3-(1,1,2,2-tetrafluoroethoxy))phenyl-4-thiazolidinone.

Step 1 Preparation of 3-(3-(1,1,2,2-tetrafluoroethoxy))phenyl-4-thiazolidinone 3-(1,1,2,2-tetrafluoroethoxy)aniline (12.095 g) was converted to the title compound using toluene (140 ml), thioglycollic acid (4.03 ml) and 37% aqueous formaldehyde solution (4.7 ml) by a procedure similar to that described in Preparative Example 25, Step 1. The crude product was purified by silica gel chromatography using ethyl acetate-hexane (5:95 to 15:85) as eluant to give the pure title compound, yield 3.45 g, which had:

$^1$H nmr (CDCl$_3$): δ3.74 (2H, s), 4.84 (2H, s), 5.91 (1H, tt), 7.11 (1H, m), 7.41 (3H, m)

MS: m/e 295 (M$^+$)

Step 2 Preparation of 5-chloro-3-(3-(1,1,2,2-tetrafluoroethoxy)pheny))-4-thiazolidinone 3-(3-(1,1,2,2-tetrafluoroethoxy))phenyl-4-thiazolidinone (prepared as described in Step 1 above) (3.45 g) was converted to the title compound by a procedure similar to that described in Preparative Example 25, Step 2 using dichloromethane (26 ml) and sulphuryl chloride (0.94 ml). The title compound was used immediately in Step 3.

$^1$H nmr (CDCl$_3$): δ4.71 (1H, d), 5.23 (1H, d), 5.77 (1H, s), 5.92 (1H, tt), 7.07 (1H, m), 7.46 (3H, m)

Step 3 Preparation of 5-hydroxy-3-(3-(1,1,2,2-tetrafluoroethoxy))phenyl-4-thiazolidinone 5-Chloro-3-(3-(1,1,2,2-tetrafluoroethoxy))phenyl-4-thiazolidinone (prepared as described in Step 2 above) was converted to the title compound by a procedure similar to that described in Preparative Example 25, Step 3 using a mixture of tetrahydrofuran (7 ml) and saturated sodium bicarbonate solution (10 ml). The crude product (4 g) was chromatographed on silica gel using ethyl acetate-hexane (35:65) as eluant. The title compound was obtained as a golden oil, yield 2.942.

$^1$H nmr (CDCl$_3$): δ4.20 (1H, broad s), 4.71 (1H, d), 5.02 (1H, dd), 5.72 (1H, s), 5.92 (1H, tt), 7.14 (1H, m), 7.44 (3H, m)

MS: m/e 311 (M$^+$)

PREPARATIVE EXAMPLE 29

Preparation of 5-hydroxy-3-(3-methyl)phenyl-4-thiazolidinone

Step 1 Preparation of 2-mercapto-N-(3-methylphenyl)acetamide

Freshly distilled meta-toluidine (10.168 g) was dissolved in toluene (50 ml) and treated with thioglycollic acid (7 ml).

The mixture was heated under reflux, and water collected in a Dean and Stark apparatus overnight. The reaction mixture was then cooled and poured into hexane (50 ml). The product separated as an oil and the solvents were removed under reduced pressure to give a white solid (17.975 g). Attempts at recrystallisation resulted in failure and the residue was chromatographed on silica gel. The product (14.84 g), still contaminated with meta toluidine, was taken up in ethyl acetate and washed with 2M hydrochloric acid. The title compound was then isolated in the usual manner as a white solid, yield 13.13 g, mp 58°–60° C.

$^1$H nmr (CDCl$_3$): δ2.00 (1H, t, exchanges with D$_2$O), 2.35 (3H, s), 3.40 (2H, d), 6.95 (1H, d), 7.20–7.30 (2H, m), 7.35 (1H, d), 7.40 (1H, s), 8.4–8.55 (1H, broad s, exchanges with D$_2$O)

Step 2 Preparation of 3-(3-methyl)phenyl-4-thiazolidinone

2-Mercapto-N-(3-methylphenyl)acetamide (prepared as described in Step 1) (2.0455 g) was dissolved (with warming) in toluene (25 ml) and the solution treated with p-toluenesulphonic acid (0.215 g) and paraformaldehyde (0.339 g). An exotherm took place and a thick white suspension resulted. The reaction mixture was then heated to reflux, and water was collected in a Dean and Stark apparatus. An orange oil was deposited and after 3 hours at reflux the reaction mixture was allowed to cool to room temperature. The toluene was decanted from the deposited reddish oil and evaporated to give an orange oil (0.707 g). This was chromatographed on silica gel using ethyl acetate-hexane (35:65) to give the title compound as an oil, yield 0.388 g.

$^1$H nmr (CDCl$_3$): δ2.38 (3H, s), 3.75 (2H, s), 4.81 (2H, s), 7.08 (1H, d), 7.15–7.35 (3H, m)

MS: m/e 193 (M$^+$)

Step 3 Preparation of 5-chloro-3-(3-methyl)phenyl-4-thiazolidinone 3-(3-Methyl)phenyl-4-thiazolidinone (prepared as described in Step 2) (0.369 g) was converted to the title compound by a procedure similar to that described in Preparative Example 25, Step 2 using dichloromethane (5 ml) and sulphuryl chloride (0.169 ml). The title compound was used immediately in Step 4.

$^1$H nmr (CDCl$_3$): δ2.41 (3H, s), 4.67 (1H, d), 5.19 (1H, d), 5.77 (1H, s), 7.11 (1H, d), 7.20–7.40 (3H, m)

Step 4 Preparation of 5-hydroxy-3-(3-methyl)phenyl-4-thiazolidinone

5-Chloro-3-(3-methyl)phenyl-4-thiazolidinone (prepared as described in Step 3) was converted to the title compound by a procedure similar to that described in Preparative Example 25, Step 3 using a (1:1) mixture of tetrahydrofuran and saturated sodium bicarbonate solution (15 ml). The title compound was obtained as an orange oil, yield 0.309 g.

$^1$H nmr (CDCl$_3$): δ2.35 (3H, s), 4.45–4.60 (1H, broad s), 4.67 (1H, d), 4.95 (1H, d), 5.74 (1H, s), 7.10 (1H, d), 7.20–7.40 (3H, m)

PREPARTIVE EXAMPLE 30

Preparation of 5-hydroxy-3-(3-methoxy)phenyl-4-thiazolidinone

Step 1 Preparation of 2-mercapto-N-(3-methoxyphenyl)acetamide

Freshly distilled 3-methoxyaniline (7.6615 g) was dissolved in toluene (35 ml) and treated with thioglycollic acid (4.75 ml). The mixture was heated under reflux, and water collected in an Dean and Stark apparatus overnight. Upon cooling to room temperature crystals formed which were collected at the pump. The title compound (which was sufficiently pure for the next reaction) was obtained as a white solid, yield 9.233 g.

$^1$H nmr (CDCl$_3$): δ2.03 (1H, t), 3.38 (2H, d), 3.80 (3H, s), 6.70 (1H, dd), 7.00 (1H, d), 7.20–7.34 (2H, m), 8.4–8.65 (1H, broad s)

MS: m/e 197 (M$^+$)

Step 2 Preparation of 3-(3-methoxy)phenyl-4-thiazolidinone

Dry acetone (250 ml) was cannulated into a 3-necked flask fitted with a condenser, a dropping funnel and a septum inlet. The dropping funnel was charged with a solution of 2-mercapto-N-(3-methoxyphenyl)acetamide (prepared as described in Step 1 above) (2.36 g) and diiodomethane (2 ml) in acetone (100 ml). Freshly ground potassium hydroxide (4.0 g) was rapidly added to the acetone in the 3-necked flask and the stirred suspension was then plunged into an oil bath pre-heated to 60° C. When the solvent began to reflux the contents of the dropping funnel were introduced over 30 minutes. After the addition was complete the reaction mixture was allowed to cool to room temperature and was filtered through a bed of 'Celite'. The solution was then mixed with chloroform and water and the organic layer separated. The water layer was extracted with a further portion of chloroform and the combined organic layers were washed with brine and then dried (Na$_2$SO$_4$). The solvent was removed under reduced pressure to give a brown oil (5.36 g), which was chromatographed on silica gel using ethyl acetate-hexane mixtures (3:7 to 10:0) as eluant to give the title compound, yield 0.659 g.

$^1$H nmr (CDCl$_3$): δ3.74 (2H, s), 3.82 (3H, s), 4.81 (2H, s), 6.80 (1H, dd), 6.98 (1H, dd), 7.08 (1H, t), 7.31 (1H, t)

MS: m/e 209 (M$^+$)

Step 3 Preparation of 5-chloro-3-(3-methoxy)phenyl-4-thiazolidinone 3-(3-Methoxy)phenyl-4-thiazolidinone (prepared as described in Step 2 above) (0.629 g) was converted to the title compound by a procedure similar to that described in Preparative Example 25, Step 2 using dichloromethane (10 ml) and sulphuryl chloride (0.266 ml). The title compound was used immediately in Step 4.

Step 4 Preparation of 5-hydroxy 3-(3-methoxy)phenyl-4-thiazolidinone

5-Chloro-3-(3-methoxy)phenyl-4-thiazolidinone (prepared as described in Step 3 above) was converted to the title compound by a procedure similar to that described in Preparative Example 25, Step 3 using a (1:1) mixture of tetrahydrofuran and saturated sodium bicarbonate solution (20 ml). The title compound (0.36 g) had:

$^1$H nmr (CDCl$_3$): δ3.81 (3H, s), 4.67 (1H, d), 4.75–4.95 (1H, broad s), 4.99 (1H, d), 5.75 (1H, s), 6.83 (1H, dd), 7.00 (1H, dd), 7.09 (1H, t), 7.35 (1H, m)

MS: m/e 225 (M$^+$)

PREPARATIVE EXAMPLE 31

Preparation of 5-hydroxy-3-(3-methoxycarbonyl)phenyl-4-thiazolidinone

Step 1 Preparation of 3-(3-methoxycarbonyl)phenyl-4-thiazolidinone

3-Methoxycarbonyl aniline (5 g) was converted to the title compound using toluene (125 ml), thioglycollic acid (2.3 ml) and 37% aqueous formaldehyde solution (2.68 ml) by a procedure similar to that described in Preparative Example 25, Step 1. The crude product (3.95 g) was recrystallised from ethyl acetate-hexane to give the title compound as a white solid, yield 3.322 g, mp 118°–119.5° C.

$^1$H nmr (CDCl$_3$): δ3.76 (2H, s), 3.94 (3H, s), 4.87 (2H, s), 7.50 (1H, t), 7.80 (1H, dd), 7.93 (1H, d), 8.02 (1H, broad s)

Step 2 Preparation of 5-chloro-3-(3-methoxycarbonyl)phenyl-4-thiazolidinone 3-(3-Methoxycarbonyl)phenyl-4-thiazolidinone (prepared as described in Step 1 above) (3.08 g) was converted to the title compound by a procedure similar to that described in Preparative Example 25, Step 2 using dichloromethane (25 ml) and sulphuryl chloride (1.04 ml). The title compound was used immediately in Step 3.

$^1$H nmr (CDCl$_3$): δ3.94 (3H, s), 4.74 (1H, d), 5.25 (1H, d), 5.79 (1H, d), 7.53 (1H, t), 7.85 (1H, dd), 7.97 (1H, d), 8.08 (1H, m)

Step 3 Preparation of 5-hydroxy-3-(3-methoxycarbonyl) phenyl-4-thiazolidinone

5-Chloro-3-(3-methoxycarbonyl)phenyl-4-thiazolidinone (prepared as described in Step 2 above) was converted to the title compound by a procedure similar to that described in Preparative Example 25, Step 3 using a mixture of tetrahydrofuran (20 ml) and saturated sodium bicarbonate solution (15 ml). The crude product (2.95 g of a red brown oil) was purified on silica gel using ethyl acetate-hexane (1:1 then 6:4) as eluant. The title compound was obtained as a sticky orange solid, yield 2.34 g.

$^1$H nmr (CDCl$_3$): δ3.92 (3H, s), 4.05 (1H, broad s), 4.75 (1H, d), 5.03 (1H, d), 5.75 (1H, s), 7.51 (1H, t), 7.82 (1H, dd), 7.96 (1H, d), 8.06 (1H, broad s)

PREPARATIVE EXAMPLE 32

Preparation of 5-hydroxy-3-(3-bromo)phenyl-4-thiazolidinone

Step 1 Preparation of 3-(3-bromo)phenyl-4-thiazolidinone

3-Bromoaniline (13.315 g) was converted to the title compound using toluene (170 ml), thioglycollic acid (5.4 ml) and 37% aqueous formaldehyde solution (6.24 ml) by a procedure similar to that described in Preparative Example 25, Step 1. The toluene layer was decanted from the precipitated orange oil and washed with saturated sodium bicarbonate solution. The organic layer was dried (MgSO$_4$) and evaporated to give an oil (7.92 g) which was chromatographed on silica gel using ethyl acetate-hexane (15:85) as eluant. The title compound (3.81 g) had:

$^1$H nmr (CDCl$_3$): δ3.73 (2H, s), 4.80 (2H, s), 7.24–7.45 (3H, m), 7.65 (1H, m)

MS: m/e 257 (M$^+$; Br=79)

Step 2 Preparation of 5-chloro-3-(3-bromo)phenyl-4-thiazolidinone 3-(3-Bromo)phenyl-4-thiazolidinone (prepared as described in Step 1 above) (3.08 g) was converted to the title compound by a procedure similar to that described in Preparative Example 25, Step 2 using dichloromethane (25 ml) and sulphuryl chloride (0.96 ml). The title compound was used immediately in Step 3.

$^1$H nmr (CDCl$_3$): δ4.68 (1H, d), 5.20 (1H, d), 5.75 (1H, s), 7.30 (1H, t), 7.45 (2H, m), 7.70 (1H, m)

Step 3 Preparation of 5-hydroxy-3-(3-bromo)phenyl-4-thiazolidinone

5-Chloro-3-(3-bromo)phenyl-4-thiazolidinone (prepared as described in Step 2 above) was mixed with tetrahydrofuran (15 ml) and saturated sodium bicarbonate solution (10 ml) and stirred at room temperature for 45 minutes. The reaction mixture was worked up as in Preparative Example 25, Step 3 but nmr indicated incomplete reaction together with impurities. The material was chromatographed on silica using ethyl acetate-hexane (35:65) which indicated both product and starting material. This was reacted further in tetrahydrofuran (15 ml) and sat sodium bicarbonate (10 ml) overnight and then again worked up as in Preparative Example 25, Step 3. The residue (2 g) was chromatographed on silica using ethyl acetate/hexane as eluant (3:7) to give the title compound, yield 0.964 g, which had:

$^1$H nmr (CDCl$_3$): δ4.08 (1H, broad s), 4.69 (1H, d), 4.99 (1H, d), 5.71 (1H, s), 7.23–7.48 (3H, m), 7.69 (1H, m)

PREPARATIVE EXAMPLE 33

Preparation of 5-hydroxy-3-(3-iodo)phenyl-4-thiazolidinone.

Step 1 Preparation of 3-(3-iodo)phenyl-4-thiazolidinone

3-Iodoaniline (11.757 g) was converted to the title compound using toluene (140 ml), thioglycollic acid (3.73 ml) and 37% aqueous formaldehyde solution (4.35 ml) by a procedure similar to that described in Preparative Example 25, Step 1. The toluene layer was decanted from the precipitated red oil and was washed with 2M hydrochloric acid, sodium bicarbonate and brine. The toluene layer was dried (MgSO$_4$) and evaporated to give a residue (6.5 g) which was chromatographed on silica using ethyl acetate-hexane (15:85) as eluant. The title compound was obtained as an off-white solid, yield 4.00 g, mp 88°–88.5° C.

$^1$H nmr (CDCl$_3$): δ3.73 (2H, s), 4.79 (2H, s), 7.12 (1H, t), 7.43 (1H, dd), 7.59 (1H, d), 7.80 (1H ,m)

MS: m/e 305 (M$^+$)

Step 2 Preparation of 5-chloro-3-(3-iodo)phenyl-4-thiazolidinone 3-(3-Iodo)phenyl-4-thiazolidinone (prepared as described in Step 1 above (2.91 g) was converted to the title compound by a procedure similar to that described in Preparative Example 25, Step 2 using dichloromethane (27 ml) and sulphuryl chloride (0.77 ml). The title compound was used immediately in Step 3.

$^1$H nmr (CDCl$_3$): δ4.66 (1H, d), 5.19 (1H, d), 5.75 (1H, s), 7.17 (1H, t), 7.50 (1H, m), 7.64 (1H, d), 7.68 (1H, m)

Step 3 Preparation of 5-hydroxy-3-(3-iodo)phenyl-4-thiazolidinone

5-Chloro-3-(3-iodo)phenyl-4-thiazolidinone (prepared as described in Step 2 above) was converted to the title compound by a procedure similar to that described in Preparative Example 25, Step 3 using a mixture of tetrahydrofuran (7 ml) and saturated sodium bicarbonate solution (10 ml). The crude product (3.04 g) was purified on silica gel using ethyl acetate hexane (35:65) as eluant. The title compound was obtained as a yellow solid, yield 1.85 g, mp 141°–142° C.

$^1$H nmr (CDCl$_3$): δ3.59 (1H, d), 4.69 (1H, d), 4.96 (1H, d), 5.70 (1H, d), 7.15 (1H, t), 7.49 (1H, dd), 7.63 (1H, d), 7.84 (1H, m)

PREPARATIVE EXAMPLE 34

Preparation of 5-hydroxy-3-(3-phenoxy)phenyl-4-thiazolidinone.

Step 1 Preparation of 2-mercapto-N-(3-phenoxyphenyl) acetamide

Freshly distilled 3-phenoxyaniline (5.94 g) was dissolved in toluene (30 ml) under nitrogen and treated with thioglycollic acid (2.45 ml). The mixture was refluxed, and water collected in a Dean and Stark apparatus overnight. The solvent was removed under reduced pressure and the residue taken up in ethyl acetate. This was washed successively with 2M hydrochloric acid, saturated sodium bicarbonate solution and brine. The organic layer was processed in the usual manner to give the title compound (which was sufficiently pure for the next reaction) as a pale yellow oil, yield 6.824 g.

$^1$H nmr (CDCl$_3$): δ1.95–2.10 (1H, broad s), 3.3–3.45 (2H, broad s), 6.80 (1H, m), 7.03 (2H, d), 7.12 (1H, t), 7.25–7.40 (5H, m), 8.40–8.60 (1H, broad s)

Step 2 Preparation of 3-(3-phenoxy)phenyl-4-thiazolidinone

2-Mercapto-N-(3-phenoxyphenyl)acetamide (prepared as described in Step 1 above) (3.102 g) was converted to the title compound by a procedure similar to that described in Preparative Example 30, Step 2 using diiodomethane (2 ml) and ground potassium hydroxide (4.0 g) except that tetrahydrofuran (350 ml) was used as solvent in place of acetone. The crude product was purified on silica gel using ethyl acetate/hexane (15:85) to give the title compound, yield 0.505 g.

$^1$H nmr (CDCl$_3$): δ3.72 (2H, s), 4.80 (2H, s), 6.87 (1H, dd), 7.00–7.40 (8H, m)

Step 3 Preparation of 5-chloro-3-(3-phenoxy)phenyl-4-thiazolidinone 3-(3-Phenoxy)phenyl-4-thiazolidinone (prepared as described in Step 2 above (0.500 g) was converted to the title compound by a procedure similar to that described in Preparative Example 25, Step 2 using dichloromethane (5 ml) and sulphuryl chloride (0.163 ml). The title compound was used immediately in Step 4.

Step 4 Preparation of 5-hydroxy 3-(3-phenoxy)phenyl-4-thiazolidinone

5-Chloro-3-(3-phenoxy)phenyl-4-thiazolidinone (prepared as described in Step 3) was converted to the title compound by a procedure similar to that described in Preparative Example 25, Step 3 using a mixture of tetrahydrofuran (10 ml) and saturated sodium bicarbonate solution (5 ml). The title compound was purified on silica gel using ethyl acetate/hexane (35:65) as eluant, and was obtained as an oil which slowly crystallised on standing, yield 0.263 g.

$^1$H nmr (CDCl$_3$): δ4.15–4.30 (1H, broad s), 4.67 (1H, d), 4.96 (1H, d), 5.70 (1H, s), 6.90 (1H, dd), 7.00–7.40 (8H, m)

MS: m/e 287 (M$^+$)

PREPARATIVE EXAMPLE 35

Preparation of 5-hydroxy-3-(3-methanesulphonyl)phenyl-4-thiazolidinone

Step 1 Preparation of (3-nitro)phenyl methyl sulphone

Phenyl methyl sulphone (4.0 g) was added, portionwise, to fuming nitric acid stirred at 0° C. The reaction mixture was allowed to warm to room temperature, stirred for 1 hour, and then poured carefully onto ice. The solution was carefully neutralised with sodium bicarbonate and the mixture filtered at the pump. The solid collected was washed with water and dried under reduced pressure over potassium hydroxide to give the title compound as a white solid (5.63 g) in a sufficient state of purity for the next reaction.

$^1$H nmr (CDCl$_3$): δ3.13 (3H, s), 7.83 (1H, t), 8.30 (1H, d), 8.54 (1H, d), 8.82 (1H, s)

Step 2 Preparation of (3-amino)phenyl methyl sulphone (3-Nitro)phenyl methyl sulphone (prepared as described in Step 1 above) (5.396 g) reduced iron (7.5 g) and ammonium chloride (7.18 g) were mixed together in ethanol/water (2:1) (150 ml) and heated under reflux for 2 hours. The black solution was filtered through 'Celite' and the pad washed with ethyl acetate. The solvents were removed under reduced pressure and the residue taken up in ethyl acetate/water. The organic layer was separated and the aqueous layer extracted with 3 further portions of ethyl acetate. The combined organic layers were washed with brine and the solvent removed under reduced pressure to give a dark orange oil (3.9275 g). This was chromatographed on silica gel using ethyl acetate-hexane (45:55 to 50:50) as eluant to give the title compound as an orange oil, yield 3.607 g.

$^1$H nmr (CDCl$_3$): δ3.02 (3H, s), 3.8–4.2 (2H, broad s), 6.90 (1H, m), 7.18–7.38 (3H, m)

Step 3 Preparation of 3-(3-methanesulphonyl)phenyl-4-thiazolidinone (3-Amino)phenyl methyl sulphone (prepared as described in Step 2 above) (3.6 g) was converted to the title compound using toluene (175 ml), thioglycollic acid (1.46 ml) and 37% aqueous formaldehyde solution (1.71 ml) by a procedure similar to that described in Preparative Example 25, Step 1. The crude product was purified by silica gel chromatography using ethyl acetate-hexane (1:1) as eluant. The title compound was obtained as a pale yellow solid, yield 1.105 g, mp 92°–95.5° C.

$^1$H nmr (CDCl$_3$): δ3.08 (3H, s), 3.77 (2H, s), 4.88 (2H, s), 7.63 (1H, t), 7.82 (1H, d), 7.89 (1H, d), 7.99 (1H, m)

Step 4 Preparation of 5-chloro-3-(3-methanesulphonyl)phenyl-4-thiazolidinone 3-(3-Methanesulphonyl)phenyl-4-thiazolidinone (prepared as described in Step 3 above) (1 g) was converted to the title compound by a procedure similar to that described in Preparative Example 25, Step 2 using dichloromethane (10 ml) and sulphuryl chloride (0.31 ml). The title compound was used immediately in Step 5.

Step 5 Preparation of 5-hydroxy-3-(3-methanesulphonyl)phenyl-4-thiazolidinone

5-Chloro-3-(3-methoxyphenyl)thiazolidine-4-one (prepared as described in Step 4 above) was converted to the title compound by a procedure similar to that described in Preparative Example 25, Step 3 using a mixture of tetrahydrofuran (15 ml) and saturated sodium bicarbonate solution (5 ml). The crude product (0.892 g) was purified by silica gel chromatography using ethyl acetate hexane (3:1) as eluant. The title compound was obtained as a soft yellow solid, yield 0.679 g.

$^1$H nmr (CDCl$_3$): δ3.09 (3H, s), 4.25–4.35 (1H, broad s), 4.75 (1H, d), 5.08 (1H, d), 5.72 (1H, s), 7.63 (1H, t), 7.84 (2H, m), 8.07 (1H, m)

PREPARATIVE EXAMPLE 36

Preparation of 5-hydroxy-3-(3,4,5-trichloro)phenyl-4-thiazolidinone

Step 1 Preparation of 3-(3,4,5-trichloro)phenyl-4-thiazolidinone 3,4,5-Trichloroaniline (5.167 g) was converted to the title compound using toluene (250 ml), thioglycollic acid (2.75 ml) and 37% aqueous formaldehyde solution (2.35 ml) by a procedure similar to that described in Preparative Example 25, Step 1. No oil was deposited in this reaction but on cooling some pale brown needles formed which were removed by filtration. The filtrate was concentrated to give a white solid which was taken up in dichloromethane and washed successivly with 2M hydrochloric acid, saturated sodium bicarbonate solution and brine. The organic layer was dried (MgSO$_4$) and evaporated to give an off white solid (2.8 g). The crude product was chromatographed on silica using ethyl acetate-hexane (15:85) as eluant to give the title compound as a white solid, yield 2.27 g, mp 161°–163° C.

$^1$H nmr (CDCl$_3$): δ3.73 (2H, s), 4.79 (2H, s), 7.61 (2H, s)

Step 2 Preparation of 5-chloro-3-(3,4,5-trichloro)phenyl-4-thiazolidinone 3-(3,4,5-Trichloro)phenyl-4-thiazolidinone (prepared as described in Step 1 above (2.00 g) was converted to the title compound by a procedure similar to that described in Preparative Example 25, Step 2 using dichloromethane (20 ml) and sulphuryl chloride (0.63 ml). The title compound was used immediately in Step 3.

Step 3 Preparation of 5-hydroxy-3-(3,4,5-trichloro)phenyl-4-thiazolidinone

5-Chloro-3-(3,4,5-trichloro)phenyl-4-thiazolidinone (prepared as described in Step 2 above) was converted to the title compound by a procedure similar to that described in Preparative Example 25, Step 3 using a mixture of tetrahydrofuran (10 ml) and saturated sodium bicarbonate solution (10 ml). The crude product (2.15 g) was purified on silica gel using ethyl acetate-hexane (35:65) as eluant. The title compound was obtained as a brown solid (1.3 g) and had:

$^1$H nmr (CDCl$_3$/d$_6$_DMSO): δ4.63 (1H, d), 5.05 (1H, d), 5.59 (1H, d), 6.96 (1H, d), 7.72 (2H, s)

PREPARATIVE EXAMPLE 37

Preparation of 5-hydroxy-3-(3-methylthio)phenyl-4-thiazolidinone

Step 1 Preparation of 2-mercapto-N-(3-methylthiophenyl) acetamide

3-Methylmercaptoaniline (5.041 g) was converted to the title compound by a procedure similar to that described in Preparative Example 34, Step 1 using toluene (25 ml) and thioglycollic acid (3.78 ml). The crude product was purified on silica gel using ethyl acetate-hexane (0:1 to 1:7 to 1:3) as eluant. The title compound was obtained as a creamy white solid, yield 6.55 g.

$^1$H nmr (CDCl$_3$): δ2.03 (1H, t), 2.50 (3H, s), 3.40 (2H, d), 7.02 (1H, m), 7.25 (2H, m), 7.53 (1H, m), 8.50 (1H, broad s)

Step 2 Preparation of 3-(3-methylthio)phenyl-4-thiazolidinone

2-Mercapto-N-(3-methylthiophenyl)acetamide (prepared as described in Step 1 above) (5 g) was converted into the title compound by a procedure similar to that described in Preparative Example 30, Step 2 using diiodomethane (3.89 ml) and ground potassium hydroxide (7.89 g) except that tetrahydrofuran (500 ml) was used as solvent in place of acetone. The crude product was purified on silica gel using ethyl acetate-hexane (1:4)) as eluant to give a brown oil (1.302 g) still contaminated with a little of the aniline which was removed by extraction of an ethyl acetate solution of the material with 2M hydrochloric acid. This solution was processed in the usual manner to give the title compound as an orange/brown oil (0.97 g) in a sufficient state of purity for the next stage of the synthesis.

$^1$H nmr (CDCl$_3$): δ2.48 (3H, s), 3.75 (2H, s), 4.81 (2H, s), 7.10–7.37 (4H, m)

Step 3 Preparation of 5-chloro-3-(3-methylthio)phenyl-4-thiazolidinone 3-(3-Methylthio)phenyl-4-thiazolidinone (prepared as described in Step 3 above) (0.97 g) was converted to the title compound by a procedure similar to that described in Preparative Example 25, Step 2 using dichloromethane (20 ml) and sulphuryl chloride (0.35 ml). The title compound was used immediately in Step 4.

$^1$H nmr (CDCl$_3$): δ2.48 (3H, s), 4.68 (1H, d), 5.19 (1H, d), 5.77 (1H, s), 7.15–7.45 (4H, m)

Step 4 Preparation of 5-hydroxy-3-(3-methylthio)phenyl-4-thiazolidinone

5-Chloro-3-(3-methylthio)phenyl-4-thiazolidinone (prepared as described in Step 3) was converted to the title compound by a procedure similar to that described in Preparative Example 25, Step 3 using a mixture of tetrahydrofuran (20 ml) and saturated sodium bicarbonate (15 ml). The crude product was purified by chromatography on silica gel using ethyl acetate-hexane (1:1) as eluant. The title compound was obtained as a brown gum, yield 0.578 g.

$^1$H nmr (CDCl$_3$): δ2.48 (3H, s), 4.14 (1H, broad s), 4.70 (1H, d), 4.98 (1H, d), 5.72 (1H, s), 7.10–7.40 (4H, m)

PREPARATIVE EXAMPLE 38

Preparation of 5-hydroxy-3-(3-trifluoromethoxy) phenyl-4-thiazolidinone.

Step 1 Preparation of 3-(3-trifluoromethoxy)phenyl-4-thiazolidinone 3-(Trifluoromethoxy)aniline (5.076 g) was converted to the title compound using toluene (150 ml), thioglycollic acid (2.99 ml) and 37% aqueous formaldehyde solution (2.56 ml) by a procedure similar to that described in Preparative Example 25, Step 1. The crude product (8.583 g) was purified by silica gel chromatography using ethyl acetate-hexane (15:85) as eluant. The title compound was obtained a mobile pale yellow oil, yield 3.818 g.

$^1$H nmr (CDCl$_3$): δ3.73 (2H, s), 4.82 (2H, s), 7.10 (1H, m), 7.42 (3H, m)

MS: m/e 263 (M$^+$)

Step 2 Preparation of 5-chloro-3-(3-trifluoromethoxy) phenyl-4-thiazolidinone 3-(3-Trifluoromethoxy)phenyl-4-thiazolidinone (prepared as described in Step 1 above) (3.468 g) was converted to the title compound by a procedure similar to that described in Preparative Example 25, Step 2 using dichloromethane (25 ml) and sulphuryl chloride (1.06 ml). The title compound was used immediately in Step 3.

$^1$H nmr (CDCl$_3$): δ4.70 (1H, d), 5.22 (1H, d), 5.76 (1H, s), 7.16 (1H, m), 7.48 (3H, m)

Step 3 Preparation of 5-hydroxy-3-(3-trifluoromethoxy) phenyl-4-thiazolidinone

5-Chloro-3-(3-trifluoromethoxy)phenyl-4-thiazolidinone (prepared as described in Step 2 above) was converted to the title compound by a procedure similar to that described in Preparative Example 25, Step 3 using a 1:1 mixture of tetrahydrofuran and saturated sodium bicarbonate solution (40 ml). The crude product (4.512 g) was purified by silica gel chromatography using ethyl acetate-hexane mixtures as eluant. The title compound was obtained as a yellow solid, yield 1.514 g.

$^1$H nmr (CDCl$_3$): δ3.63 (1H, broad s), 4.73 (1H, d), 5.00 (1H, d), 5.72 (1H, s), 7.15 (1H, m), 7.47 (3H, m)

PREPARATIVE EXAMPLE 39

Preparation of 5-hydroxy-3-(3-methoxy-5-trifluoromethyl)phenyl-4-thiazolidinone

Step 1 Preparation of 3-(3-methoxy-5-trifluoromethyl) phenyl-4-thiazolidinone.

5-methoxy-αααtrifluoro-m-toluidine (5.286 g) was converted to the title compound using toluene (80 ml), thioglycollic acid (2.1 ml) and 37% aqueous formaldehyde solution (2.51 ml) by a procedure similar to that described in Preparative Example 25, Step 1. Evaporation of the toluene gave a yellow solid, which was dissolved in diethyl ether and washed successively with 2M hydrochloric acid, saturated sodium bicarbonate solution and brine. The organic layer was dried (MgSO$_4$) and the solvent removed under reduced pressure to give a residue (4.2 g) which was chromatographed on silica using ethyl acetate-hexane (20:80 to 25:75) as eluant. The title compound (3.459 g) had:

$^1$H nmr (CDCl$_3$): δ3.75 (2H, s), 3.87 (3H, s), 4.85 (2H, s), 7.01 (1H, s), 7.25 (1H, s), 7.34 (1H, s)

MS: m/e 277 (M$^{30}$ )

Step 2 Preparation of 5-chloro-3-(3-methoxy-5-trifluoromethyl)phenyl-4-thiazolidinone 3-(3-Methoxy-5-trifluoromethyl)phenyl-4-thiazolidinone (prepared as described in Step 1 above) (3.45 g) was converted to the title compound by a procedure similar to that described in Preparative Example 25, Step 2 using dichloromethane (24 ml) and sulphuryl chloride (1.05 ml). The title compound was used immediately in Step 3.

Step 3 Preparation of 5-hydroxy-3-(3-methoxy-5-trifluoromethyl)phenyl-4-thiazolidinone 5-Chloro-3-(3-methoxy-5-trifluoromethyl)phenyl-4-thiazolidinone (prepared as described in Step 2 above) was converted to the title compound by a procedure similar to that described in Preparative Example 25, Step 3 using a mixture of tetrahydrofuran (10 ml) and saturated sodium bicarbonate solution (10 ml). The crude product (3.2 g) was purified on silica gel using ethyl acetate-hexane (2:3) to give the title compound (2.56 g) which had:

$^1$H nmr (CDCl$_3$): δ3.87 (3H, s), 4.15 (1H, broad s), 4.72 (1H, d), 5.01 (1H, d), 5.71 (1H, s), 7.03 (1H, s), 7.27 (1H, d), 7.36 (1H, d)

MS: m/e 293 (M$^+$)

PREPARATIVE EXAMPLE 40

Preparation of 5-hydroxy-3-(3-nitro-5-trifluoromethyl)phenyl-4-thiazolidinone

Step 1 Preparation of 3-nitro-5-trifluoromethylaniline (ref J. Med Chem. 1981, 24, 742)

3,5-Dinitrobenzotrifluoride (10 g) was dissolved in a mixture of methanol (200 ml) and 1,4-dioxane (125 ml) and heated under reflux. To this solution was added concentrated hydrochloric acid (30 ml) and then in small portions, reduced iron powder (9 g). CARE: violent effervescence. Refluxing was continued for a further 1 hour and the reaction mixture allowed to cool to room temperature. The mixture was filtered through 'Celite' and the pad washed well with dichloromethane. The solvents were removed under reduced pressure to give a residue which was partitioned between dichloromethane and water. The organic layer was washed with brine, dried (MgSO$_4$) and evaporated under reduced pressure to give a brown semi-solid (8 g). This was chromatographed on silica gel using ethyl acetate-hexane (1:9) as eluant to give the title compound as fine golden crystals, yield 4.98 g.

$^1$H nmr (CDCl$_3$): δ4.10–4.40 (2H, broad s), 7.15 (1H, broad s), 7.63 (1H, m), 7.81 (1H, broad s)

Step 2 Preparation of 3-(3-nitro-5-trifluoromethyl)phenyl-4-thiazolidinone

3-Nitro-5-trifluoromethylaniline (prepared as described in Step 1 above) (4.98 g) was converted to the title compound using toluene (90 ml), thioglycollic acid (2.30 ml) and 37% aqueous formaldehyde solution (2.75 ml) by a procedure similar to that described in Preparative Example 25, Step 1. A solid precipitated upon cooling, this was removed by filtration and the filterate evaporated under reduced pressure to give a semi-solid residue (3.965 g). This residue was taken up in ethyl acetate and washed successively with 2M hydrochloric acid, saturated sodium bicarbonate solution and brine. The organic layer was dried (MgSO$_4$) and evaporated under reduced pressure to give the crude product (2.82 g). this was chromatographed on silica gel using ethyl acetate/hexane (3:7) as eluant to give the title compound, yield 1.784 g.

$^1$H nmr (CDCl$_3$): δ3.81 (2H, s), 4.94 (2H, s), 8.28 (1H, s), 8.34 (1H, s), 8.58 (1H, m)

MS: m/e 292 (M$^+$)

Step 3 Preparation of 5-chloro-3-(3-nitro-5-trifluoromethyl) phenyl-4-thiazolidinone 3-(3-Nitro-5-trifluoromethylphenyl)thiazolidine-4-one (prepared as described in Step 1 above) (1.78 g) was converted to the title compound by a procedure similar to that described in Preparative Example 25, Step 2 using dichloromethane (20 ml) and sulphuryl chloride (0.54 ml). The title compound was used immediately in Step 4.

Step 4 Preparation of 5-hydroxy-3-(3-nitro-5-trifluoromethyl)phenyl-4-thiazolidinone 5-Chloro-3-(3-nitro-5-trifluoromethyl)phenyl-4-thiazolidinone (prepared as described in Step 1 above) was converted to the title compound by a procedure similar to that described in Preparative Example 25, Step 3 using a mixture of tetrahydrofuran (10 ml) and saturated sodium bicarbonate solution (10 ml). The crude product (1.67 g) was purified on silica gel using ethyl acetate-hexane (2:3) as eluant. The title compound was obtained as a yellow solid, yield 1.118 g.

$^1$H nmr (CDCl$_3$): δ4.78 (1H, d), 5.21 (1H, d), 5.65 (1H, d), 6.94 (1H, d), 8.33 (2H, s), 8.67 (1H, m)

MS: m/e 308 (M$^+$)

PREPARATIVE EXAMPLE 41

Preparation of 5-hydroxy-3-(3-trifluoromethanesulphonylphenyl)thiazolidine-4-one Step 1 Preparation of 3-nitrobenzenesulphonyl fluoride 3-Nitrobenzenesulphonyl chloride (10 g) was dissolved in 1,4-dioxane (30 ml) and stirred at room temperature. To this solution was added a solution of potassium fluoride (3.9 g) in water (5 ml) and the stirring continued at room temperature for 5 hours. The reaction mixture was allowed to stand at room temperature overnight and was poured into ice/water. The product was extracted into dichloromethane, the solvent was dried (MgSO$_4$) and evaporated under reduced pressure to give the title compound (8 g). This material was sufficiently pure for the next stage of the synthesis.

$^1$H nmr (CDCl$_3$): δ7.93 (1H, t), 8.37 (1H, d), 8.67 (1H, dd), 8.89 (1H, m)

MS: m/e 205 (M$^+$)

Step 2 Preparation of 3-trifluoromethylsulphonyl nitrobenzene (ref Synthesis, 1990, 1151)

3-Nitrobenzenesulphonyl fluoride (prepared as described in Step 1 above) (6.79 g) was suspended in petroleum ether (60/80) (35 ml) and was stirred at room temperature under nitrogen. To this solution was added tris(dimethylamino) sulphur(trimethylsilyl)difluoride (0.92 g) and then (trifluoromethyl)trimethylsilane (9.77 ml) dissolved in dry tetrahydrofuran (35 ml). The reaction mixture was stirred at room temperature for 3.5 hours when g.c. analysis revealed 25% starting material and 75% product. The mixture was then treated with water and the product and unchanged starting material were extracted into hexane. The combined organic layers were dried and evaporated to give a residue (4.62 g) which was treated with an aqueous ammonia/tetrahydrofuran mixture to convert the unchanged sulphonyl fluoride into the corresponding sulphonamide. When tlc had shown that all the sulphonyl fluoride had been converted the mixture was diluted with water, the organic layer separated, dried (MgSO$_4$) and evaporated under reduced pressure to give a residue (3.8 g) which was chromatographed on silica gel using ethyl acetate-hexane (1:9) as eluant. The title compound (2.77 g) had:

$^1$H nmr (CDCl$_3$): δ7.96 (1H, t), 8.39 (1H, d), 8.71 (1H, d), 8.90 (1H, s)

MS: m/e 255 (M$^+$)

Step 3 Preparation of 3-(trifluoromethanesulphonyl)aniline

3-Trifluoromethylsulphonyl nitrobenzene (prepared as described in Step 2 above) (3.27 g) was mixed with water (30 ml), ethanol (60 ml), ammonium chloride (3.4245 g) and reduced iron (3.584 g) and refluxed for 30 minutes. The reaction mixture was allowed to cool to room temperature and was filtered through 'Celite'. The filtrate was diluted with water and the product extracted with dichloromethane (×3). The combined organic layers were dried and evaporated under reduced pressure to give a residue (2.752 g) which was combined with a similar residue (0.15 g) from an earlier preparation using (0.2 g) of 3-trifluoromethanesulphonyl nitrobenzene. This was chromatographed on silica gel using ethyl acetate-hexane (1:4) as eluant to give the title compound (2.466 g) which had:

$^1$H nmr (CDCl$_3$): δ3.90–4.20 (2H, broad s), 7.05 (1H, m), 7.25 (1H, s), 7.40 (2H, m)

MS: m/e 225 (M$^+$)

Step 4 Preparation of 3-(3-trifluoromethanesulphonyl) phenyl-4-thiazolidinone 3-(Trifluoromethanesulphony)laniline (prepared as described in Step 3 above) (2.46 g) was converted (in part) to the title compound using toluene (30 ml), thioglycollic acid (1.386 g) and 37% aqueous formaldehyde solution (1.25 ml) by a procedure similar to that described in Preparative Example 25, Step 1. The solvent was removed to give a golden coloured oil which was taken up in ethyl acetate and washed successively with 2M hydrochloric acid, saturated sodium bicarbonate solution and brine. The ethyl acetate was dried and evaporated to give a residue (0.87 g), which contained the product. Because of the poor recovery the sodium bicarbonate washings were taken to pH4 using 2M hydrochloric acid and extracted into ethyl acetate. This was dried (MgSO$_4$) and evaporated under reduced pressure to give a residue (2.90 g) which was found to be the intermediate acyclic acid, S-(N(3-(trifluoromethanesulphonyl)phenylamino)methyl) thioglycollic acid. This was converted to the title compound by a procedure similar to that described in Preparative Example 26, Step 1 using dichloromethane (50 ml), thionyl chloride (0.65 ml) and triethylamine (1.25 ml). This yielded a further sample (2.07 g) containing the title compound which was combined with the earlier residue (0.87 g) and purified on silica gel using ethyl acetate-hexane (35:65) as eluant. The title compound (1.634 g) was obtained as a yellow solid and had:

$^1$H nmr (CDCl$_3$): δ3.78 (2H, s), 4.90 (2H, s), 7.72 (1H, t), 7.89 (1H, d), 8.05 (1H, s), 8.15 (1H, d)

MS: m/e 311 (M$^+$)

Step 5 Preparation of 5-chloro-3-(3-trifluoromethanesulphonyl)phenyl-4-thiazolidinone 3-(3-Trifluoromethylsulphonyl)phenyl-4-thiazolidinone prepared as described in Step 4 above) (1.63 g) was converted to the title compound by a procedure similar to that described in Preparative Example 25, Step 2) using dichloromethane (20 ml) and sulphuryl chloride (0.46 ml). The title compound was used immediately in Step 6.

Step 6 Preparation of 5-hydroxy-3-(3-trifluoromethanesulphonyl)-4-thiazolidinone 5-Chloro-3-(3-trifluoromethanesulphonyl)phenyl-4-thiazolidinone (prepared as described in Step 5 above) was converted to the title compound by a procedure similar to that described in Preparative Example 25, Step 3 using a mixture of tetrahydrofuran (10 ml) and saturated sodium bicarbonate solution (10 ml). The crude product (1.09 g) was purified on silica gel using ethyl acetate-hexane (1:1) as eluant. The title compound (0.47 g) had:

$^1$H nmr (CDCl$_3$): δ3.64 (1H, broad s), 4.79 (1H, d), 5.10 (1H, d), 5.75 (1H, s), 7.76 (1H, t), 7.93 (1H, d), 8.18 (2H, m)

MS: m/e 327 (M$^+$)

PREPARATIVE EXAMPLE 42

Preparation of 3-hydroxy-1-(3-trifluoromethyl) phenyl-2-pyrrolidinone

Step 1 Preparation of 1-(3-trifluoromethyl)phenyl-2-pyrrolidinone-3-carboxylic acid A suspension of 6,6-dimethyl-5,7-dioxaspiro[2.5]octane-4,8-dione (prepared as described in Organic Syntheses, Volume 60, p 66–68) (8.00 g) in 3-trifluoromethylaniline (8.05 g) was stirred at room temperature for 24 hours. The mixture was filtered, and the insoluble solid was washed with chloroform. The combined filtrates were washed with 2M hydrochloric acid, brine and then dried (MgSO$_4$). Evaporation of the solvent under reduced pressure left a brown solid, which was recrystallised from chloroform/hexane to give the product as a white, crystalline solid, yield 4.10 g, mp 135°–136° C. (dec).

$^1$H nmr (CDCl$_3$): δ2.47–2.67 (2H, m), 3.70 (1H, t), 3.92–4.01 (2H, m), 7.00 (broad), 7.45–7.60 (2H, m), 7.81–7.90 (2H, m)

Step 2 Preparation of 1-(3-trifluoromethyl)phenyl-2-pyrrolidinone 1-(3-trifluoromethyl)phenyl-2-pyrrolidinone-3-carboxylic acid (prepared as in Step 1 above) (3.60 g) was heated to its melting point, and heating was continued until effervescence ceased (ca 50 minutes). The melt was cooled, dissolved in diethyl ether, and treated with decolourising charcoal. The charcoal was filtered off, and the solvent was removed under reduced pressure to leave a solid residue. This was recrystallised from hexane to give the product as colourless needles, yield 2.20 g, mp 67°–68° C.

$^1$H nmr (CDCl$_3$): δ2.19 (2H, quin), 2.62 (2H, t), 3.89 (2H, t), 7.35–7.53 (2H, m), 7.81–7.93 (2H, m)

MS: m/e 229 (M$^+$)

Step 3 Preparation of 3-hydroxy-1-(3-trifluoromethyl) phenyl-2-pyrrolidinone

A stirred solution of 1-(3-trifluoromethyl)phenyl-2-pyrrolidinone (prepared as in Step 2 above) (1.10 g) in dry tetrahydrofuran (5 ml) was cooled to −70° C. under a nitrogen atmosphere, and a solution of lithium hexamethyldisilazide in hexanes (1.0M, 4.9 ml) was added dropwise. The resultant pale yellow suspension was then treated with a solution of N-toluenesulphonyl-3-phenyloxaziridine (prepared as described in Journal of Organic Chemistry, 1988, 53, 2087) (2.00 g) in dry tetrahydrofuran (5 ml). The resultant pale yellow solution was allowed to warm to room temperature, and was then quenched with water and acidified to pH5 using 2M hydrochloric acid. The mixture was extracted with diethyl ether (×2), and the combined extracts were washed with water, dried (MgSO$_4$) and evaporated under reduced pressure to leave an oil. Purification by silica gel chromatography, eluting with ethyl acetate/hexane mixtures, afforded the title compound as a clear gum, yield 0.26 g.

$^1$H nmr (CDCl$_3$): δ1.62 (1H, broad s), 2.12 (1H, m), 2.63 (1H, m), 3.72–3.90 (2H, m), 4.51 (1H, m), 7.39–7.58 (2H, m), 7.77–8.02 (2H, m)

MS: m/e 245 (M$^+$)

PREPARATIVE EXAMPLE 43

Preparation of 1-(2-chloro-6-fluoro-4-trifluoromethyl)phenyl-3-hydroxy-2-pyrrolidinone Step 1 Preparation of 1-(2-chloro-6-fluoro-4-trifluoromethyl)phenyl-2-pyrrolidinone A stirred suspension of 2-pyrrolidinone (2.60 g) and finely ground potassium hydroxide (1.80 g) in dry dimethyl sulphoxide (40 ml) was treated with 1-chloro-2,3-difluoro-5- trifluoromethylbenzene (6.50 g). The mixture was stirred at room temperature for 1 hour, then made slightly acid using 2M hydrochloric acid. The crystalline preciptate which formed was filtered off, washed with water and dried, affording the product as a white crystalline compound, yield 6.30 g, mp 115°–116° C.

$^1$H nmr (CDCl$_3$): δ2.22–2.37 (2H, m), 2.56–2.66 (2H, m), 3.70 (1H, m), 3.79 (1H, m), 7.38 (1H, m), 7.57 (1H, m)

Step 2 Preparation of 1-(2-chloro-6-fluoro-4-trifluoromethyl)phenyl-3-hydroxy-2-pyrrolidinone By a procedure similar to that described in Preparative Example 42, Step 3 above, but using 1-(2-chloro-6-fluoro-4-trifluoromethyl)phenyl-2-pyrrolidinone (prepared as in Step 1 above) (11.40 g), N-toluenesulphonyl-3-phenyloxaziridine (prepared as described in Journal of Organic Chemistry, 1988, 53, 2087) (15.00 g), tetrahydrofuran (200 ml) and a solution of lithium hexamethyldisilazide in tetrahydrofuran (1.0M, 41.0 ml), and purification of the crude product by silica gel chromatography, eluting with ethyl acetate/hexane mixtures, the title compound was obtained as a crystalline solid, yield 2.40 g, mp 102°–104° C.

$^1$H nmr (CDCl$_3$): δ2.28 (1H, m), 2.64 (1H, m), 3.52–3.81 (3H, m), 5.52 (1H, m), 7.38 (1H, m), 7.59 (1H, m)

PREPARATIVE EXAMPLE 44

Preparation of dihydro-2-hydroxy-4-(3-trifluoromethyl)phenyl-4H-1,4-oxazin-3-(2H)-one Step 1 Preparation of dihydro-4-(3-trifluoromethyl)phenyl-4H-1,4-oxazin-3-(2H)-one A stirred solution of N-(3-trifluoromethylphenyl) ethanolamine (8.20 g) in dry tetrahydrofuran (25 ml) was treated dropwise with chloroacetyl chloride (4.50 g). The resultant solution was cooled in an ice bath, and sodium hydride (3.20 g of a 60% dispersion in mineral oil) was added portionwise. The mixture was then allowed to warm to room temperature, and was stirred for a further 5 hours. Water was added, and the mixture was extracted thoroughly with diethyl ether. The combined ether extracts were washed with brine, dried (MgSO$_4$), and evaporated under reduced pressure to leave a brown oil. Purification by silica gel chromatography, eluting with ethyl acetate/hexane mixtures, afforded the title compound as a white crystalline solid, yield 2.80 g, mp 47°–48° C.

$^1$H nmr (CDCl$_3$): δ3.79 (2H, m), 4.05 (2H, m), 4.37 (2H, s), 7.50–7.58 (3H, m), 7.62 (1H, m)

Step 2 Preparation of dihydro-2-hydroxy-4-(3-trifluoromethyl)phenyl-4H-1,4-oxazin-3-(2H)-one A stirred solution of dihydro-4-(3-trifluoromethyl) phenyl-4H-1,4-oxazin-3-(2H)-one (prepared as in Step 1 above) (0.49 g) in dry tetrahydrofuran (20 ml) was cooled to 0° C. under a nitrogen atmosphere, and a solution of lithium hexamethyldisilazide in tetrahydrofuran (1.0M, 2.1 ml) was added dropwise. The resultant pale yellow suspension was then added to a solution of N-toluenesulphonyl-3-phenyloxaziridine (prepared as described in Journal of Organic Chemistry, 1988, 53, 2087) (1.10 g) in dry tetrahydrofuran (10 ml). The resultant pale yellow solution was allowed to warm to room temperature, and was stirred for 1 hour before being quenched with water and acidified to pH5 using 2M hydrochloric acid. The mixture was extracted with diethyl ether (×2), and the combined extracts were washed with brine, dried (MgSO$_4$) and evaporated under reduced pressure to leave an oil. Purification by silica gel chromatography, eluting with ethyl acetate/hexane mixtures, afforded the title compound as a white solid, yield 0.14 g, mp 113°–119° C.

$^1$H nmr (CDCl$_3$): δ3.59 (1H, m), 3.91–4.05 (2H, m), 4.49 (1H, m), 5.04 (1H, broad s), 5.43 (1H, s), 7.50–7.63 (4H, m)

PREPARATIVE EXAMPLE 45

Preparation of dihydro-2-hydroxy-4-(3-trifluoromethyl)phenyl-4H-1,4-thiazin-3-(2H)-one Step 1 Preparation of N-(2-bromoethyl)-α,α,αtrifluoro-m-toluidine N-(3-trifluoromethylphenyl)ethanolamine (4.17 g) and triphenyl phosphine (5.50 g) were dissolved in dry pyridine (35 ml) and stirred at 0° C. To this solution was added, portionwise, carbon tetrabromide (7.08 g). Stirring was continued for 1 hour and the reaction mixture was left to stand at room temperature overnight. A little more triphenyl phosphine (0.20 g) was added, and when virtually all starting alcohol had been consumed the pyridine was removed under reduced pressure to leave a brown residue (14.10 g). This was chromatographed on silica gel, eluting with ethyl acetate/hexane (1:9) as eluant to give the title compound as a light brown oil, yield 3.35 g.

$^1$H nmr (CDCl$_3$): δ3.58 (4H, m), 4.25 (1H, broad s), 6.77 (1H, d), 6.81 (1H, s), 6.98 (1H, d), 7.29 (1H, d)

Step 2 Preparation of ethyl S-(2-(3-trifluoromethylphenylamino)ethyl)thioglycollate A solution of N-(2-bromoethyl)-α,α,αtrifluoro-m-toluidine (prepared as in Step 1 above) (2.80 g) in dimethylformamide was added to a solution af the the sodium anion of ethyl thioglycollate [prepared using ethyl thioglycollate (1.25 g) and sodium hydride (1.25 g of a 60% dispersion in mineral oil)] in dimethylformamide (total volume 100 ml), and was allowed to stir at room temperature for approximately 2 hours. The reaction was cautiously quenched with 5% aqueous ammonium chloride solution, and the product was extracted with diethyl ether (×3). The combined organic layers were washed successively with water (×2) and brine, then dried (Na$_2$SO$_4$) and evaporated under reduced pressure. The residue (3.00 g) was chromatographed on silica gel, eluting with ethyl acetate/hexane (15:85) to give the title compound as an oil, yield 2.07 g.

$^1$H nmr (CDCl$_3$): δ1.36 (3H, t), 2.92 (2H, t), 3.25 (2H, s), 3.40 (1H, q), 4.29 (2H, q), 4.39 (1H, broad t), 6.77 (1H, d), 6.82 (1H, s), 6.95 (1H, d), 7.27 (1H, t)

MS: m/e 307 (M$^+$)

Step 3 Preparation of dihydro-4-(3-trifluoromethyl)phenyl-4H-1,4-thiazin, 3-(2H)-one Ethyl S-(2-(3-trifluoromethylphenylamino)ethyl) thioglycollate (prepared as in Step 2 above) (2.05 g) was dissolved in xylene (25 ml) and p-toluenesulphonic acid (0.127 g) was added. The solution was heated under gentle reflux for 28 hours, then cooled and the solvent was removed under reduced pressure to leave a brown oil (1.88 g). This was chromatographed on silica gel, eluting with ethyl acetate/hexane (45:65) to give the title compound as a light brown solid, yield 1.31 g.

$^1$H nmr (CDCl$_3$): δ3.05 (2H, t), 3.48 (2H, s), 4.02 (2H, t), 7.52 (4H, m)

MS: m/e 261 (M$^+$)

Step 4 Preparation of dihydro-2-chloro-4-(3-trifluoromethyl)phenyl-4H-1,4-thiazin-3-(2H)-one dihydro-4-(3-trifluoromethyl)phenyl-4H-1,4-thiazin-3-(2H)-one (prepared as in Step 3 above) (1.31 g) was converted to the title compound by a procedure similar to that described in Preparative Example 25, Step 2 using dichloromethane (17 ml) and sulphuryl chloride (0.403 ml). This product was used immediately in Step 5.

Step 5 Preparation of dihydro-2-hydroxy-4-(3-trifluoromethyl)phenyl-4H-1,4-thiazin-3-(2H)-one Dihydro-2-chloro-4-(3-trifluoromethyl)phenyl-4H-1,4-thiazin-3-(2H)-one (prepared as in Step 4 above) was converted to the title compound by a procedure similar to that described in Preparative Example 25, Step 3 using tetrahydrofuran (7 ml) and saturated sodium bicarbonate solution (10 ml). The crude preoduct (1.33 g) was purified by silica gel chromatography, eluting with ethyl acetate/hexane (35:65). The title compound (0.68 g) had:

$^1$H nmr (CDCl$_3$): δ3.20 (2H, m), 4.10 (3H, m), 55.62 (1H, d), 7.55 (4H, m)

MS: m/e 277 (M$^+$)

PREPARATIVE EXAMPLE 46

Preparation of 3-hydroxy-1-(3-trifluoromethyl)phenyl-2-imidazolidinone

Step 1 Preparation of N-benzyloxy-N'-(3-trifluoromethyl)phenyl urea

O-Benzylhydroxylamine hydrochloride (1.71 g) was suspended in ethyl acetate, and the mixture was washed thoroughly with saturated aqueous sodium bicarbonate solution. the organic layer was dried (MgSO$_4$), and evaporated under reduced pressure to leave O-benzylhydroxylamine as an oil. This was added dropwise to 3-trifluoromethylphenyl isocyanate (2.00 g), and the mixture was left to stand for 1 hour. The mixture was then dissolved in ethyl acetate and washed with 2M hydrochloric acid. The organic layer was separated, dried (MgSO$_4$), and evaporated under reduced pressure to afford the product, yield 2.91 g.

$^1$H nmr (CDCl$_3$): δ4.90 (2H, s), 7.18–7.59 (11H, m)

Step 2 Preparation of 1-benzyloxy-3-(3-trifluoromethyl)phenyl-2-imidazolidinone

A stirred solution of N-benzyloxy-N'-(3-trifluoromethyl)phenyl urea (prepared as in Step 1 above) (0.815 g) in dimethylformamide (30 ml) was treated portionwise with sodium hydride (0.113 g of a 55% dipersion in mineral oil). The solution was stirred for 30 minutes, then 1,2-dibromoethane (0.494 g) was added. The mixture was stirred for a further 30 minutes, and was then treated portionwise with sodium hydride (0.113 g of a 55% dipersion in mineral oil). The mixture was stirred for a further 18 hours, then diethyl ether was added, and the mixture was washed thoroughly with water, dried (MgSO$_4$) and evaporated under reduced pressure. Purification by silica gel chromatography, eluting with ethyl acetate/hexane mixtures, afforded the title compound, yield 0.410 g.

$^1$H nmr (CDCl$_3$): δ3.43 (2H, t), 3.70 (2H, t), 5.05 (2H, s), 7.22–7.52 (7H, m), 7.74–7.89 (2H, m)

Step 3 Preparation of 3-hydroxy-1-(3-trifluoromethyl)phenyl-2-imidazolidinone

A stirred solution of 1-benzyloxy-3-(3-trifluoromethyl)phenyl-2-imidazolidinone (prepared as in Step 2 above) (0.223 g) in methanol (30 ml) was hydrogenated over a 5% palladium on carbon catalyst (0.025 g) for 1 hour. A further quantity (0.025 g) of the catalyst was then added, and the mixture was hydrogenated for a further 1 hour. The mixture was filtered through Hyflo, washing through with more methanol, and the combined filtrates were evaporated under reduced pressure to leave a gum. Purification by silica gel chromatography, eluting with ethyl acetate/hexane mixtures, afforded-the title compound, yield 0.049 g.

$^1$H nmr (CDCl$_3$): δ3.65–3.76 (2H, m), 3.76–3.87 (2H, m), 7.38 (1H, d), 7.48 (1H, t), 7.75 (1H, s), 7.80 (1H, d), 8.72 (1H, broad)

MS: m/e 246 (M$^+$)

PREPARATIVE EXAMPLE 47

Preparation of tetrahydro-3-hydroxy-1-(3-trifluoromethyl)phenyl-2-(1H)-pyrimidinone Step 1 Preparation of tetrahydro-1-benzyloxy-3-(3-trifluoromethyl)phenyl-2-(1H)-pyrimidinone By a procedure similar to that described in Preparative Example 46, Step 2 above, but using N-benzyloxy-N'-(3-trifluoromethyl)phenyl urea (prepared as in Preparative Example 46, Step 1 above) (0.714 g), dimethylformamide (30 ml), sodium hydride (0.100 g of a 55% dispersion in mineral oil), 1,3-dibromopropane (0.465 g) and a second quantity of sodium hydride (0.100 g of a 55% dispersion in mineral oil), and purification of the crude product by silica gel chromatography, eluting with ethyl acetate/hexane mixtures, the title compound was obtained, 0.510 g.

$^1$H nmr (CDCl$_3$): δ2.11 (2H, quin), 3.52 (2H, t), 3.63 (2H, t), 4.99 (2H,s), 7.30–7.58 (9H, m)

Step 2 Preparation of tetrahydro-3-hydroxy-1-(3-trifluoromethyl)phenyl-2-(1H)-pyrimidinone By a procedure similar to that described in Preparative Example 46, Step 3 above, but hydrogenating tetrahydro-1-benzyloxy-3-(3-trifluoromethyl)phenyl-2-(1H)-pyrimidinone (prepared as in Step 2 above) (0.075 g) over a 5% palladium on carbon catalyst (0.015 g) in methanol (5 ml), the title compound was obtained.

$^1$H nmr (CDCl$_3$): δ2.28 (2H, quin), 3.74 (4H, t), 7.40–7.53 (4H, m) (OH broad—not observed)

m/e 260 (M$^+$)

PREPARATIVE EXAMPLE 48

Preparation of 3-hydroxy-1-(3-trifluoromethyl)phenyl-2-piperidinone

Step 1 Preparation of N-(3-trifluoromethyl)phenyl-5-chlorovaleramide

5-Chlorovaleryl chloride (4.00 g) was added to 3-trifluoromethyl aniline (5.00 g). The resultant solid mass was dissolved in ethyl acetate, and the solution was washed with 2M hydrochloric acid, water and saturated sodium biocarbonate solution. The organic layer was dried (MgSO$_4$) and evaporated under reduced pressure to afford the product as an oil, yield 8.06 g.

$^1$H nmr (CDCl$_3$): δ1.78–1.95 (4H, m), 2.42 (2H, t), 3.55 (2H, t), 7.31–7.47 (2H, m), 7.59 (1H, broad s), 7.71 (1H, d), 7.82 (1H, s)

Step 2 Preparation of 1-(3-trifluoromethyl)phenyl-2-piperidinone

A solution of N-(3-trifluoromethyl)phenyl-5-chlorovaleramide (prepared as in Step 1 above) (7.91 g) in dimethylformamide (100 ml) was treated portionwise with sodium hydride (1.23 g of a 55% dispersion in mineral oil). The mixture was stirred at room temperature for 16 hours, then heated to 60° C. for a further 2 hours. The mixture was then cooled, diluted with diethyl ether, and extracted thoroughly with water, and the organic phase was then dried (MgSO$_4$). Evaporation of the solvent under reduced pressure afforded the product as a solid, yield 3.24 g.

$^1$H nmr (CDCl$_3$): δ1.88–2.03 (4H, m), 2.58 (2H, t), 3.67 (2H, t), 7.44–7.56 (4H, m)

Step 3 Preparation of 3-hydroxy-1-(3-trifluoromethyl)phenyl-2-piperidinone

A stirred solution of 1-(3-trifluoromethyl)phenyl-2-piperidinone (prepared as in Step 2 above) (1.03 g) in tetrahydrofuran (15 ml) was cooled to 0° C. under a nitrogen atmosphere, and a lithium hexamethyl disilazide (4.2 ml of a 1M solution in tetrahydrofuran) was added dropwise. The resultant orange solution was then treated with a solution of N-toluenesulphonyl-3-phenyloxaziridine (prepared as described in Journal of Organic Chemistry, 1988, 53, 2087) (1.16 g) in tetrahydrofuran (5 ml). The mixture was left to stand for 66 hours, then was diluted with water and extracted with diethyl ether. The ether extract was dried (MgSO$_4$), evaporated under reduced pressure, and the mixture was separated by silica gel chromatography, eluting with ethyl acetate/hexane mixtures, to afford the product, which was obtained as a 2:1 mixture with unreacted 1-(3-trifluoromethyl)phenyl-2-piperidinone, from which it could not be separated. This mixture was used directly in Example 91.

$^1$H nmr (CDCl$_3$): inter alia δ1.80–2.12 (3H, m), 2.43 (1H, m), 3.60–3.71 (2H, m), 3.79 (1H, m), 4.25 (1H, m), 7.42–7.58 (4H, m)

PREPARATIVE EXAMPLE 49

Preparation of dihydro-6-hydroxy-3-methyl-4-(3,5-bis(trifluoromethyl))phenyl-2H-1,3,4-thiadiazin-5-(6H)-one Step 1 Preparation of dihydro-4-(3,5-bis(trifluoromethyl)) phenyl-2H-1,3,4-thiadiazin-5-(6H)-one A stirred solution of 3,5-bis(trifluoromethyl)hydrazine (1.22 g) in toluene (20 ml) was treated dropwise with 37% aqueous formaldehyde (0.385 ml), then para-toluenesulphonic acid (2 mg) was added. The mixture was stirred for 10 minutes, then thioglycollic acid (0.46 g) was added, and the mixture was heated under reflux, and water was collected in a Dean and Stark apparatus. After 3.5 hours the mixture was cooled, diluted with ethyl acetate (30 ml), extracted with saturated aqueous sodium bicarbonate solution (2×50 ml), washed with water (30 ml), 2M hydrochloric acid (30 ml), dried (MgSO$_4$) and evaporated under reduced pressure to leave a pale yellow solid. Trituration with diethyl ether afforded the title compound, yield 0.821 g.

$^1$H nmr (CDCl$_3$): δ3.65 (2H, s), 4.57 (2H, s), 6.99 (1H, s), 7.05 (2H, s), 7.39 (1H, s)

Step 2 Preparation of dihydro-3-methyl-4-(3,5-bis (trifluoromethyl))phenyl-2H-1,3,4-thiadiazin-5-(6H)-one A solution of dihydro-4-(3,5-bis(trifluoromethyl))phenyl-2H-1,3,4-thiadiazin-5(6H)-one (prepared as in Step 1 above) (0.330 g) in tetrahydrofuran (2 ml) was added dropwise to a stirred slurry of sodium hydride (24 mg) in tetrahydrofuran (3 ml). After 15 minutes the red solution was treated with methyl iodide (0.142 g), and the mixture was stirred for 2 hours. A further quantity of methyl iodide (1.0 ml) was added, and the mixture was stirred for another 30 minutes before being diluted with diethyl ether (30 ml) and washed with water (30 ml). The organic layer was separated, dried (MgSO$_4$) and evaporated under reduced pressure to afford the title compound as a pale yellow solid, yield 0.321 g.

$^1$H nmr (CDCl$_3$): δ3.29 (3H, s), 3.59 (2H, s), 4.50 (2H, broad), 7.03 (2H, s), 7.37 (1H, s)

Step 3 Preparation of dihydro-6-hydroxy-3-methyl-4-(3,5-bis(trifluoromethyl)) phenyl-2H-1,3,4-thiadiazin-5(6H)-one A stirred solution of dihydro-3-methyl-4-(3,5-bis (trifluoromethyl))phenyl-2H-1,3,4-thiadiazin-5(6H)-one (prepared as in Step 2 above) (0.321 g) in dichloromethane (8 ml) was cooled in an ice bath. A stream of nitrogen was bubbled through the solution, and sulphuryl chloride (0.08 ml) was added. After the addition the solution was stirred with cooling for 10 minutes, allowed to warm to room temperature, and was then stirred for a further 30 minutes whilst maintaining the nitrogen flow. The solution was evaporated under reduced pressure, and the residue was dissolved in tetrahydrofuran (5 ml). This solution was treated with aqueous sodium bicarbonate solution (5 ml), and the mixture was stirred vigorously for 15 minutes, then left to stand for 16 hours. The mixture was extracted with ethyl acetate (2×30 ml), and the combined extracts were dried (MgSO$_4$). Evaporation of the solvent under reduced pressure left a gum, which was triturated with ethyl acetate/ hexane and filtered to remove a solid. The filtrate was evaporated under reduced pressure, and the residue was chromotographed on silica gel, eluting with hexane/ethyl acetate mixtures, to afford the title compound as a gum, yield 0.037 g.

$^1$H nmr (CDCl$_3$): δ3.30 (3H, s), 3.95 (1H, broad s), 4.39 (1H, broad d), 4.78 (1H, d) 5.55 (1H, s), 7.02 (2H, s), 7.36 (1H, s)

PREPARATIVE EXAMPLE 50

Preparation of dihydro-4-hydroxy-2-(3-trifluoromethyl)phenyl-2H-1,2-oxazin-3-(4H)-one Step 1 Preparation of N-(3-trifluoromethyl)phenyl hydroxylamine A solution of 3-nitro-(α,α,αtrifluorotoluene (4.95 g) in ethanol (100 ml) was stirred vigorously with an air-stirrer and treated successively with a solution of ammonium chloride (15.00 g) in water (50 ml), then zinc powder (12.00 g). After 5 minutes, when the exotherm had begun to subside, the mixture was filtered through Hyflo Super-cel, diluted with water (100 ml) and extracted with ethyl acetate (3×100 ml). The combined extracts were washed with brine, dried (MgSO$_4$), and evaporated under reduced pressure to give a yellow oil. This was chromatographed on silica gel, eluting with dichloromethane/ethyl acetate (19:1), to give the title compound, yield 3.75 g, mp 44°–45° C.

Step 2 Preparation of a mixture of dihydro-4-bromo-2-(3-trifluoromethyl)phenyl-2H-1,2-oxazin-3-(4H)-one and dihydro-4-chloro-2-(3-trifluoromethyl)phenyl-2H-1,2-oxazin-3-(4H)-one A solution of N-(3-trifluoromethyl)phenyl hydroxylamine (prepared as in Step 1 above) (3.60 g) and triethylamine (4.12 g) in dry tetrahydrofuran (10 ml) was added over 20 minutes to a stirred, ice-cooled solution of 2,4-dibromobutanoyl chloride (92% pure, prepared as described in Journal of Medicinal Chemistry, 1987, 30, 1995) (5.81 g) in dry tetrahydrofuran (10 ml). The mixture was stirred for a further 3 hours, filtered and the filtrate was evaporated under reduced pressure. The residue was diluted with ethyl acetate, washed with 2M sulphuric acid, water, aqueous sodium carbonate (×3) and brine, dried (MgSO$_4$) and evaporated under reduced pressure. The residue was chromatographed on silica gel, eluting with ethyl acetate/hexane (1:5), to give a 1:1 mixture of the title compounds as an orange oil, yield 1.42 g.

$^1$H nmr (CDCl$_3$): δ2.4–2.7 (1H, m), 2.8–3.0 (1H, 2m), 4.3–4.5 (2H, 2m), 4.8–4.9 (1H, 2m), 7.4–7.6 (2H, 2m)

Step 3 Preparation of dihydro-4-iodo-2-(3-trifluoromethyl) phenyl-2H-1,2-oxazin-3-(4H)-one A 1:1 mixture of dihydro-4-bromo-2-(3-trifluoromethyl) phenyl-2H-1,2-oxazin-3-(4H)-one and dihydro-4-chloro-2-(3-trifluoromethyl)phenyl-2H-1,2-oxazin-3-(4H)-one (prepared as in Step 2 above) (1.20 g), sodium iodide (1.11 g) and dry acetone (25 ml) was heated under reflux for 2 hours, allowed to cool, diluted with water and extracted with ethyl acetate (×3). the combined organic extracts were washed with brine, dried (MgSO$_4$) and evaporated to dryness under reduced pressure. The residue was shown to be 93% dihydro-4-iodo-2-(3-trifluoromethyl)phenyl-2H-1,2-oxazin-3-(4H)-one and 7% dihydro-4-chloro-2-(3-trifluoromethyl)phenyl-2H-1,2-oxazin-3-(4H)-one, yield 1.50 g.

$^1$H nmr (CDCl$_3$): inter alia δ2.86 (1H, m), 2.84 (1H, m), 4.33 (1H, m), 4.46 (1H, m), 4.88 (1H, t), 7.40–7.55 (2H, m), 7.92–8.00 (2H, d and s).

MS: m/e 371 (M$^+$)

Step 4 Preparation of dihydro-4-hydroxy-2-(3-trifluoromethyl)phenyl-2H-1,2-oxazin-3-(4H)-one A mixture of dihydro-4-iodo-2-(3-trifluoromethyl)phenyl-2H-1,2-oxazin-3-(4H)-one (prepared as in Step 3 above) (1.20 g) and bis(trifluoroacetoxy)iodobenzene (1.68 g) in dry dichloromethane (25 ml) was stirred for 24 hours. The mixture was then diluted with diethyl ether, washed with aqueous sodium bisulphite, aqueous sodium bicarbonate and brine, dried (MgSO$_4$) and evaporated under reduced pressure to give the triflouroacetate ester of the title compound. This was filtered through silica gel in dichloromethane/methanol (49:1) to generate the alcohol, then chromatographed on silica gel, eluting with ethyl acetate/hexane (1:3), to give the title compound as an oil, which crystallised on standing, yield 0.44 g, mp 45°–46° C.

$^1$H nmr (CDCl$_3$): δ1.97 (1H, m), 2.87 (1H, m), 3.55 (1H, d), 4.30 (1H, m), 4.45 (1H, m), 4.69 (1H, dt), 7.49 (2H, d+t), 8.00 (2H, s+d)

MS: m/e 261 (M$^+$)

PREPARATIVE EXAMPLE 51

Preparation of 5-hydroxy-3-(3-(N,N-dibenzyl) sulphonamino)phenyl-4 thiazolidinone.

Step 1 Preparation of 3-(N,N-dibenzylsulphonamino) nitrobenzene.

Dibenzylamine (10.9 ml) was dissolved in dry dichloromethane (40 ml) and stirred at 0° C. To this solution was added, portionwise, 3-nitrophenyl-sulphonylchloride (4.18 g) and the stirring was continued at 0° C. for 30 minutes. The cooling bath was then removed and the reaction mixture allowed to warm to room temperature over 2 hours. Water was then added and the product extracted into dichloromethane (3×). The combined organic layers were washed with 2M hydrochloric acid and brine and then dried (MgSO$_4$). The solvent was removed under reduced pressure to give a residue (11.60 g) which was chromatographed on silica gel using ethyl acetate-hexane (1:4) as eluant. The title compound (3.2 g) had:

$^1$H nmr (CDCl$_3$): δ4.42 (4H,s), 7.12 (4H,m), 7.24 (6H,m), 7.65 (1H,t), 8.06 (1H,d), 8.38 (1H,d), 8.51 (1H,s).

MS : 382 (M+)

Step 2 Preparation of 3-((N,N-dibenzyl)sulphonamido) aniline.

3-(Dibenzylsulphonamido)nitrobenzene (prepared as described in Step 1 above) iron (2.35 g), ammonium chloride (2.24 g), ethanol (140 ml) and water were mixed and then refluxed together for 1.5 hours. The reaction mixture was cooled to room temperature and then filtered through 'Celite'. The filtrate was mixed with water and the product extracted into dichloromethane (3×). The combined organic layers were dried (MgSO$_4$) and evaporated under reduced pressure to give a residue (3.022 g). The residue was chromatographed on silica gel using ethyl acetate-hexane (1:4 to 1:3) to give the title compound (2.47 g) which had:

$^1$H nmr (CDCl$_3$): δ3.90 (2H,broad s), 4.33 (4H,s), 6.85 (1H,dd), 7.15 (5H,m), 7.25 (8H,m).

MS: 352 (M+)

Step 3 Preparation of 3-(3-N,N-dibenzyl)sulphonamido) phenyl-4-thiazolidinone.

3-(Dibenzylsulphonamido)aniline (prepared as described in Step 3 above) (2.664 g) was converted to the title compound using toluene (20 ml), thiogylycollic acid (0.63 ml) and 37% aqueous formaldehyde solution (0.74 ml) by a procedure similar to that described in preparative example 25 Step 1. The solvent was removed under reduced pressure to give a gum which was taken up in dichloromethane and washed with 2M hydrochloric acid, saturated sodium bicarbonate solution and water. The solvent was dried (MgSO$_4$) and evaporated under reduced pressure to give an off-white solid (1.5 g), which was sufficiently pure for the next stage of the synthesis.

1H nmr (CDCl$_3$) δ: 3.75 (2H,s), 4.35 (4H,s), 4.75 (2H,s), 7.09 (4H,m), 7.23 (6H,m), 7.53 (1H,t), 7.69 (1H,d), 7.75 (1H,s), 7.82 (1H,d).

Step 4 Preparation of 5-chloro-3-(3-(N,N-dibenzyl) sulphonoamidophenyl)-4-thiazolidinone.

3-(Dibenzylsulphonamido)phenyl-4-thiazolidinone (prepared as described in Step 3 above) (1.5 g) was converted to the title compound by a procedure similar to that described in prepatative Example 25 Step 2 using dichloromethane (15 ml) and sulphonyl chloride (0.29 ml). The title compound was used immediately in Step 5.

Step 5 Preparation of 5-hydroxy-3-(dibenzylsulphonamido) phenyl-4-thiazolidinone.

5-Chloro-3-(3-(N,N-dibenzyl)sulphonamido)phenyl)-4-thiazolidinone (prepared as described in Step 4 above) was converted to the title compound by a procedure similar to that described in preparative Example 25 Step 3 using a mixture of tetrahydrofuran (10 ml) and saturated sodium bicarbonate solution (10 ml). The crude product (1.34 g) was purified on silica gel using ethyl acetate-hexane (55:45) as eluant to give the title compound as a brittle yellow foam (0.83 g) which had:

$^1$H nmr (CDCl$_3$): δ3.83 (1H,broad s), 4.35 (4H,s), 4.62 (1H,d), 4.93 (1H,d), 5.71 (1H,s), 7.09 (4H,m), 7.23 (6H,m), 7.54 (1H,t), 7.71 (1H,d), 7.80 (2H,m).

EXAMPLE 1

PREPARATION OF COMPOUND 1

5-t-butylcarbamoyloxy-3-(3,4-dichloro)phenyl-4-thiazolidinone

A stirred solution of 3-(3,4-dichloro)phenyl-5-hydroxy-4-thiazolidinone (prepared as in Preparative Example 1 above) (1.50 g) in dichloromethane (40 ml) was treated dropwise with tert-butyl isocyanate (0.56 g) and triethylamine (0.58 g). The solution was stirred for 6 hours, and then left to stand for a further 18 hours. The solution was then washed with 2M hydrochloric acid (30 ml), dried (MgSO$_4$), and the solvent was removed under reduced pressure to leave a pale yellow solid. Recrystallisation from chloroform/hexane afforded the title compound as a crystalline solid, yield 1.31 g, mp 133°–134° C.

$^1$H nmr (CDCl$_3$): δ1.32 (9H, s), 4.62 (1H, d), 4.89 (1H, broad s), 4.98 (1H, d), 6.18 (1H, s), 7.33–7.50 (2H, m), 7.68 (1H, s)

EXAMPLE 2

PREPARATION OF COMPOUND 5

5-i-propylcarbamoyloxy-3-(3-trifluoromethyl)phenyl-4-thiazolidinone

A stirred solution of 5-hydroxy-3-(3-trifluoromethyl) phenyl-4-thiazolidinone (prepared as in Preparative Example 2 above) (3.00 g) and triethylamine (0.1 ml) in chloroform (40 ml) was treated dropwise with a solution of iso-propyl isocyanate (1.08 g) in chloroform (10 ml). The mixture was stirred for 2 hours, then a further quantity of iso-propyl isocyanate (1 ml) was added. The mixture was stirred for a further 30 minutes, then evaporated under reduced pressure to leave a white solid. This was triturated with hexane, and recrystallised from ethyl acetate/hexane to give the title compound as a white crystalline solid, yield 2.88 g, mp 167–168° C.

$^1$H nmr (CDCl$_3$): δ1.19 (6H, d), 3.83 (1H, m), 4.69 (1H, d), 4.78 (1H, broad d), 5.07 (1H, d), 6.21 (1H, s), 7.51–7.62 (2H, m), 7.71–7.79 (2H, m)

EXAMPLE 3

PREPARATION OF COMPOUND 9

5-methylcarbamoyloxy-3-(3-trifluoromethyl)phenyl-4-thiazolidinone

By a procedure similar to that described in Example 2, but using 5-hydroxy-3-(3-trifluoromethyl)phenyl-4-thiazolidinone (prepared as in Preparative Example 2 above), methyl isocyanate and triethylamine, the title compound was obtained, mp 156° C.

EXAMPLE 4

PREPARATION OF COMPOUND 16

5-ethylcarbamoyloxy-3-(3-trifluoromethyl)phenyl-4-thiazolidinone

By a procedure similar to that described in Example 2, but using 5-hydroxy-3-(3-trifluoromethyl)phenyl-4-thiazolidinone (prepared as in Preparative Example 2 above) (1.00 g), ethyl isocyanate (0.25 ml), triethylamine (0.01 ml) and chloroform (5 ml), the title compound was obtained, mp 152°–153° C.

$^1$H nmr (CDCl$_3$): δ1.25 (3H, t), 3.36 (2H, m), 4.69 (1H, d), 4.89 (1H, broad t), 5.08 (1H, dd), 6.21 (1H, d), 7.51–7.59 (2H, m), 7.71–7.80 (2H, m)

EXAMPLE 5

PREPARATION OF COMPOUND 17

5-benzylcarbamoyloxy-3-(3-trifluoromethyl)phenyl-4-thiazolidinone

By a procedure similar to that described in Example 2, but using 5-hydroxy-3-(3-trifluoromethyl)phenyl-4-thiazolidinone (prepared as in Preparative Example 2 above) (0.90 g), benzyl isocyanate (0.46 g), triethylamine (0.01 ml) and chloroform (3 ml), the title compound was obtained, mp 153°–154° C.

$^1$H nmr (CDCl$_3$): δ4.39 (2H, d), 4.68 (1H, d), 5.07 (1H, dd), 5.25 (1H, broad t), 6.24 (1H, d), 7.23–7.38 (5H, m), 7.50–7.60 (2H, m), 7.70–7.79 (2H, m)

EXAMPLE 6

PREPARATION OF COMPOUND 20

5-phenylcarbamoyloxy-3-(3-trifluoromethyl)phenyl-4-thiazolidinone

By a procedure similar to that described in Example 2, but using 5-hydroxy-3-(3-trifluoromethyl)phenyl-4-thiazolidinone (prepared as in Preparative Example 2 above) (0.80 g), phenyl isocyanate (0.33 ml), triethylamine (0.01 ml) and chloroform (3 ml), the title compound was obtained, mp 192°–194° C.

$^1$H nmr (CDCl$_3$/d$_6$-DMSO): δ4.71 (1H, dd), 5.12 (1H, dd), 6.29 (1H, dd), 7.02 (1H,m), 7.20–7.31 (2H, m), 7.40–7.65 (4H, m), 7.72 (1H, m), 7.85 (1H, m), 9.01 (1H, broad s)

EXAMPLE 7

PREPARATION OF COMPOUND 26

5-t-butylcarbamoyloxy-3-(3-trifluoromethyl)phenyl-4-thiazolidinone

A stirred slurry of 5-hydroxy-3-(3-trifluoromethyl)phenyl-4-thiazolidinone (prepared as in Preparative Example 2 above) (0.84 g) in chloroform (5 ml) was treated with triethylamine (0.01 ml), then tert-butyl isocyanate (0.32 g). The resultant solution was stirred for 2 hours, then evaporated under reduced pressure. The solid residue was recrystallised from hexane to give the title compound as a white, crystalline compound, yield 0.90 g, mp 98°–99° C.

$^1$H nmr (CDCl$_3$): δ1.32 (9H, s), 4.69 (1H, d), 4.90 (1H, broad s), 5.04 (1H, d), 6.21 (1H, s), 7.52–7.59 (2H, m), 7.71–7.79 (2H, m)

MS: m/e 362 (M$^+$)

EXAMPLE 8

PREPARATION OF COMPOUND 30

5-i-propylcarbamoyloxy-3-(3,5-bis(trifluoromethyl))phenyl-4-thiazolidinone

By a procedure similar to that described in Example 2, but using 5-hydroxy-3-(3,5-bis(trifluoromethyl))phenyl-4-thiazolidinone (prepared as in Preparative Example 3 above) (1.50 g), iso-propyl isocyanate (0.39 g), triethylamine (0.01 ml) and chloroform (5 ml), and recrystallising the crude product from chloroform/hexane, the title compound was obtained as a white solid, yield 1.30 g, mp 141°–142° C.

$^1$H nmr (CDCl$_3$): δ1.19 (6H, d), 3.82 (1H, m), 4.72 (1H, d), 4.76 (1H, broad d), 5.13 (1H, d), 6.20 (1H, s), 7.78 (1H, s), 8.04 (2H, s)

EXAMPLE 9

PREPARATION OF COMPOUND 33

5-i-propylcarbamoyloxy-3-(4-trifluoromethyl)phenyl-4-thiazolidinone

By a procedure similar to that described in Example 2, but using 5-hydroxy-3-(4-trifluoromethyl)phenyl-4-thiazolidinone (prepared as in Preparative Example 4 above) (0.185 g), iso-propyl isocyanate (0.060 g), triethylamine (0.01 ml) and chloroform (5 ml), and recrystallising the crude product from chloroform/hexane, the title compound was obtained as a white solid, yield 0.180 g, mp 198° C.

$^1$H nmr (CDCl$_3$): δ1.19 (6H, d), 3.81 (1H, m), 4.69 (1H, d), 4.76 (1H, broad d), 5.09 (1H, d), 6.21 (1H, s), 7.63–7.71 (4H, m)

EXAMPLE 10

PREPARATION OF COMPOUND 35

5-t-butylcarbamoyloxy-3-(3-chloro)phenyl-4-thiazolidinone

A stirred suspension of 3-(3-chloro)phenyl-5-hydroxy-4-thiazolidinone (prepared as in Preparative Example 5 above) (16.60 g) in dichloromethane (100 ml) was treated with triethylamine (10 ml) followed by tert-butyl isocyanate (8.5 ml). The solution was stirred for 8 hours, then left to stand for 18 hours. The solution was washed with 2M hydrochloric acid (50 ml), then with brine, and was then dried (MgSO$_4$). Evaporation of the solvent under reduced pressure left a solid residue, which was recrystallised from carbon tetrachloride to give the title compound as a white solid, yield 21.20 g, mp 117°–118° C.

$^1$H nmr (CDCl$_3$): δ1.32 (9H, s), 4.76 (1H, d), 4.90 (1H, broad s), 4.98 (1H, d), 6.19 (1H, s), 7.20–7.40 (3H, m), 7.53 (1H, m)

EXAMPLE 11

PREPARATION OF COMPOUND 40

5-t-butylcarbamoyloxy-3-(3,5-dichloro)phenyl-4-thiazolidinone

By a procedure similar to that described in Example 10, but using 3-(3,5-dichloro)phenyl-5-hydroxy-4-thiazolidinone (prepared as in Preparative Example 6 above) (14.30 g), tert-butyl isocyanate (7.0 ml), triethylamine (7.6 ml) and chloroform as the solvent (100 ml), and recrystallising the crude product from carbon tetrachloride, the title compound was obtained as a white solid, yield 17.00 g, mp 150°–152° C.

$^1$H nmr (CDCl$_3$): δ1.32 (9H, s), 4.61 (1H, d), 4.88 (1H, broad s), 4.99 (1H, d), 6.14 (1H, s), 7.25 (1H, t), 7.47 (2H, d)

EXAMPLE 12

PREPARATION OF COMPOUND 44

3-(3-chloro-4-fluoro)phenyl-5-i-propylcarbamoyloxy-4-thiazolidinone

By a procedure similar to that described in Example 10, but using 3-(3-chloro-4-fluoro)phenyl-5-hydroxy-4-thiazolidinone (prepared as in Preparative Example 7 above) (2.50 g), iso-propyl isocyanate (0.86 g), triethylamine (1.3 ml) and dichloromethane (25 ml), and recrystallising the crude product from chloroform, the title compound was obtained as a white solid, yield 3.20 g, mp 190°–191° C.

$^1$H nmr (CDCl$_3$): δ1.18 (6H, d), 3.83 (1H, m), 4.61 (1H, d), 4.78 (1H, broad d), 4.99 (1H, d), 6.18 (1H, s), 7.20 (1H, m), 7.36 (1H, m), 7.60 (1H, m)

EXAMPLE 13

PREPARATION OF COMPOUND 45

5-t-butylcarbamoyloxy-3-(3-chloro-4-fluoro)phenyl-4-thiazolidinone

By a procedure similar to that described in Example 10, but using 3-(3-chloro-4-fluoro)phenyl-5-hydroxy-4-thiazolidinone (prepared as in Preparative Example 7 above) (2.50 g), tert-butyl isocyanate (1.00 g), triethylamine (1.3 ml) and dichloromethane (25 ml), and recrystallising the crude product from toluene/hexane, the title compound was obtained as a white solid, yield 2.60 g, mp 130°–133° C.

$^1$H nmr (CDCl$_3$): δ1.32 (9H, s), 4.61 (1H, d), 4.89 (1H, broad s), 4.95 (1H, d), 6.18 (1H, s), 7.21 (1H, m), 7.36 (1H, m), 7.60 (1H, m)

EXAMPLE 14

PREPARATION OF COMPOUND 48

5-t-butylcarbamoyloxy-3-(2-chloro)phenyl-4-thiazolidinone

By a procedure similar to that described in Example 10, but using 3-(2-chloro)phenyl-5-hydroxy-4-thiazolidinone (prepared as in Preparative Example 8 above) (2.74 g), tert-butyl isocyanate (1.20 g), triethylamine (1.6 ml) and dichloromethane (20 ml), the title compound was obtained as a gum.

$^1$H nmr (CDCl$_3$): δ1.31 (9H, s), 4.65 (1H, d), 4.82 (1H, d), 4.91 (1H, broad s), 6.21 (1H, s), 7.33–7.42 (3H, m), 7.51 (1H, m)

EXAMPLE 15

PREPARATION OF COMPOUND 52

5-t-butylcarbamoyloxy-3-(4-methoxy)phenyl-4-thiazolidinone

By a procedure similar to that described in Example 10, but using 5-hydroxy-3-(4-methoxy)phenyl-4-thiazolidinone (prepared as in Preparative Example 9 above) (1.60 g), tert-butyl isocyanate (0.70 g), triethylamine (0.94 ml) and dichloromethane (25 ml), and trituration of the crude product with diethyl ether, the title compound was obtained as a white solid, yield 1.90 g, mp 127°–129° C.

$^1$H nmr (CDCl$_3$): δ1.32 (9H, s), 3.80 (3H, s), 4.62 (1H, d), 4.89 (1H, broad s), 4.92 (1H, d), 6.20 (1H, s), 6.95 (2H, m), 7.33 (2H, m)

EXAMPLE 16

PREPARATION OF COMPOUND 56

5-t-butylcarbamoyloxy-3-(2,3-dichloro)phenyl-4-thiazolidinone

By a procedure similar to that described in Example 10, but using 3-(2,3-dichloro)phenyl-5-hydroxy-4-thiazolidinone (prepared as in Preparative Example 10 above) (0.50 g), tert-butyl isocyanate (0.19 g), triethylamine (0.26 ml) and dichloromethane (15 ml), and trituration of the crude product with hexane, the title compound was obtained as a white solid, yield 0.58 g, mp 145°–147° C.

$^1$H nmr (CDCl$_3$): δ1.32 (9H, s), 4.63 (1H, d), 4.82 (1H, d), 4.93 (1H, broad s), 6.19 (1H, s), 7.21–7.36 (2H, m), 7.53 (1H, m)

EXAMPLE 17

PREPARATION OF COMPOUND 59

5-i-propylcarbamoyloxy-3-(3,5-dichloro)phenyl-4-thiazolidinone

By a procedure similar to that described in Example 10, but using 3-(3,5-dichloro)phenyl-5-hydroxy-4-thiazolidinone (prepared as in Preparative Example 6 above), iso-propyl isocyanate, and triethylamine, the title compound was obtained, mp 195°–198° C.

EXAMPLE 18

PREPARATION OF COMPOUND 61

3-(2-chloro)phenyl-5-i-propylcarbamoyloxy-4-thiazolidinone

By a procedure similar to that described in Example 10, but using 3-(2-chloro)phenyl-5-hydroxy-4-thiazolidinone (prepared as in Preparative Example 8 above), iso-propyl isocyanate, and triethylamine, the title compound was obtained.

$^1$H nmr (CDCl$_3$): δ1.19 (3H, d), 1.20 (3H, d), 3.87 (1H, m), 4.58 (1H, d), 4.83 (1H, broad), 4.86 (1H, dd), 6.12 (1H, d), 7.33–7.41 (3H, m), 7.51 (1H, m)

EXAMPLE 19

PREPARATION OF COMPOUND 62

5-cyclohexylcarbamoyloxy-3-(3-trifluoromethyl)phenyl-4-thiazolidinone

By a procedure similar to that described in Example 10, but using 5-hydroxy-3-(3-trifluoromethyl)phenyl-4-thiazolidinone (prepared as in Preparative Example 2 above) (0.53 g), cyclohexyl isocyanate (0.25 g), triethylamine (0.28 ml) and dichloromethane (10 ml), and recrystallising the crude product from ethyl acetate/hexane, the title compound was obtained as a white, crystalline solid, yield 0.52 g, mp 183°–185° C.

$^1$H nmr (CDCl$_3$): δ1.05–1.45 (5H, m), 1.52–1.78 (3H, m), 1.87–2.00 (2H, m), 3.50 (1H, m), 4.69 (1H, d), 4.78 (1H broad d), 5.07 (1H, d), 6.19 (1H, s), 7.49–7.61 (2H, m), 7.71–7.80 (2H, m)

EXAMPLE 20

PREPARATION OF COMPOUND 66

5-(1-methylcyclopropyl)carbamoyloxy-3-(3-trifluoromethyl)phenyl-4-thiazolidinone A stirred solution of 1-methylcyclopropane-1-carboxylic acid (0.057 g) and diphenyl phosphoryl azide (0.165 g) in toluene (15 ml) was treated with triethylamine (0.079 ml). The mixture was stirred for 1 hour, then 5-hydroxy-3-(3-trifluoromethyl)phenyl-4-thiazolidinone (prepared as in Preparative Example 2 above) (0.150 g) was added, and the mixture was heated under reflux for 3 hours. The mixture was cooled, extracted with 2M hydrochloric acid, dried (MgSO$_4$) and evaporated under reduced pressure to leave a gum. The crude product was separated from this by silica gel chromatography, eluting with ethyl acetate/hexane mixtures. This was dissolved in ethyl acetate, washed with saturated sodium carbonate solution, dried (MgSO$_4$) and evaporated under reduced pressure, affording the pure title compound as a white solid, yield 0.016 g, mp 203°–206° C.

$^1$H nmr (CDCl$_3$): δ0.60–0.67 (2H, m), 0.77–0.84 (2H, m), 1.38 (3H, s), 4.70 (1H, d), 5.07 (1H, d), 5.25 (1H, broad s), 6.20 (1H, s), 7.50–7.60 (2H, m), 7.69–7.80 (2H, m)

EXAMPLE 21

PREPARATION OF COMPOUND 69

5-(α,αdimethylbenzyl)carbamoyloxy-3-(3-trifluoromethyl)phenyl-4-thiazolidinone

By a procedure similar to that described in Example 10, but using 5-hydroxy-3-(3-trifluoromethyl)phenyl-4-thiazolidinone (prepared as in Preparative Example 2 above) (0.53 g), α,αdimethylbenzyl isocyanate (0.26 g), triethylamine (0.28 ml) and dichloromethane (10 ml), and purification of the crude product by silica gel chromatography eluting with ethyl acetate/hexane followed by crystallisation from chloroform/hexane, the title compound was obtained as a white, crystalline solid, yield 0.42 g, mp 100°–101° C.

$^1$H nmr (CDCl$_3$): δ1.69 (6H, s), 4.68 (1H, d), 5.02 (1H, d), 5.30 (1H, broad s), 6.18 (1H, s), 7.18–7.42 (5H, m), 7.48–7.58 (2H, m), 7.61–7.78 (2H, m)

EXAMPLE 22

PREPARATION OF COMPOUND 77

5-t-butylcarbamoyloxy-3-(4-methyl)phenyl-4-thiazolidinone

By a procedure similar to that described in Example 10, but using 5-hydroxy-3-(4-methyl)phenyl-4-thiazolidinone (prepared as in Preparative Example 11 above) (2.00 g), tert-butyl isocyanate (0.95 g), triethylamine (1.3 ml) and dichloromethane (25 ml), and recrystallisation of the crude product from chloroform/hexane, the title compound was obtained as a white, crystalline solid, yield 1.90 g, mp 142°–143° C.

$^1$H nmr (CDCl$_3$): δ1.31 (9H, s), 2.38 (3H, s), 4.63 (1H, d), 4.89 (1H, broad s), 4.94 (1H, d), 6.20 (1H, s), 7.18–7.26 (2H, m), 7.29–7.35 (2H, m)

EXAMPLE 23

PREPARATION OF COMPOUND 84

5-t-butylcarbamoyloxy-3-(4-chloro)phenyl-4-thiazolidinone

By a procedure similar to that described in Example 10, but using 3-(4-chloro)phenyl-5-hydroxy-4-thiazolidinone (prepared as in Preparative Example 12 above) (2.00 g), tert-butyl isocyanate (0.86 g), triethylamine (1.15 ml) and dichloromethane (25 ml), and recrystallisation of the crude product from chloroform/hexane, the title compound was obtained as a white, crystalline solid, yield 2.80 g, mp 152°–153° C.

$^1$H nmr (CDCl$_3$): δ1.31 (9H, s), 4.62 (1H, d), 4.88 (1H, broad s), 4.98 (1H, d), 6.19 (1H, s), 7.35–7.49 (4H, m)

EXAMPLE 24

PREPARATION OF COMPOUND 91

5-t-butylcarbamoyloxy-3-(2,5-dichloro)phenyl-4-thiazolidinone

By a procedure similar to that described in Example 10, but using 3-(2,5-dichloro)phenyl-5-hydroxy-4-thiazolidinone (prepared as in Preparative Example 13 above) (0.36 g), tert-butyl isocyanate (0.14 g), triethylamine (0.19 ml) and dichloromethane (15 ml), and trituration of the crude product with diethyl ether/hexane, the title compound was obtained as a white, crystalline solid, yield 0.25 g, mp 146°–147° C.

$^1$H nmr (CDCl$_3$): δ1.34 (9H, s), 4.55 (1H, d), 4.82 (1H, d), 4.90 (1H, broad s), 6.19 (1H, s), 7.31–7.48 (3H, m)

EXAMPLE 25

PREPARATION OF COMPOUND NO. 890

4-t-butylcarbamoyloxy-2-(3-trifluoromethyl)phenyl-3-isoxazolidinone.

A solution of 4-hydroxy-2-(3-trifluoromethyl)phenyl-3-isoxazolidinone (0.05 g, prepared as described in Preparative Example 14 and containing toluene p-sulphonamide), t-butylisocyanate (0.042 g) and triethylamine (0.043 g) in dichloromethane (2 ml) was allowed to stand overnight at room temperature. Further aliquots of isocyanate and triethylamine were added and, after a further four hours, the mixture was evaporated under reduced pressure. The residue was dissolved in ethyl acetate, washed with water and brine, dried over magnesium sulphate and evaporated under reduced pressure. Chromatography on silica, using hexane-ethyl acetate (3:1) gave product (0.02 g) free of toluene p-sulphonamide but contaminated with N,N'-di-t-butyl urea. 1H nmr (CDCl$_3$), title compound signals only: δ1.35 (9H,s), 4.4 (1H,dd), 4.85 (1H,dd), 5.0 (1H,bs), 5.6 (1H,t), 7.5 (2H,m), 8.0 (2H,m).

M/S: 346 M+

EXAMPLE 26

PREPARATION OF COMPOUND 100

5-t-butylcarbamoyloxy-3-(2-fluoro-5-trifluoromethyl)phenyl-4-thiazolidinone

By a procedure similar to that described in Example 10, but using 3-(2-fluoro-5-trifluoromethyl)phenyl-5-hydroxy-4-thiazolidinone (prepared as in Preparative Example 15 above) (1.40 g), tert-butyl isocyanate (0.5 g), triethylamine (0.70 ml) and dichloromethane (10 ml), and silica gel chromatography of the crude product, eluting with ethyl acetate/hexane, the title compound was obtained as a clear glass, yield 1.90 g.

$^1$H nmr (CDCl$_3$): δ1.32 (9H, s), 4.60 (1H, d), 4.91 (2H, d+broad s), 6.19 (1H, s), 7.34 (1H, m), 7.60–7.75 (2H, m)

EXAMPLE 27

PREPARATION OF COMPOUNDS 107 and 108

5-t-butylcarbamoyloxy-3-(3-trifluoromethyl)phenyl-4-thiazolidinone-S,S-dioxide and 5-t-butylcarbamoyloxy-3-(3-trifluoromethyl)phenyl-4-thiazolidinone-S-oxide A stirred solution of Compound 26 (3.62 g) in dichloromethane (70 ml) was treated portionwise with solid 50–60% m-chloroperbenzoic acid (3.10 g) over 1 hour. The resultant suspension was extracted with saturated aqueous sodium bicarbonate, and the organic layer was dried (MgSO$_4$) and evaporated under reduced pressure to leave a white foam. Silica gel chromatography, eluting with ethyl acetate/hexane mixtures, afforded firstly Compound 107, 5-t-butylcarbamoyloxy-3-(3-trifluoromethyl)phenyl-4-thiazolidinone-S,S-dioxide, as a white solid, yield 1.20 g, mp 181°–184° C.;

$^1$H nmr (CDCl$_3$): δ1.33 (9H, s), 4.98 (1H, d), 5.04 (1H, d), 5.71 (1H, s), 5.96 (1H, broad s), 7.55–7.66 (3H, m), 7.75 (1H, m)

followed by Compound 108, 5-t-butylcarbamoyloxy-3-(3-trifluoromethyl)phenyl-4-thiazolidinone-S-oxide, yield 2.70 g, which was obtained as a 3:1 mixture of diastereoisomers.

$^1$H nmr (CDCl$_3$): major diastereoisomer δ1.36 (9H, s), 4.69 (1H, d), 4.99 (1H, d), 5.59 (1H, broad s), 6.18 (1H, s), 7.49–7.59 (2H, m), 7.62–7.78 (2H, m); minor diastereoisomer δ1.30 (9H, s), 4.59 (1H, d), 5.31 (1H, d), 5.35 (1H, broad s), 5.44 (1H, s), 7.55–7.66 (3H, m), 7.75 (1H, m)

EXAMPLE 28

PREPARATION OF COMPOUND 112

5-t-butylcarbamoyloxy-3-(3-chloro-4-methyl)phenyl-4-thiazolidinone

By a procedure similar to that described in Example 10, but using 3-(3-chloro-4-methyl)phenyl-5-hydroxy-4-thiazolidinone (prepared as in Preparative Example 16 above) (2.44 g), tert-butyl isocyanate (1.0 g), triethylamine (1.4 ml) and dichloromethane (25 ml), and recrystallisation of the crude product from ethyl acetate/hexane, the title compound was obtained as a white solid, yield 2.80 g, mp 144°–147° C.

$^1$H nmr (CDCl$_3$): δ1.32 (9H, s), 4.62 (1H, d), 4.90 (1H, broad s), 4.95 (1H, d), 6.19 (1H, s), 7.22–7.30 (2H, m), 7.50 (1H, s)

EXAMPLE 29

PREPARATION OF COMPOUND 119

5-(N-(1,1-dimethyl)propyl)carbamoyloxy-3-(3-trifluoromethyl)phenyl-4-thiazolidinone A stirred solution of 5-hydroxy-3-(3-trifluoromethyl)phenyl-4-thiazolidinone (prepared as in Preparative Example 2 above) (0.56 g) in dichloromethane (10 ml) was cooled in an ice bath and treated dropwise with tetrachlorethyl chloroformate (0.62 g) followed by pyridine (0.20 g). The mixture was stirred for a further 2 hours, treated with 1,1-dimethyl-1-propylamine (0.44 g), then allowed to stand for 65 hours. The solution was washed with 2M hydrochloric acid (2×20 ml), dried (MgSO$_4$), and evaporated under reduced pressure to leave a gum. Silica gel chromatography, eluting with ethyl acetate/hexane, afforded the crude product as a solid, which was triturated twice with diethyl ether to afford the title compound as a white solid, yield 0.14 g.

$^1$H nmr (CDCl$_3$): δ0.89 (3H, t), 1.28 (6H, s), 1.67 (2H, m), 4.68 (1H, d), 4.82 (1H, broad s), 5.04 (1H, d), 6.19 (1H, s), 7.49–7.58 (2H, m), 7.68–7.79 (2H, m)

EXAMPLE 30

PREPARATION OF COMPOUND 122

5-(N,N-diethyl)carbamoyloxy-3-(3-trifluoromethyl)phenyl-4-thiazolidinone

By a procedure similar to that described in Example 29, but using 5-hydroxy-3-(3-trifluoromethyl)phenyl-4-thiazolidinone (prepared as in Preparative Example 2 above) (0.30 g), tetrachlorethyl chloroformate (0.31 g), pyridine (0.13 ml) and diethylamine (0.10 g), and silica gel chromatography of the crude product (eluting with ethyl acetate/hexane), the title compound was obtained, yield 0.10 g.

$^1$H nmr (CDCl$_3$): δ1.14 (6H, t), 3.20–3.45 (4H, m), 4.68 (1H, d), 5.12 (1H, dd), 6.21 (1H, d), 7.49–7.61 (2H, m), 7.68–7.85 (2H, m)

EXAMPLE 33

PREPARATION OF COMPOUNDS 133 and 134

5-i-propylcarbamoyloxy-3-(3-trifluoromethyl)phenyl-4-thiazolidinone-S,S-dioxide and 5-i-propylcarbamoyloxy-3-(3-trifluoromethyl)phenyl-4-thiazolidinone-S-oxide By a procedure similar to that described in Example 27, but using Compound 5 instead of Compound 26, Compound 133 (5-i-propylcarbamoyloxy-3-(3-trifluoromethyl)phenyl-4-thiazolidinone-S,S-dioxide):

$^1$H nmr (CDCl$_3$/d$_6$DMSO): δ1.06 (6H, d), 3.56 (1H, m), 5.29 (1H, d), 5.43 (1H, d), 6.36 (1H, s), 7.30–8.10 (5H, m)

and Compound 134 (5-i-propylcarbamoyloxy-3-(3-trifluoromethyl)phenyl-4-thiazolidinone-S-oxide):

$^1$H nmr (CDCl$_3$/d$_6$DMSO): δ1.19 (6H, 2d), 3.76 (1H, m), 4.82 (1H, d), 5.27 (1H, d), 6.51 (1H, s), 7.53–7.69 (2H, m), 7.75–7.89 (2H, m), 7.95 (1H, m) were obtained.

EXAMPLE 34

PREPARATION OF COMPOUND 138

5-t-butylcarbamoyloxy-3-(3,5-bis(trifluoromethyl))phenyl-4-thiazolidinone

By a procedure similar to that described in Example 10, but using 5-hydroxy-3-(3,5-bis(trifluoromethyl))phenyl-4-thiazolidinone (prepared as in Preparative Example 3 above) (1.70 g), tert-butyl isocyanate (0.51 g), triethylamine (0.7 ml) and dichloromethane (10 ml), and recrystallisation of the crude product from carbon tetrachloride, the title compound was obtained as a white solid, yield 1.90 g, mp 147°–148° C.

$^1$H nmr (CDCl$_3$): δ1.33 (9H, s), 4.74 (1H, d), 4.88 (1H, broad s), 5.11 (1H, d), 6.20 (1H, s), 7.78 (1H, s), 8.05 (2H, s)

EXAMPLE 35

PREPARATION OF COMPOUND 146

5-(N,N-dimethyl)carbamoyloxy-3-(3,5-bis (trifluoromethyl))phenyl-4-thiazolidinone A stirred solution of 5-hydroxy-3-(3,5-bis (trifluoromethyl))phenyl-4-thiazolidinone (prepared as in Preparative Example 3 above) (1.55 g) and triethylamine (0.68 ml) in dichloromethane (10 ml) was treated with dimethylcarbamoyl chloride (0.50 g). The mixture was stirred for 24 hours, then evaporated under reduced pressure. The residue was triturated with dichloromethane/hexane, and a solid was filtered off. Evaporation of the filtrate under reduced pressure left an oil, which was separated by silica gel chromatography (eluting with chloroform/methanol) to afford the title compound as a gum, yield 0.41 g.

$^1$H nmr (CDCl$_3$): δ2.95 (6H, s), 4.71 (1H, d), 5.17 (1H, d), 6.19 (1H, s), 7.77 (1H, s), 8.07 (2H, s)

EXAMPLE 36

PREPARATION OF COMPOUND 159

5-(N,N-dimethyl)carbamoyloxy-3-(3-trifluoromethyl) phenyl-4-thiazolidinone

A stirred solution of 5-hydroxy-3-(3-trifluoromethyl) phenyl-4-thiazolidinone (prepared as in Preparative Example 2 above) (1.00 g) in pyridine (2 ml) was treated with dimethylcarbamoyl chloride (0.48 g). After 20 minutes, water was added, and the mixture was extracted with diethyl ether. The ether layer was separated, washed with 2M hydrochloric acid and brine, then dried (MgSO$_4$). Evaporation of the solvent under reduced pressure left a gum, which was separated by silica gel chromatography (eluting with chloroform/methanol) to afford the crude product as a yellow solid. Trituration with diethyl ether/hexane afforded the title compound as a pale yellow solid, yield 0.60 g, mp 67°–69° C.

$^1$H nmr (CDCl$_3$): δ2.94 (6H, s), 4.68 (1H, d), 5.10 (1H, dd), 6.21 (1H, d), 7.50–7.60 (2H, m), 7.72–7.81 (2H, m)

EXAMPLE 37

PREPARATION OF COMPOUND 166

5-i-propylcarbamoyloxy-3-phenyl-4-thiazolidinone

A stirred solution of 5-hydroxy-3-phenyl-4-thiazolidinone (prepared as in Preparative Example 17 above) (0.24 g) and triethylamine (0.01 ml) in chloroform (5 ml) was treated with iso-propyl isocyanate (0.116 g). The mixture was stirred for 4 hours, then evaporated under reduced pressure. Recrystallisation of the solid residue from diethyl ether/hexane afforded the title compound as colourless needles, yield 0.14 g, mp 130°–132° C.

$^1$H nmr (CDCl$_3$): δ1.18 (6H, d), 3.82 (1H, m), 4.66 (1H, d), 4.75 (1H, broad d), 5.02 (1H, dd), 6.22 (1H, d), 7.29 (1H, m), 7.39–7.51 (4H, m)

EXAMPLE 38

PREPARATION OF COMPOUND 171

5-(N-(1,1-dimethyl)-2-propynyl)carbamoyloxy-3-(3-trifluoromethyl)phenyl-4-thiazolidinone A stirred solution of phosgene in toluene (1.93M; 7.25 ml) was cooled in an ice bath, and simultaneously treated with solutions of 1-amino-1,1-dimethyl-2-propyne (1.00 g) in diethyl ether (5 ml) and sodium hydroxide (1.15 g) in water (4 ml). The mixture was stirred vigorously for 20 minutes, with cooling, then the organic layer was separated and passed through phase separating paper to dry it. An infrared spectrum showed the presence of an isocyanate in the solution (2200 cm$^{-1}$). 5-Hydroxy-3-(3-trifluoromethyl) phenyl-4-thiazolidinone (prepared as in Preparative Example 2 above) (0.10 g) and triethylamine (1.0 ml) were added to this solution, and the mixture was allowed to stand for 18 hours, before being evaporated to dryness under reduced pressure. The residue was triturated with ethyl acetate/hexane and a solid was filtered off. The filtrate was evaporated under reduced pressure, and the residual mixture was separated by silica gel chromatography (eluting with ethyl acetate/hexane), to afford the title compound as a white solid, yield 0.10 g, mp 97°–99° C.

$^1$H nmr (CDCl$_3$): δ1.63 (6H, s), 1.37 (1H, s), 4.69 (1H, d), 5.05 (1H, d), 5.21 (1H, broad s), 6.24 (1H, s), 7.51–7.60 (2H, m), 7.70–7.78 (2H, m)

EXAMPLE 39

PREPARATION OF COMPOUND 174

5-(N-(1-cyano-1-methyl)ethyl)carbamoyloxy-3-(3-trifluoromethyl)phenyl-4-thiazolidinone By a procedure similar to that described in Example 38, but using alpha-amino isobutyronitrile (1.00 g) instead of 1-amino-1,1-dimethyl-2-propyne, the title compound was obtained as a white solid, yield 0.08 g, mp 119°–122° C.

$^1$H nmr (CDCl$_3$): δ1.70 (6H, s), 4.71 (1H, d), 5.09 (1H, d), 5.37 (1H, broad s), 6.27 (1H, s), 7.51–7.62 (2H, m), 7.68–7.79 (2H, m)

MS: m/e 373 (M$^+$)

EXAMPLE 40

PREPARATION OF COMPOUND 178

5-(N-(1-cyano)cyclopentyl)carbamoyloxy-3-(3-trifluoromethyl)phenyl-4-thiazolidinone By a procedure similar to that described in Example 38, but using 1-amino-1-cyano cyclopentane (1.00 g) instead of 1-amino-1,1-dimethyl-2-propyne, the title compound was obtained, yield 0.18 g.

$^1$H nmr (CDCl$_3$): δ1.75–1.92 (4H, m), 2.02–2.18 (2H, m), 2.27–2.43 (2H, m), 4.69 (1H, d), 5.09 (1H, m), 5.24 (1H, broad s), 6.26 (1H, s), 7.52–7.61 (2H, m), 7.68–7.78 (2H, m)

EXAMPLE 41

PREPARATION OF COMPOUND 197

3-(4-fluoro-3-trifluoromethyl)phenyl-5-i-propylcarbamoyloxy-4-thiazolidinone

By a procedure similar to that described in Example 10, but using 3-(4-fluoro-3-trifluoromethyl)phenyl-5-hydroxy-4-thiazolidinone (prepared as in Preparative Example 18 above) (2.00 g), iso-propyl isocyanate (0.64 g), triethylamine (1.0 ml) and dichloromethane (25 ml), and recrystallisation of the crude product from carbon tetrachloride/chloroform, the title compound was obtained as colourless crystals, yield 2.15 g, mp 186°–188° C.

$^1$H nmr (CDCl$_3$): δ1.19 (6H, d), 3.82 (1H, m), 4.61 (1H, d), 4.73 (1H, broad d), 5.01 (1H, d), 6.17 (1H, s), 7.27 (1H, m), 7.68–7.76 (2H, m)

EXAMPLE 42

PREPARATION OF COMPOUND 206

5-t-butylcarbamoyloxy-3-(4-fluoro-3-trifluoromethyl)phenyl-4-thiazolidinone

By a procedure similar to that described in Example 10, but using 3-(4-fluoro-3-trifluoromethyl)phenyl-5-hydroxy-4-thiazolidinone (prepared as in Preparative Example 18 above) (2.00 g), tert-butyl isocyanate (0.75 g), triethylamine (1.0 ml) and dichloromethane (25 ml), and recrystallisation of the crude product from carbon tetrachloride/hexane, the title compound was obtained as white crystals, yield 2.20 g, mp 116°–118° C.

$^1$H nmr (CDCl$_3$): δ1.34 (9H, s), 4.65 (1H, d), 4.88 (1H, broad s), 4.99 (1H, d), 6.18 (1H, s), 7.28 (1H, m), 7.65–7.76 (2H, m)

EXAMPLE 43

PREPARATION OF COMPOUND 211

3-(3-pentafluorosulphanyl)phenyl-5-i-propylcarbamoyloxy-4-thiazolidinone

By a procedure similar to that described in Example 10, but using 3-(3-pentafluorosulphanyl)phenyl-5-hydroxy-4-thiazolidinone (prepared as in Preparative Example 19 above) (0.42 g), iso-propyl isocyanate (0.15 g), triethylamine (0.1 ml) and dichloromethane (10 ml), and trituration of the crude product with diethyl ether, the title compound was obtained as a white crystaline solid, yield 0.36 g, mp 171°–173° C.

$^1$H nmr (CDCl$_3$): δ1.19 (6H, d), 3.83 (1H, m), 4.70 (1H, d), 4.74 (1H, broad d), 5.07 (1H, d), 6.20 (1H, s), 7.55 (1H, m), 7.63–7.73 (2H, m), 7.91 (1H, m)

EXAMPLE 44

PREPARATION OF COMPOUND 216

5-t-butylcarbamoyloxy-3-(3-pentafluorosulphanyl)phenyl-4-thiazolidinone

By a procedure similar to that described in Example 10, but using 3-(3-pentafluorosulphanyl)phenyl-5-hydroxy-4-thiazolidinone (prepared as in Preparative Example 19 above) (0.42 g), tert-butyl isocyanate (0.16 g), triethylamine (0.1 ml) and dichloromethane (10 ml), and recrystallisation of the crude product from ethyl acetate/hexane, the title compound was obtained as a white crystaline solid, yield 0.34 g, mp 131°–133° C.

$^1$H nmr (CDCl$_3$): δ1.31 (9H, s), 4.69 (1H, d), 4.86 (1H, broad s), 5.04 (1H, d), 6.20 (1H, s), 7.55 (1H, m), 7.64–7.72 (2H, m), 7.92 (1H, m)

EXAMPLE 45

PREPARATION OF COMPOUND 220

3-(3-trifluoromethyl)phenyl-5-(N-(1,1-dimethyl)-2-butynyl)carbamoyloxy-4-thiazolidinone A stirred suspension of 1-amino-1,1-dimethyl-2-butyne hydrochloride (0.84 g) in a solution of phosgene in toluene (12.5% w/v; 10 ml) was treated with triethylamine (1.83 ml), and the resulting mixture was heated under reflux for 2 hours, then cooled. A solution of 5-hydroxy-3-(3-trifluoromethyl)phenyl-4-thiazolidinone (prepared as in Preparative Example 2 above) (1.65 g) in toluene (54 ml) was added, and the mixture was stirred at room temperature for 3 days. The solution was extracted with water, then dried (MgSO$_4$) and evaporated under reduced pressure. Silica gel chromatography, eluting with diethyl ether/hexane, followed by crystallisation from hexane afforded the title compound as a white, crystalline solid, yield 0.07 g.

$^1$H nmr (CDCl$_3$): δ1.58 (6H, s), 1.80 (3H, s), 4.69 (1H, d), 5.06 (1H, d), 5.13 (1H, broad s), 6.23 (1H, s), 7.50–7.60 (2H, m), 7.71–7.79 (2H, m)

EXAMPLE 46

PREPARATION OF COMPOUND 221

5-t-butylcarbamoyloxy-3-(2-fluoro-3-trifluoromethyl)phenyl-4-thiazolidinone

By a procedure similar to that described in Example 10, but using 3-(2-fluoro-3-trifluoromethyl)phenyl-5-hydroxy-4-thiazolidinone (prepared as in Preparative Example 20 above) (4.00 g), tert-butyl isocyanate (1.41 g), triethylamine (1.43 g) and dichloromethane (60 ml), and trituration of the crude product with diethyl ether/hexane, the title compound was obtained as white crystals, yield 4.70 g, mp 136°–137° C.

$^1$H nmr (CDCl$_3$): δ1.32 (9H, s), 4.59 (1H, d), 4.92 (2H, d+broad s), 6.18 (1H, s), 7.33 (1H, m), 7.58–7.69 (2H, m)

EXAMPLE 47

PREPARATION OF COMPOUND 227

5-t-butylcarbamoyloxy-2-phenyl-3-(3-trifluoromethyl)phenyl-4-thiazolidinone

By a procedure similar to that described in Example 10, but using 5-hydroxy-2-phenyl-3-(3-trifluoromethyl)phenyl-4-thiazolidinone (prepared as in Preparative Example 21 above) (36 mg), tert-butyl isocyanate (11 mg), triethylamine (0.01 ml) and dichloromethane (5 ml), and purification of the crude product by silica gel chromatography, eluting with ethyl acetate/hexane, the title compound was obtained as a mixture of diastereomers.

$^1$H nmr (CDCl$_3$): major diastereoisomer δ1.33 (9H, s), 4.95 (1H, broad s), 6.00 (1H, s), 6.49 (1H, s), 7.22–7.35 (5H, m), 7.35–7.50 (4H, m); minor diastereoisomer δ1.30 (9H, s), 4.89 (1H, broad s), 6.27 (1H, s), 6.38 (1H, s), 7.22–7.35 (5H, m), 7.35–7.50 (4H, m)

EXAMPLE 48

PREPARATION OF COMPOUND 231

5-t-butylcarbamoyloxy-3-(4-chloro-3-trifluoromethyl)phenyl-4-thiazolidinone

By a procedure similar to that described in Example 10, but using 3-(4chloro-3-trifluoromethyl)phenyl-5-hydroxy-4-thiazolidinone (prepared as in Preparative Example 22 above) (2.00 g), tert-butyl isocyanate (0.66 g), triethylamine (0.93 ml) and dichloromethane (20 ml), and recrystallisation of the crude product from ethyl acetate/hexane, the title compound was obtained as white crystals, yield 1.90 g, mp 141°–143° C.

$^1$H nmr (CDCl$_3$): δ1.31 (9H, s), 4.65 (1H, d), 4.89 (1H, broad s), 5.02 (1H, d), 6.19 (1H, s), 7.56 (1H, d), 7.69 (1H, dd), 7.84 (1H, d)

EXAMPLE 49

PREPARATION OF COMPOUND 233

5-methyl-5-i-propylcarbamoyloxy-3-(3-trifluoromethyl)phenyl-4-thiazolidinone

By a procedure similar to that described in Example 10, but using 5-hydroxy-5-methyl-3-(3-trifluoromethyl)phenyl-4-thiazolidinone (prepared as in Preparative Example 23 above) (1.70 g), iso-propyl isocyanate (0.52 g), triethylamine (0.83 ml) and dichloromethane (10 ml), and purification of the crude product by silica gel chromatography, the title compound was obtained as a white solid, yield 0.28 g, mp 77°–83° C.

$^1$H nmr (CDCl$_3$): δ1.16 (6H, d), 1.91 (3H, s), 3.78 (1H, m), 4.58 (1H, d), 4.72 (1H, broad d), 5.07 (1H, d), 7.49–7.58 (2H, m), 7.68–7.80 (2H, m)

EXAMPLE 50

PREPARATION OF COMPOUND 241

5-t-butylcarbamoyloxy-3-(2-methoxy)phenyl-4-thiazolidinone

By a procedure similar to that described in Example 10, but using 5-hydroxy-3-(2-methoxy)phenyl-4-thiazolidinone (prepared as in Preparative Example 24 above) (0.29 g), tert-butyl isocyanate (0.13 g), triethylamine (0.18 ml) and dichloromethane (10 ml), and purification of the crude product by silica gel chromatography, eluting with ethyl acetate/hexane, the title compound was obtained as a colourless gum which contained ethyl acetate, yield 0.40 g.

$^1$H nmr (CDCl$_3$): δ1.34 (9H, s), 3.85 (3H, s), 4.57 (1H, dd), 4.81 (1H, d), 4.92 (1H, broad s), 6.21 (1H, d), 6.94–7.05 (2H, m), 7.26 (1H, m), 7.37 (1H, m)

EXAMPLE 51

PREPARATION OF COMPOUNDS 248 and 249

Diastereoisomers of 5-((S)-αmethylbenzyl)carbamoyloxy-3-(3-trifluoromethyl)phenyl-4-thiazolidinone By a procedure similar to that described in Example 10, but using 5-hydroxy-3-(3-trifluoromethyl)phenyl-4-thiazolidinone (prepared as in Preparative Example 2 above) (0.975 g), (S)-αmethylbenzyl isocyanate (0.545 g), triethylamine (0.20 ml) and dichloromethane (5 ml), the title compounds were prepared as a 3:2 mixture of diastereoisomers. Fractional crystallisation of the crude product mixture from ethanol (×2) afforded one diastereoisomer (Compound 248) pure, yield 0.140 g, mp 178°–179° C.

$^1$H nmr (CDCl$_3$): δ1.53 (3H, d), 4.68 (1H, d), 4.88 (1H, m), 5.05 (1H, d), 5.19 (1H, broad d), 6.25 (1H, s), 7.21–7.40 (5H, m), 7.51–7.60 (2H, m), 7.68–7.78 (2H, m)

Recrystallisation of the material left in the mother liquors from the above crystallisations from ethyl acetate/hexane afforded a 1:1 mixture of diastereoisomers (Compounds 248 and 249), yield 0.150 g, mp 148°–151° C.

$^1$H nmr (CDCl$_3$): (Compound 249 only) δ1.55 (3H, d), 4.68 (1H, d), 4.88 (1H, m), 5.08 (1H, d), 5.20 (1H, broad), 6.18 (1H, s), 7.21–7.40 (5H, m), 7.51–7.60 (2H, m), 7.68–7.78 (2H, m)

EXAMPLE 52

PREPARATION OF COMPOUNDS 255 and 256

Diastereoisomers of 5-((R)-αmethylbenzyl)carbamoyloxy-3-(3-trifluoromethyl)phenyl-4-thiazolidinone By a procedure similar to that described in Example 10, but using 5-hydroxy-3-(3-trifluoromethyl)phenyl-4-thiazolidinone (prepared as in Preparative Example 2 above) (2.00 g), (R)-αmethylbenzyl isocyanate (1.10 ml), triethylamine (0.10 ml) and dichloromethane (25 ml), the title compounds were prepared as a 3:2 mixture of diastereoisomers. Fractional crystallisation of the crude product mixture from ethanol (×2) afforded one diastereoisomer (Compound 255) pure, yield 0.368 g, mp 176°–179° C.

$^1$H nmr (CDCl$_3$): δ1.52 (3H, d), 4.68 (1H, d), 4.88 (1H, m), 5.05 (1H, d), 5.20 (1H, broad d), 6.25 (1H, s), 7.21–7.40 (5H, m), 7.51–7.60 (2H, m), 7.68–7.78 (2H, m)

Recrystallisation of the material left in the mother liquors from the above crystallisations from ethyl acetate/hexane afforded a 1:1 mixture of diastereoisomers (Compounds 255 and 256), yield 0.163 g, mp 148°–151° C.

$^1$H nmr (CDCl$_3$): (Compound 256 only) δ1.55 (3H, d), 4.68 (1H, d), 4.88 (1H, m), 5.07 (1H, d), 5.18 (1H, broad), 6.18 (1H, s), 7.21–7.40 (5H, m), 7.51–7.60 (2H, m), 7.68–7.78 (2H, m)

EXAMPLE 53

PREPARATION OF COMPOUND 260

5-(3-morpholino)carbonyloxy-3-(3-trifluoromethyl)phenyl-4-thiazolidinone

By a procedure similar to that described in Example 35, but using 5-hydroxy-3-(3-trifluoromethyl)phenyl-4-thiazolidinone (prepared as in Preparative Example 2 above) (0.100 g), morpholinocarbamoyl chloride (0.057 g), triethylamine (0.055 ml) and dichloromethane (10 ml), and purification of the crude product by silica gel chromatography, eluting with ethyl acetate/hexane, the title compound was obtained, yield 0.092 g.

$^1$H nmr (CDCl$_3$): δ3.45–3.56 (4H, m), 3.60–3.72 (4H, m), 4.69 (1H, d), 5.09 (1H, d), 6.22 (1H, s), 7.50–7.61 (2H, m), 7.70–7.81 (2H, m)

EXAMPLE 54

PREPARATION OF COMPOUND 262

5-(N-(2-chloro)ethyl)carbamoyloxy-3-(3-trifluoromethyl)phenyl-4-thiazolidinone

By a procedure similar to that described in Example 10, but using 5-hydroxy-3-(3-trifluoromethyl)phenyl-4-thiazolidinone (prepared as in Preparative Example 2 above) (0.25 g), 2-chloroethyl isocyanate (0.11 g), triethylamine (0.13 ml) and chloroform (10 ml) as the solvent, the title compound was obtained as a pale yellow solid, yield 0.30 g.

$^1$H nmr (CDCl$_3$): δ3.47–3.69 (4H, m), 4.69 (1H, d), 5.08 (1H, d), 5.32 (1H, broad t), 6.23 (1H, s), 7.50–7.60 (2H, m), 7.69–7.80 (2H, m)

EXAMPLE 55

PREPARATION OF COMPOUND 270

5-(4-(2,6-dichloropyridyl)amino)carbonyloxy-3-(3-trifluoromethyl)phenyl-4-thiazolidinone By a procedure similar to that described in Example 10, but using 5-hydroxy-3-(3-trifluoromethyl)phenyl-4-thiazolidinone (prepared as in Preparative Example 2 above) (0.100 g), 4-(2,6-dichloro)pyridyl isocyanate (0.072 g), triethylamine (0.056 ml) and chloroform (10 ml) as the solvent, and purification of the crude product by silica gel chromatography, eluting with diethyl ether mixtures, the title compound was obtained, yield 0.035 g.

$^1$H nmr (CDCl$_3$): δ4.77 (1H, d), 5.13 (1H, dd), 6.30 (1H, d), 7.17 (1H, broad s), 7.33 (2H, s), 7.56–7.67 (2H, m), 7.72–7.80 (2H, m)

EXAMPLE 56

PREPARATION OF COMPOUND 274

5-(N-(1,1-dimethyl)-2-propenyl)carbamoyloxy-3-(3-trifluoromethyl)phenyl-4-thiazolidinone A stirred solution of Compound 171 (0.150 g) in ethyl acetate (10 ml) was treated with a lead-poisoned 5% palladium on calcium carbonate catalyst (0.015 g), and the mixture was hydrogenated for 4 hours. A further quantity (0.015 g) of catalyst was added, and the mixture was then hydrogenated for a further 5 hours. The mixture was filtered through 'Celite', and the filtrate was evaporated under reduced pressure to leave the title compound as a gum which crystallised on standing, yield 0.090 g, mp 106°–108° C.

$^1$H nmr (CDCl$_3$): δ1.42 (6H, s), 4.69 (1H, d), 4.92–5.21 (4H, m), 5.95 (1H, dd), 6.21 (1H, s), 7.51–7.60 (2H, m), 7.69–7.80 (2H, m)

m/e 374 (M$^+$)

EXAMPLE 57

PREPARATION OF COMPOUND 278

5-(N-diphenylmethyl)carbamoyloxy-3-(3-trifluoromethyl)phenyl-4-thiazolidinone

By a procedure similar to that described in Example 38, but using 5-hydroxy-3-(3-trifluoromethyl)phenyl-4-thiazolidinone (prepared as in Preparative Example 2 above) (0.109 g), triethylamine (0.20 ml) and the isocyanate prepared in situ from diphenylmethylamine (1.00 g), phosgene in toluene (1.93M; 3.21 ml), diethyl ether (5 ml) and aqueous sodium hydroxide (0.480 g in 10 ml), and purification of the crude product by silica gel chromatography, eluting with ethyl acetate/hexane mixtures, the title compound was obtained as a white solid, yield 0.058 g, mp 170°–172° C.

$^1$H nmr (CDCl$_3$): δ4.69 (1H, d), 5.07 (1H, d), 5.55 (1H, broad d), 5.96 (1H, d), 6.24 (1H, d), 7.15–7.39 (10H, m), 7.51–7.59 (2H, m), 7.67–7.77 (2H, m)

EXAMPLE 58

PREPARATION OF COMPOUND 281

5-t-butylcarbamoyloxy-3-(3-nitro)phenyl-4-thiazolidinone

5-Hydroxy-3-(3-nitro)phenyl-4-thiazolidinone (prepared as in Preparative Example 25 above) (1.7088 g) was suspended in dry dichloromethane (30 ml) and stirred at room temperature. Triethylamine (1 ml) was added and then, dropwise, tert-butyl isocyanate (0.812 ml). The suspension gradually went into solution and stirring was continued for 4 hours. The reaction mixture was diluted with dichloromethane and washed successively with 2M hydrochloric acid, saturated sodium bicarbonate solution and brine. The organic layer was dried (Na$_2$SO$_4$) and evaporated under reduced pressure to give a yellow solid (2.268 g). This material was purified by silica gel chromatography using ethyl acetate-hexane (3:7) as eluant. The title compound was obtained as a yellow solid, yield 2.176 g, mp 157°–158° C.

$^1$H nmr (CDCl$_3$): δ1.33 (9H, s), 4.72 (1H, d), 4.89 (1H, broad s), 5.10 (1H, d), 6.21 (1H, s), 7.62 (1H, t), 8.00 (1H, dd), 8.15 (1H, dd), 8.35 (1H, t)

EXAMPLE 59

PREPARATION OF COMPOUND 282

5-t-butylcarbamoyloxy-3-(3-cyano)phenyl-4-thiazolidinone.

5-Hydroxy-3-(3-cyano)phenyl-4-thiazolidinone (prepared as in Preparative Example 26 above) (1.62 g) was converted to the title compound by a procedure similar to that described in Example 58 using dichloromethane (15 ml), triethylamine (1.02 ml) and tert-butyl isocyanate (0.84 ml). The crude product (2.3 g) was purified by silica gel chromatography using ethyl acetate-hexane (3:7) as eluant. The title compound was obtained as a solid, yield 2.20 g, mp 149°–151° C.

$^1$H nmr (CDCl$_3$): δ1.33 (9H, s), 4.68 (1H, d), 4.89 (1H, broad s), 5.06 (1H, d), 6.20 (1H, s), 7.58 (2H, m), 7.80 (1H, m), 7.88 (1H, s)

EXAMPLE 60

PREPARATION OF COMPOUND 285

5-t-butylcarbamoyloxy-3-(3-fluoro)phenyl-4-thiazolidinone

5-Hydroxy-3-(3-fluoro)phenyl-4-thiazolidinone (prepared as in Preparative Example 27 above) (0.42 g) was converted to the title compound by a procedure similar to that described in Example 58 using dichloromethane (4 ml), triethylamine (0.274 ml) and tert-butyl isocyanate (0.225 ml). The crude product was purified by silica gel chromatography using ethyl acetate -hexane (1:4) as eluant. The title compound was obtained as a white solid, yield 0.56 g, mp 112°–114° C.

$^1$H nmr (CDCl$_3$): δ1.33 (9H, s), 4.66 (1H, d), 4.87 (1H, broad s), 5.02 (1H, dd), 6.20 (1H, broad s), 6.99 (1H, td), 7.22–7.45 (3H, m)

EXAMPLE 61

PREPARATION OF COMPOUND 301

5-t-butylcarbamoyloxy-3-(3-(1,1,2,2-tetrafluoroethoxy))phenyl-4-thiazolidinone.

5-Hydroxy-3-(3-(1,1,2,2-tetrafluoroethoxy))phenyl-4-thiazolidinone (prepared as in Preparative Example 28 above) (1.9 g) was converted to the title compound by a procedure similar to that described in Example 58 using dichloromethane (20 ml), triethylamine (0.85 ml) and tert-butylisocyanate (0.70 ml). The crude product was purified by silica gel chromatography using ethyl acetate hexane (1:4) as eluant. The title compound (2.063 g) was obtained as a white solid which was further purified by recrystallisation from ethyl acetate-hexane to give white crystals, yield 1.338 g, mp 74°–75° C.

$^1$H nmr (CDCl$_3$): δ1.34 (9H, s), 4.68 (1H, d), 4.86 (1H, broad s), 5.03 (1H, d), 5.92 (1H, tt), 6.21 (1H, s), 7.15 (1H, m), 7.46 (3H, m)

EXAMPLE 62

PREPARATION OF COMPOUND 307

5-t-butylcarbamoyloxy-3-(3-amino)phenyl-4-thiazolidinone.

5-t-Butylcarbamoyloxy-3-(3-nitro)phenyl-4-thiazolidinone (prepared as described in Example 58 above) (1.424 g) was dissolved in ethyl acetate (25 ml) and 5% palladium on charcoal (0.25 g) introduced. The reaction mixture was stirred vigorously under an atmosphere of hydrogen overnight, and the catalyst was then removed by filtration through 'Celite'. After removal of the solvent under reduced pressure, the residue was redissolved in ethyl acetate (25 ml) and fresh 5% palladium on charcoal (0.25 g) introduced. Hydrogenation was continued for 72 hours and the catalyst again removed by filtration through 'Celite'. The solvent was removed under reduced pressure giving a solid (1.166 g). This was recrystallised from ethyl acetate/hexane to give the title compound as a solid, yield 0.488 g, mp 134°–136° C.

$^1$H nmr (CDCl$_3$): δ1.33 (9H, s), 3.80 (2H, broad s), 4.63 (1H, d), 4.85–5.0 (2H, m), 6.20 (1H, s), 6.60 (1H ,dd), 6.75 (1H ,dd), 6.9 (1H, t), 7.18 (1H, t)

EXAMPLE 63

PREPARATION OF COMPOUND 316

5-t-butylcarbamoyloxy-3-(3-methyl)phenyl-4-thiazolidinone.

5-Hydroxy-3-(3-methyl)phenyl-4-thiazolidinone (prepared as described in Preparative Example 29 above) (0.300 g) was dissolved in dry dichloromethane (5 ml) and stirred at room temperature under nitrogen. Triethylamine (0.220 ml) was added and then, dropwise, tert-butyl isocyanate (0.180 ml). The mixture was stirred at room temperature for approximately 72 hours and then diluted with dichloromethane. This was washed successively with 2M hydrochloric acid, saturated sodium bicarbonate solution and brine. The organic later was dried (Na$_2$SO$_4$) and evaporated under reduced pressure to give the crude product (0.401 g). This was purified by silica gel chromatography using ethyl acetate-hexane (3:7) as eluant to give a white semi-solid (0.357 g) which was recrystallised from ethyl acetate-hexane. The title compound was obtained as a white solid, yield 0.300 g, mp 141°–142° C.

$^1$H nmr (CDCl$_3$): δ1.33 (9H, s), 2.38 (3H, s), 4.66 (1H, d), 4.89 (1H, broad s), 4.97 (1H, d), 6.21 (1H, s), 7.11 (1H, d), 7.20–7.36 (3H, m)

EXAMPLE 64

PREPARATION OF COMPOUND 318

5-t-butylcarbamoyloxy-3-(3-N,N-(bismethanesulphonyl)amino)phenyl-4-thiazolidinone 5-t-Butylcarbamoyloxy-3-(3-amino)phenyl-4-thiazolidinone (prepared as described in Example 62 above) (0.3447 g) was dissolved in dichloromethane (5 ml) and stirred at room temperature under nitrogen. Triethylamine (0.194 ml) and methanesulphonyl chloride (0.095 ml) were added and the reaction mixture stirred at room temperature for 72 hours. Further portions of triethylamine (0.194 ml) and methanesulphonyl chloride (0.095 ml) were added and after 1 hour the reaction mixture was diluted with dichloromethane and washed successively with 2M hydrochloric acid, saturated sodium bicarbonate solution and brine. The organic layer was dried (Na$_2$SO$_4$) and evaporated to give a yellow solid (0.464 g). This was chromatographed on silica gel using ethyl acetate-hexane (2:3) as eluant to give the title compound, yield 0.236 g, which had:

$^1$H nmr (CDCl$_3$): δ1.33 (9H, s), 3.44 (6H, s), 4.72 (1H, d), 4.86 (1H, broad s), 5.06 (1H, d), 6.22 (1H, s), 7.28 (1H, m), 7.53 (2H, m), 7.77 (1H, s)

MS: m/e 465 (M+)

EXAMPLE 65

PREPARATION OF COMPOUND 321

5-t-butylcarbamoyloxy-3-(3-methoxy)phenyl-4-thiazolidinone

5-Hydroxy-3-(3-methoxy)phenyl-4-thiazolidinone (prepared as described in Preparative Example 30 above) (0.350 g) was converted to the title compound by a procedure similar to that described in Example 58 using dichloromethane (5 ml), triethylamine (0.26 ml) and tert-butylisocyanate (0.195 ml). The crude product (0.45 g) was purified by silica gel chromatography using ethyl acetate-hexane (3:7) to give a foam (0.389 g) which was in turn purified on silica gel using methanol-dichloromethane (0.5:99.5). The title compound was obtained as a hygroscopic white solid, yield 0.227 g.

$^1$H nmr (CDCl$_3$): δ1.33 (9H, s), 3.82 (3H, s), 4.67 (1H, d), 4.85–4.95 (1H, broad s), 4.99 (1H, d), 6.21 (1H, s), 6.84 (1H, dd), 7.00 (1H, dd), 7.12 (1H, t), 7.34 (1H, t)

MS: m/e 324 (M+)

EXAMPLE 66

PREPARATION OF COMPOUND 326

5-t-butylcarbamyloxy-3-(3-methoxycarbonyl)phenyl-4-thiazolidinone

5-Hydroxy-3-(3-methoxycarbonyl)phenyl-4-thiazolidinone (prepared as described in Preparative Example 31 above) (2.258 g) was converted to the title compound by a procedure similar to that described in Example 58 using dichloromethane (35 ml), triethylamine (1.37 ml) and tert-butylisocyanate (1.12 ml). The crude product was purified by silica gel chromatography using ethyl acetate hexane (1:3). The title compound was obtained as a white solid, yield 2.881 g, mp 123°–125° C.

$^1$H nmr (CDCl$_3$): δ1.33 (9H, s), 3.93 (3H, s), 4.70 (1H, d), 4.90 (1H, broad s), 5.07 (1H, d), 6.22 (1H, s), 7.52 (1H, t), 7.83 (1H, dd), 7.97 (1H, dd), 8.0 6 (1H, m)

EXAMPLE 67

PREPARATION OF COMPOUND 328

5-t-butylcarbamoyloxy-3- (3-bromo)phenyl-4-thiazolidinone

5-Hydroxy-3- (3-bromo)phenyl-4-thiazolidinone (prepared as described in Preparative Example 32 above) (0.964 g) was converted to the title compound by a procedure similar to that described in Example 58 using dichloromethane (10 ml), triethylamine (0.48 ml) an d tert-butylisocyanate (0.39 ml). The crude product was purified by silica gel chromatography using ethyl acetate-hexane (1:4) as eluant to give a solid residue (1.07 g). This in turn was further purified by recrystallisation from ethyl acetate-hexane to give the title compound as a white powdery solid, yield 0.83 g, mp 153°–155° C.

$^1$H nmr (CDCl$_3$): δ1.33 (9H, s), 4.64 (1H, d), 4.85 (1H, broad s), 5.00 (1H, d), 6.19 (1H, s), 7.30 (1H, t), 7.45 (2H, m), 7.69 (1H, t)

EXAMPLE 68

PREPARATIVE OF COMPOUND 331

Preparation of 5-t-butylcarbamoyloxy-3-(3-iodo)phenyl-4-thiazolidinone

5-Hydroxy-3-(3-iodo)phenyl-4-thiazolidinone (prepared as described in Preparative Example 33 above) (1.68 g) was converted to the title compound by a procedure similar to that described in Example 58 using dichloromethane (15 ml), triethylamine (0.73 ml) and tert-butylisocyanate (0.59 ml). The crude product was purified by silica gel chromatography using ethyl acetate-hexane (1:4) to give the title compound as a solid, yield 1.2 g, mp 161°–162.5° C.

$^1$H nmr (CDCl$_3$): δ1.33 (9H, s), 4.62 (1H, d), 4.85 (1H, broad s), 4.98 (1H, d), 6.19 (1H, s), 7.16 (1H, t), 7.49 (1H, dd), 7.63 (1H, d), 7.84 (1H, m)

EXAMPLE 69

PREPARATION OF COMPOUND 336

5-t-butylcarbamoyloxy-3-(3-phenoxy)phenyl-4-thiazolidinone

5-Hydroxy 3-(3-phenoxy)phenyl-4-thiazolidinone (prepared as described in Preparative Example 34 above) (0.255 g) was converted to the title compound by a procedure similar to that described in Example 58 using dichloromethane (5 ml), triethylamine (0.136 ml) and tert-butylisocyanate (0.111 ml). The crude product was purified by silica gel chromatography using ethyl acetate-hexane (1:4) as eluant to give a sticky orange solid. This was recrystallised from ethyl acetate-hexane to give the title compound as a white solid, yield 0.195 g, mp 131°–132° C.

$^1$H nmr (CDCl$_3$): δ1.33 (9H, s), 4.63 (1H, d), 4.80–4.95 (1H, broad s), 4.98 (1H, d), 6.20 (1H, s), 6.92 (1H, dd), 7.00–7.42 (8H, m)

EXAMPLE 70

PREPARATION OF COMPOUND 337

5-t-butylcarbamoyloxy-3-phenyl-4-thiazolidinone

5-Hydroxy-3-phenyl-4-thiazolidinone (prepared as described in Preparative Example 17 above) (0.095 g) was converted to the title compound by a procedure silimar to that described in Example 58 using dichloromethane (2 ml), triethylamine (0.068 ml) and tert-butyl isocyanate (0.056 ml). The crude product was purified by silica gel chromatography using ethyl acetate-hexane (1:4) as eluant. The title compound was further purified by recrystallisation from ethyl acetate-hexane (2×) (0.065 g). mp 146°–148° C. (but still contained 9% di-t-butyl urea).

$^1$H nmr (CDCl$_3$): inter alia δ1.33 (9H, s), 4.67 (1H, d), 4.88 (1H, broad s), 5.01 (1H, d), 6.22 (1H, s), 7.28 (1H, m), 7.45 (4H, m)

MS: m/e 294 (M+)

EXAMPLE 71

PREPARATION OF COMPOUND 339

5-t-butylcarbamoyloxy-3-(3-(N-acetyl)amino)phenyl-4-thiazolidinone 5-t-butylcarbamoyloxy-3-(3-amino)phenyl-4-thiazolidinone (prepared as in Example 62) (0.350 g) was dissolved in dry dichloromethane (5 ml) and treated with dry triethylamine (0.198 ml) under nitrogen. Acetyl chloride (0.089 ml) was added cautiously and the reaction mixture stirred at room temperature for 72 hours. The reaction mixture was diluted with dichloromethane and washed successively with 2M hydrochloric acid, saturated sodium bicarbonate and brine. The organic layer was dried (Na$_2$SO$_4$) and evaporated under reduced pressure to give an off-white solid (0.349 g). The crude product was purified by silica gel chromatography using ethyl acetate-hexane (7:3) as eluant to give a solid (0.261 g). This was recrystallised from ethyl acetate-hexane to give the title compound as a white solid, yield 0.176 g, mp 160°–162° C.

$^1$H nmr (CDCl$_3$): δ1.33 (9H, s), 2.08 (3H, s), 4.62 (1H,d), 4.78 (1H, broad s), 4.97 (1H, d), 5.05 (1H, broad s), 6.22 (1H, s), 7.11 (1H, m), 7.30 (2H, m), 7.75 (1H,broad s), 7.98 (1H, broad s)

EXAMPLE 72

PREPARATION OF COMPOUND 340

5-t-butylcarbamoyloxy-3-(3-methanesulphonyl)phenyl-4-thiazolidinone

5-Hydroxy 3-(3-methanesulphonyl)-4-thiazolidinone (prepared as in Preparative Example 35 above) (0.67 g) was converted to the title compound by a procedure similar to that described in Example 58 using dichloromethane (17 ml), triethylamine (0.38 ml) and tert-butylisocyanate (0.31 ml). The crude product (0.917 g) was purified on silica gel using ethyl acetate-hexane (1:1) as eluant. The title compound was obtained as a white solid, yield 0.845 g, and had:

$^1$H nmr (CDCl$_3$): δ1.33 (9H, s), 3.08 (3H, s), 4.72 (1H, d), 4.87 (1H, broad s), 5.09 (1H, d), 6.21 (1H, s), 7.66 (1H, t), 7.88 (2H, m), 8.04 (1H, m)

MS: m/e 372 (M+)

EXAMPLE 73

PREPARATION OF COMPOUND 341

5-t-butylcarbamoyloxy-3-(3,4,5-trichloro)phenyl-4-thiazolidinone

5-Hydroxy-3-(3,4,5-trichloro)phenyl-4-thiazolidinone (prepared as described in Preparative Example 36 above) (1.2 g) was converted to the title compound by a procedure similar to that described in Example 58 using dichloromethane (20 ml), triethylamine (0.6 ml) and tert-butyl isocyanate (0.48 ml). The crude product (1.57 g) was purified by silica gel chromatography using ethyl acetate-hexane (15:85 to 20:80) as eluant to give an orange solid (1.35 g). This was in turn further purified by recrystallisation from ethyl acetate-hexane to give the title compound as a light pink solid. mp 163°–165° C.

$^1$H nmr (CDCl$_3$): δ1.34 (9H, s), 4.62 (1H, d), 4.85 (1H, broad s), 4.99 (1H, d), 6.16 (1H, s), 7.64 (2H, s)

EXAMPLE 74

PREPARATION OF COMPOUND 342

5-t-butylcarbamoyloxy-3-(3-methylthio)phenyl-4-thiazolidinone

5-Hydroxy-3-(3-methylthio)phenyl-4-thiazolidinone (prepared as described in Preparative Example 37) (0.578 g) was converted to the title compound by a procedure similar to that described in Example 58 using dichloromethane (20 ml), triethylamine (0.37 ml) and tert-butylisocyanate (0.30 ml). The crude product (0.765 g) was chromatographed on silica gel using ethyl acetate:hexane (1:3) as eluant but this material still contained some impurities and the sample was rechromographed using ethyl acetate-hexane (18:88). This yielded a yellow/white solid (0.42 g) which was recrystallised from ethyl acetate/hexane. The title compound was obtained as white needles, yield 0.32 g, mp 144.2°–146.2° C.

$^1$H nmr (CDCl$_3$): δ1.33 (9H, s), 2.50 (3H, s), 4.65 (1H, d), 4.88 (1H, broad s), 5.00 (1H, d), 6.21 (1H, s), 7.15–7.42 (4H, m)

EXAMPLE 75

PREPARATION OF COMPOUND 344

5-t-butylcarbamoyloxy-3-(3-trifluoromethoxy)phenyl-4-thiazolidinone

5-Hydroxy 3-(3-trifluoromethoxy)phenyl-4-thiazolidinone (prepared as described in Preparative Example 38 above) (2.698 g) was converted to the title compound by a procedure similar to that described in Example 58 using dichmoromethane (70 ml), triethylamine (1.48 ml) and tert-butyl isocyanate (1.21 ml). The crude product (3.483 g) was purified on silica gel using ethyl acetate hexane (20:80) as eluant. The pale yellow solid obtained was further purified by recrystallisation from ethyl acetate-hexane to give the title compound as a white solid, yield 2.26 g, mp 103°–105° C.

$^1$H nmr (CDCl$_3$): δ1.33 (9H, s), 4.68 (1H, d), 4.87 (1H, broad s), 5.03 (1H, d), 6.21 (1H, s), 7.15 (1H, m), 7.47 (3H, m)

EXAMPLE 76

PREPARATION OF COMPOUND 346

5-t-butylcarbamoyloxy-3-(3-methoxy-5-trifluoromethyl)phenyl-4-thiazolidinone

5-Hydroxy-3-(3-methoxy-5-trifluoromethyl)phenyl-4-thiazolidinone (prepared as in Preparative Example 39 above) (2.49 g) was converted to the title compound by a procedure similar to that described in Example 58 using dichloromethane (25 ml), triethylamine (1.25 ml) and tert-butyl isocyanate (1.02 ml). The crude product (3.521 g) was purified by silica gel chromatography using ethyl acetate-hexane (1:4 to 3:7) as eluant to give a white solid (3.0 g). This in turn was purified by recrystallisation from ethyl acetate-hexane to give the title compound as a white solid, yield 2.673 g, mp 111°–112° C.

$^1$H nmr (CDCl$_3$): δ1.33 (9H, s), 3.87 (3H, s), 4.69 (1H, d), 4.89 (1H, broad s), 5.04 (1H, d), 6.21 (1H ,s), 7.05 (1H, s), 7.29 (1H, s), 7.38 (1H, s)

EXAMPLE 77

PREPARATION OF COMPOUND 348

5-t-butylcarbamoyloxy-3-(3-nitro-5-trifluoromethyl)phenyl-4-thiazolidinone

5-Hydroxy-3-(3-nitro-5-trifluoromethyl)phenyl-4-thiazolidinone (prepared as in Preparative Example 40 above) (1.11 g) was converted to the title compound by a procedure similar to that described in Example 58 using dichloromethane (30 ml), triethylamine (0.53) and tert-butylisocyanate (0.43 ml). The crude product (1.43 g) was purified by silica gel chromatography using ethyl acetate-hexane (1:3) as eluant to give a yellow/orange solid (1.17 g). This in turn was further purified by recrystallisation from ethyl acetate-hexane to give the title compound as a pale yellow solid, yield 0.437 g.

$^1$H nmr (CDCl$_3$): δ1.33 (9H, s), 4.76 (1H, d), 4.87 (1H, broad s), 5.16 (1H, d), 6.20 (1H, s), 8.31 (1H, s), 8.38 (1H, s), 8.61 (1H, m)

MS: m/e 408 (M$^+$+H)

EXAMPLE 78

PREPARATION OF COMPOUND 350

5-t-butyl-3-(3-trifluoromethanesulphonyl)phenyl-4-thiazolidinone

5-Hydroxy-3-(3-trifluoromethanesulphonyl)phenyl-4-thiazolidinone (prepared as in Preparative Example 41 above) (0.46 g) was converted to the title compound by a procedure similar to that described in Example 58 using dichloromethane (10 ml), triethylamine (0.21 ml) and tert-butylisocyanate (0.17 ml). The crude product (0.65 g) was purified by silica gel chromatography using ethyl acetate-hexane (35:65) as eluant. The title compound was obtained as a white solid, yield 0.47 g.

$^1$H nmr (CDCl$_3$): δ1.33 (9H, s), 4.73 (1H, d), 4.88 (1H, broad s), 5.12 (1H, d), 6.21 (1H, s), 7.76 (1H, t), 7.94 (1H, d), 8.12 (1H, s), 8.18 (1H, d)

MS: 427 (M$^+$+H)

EXAMPLE 79

PREPARATION OF COMPOUNDS 359 AND 360

(+)-5-t-butylcarbamoyloxy-3-(3-trifluoromethyl)phenyl-4-thiazolidinone and (−)-5-t-butylcarbamoyloxy-3-(3-trifluoromethyl)phenyl-4-thiazolidinone Racemic Compound 26 (prepared as descibed in Example 7) was separated on a covalently bonded D-phenylglycine Pirkle column, eluting with a mixture of hexane/tetrahydrofuran/acetonitrile (90:10:0.26). The column dimensions were 25 cm (length)×0.8 cm (diameter), and the compound was separated in quantities of ca 0.4–0.5 mg per run (75 runs in all). By this method, Compound 359, (+)-5-t-butylcarbamoyloxy-3-(3-trifluoromethyl)phenyl-4-thiazolidinone, was obtained as a white solid, yield 14.0 mg, $[\alpha]_D^{29}$=+118° (c=0.14 g/100 ml; toluene), followed by Compound 360, (−)-5-t-butylcarbamoyloxy-3-(3-trifluoromethyl)phenyl-4-thiazolidinone, also a white solid, yield 11.8 mg, $[\alpha]_D^{29}$=−71° (c=0.12 g/100 ml; toluene).

EXAMPLE 80

PREPARATION OF COMPOUND 361

3-t-butylcarbamoyloxy-1-(3-trifluoromethyl)phenyl-2-pyrrolidinone

A stirred solution of 3-hydroxy-1-(3-trifluoromethyl)phenyl-2-pyrrolidinone (prepared as in Preparative Example 42 above) (0.220 g) in dichloromethane (2 ml) was treated with tert-butyl isocyanate (0.063 g) followed by triethylamine (0.084 ml). The solution was stirred for 24 hours, then evaporated under reduced pressure. Purification of the residue by silica gel chromatography, eluting with ethyl acetate/hexane mixtures, afforded the title compound as a clear gum, yield 0.060 g.

$^1$H nmr (CDCl$_3$): δ1.35 (9H, s), 2.13 (1H, m), 2.73 (1H, m), 3.80–3.89 (2H, m), 4.94 (1H, broad s), 5.38 (1H, t), 7.38–7.53 (2H, m), 7.89–7.95 (2H, m)

EXAMPLE 81

PREPARATION OF COMPOUND 369

3-i-propylcarbamoyloxy-1-(3-trifluoromethyl)phenyl-2-pyrrolidinone

By a procedure similar to that described in Example 80, but using 3-hydroxy-1-(3-trifluoromethyl)phenyl-2-pyrrolidinone (prepared as in Preparative Example 42 above) (0.085 g), iso-propyl isocyanate (0.030 g), triethylamine (0.01 ml) and dichloromethane (1 ml), and purification of the residue by silica gel chromatography, eluting with ethyl acetate/hexane mixtures, the title compound was obtained as a white crystaline solid, yield 0.095 g, mp 114°–117° C.

$^1$H nmr (CDCl$_3$): δ1.19 (3H, d), 1.20 (3H, d), 2.18 (1H, m), 2.78 (1H, m), 3.77–3.93 (3H, m), 4.79 (1H, broad d), 5.41 (1H, t), 7.40–7.58 (2H, m), 7.88–7.96 (2H, m)

EXAMPLE 82

PREPARATION OF COMPOUND 383

1-(2-chloro-6-fluoro-4-trifluoromethyl)phenyl-3-i-propylcarbamoyloxy-2-pyrrolidinone A stirred solution of 1-(2-chloro-6-fluoro-4-trifluoromethyl)phenyl-3-hydroxy-2-pyrrolidinone (prepared as in Preparative Example 43 above) (0.500 g) in chloroform (5 ml) was treated with triethylamine (0.25 ml), followed by iso-propyl isocyanate (0.150 g). The clear solution was stirred at room temperature for 24 hours, and was then quenched with water and acidified with 2M hydrochloric acid. The organic phase was separated, washed with 2M hydrochloric acid, dried (MgSO$_4$) and evaporated under reduced pressure to leave a white solid. This was recrystallised from chloroform/hexane to afford the title compound as colourless needles, yield 0.507 g, mp 133°–136° C.

$^1$H nmr (CDCl$_3$): δ1.18 (6H, d), 2.26 (1H, m), 2.79 (1H, m), 3.68 (1H, m), 3.75–3.92 (2H, m), 4.81 (1H, broad d), 5.45 (1H, dt), 7.39 (1H, d), 7.59 (1H, s)

EXAMPLE 83

PREPARATION OF COMPOUND 390

1-(2-chloro-6-fluoro-4-trifluoromethyl)phenyl-3-t-butylcarbamoyloxy-2-pyrrolidinone By a procedure similar to that described in Example 82, but using 1-(2-chloro-6-fluoro-4-trifluoromethyl)phenyl-3-hydroxy-2-pyrrolidinone (prepared as in Preparative Example 43 above) (0.500 g), tert-butyl isocyanate (0.174 g), triethylamine (0.25 ml) and chloroform (5 ml), and recrystallising the crude product from chloroform/hexane, the title compound was obtained as colourless crystals, yield 0.355 g, mp 134°–137° C.

$^1$H nmr (CDCl$_3$): δ1.31 (9H, s), 2.28 (1H, m), 2.79 (1H, m), 3.59–3.82 (2H, m), 4.92 (1H, broad s), 5.40 (1H, m), 7.39 (1H, d), 7.58 (1H, s)

EXAMPLE 84

PREPARATION OF COMPOUND 404

3-(N,N-dimethylamino)carbamoyloxy-1-(3-trifluoromethyl)phenyl-2-pyrrolidinone

A stirred solution of 3-hydroxy-1-(3-trifluoromethyl)phenyl-2-pyrrolidinone (prepared as in Preparative Example 42 above) (0.175 g) in pyridine (1 ml) was treated with dimethyl carbamoyl chloride (0.084 g). The mixture was stirred at room temperature for 24 hours, then 2M hydrochloric acid was added. The emulsion was extracted with chloroform, and the extract was washed with brine, dried (MgSO$_4$) and evaporated under reduced pressure to leave a gum. Purification by silica gel chromatography, eluting with chloroform/methanol mixtures, afforded the title compound as a gum, yield 0.178 g.

$^1$H nmr (CDCl$_3$): δ2.18 (1H, m), 2.72 (1H, m), 2.95 (3H, s), 2.97 (3H, s), 3.77–3.92 (2H, m), 5.43 (1H, t), 7.39–7.53 (2H, m), 7.88–7.98 (2H, m)

EXAMPLE 85

PREPARATION OF COMPOUND 409

1-(2-chloro-6-fluoro-4-trifluoromethyl)phenyl-3-(N,N-dimethylamino)carbamoyloxy-2-pyrrolidinone A stirred solution of 1-(2-chloro-6-fluoro-4-trifluoromethyl)phenyl-3-hydroxy-2-pyrrolidinone (prepared as in Preparative Example 43 above) (0.400 g) in pyridine (2 ml) was treated with sodium hydride (0.071 g of a 50% emulsion in oil) followed by dimethyl carbamoyl chloride (0.159 g). The mixture was stirred at room temperature for 5 hours, then 2M hydrochloric acid was added. The emulsion was extracted with diethyl ether (x2), and the combined extracts were washed with brine, dried (MgSO$_4$) and evaporated under reduced pressure to leave a gum. Purification by silica gel chromatography, eluting with chloroform/methanol mixtures, afforded the title compound as a white solid, yield 0.104 g, mp 121°–122° C.

$^1$H nmr (CDCl$_3$): δ2.30 (1H, m), 2.75 (1H, m), 2.93 (3H, m), 2.95 (3H, m), 3.58–3.85 (2H, m), 5.44 (1H, m), 7.38 (1H, d), 7.58 (1H, s)

EXAMPLE 86

PREPARATION OF COMPOUND 421

1-(3-trifluoromethyl)phenyl-3-(N-(1,1-dimethyl)-2-butynyl)carbamoyloxy-2-pyrrolidinone A stirred solution of 3-hydroxy-1-(3-trifluoromethyl)phenyl-2-pyrrolidinone (prepared as in Preparative Example 42 above) (0.090 g) and quinoline (0.050 g) in toluene (2 ml) was treated with a solution of phosgene in toluene (0.65 ml of a 12.5% w/v solution), and the resultant suspension was stirred at room temperature for 2 hours. The mixture was then filtered, and the filtrate was treated with triethylamine (0.06 ml) followed by 1-amino-1,1-dimethyl-2-butyne hydrochloride (0.041 g). This mixture was stirred for 24 hours, then 2M hydrochloric acid was added, and the organic phase was separated. The aqueous layer was further extracted with diethyl ether, and the combined organic phases were washed with brine, dried (MgSO$_4$) and evaporated under reduced pressure to leave a gum. Purification by silica gel chromatography, eluting with ethyl acetate/hexane mixtures followed by chloroform/methanol mixtures, afforded the title compound, yield 0.004 g.

$^1$H nmr (CDCl$_3$): δ1.62 (6H, s), 1.79 (3H, s), 2.15 (1H, m), 3.76 (1H, m), 3.80–3.91 (2H, m), 5.19 (1H, broad s), 5.39 (1H, t), 7.38–7.54 (2H, m), 7.85–7.95 (2H, m)

EXAMPLE 87

PREPARATION OF COMPOUND 448 dihydro-2-t-butylcarbamoyloxy-4-(3-trifluoromethyl)phenyl-4H-1,4-oxazin-3-(2H)-one A stirred solution of dihydro-2-hydroxy-4-(3-trifluoromethyl)phenyl-4H-1,4-oxazin-3-(2H)-one (prepared as in Preparative Example 44 above) (0.140 g) in dichloromethane (2 ml) was treated with tert-butyl isocyanate (0.054 g) followed by triethylamine (0.08 ml). The solution was stirred for 24 hours, then evaporated under reduced pressure. Recrystallisation from ethyl acetate/hexane afforded the title compound as a white solid, yield 0.091 g, mp 160°–162° C.

$^1$H nmr (CDCl$_3$): δ1.34 (9H, s), 3.59 (1H, m), 3.98–4.18 (2H, m), 4.35 (1H, m), 4.87 (1H, broad s), 6.18 (1H, s), 7.52–7.60 (3H, m), 7.65 (1H, m)

MS: m/e 360 (M$^+$)

EXAMPLE 88

PREPARATION OF COMPOUND 508 dihydro-2-t-butylcarbamoyloxy-4-(3-trifluoromethyl)phenyl-4H-1,4-thiazin-3(2H)-one Dihydro-2-hydroxy-4-(3-trifluoromethyl)phenyl-4H-1,4-thiazin-3-(2H)-one (prepared as in Preparative Example 45 above) (0.66 g) was converted to the title compound by a procedure similar to that described in Example 58 using dichloromethane (10 ml), triethylamine (0.33 ml) and tert-butyl isocyanate (0.27 ml). The crude product (0.877 g) was recrystallised from ethyl acetate/hexane to afford the title compound as white needles, yield 0.562 g, mp 113°–114° C.

$^1$H nmr (CDCl$_3$): δ1.34 (9H, s), 3.11 (2H, m), 4.03 (1H, m), 4.27 (1H, m), 4.83 (1H, broad s), 6.23 (1H, s), 5.53 (4H, m)

EXAMPLE 89

PREPARATION OF COMPOUND 561

3-t-butylcarbamoyloxy-1-(3-trifluoromethyl)phenyl-2-imidazolidinone

A stirred solution of 3-hydroxy-1-(3-trifluoromethyl)phenyl-2-imidazolidinone (prepared as in Preparative Example 46 above) (0.049 g) in dichloromethane (5 ml) was treated with triethylamine (0.03 ml) followed by tert-butyl isocyanate (0.020 g). The solution was stirred for 30 minutes, and was then washed with 2M hydrochloric acid, dried (MgSO$_4$) and evaporated under reduced pressure to afford the title compound, yield 0.060 g.

$^1$H nmr (CDCl$_3$): δ1.37 (9H, s), 3.78–3.85 (2H, m), 3.87–3.94 (2H, m), 5.10 (broad s), 7.38 (1H, d), 7.49 (1H, t), 7.79 (1H, s), 7.84 (1H, d)

EXAMPLE 90

PREPARATION OF COMPOUND 667 tetrahydro-3-t-butylcarbamoyloxy-1-(3-trifluoromethyl)phenyl-2-(1H)pyrimidinone

By a procedure similar to that described in Example 89, but using tetrahydro-3-hydroxy-1-(3-trifluoromethyl)phenyl-2(1H)-pyrimidinone (prepared as in Preparative Example 47 above) (0.075 g), tert-butyl isocyanate (0.029 g), triethylamine (0.039 ml) and dichloromethane (5 ml), and purification of the crude product by silica gel chromatography, eluting with ethyl acetate/hexane mixtures, the title compound was obtained, yield 0.053 g, mp 156°–158° C.

$^1$H nmr (CDCl$_3$): δ1.34 (9H, s), 2.25–2.36 (2H, m), 3.72–3.87 (4H, m), 4.95 (1H, broad s), 7.38–7.56 (4H, m)

EXAMPLE 91

PREPARATION OF COMPOUND 700

3-t-butylcarbamoyloxy-1-(3-trifluoromethyl)phenyl-2-piperidinone

A stirred solution of 3-hydroxy-1-(3-trifluoromethyl)phenyl-2-piperidinone (prepared as in Preparative Example 48 above) (0.247 g of a 2:1 mixture of 3-hydroxy-1-(3-trifluoromethyl)phenyl-2-piperidinone and 1-(3-trifluoromethyl)phenyl-2-piperidinone) in dichloromethane (10 ml) was treated with tert-butyl isocyanate (0.094 g) and triethylamine (0.13 ml). The solution was heated under reflux for 4 hours, and was then cooled and left to stand for 16 hours. The solution was then evaporated under reduced pressure, and the residue was purified by silica gel chromatography, eluting with ethyl acetate/hexane mixtures, to afford the title compound as a clear gum, yield 0.124 g.

$^1$H nmr (CDCl$_3$): δ1.32 (9H, s), 1.98–2.14 (3H, m), 2.33 (1H, m), 3.65 (1H, m), 3.75 (1H, m), 4.85 (1H, broad s), 5.29 (1H, m), 7.45–7.55 (4H, m)

EXAMPLE 92

PREPARATION OF COMPOUND 796 dihydro-6-t-butylcarbamoyloxy-3-methyl-4-(3,5-bis(trifluoromethyl))phenyl-2H-1,3,4-thiadiazin-5(6H)-one A stirred solution of dihydro-6-hydroxy-3-methyl-4-(3,5-bis(trifluoromethyl))phenyl-2H-1,3,4-thiadiazin-5-(6H)-one (prepared as described in Preparative Example 49 above) (0.037 g) in dichloromethane (1 ml) was treated successively with triethylamine (0.013 ml) and tert-butylisocyanate (0.011 ml). The solution was left to stand for 18 hours, before being evaporated under reduced pressure and dissolved in ethyl acetate (5 ml). The solution was washed with 2M hydrochloric acid (2×10 ml), saturated sodium bicarbonate solution (2×10 ml), dried (MgSO$_4$), and evaporated under reduced pressure to afford the title compound as a pale yellow gum, yield 0.042 g.

$^1$H nmr (d$_6$-DMSO, 120° C.): δ1.37 (9H, s), 3.38 (3H, s), 4.61 (1H, d), 4.82 (1H, d), 6.18 (1H, s), 7.03 (1H, broad s), 7.37–7.41 (2H, s), 7.48–7.51 (1H, s)

MS: m/e 469 (M$^+$)

EXAMPLE 93

PREPARATION OF COMPOUND 813 dihydro-4-t-butylcarbamoyloxy-2-(3-trifluoromethyl) phenyl-2H-1,2-oxazin-3(4H)-one A stirred solution of dihydro-4-hydroxy-2-(3-trifluoromethyl)phenyl-2H-1,2-oxazin-3-(4H)-one (prepared as described in Preparative Example 50 above) (0.26 g) in dichloromethane (5 ml) was treated successively with dichloromethane solutions of tert-butyl isocyanate (0.099 g in 1 ml) and triethylamine (0.101 g in 1 ml). Partial reaction occured overnight. The mixture was left for 5 days, adding further similar quantities of tert-butyl isocyanate and triethylamine at daily intervals. The mixture was then evaporated under reduced pressure, diluted with water and ethyl acetate and extracted several times with ethyl acetate. The combined extracts were washed with brine, dried ($MgSO_4$) and evaporated under reduced pressure. The residue was dissolved in ethyl acetate and N,N'-di-tert-butyl urea was precipitated with hexane and filtered off. The filtrate was evaporated under reduced pressure, and the precipitation procedure was repeated twice more, finally giving no urea. The filtrate was evaporated under reduced pressure and the residue chromatographed on silica gel, eluting with ethyl acetate/hexane (1:4), to give the title compound as a gum which crystallised on standing, yield 0.147 g, mp 83°–84° C.

$^1$H nmr ($CDCl_3$): δ1.38 (9H, s), 2.16 (1H, m), 4.28 (1H, m), 4.46 (1H, m), 5.00 (1H, s), 5.68 (1H, dd), 7.46 (2H, d+t), 7.98 (2H, s+d)

MS: m/e 360 ($M^+$)

EXAMPLE 94

PREPARATION OF COMPOUND 353

5-t-butylcarbamoyloxy-3-(3-(1-ethoxyvinyl))phenyl-4-thiazolidinone 5-t-Butylcarbamoyloxy-3-(3-iodo)phenyl-4-thiazolidinone (prepared as described in Example 68) (0.19 g) was dissolved in dry dimethylformamide (10 ml) and stirred at room temperature under nitrogen. To this solution was added αethoxyvinyl-tri-n-butylstannane (0.163 g) followed by bis(triphenylphosphine)palladium (II) chloride (0.125 g). The reaction mixture was heated in an oil bath (bath temperature 130° C.) for 4 hours. The heating bath was then removed and the reaction mixture allowed to stand at room temperature overnight. The mixture was then poured into 1M aqueous potassium fluoride solution (50 ml) and diluted with diethyl ether (30 ml). The mixture was stirred at room temperature for 2 hours and the precipitated solids removed by filtration through 'Celite'. The organic layer was separated and the aqueous phase extracted with more diethyl ether (×2). The combined organic layers were washed with water (×2), dried ($MgSO_4$) and evaporated under reduced pressure to give the crude product (0.28 g). This was chromatographed on silica gel (care: product rather unstable to prolonged exposure to silica gel) using ethyl acetate/hexane mixtures (1:4 to 3:7) as eluant to afford the title compound (0.042 g), which had:

$^1$H nmr ($CDCl_3$): δ1.33 (9H, s), 1.41 (3H, t), 3.92 (2H, q), 4.24 (1H, d), 4.67 (2H, m), 4.90 (1H, broad s), 5.01 (1H, d), 6.22 (1H, s), 7.40 (2H, m), 7.56 (1H, m), 7.69 (1H, m)

EXAMPLE 95

PREPARATION OF COMPOUND 156

5-t-butylcarbamoyloxy-3-(3-acetyl)phenyl-4-thiazolidinone 5-t-Butylcarbamoyloxy-3-(3-(1-ethoxyvinyl))phenyl-4-thiazolidinone (prepared as described in Example 94 above) (0.040 g) was dissolved in acetone (2 ml) and stirred at room temperature. 2M hydrochloric acid (0.1 ml) was added and the mixture was stirred for 30 minutes. The solvent was removed under reduced pressure, and the residue partitioned between ethyl acetate and aqueous sodium bicarbonate solution. The organic layer was separated, and the aqueous phase was extracted with further portions of ethyl acetate (×2). The combined ethyl acetate layers were washed with water, dried ($MgSO_4$) and evaporated under reduced pressure to leave a residue (0.039 g). This was chromatographed on silica gel using ethyl acetate/hexane (3:7) as eluant to afford the title compound (0.020 g), which had:

$^1$H nmr ($CDCl_3$): δ1.33 (9H, s), 2.62 (3H, s), 4.72 (1H, d), 4.90 (1H, broad s), 5.07 (1H, d), 6.22 (1H, s), 7.54 (1H, t), 7.80 (1H, d), 7.87 (1H, d), 8.03 (1H, s)

MS: m/e 336 ($M^+$)

EXAMPLE 96

PREPARATION OF COMPOUND 354

5-(N-1-adamantyl)carbamoyloxy-3-(3-trifluoromethyl)phenyl-4-thiazolidone.

By a procedure similar to that described in Example 10, but using 5-hydroxy-3-(3-trifluoromethyl)phenyl-4-thiazolidone (prepared as in Preparative Example 2 above) (0.100 g), 1-adamantyl isocyanate (0.067 g), triethylamine (0.053 ml) and chloroform (10 ml), and purification of the crude product by silica gel chromatography, eluting with ethyl acetate (hexane mixtures, the title compound was obtained, yield 0.121 g).

$^1$H nmr ($CDCl_3$): δ1.68 (6H,broad), 1.94 (6H,broad), 2.05 (3H,broad), 4.71 (1H,d), 4.78 (1H,broad s), 5.06 (1H,dd), 6.19 (1H,d), 7.55–7.61 (2H,m), 7.71–7.79 (2H,m).

MS: m/e 440 ($M^+$)

EXAMPLE 97

PREPARATION OF COMPOUND 319

5-(N-(1-ethynyl)cyclohexyl)carbamoyloxy-3-(3-trifluoromethyl)phenyl-4-thiazolidinone.

By a procedure similar to that described in Example 38, but using phosgene in toluene (1.93M; 0.93 ml), 1-ethynylcyclohexylamine (0.200 g), diethyl ether (2 ml), sodium hydroxide (0.144 g) in water (3 ml), then 5-hydroxy-3-(3-trifluoromethyl)phenyl-4-thiazolidinone (prepared as in Preparative Example 2 above) (0.156 g) and triethylamine (0.278 ml), and purification at the crude product by silica gel chromatography, eluting with ethyl acetate/hexane mixtures, the title compound was obtained, yield 0.181 g.

$^1$H nmr ($CDCl_3$): δ1.55–1.79 (7H,m), 2.03–2.17 (2H,m), 2.42 (1H,s), 4.69 (1H,d), 5.04 (1H,broad s), 5.07 (1H,dd), 6.23 (1H,d), 7.52–7.60 (2H,m), 7.70–7.80 (2H,m).

MS: m/e 412 ($M^+$)

EXAMPLE 98

PREARATION OF COMPOUND 355

5-tert-butylcarbamoyloxy-3-(3-(N,N-dibenzyl) sulphonamido)phenyl-4-thiazolidinone 5-Hydroxy-3-(3-N,N-dibenzyl)sulphonamido)phenyl-4-thiazolidinone (prepared as in Preparative Example 51) (0.823 g) was converted to the title compound by a procedure similar to that described in Example 58 using dichloromethane (25 ml), triethylamine (0.265 ml) and tert-butylisocyanate (0.217 ml). The crude product (0.95 g) was purified by silica gel chromatography using ethyl acetate-hexane (3:7) as eluant. The title compound (0.745 g) was obtained as a brittle white foam which had:

$^1$H nmr (CDCl$_3$): δ1.34 (9H,s), 4.36 (4H,s), 4.59 (1H,d), 4.89 (12H,broad s), 4.97 (1H,d), 6.21 (1H,s), 7.09 (4H,m), 7.22 (6H,m), 7.55 (1H,t), 7.72 (1H,d), 7.81 (2H,m).

EXAMPLE 99

PREPARATION OF COMPOUND 356

5-tert-butylcarbamoyloxy-3-(3-hydroxyamino-5-trifluoromethyl)phenyl-4-thiazolidinone.

5-tert-Butylcarbamoyloxy-3-(3-nitro-5-trifluoromethyl) phenyl-4-thiazolidone (prepared as described in Example 77 (0.792 g) was dissolved in ethyl acetate (20 ml) and 10% palladium in charcoal (0.2 g) added. The reaction mixture was stirred under an atmosphere of hydrogen for 5 hours (prolonged treatment under these conditions affords the amine, see Example 100). The catalyst was removed by filtration in 'Celite' and the pad well washed with ethyl acetate. The solvent was removed under reduced pressure to afford the title compound in essentially quantitative yield. A small sample (0.108 g) was withdrawn and chromatographed on silica gel using ethyl acetate-hexane (45:55) as eluant. A white solid was obtained which had:

$^1$H nmr (CDCl$_3$); δ1.33 (9H,s), 4.68 (1H,d), 4.88 (1H, broad s), 5.03 (1H,d), 5.32 (1H,broad s), 6.20 (1H,s), 6.96 (1H,broad s), 7.14 (1H,s), 7.22 (1H,s), 7.42 (1H,s).

FAB MS: 394 (MH+)

EXAMPLE 100

PREPARATION OF COMPOUND 357

5-tert-butylcarbamoyloxy-3-(3-amino-3-trifluoromethylphenyl)-4-thiazolidinone.

5-tert-Butylcarbamoyloxy-3-(3-hydroxylamino-5-trifluoromethylphenyl) 4-thiazolidinone (prepared as in example 99) (0.68 g) was dissolved in ethyl acetate (20 ml) and 10% palladium on charcoal (0.4 g) added. The reaction mixture was stirred under an atmosphere of hydrogen for 22 hours. Nmr revealed starting material to be present and the process was repeated (after removal of the catalyst on 'Celite' and introduction of a fresh batch) for 72 hours. Again the reaction was incomplete the process was repeated for a further 48 hours. The catalyst was removed on 'celite' and the solvent evaporated under reduced pressure to give a foam (0.579 g) which contained approximately 10% unchanged starting material together with a few other impurities. The title compound approx 80% pure had:

$^1$H nmr (CDCl$_3$): δ inter alia 1.33 (9H,s), 4.00 (2H,broad s), 4.64 (1H,d), 4.91 (1H,broad s), 4.99 (1H,d), 6.20 (1H,s), 6.79 (1H,s), 6.96 (1H,s), 7.12 (1H,s).

EXAMPLE 101

PREPARATION OF COMPOUND 306

5-cyclohexylthiocarbamoyloxy-3-(3-trifluoromethyl) phenyl-4-thiazolidinone.

A stirred solution of 5-hydroxy-3-(3-trifluoromethyl)phenyl-4-thiazolidinone (prepared as in Preparative Example 2 above) (0.50 g) in dichloromethane (15 ml) was treated dropwise with cyclohexylisothiocyanate (0.28 ml) and triethylamine (0.28 ml). The solution was stirred for 24 hours whereupon further cyclohexylisothiocyanate (0.28 ml) and triethylamine (0.28 ml) were added. After leaving for 72 hours the solvent was removed under reduced pressure and the residual mixture was separated by silica gel chromatography (eluting with ethyl acetate/hexane), followed by recrystallisation from ether/hexane to give the title compound as a very pale pink crystalline solid, yield 0.14 g, m.p. 132°–132.5° C.

$^1$H nmr showed a 5:1 ratio of conformational isomers. $^1$H nmr (CDCl$_3$): (Major conformer) δ: 1.10–2.20 (10H,m), 3.96–4.10 (1H,m), 4.71 (1H,d), 4.98 (1H,d), 6.42 (1H,broad ), 6.70 (1H,d), 7.55–7.62 (2H,m ), 7.74–7.82 (2H,m); (Minor conformer) δ1.10–2.20 (10H,m), 3.81–3.71 (1H,m), 4.71 (1H,d), 5.06 (1H,d), 6.68 (1H,broad), 6.77 (1H,d), 7.55–7.62 (2H,m), 7.74–7.82 (2H,m).

EXAMPLE 102

PREPARATION OF COMPOUND 358

5-isopropylthiocarbamoyloxy-3-(3-trifluoromethyl) phenyl-4- thiazolidinone.

By a procedure similar to that described in Example 101, but using 5-hydroxy-3-(3-trifluoromethyl)phenyl-4-thiazolidinone (prepared as in Preparative Example 2 above), isopropylisothiocyanate and triethylamine, the title compound was obtained, m.p. 138°–139° C.

$^1$H nmr showed a 5:1 ratio of conformational isomers. $^1$H nmr (CDCl$_3$): (Major conformer) δ1.27 (6H,d), 4.36 (1H,m), 4.71 (1H,d), 4.98 (1H,d), 6.38 (1H,broad), 6.70 (1H,d), 7.52–7.62 (2H,m), 7.74–7.82 (2H,m); (Minor conformer) δ1.21 (6H,dd), 4.07 (1H,m), 4.71 (1H,d), 5.05 (1H,d), 6.64 (1H,broad), 6.76 (1H,d), 7.52–7.62 (2H,m), 7.74–7.82 (2H, m).

Biological Data

The herbicidal activity of the compounds was tested as follows:Each chemical was formulated in one of two ways. Either the chemical was dissolved in an appropriate amount of water, dependent on the amount of solvent/surfactant blend required such that the total volume is 5 cm$^3$. Then a solvent sufficient blend comprised 78.2 gm/liter of Tween 20 and 21.8 gm/liter of Span 80 adjusted to 1 liter using methylcyclohexanone was added to the solution. Alternatively, the chemical was dissolved in water to the required concentration and 0.1% Tween added. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to 5 cm$^3$ with water, glass beads were added and this mixture was then shaken to effect dissolution or suspension of the chemical, after which the beads were removed. In all cases, the mixture was then diluted to the required spray volume. If sprayed independently, volumes of 25 cm$^3$ and 30 cm$^3$ were required for post-emergence tests; if sprayed together, 45 cm$^3$ was required. The sprayed aqueous emulsion contained 4% of the initial solvent/surfactant mix and the test chemical at an appropriate concentration.

The spray compositions so prepared were sprayed on to young pot plants (post-emergence test) at a spray volume equivalent to 1000 liters per hectare. Damage to plants was assessed 13 days after spraying by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100% damage.

In a test carried out to detect pre-emergence herbicidal activity, crop seeds were sown at 2 cm depth and weed seeds at 1 cm depth beneath compost and sprayed with the compositions at the rate of 1000 liters per hectare. 20 days after spraying, the seedlings in the sprayed plastic trays were compared with the seedlings in unsprayed control trays, the damage being assessed on the same scale of 0 to 9.

The results of the tests are given in Table XVI below.

TABLE XVI

TEST PLANTS (see TABLE XVII)

| Compound No | Rate of Application kg/ha | Pre- or Post Emergence Application | BV | GH | GM | ZM | OS | TA | PA | MI | CA | GA | AR | BP | EH | PO | IH | AT | XT | AF | AM | LR | AE | SH | SV | DS | BL | PD | EC | CE |
|---|---|---|---|---|---|---|---|---|---|---|---|---|---|---|---|---|---|---|---|---|---|---|---|---|---|---|---|---|---|---|
| 5 | 5 | Pre | 9 | 0 | 0 | 5 | 8 | 5 | 9 | — | 9 | 5 | — | 0 | 0 | — | — | 5 | — | — | 0 | — | 0 | 9 | 9 | 9 | — | — | 9 | — |
|  | 4 | Post | 2 | 0 | 0 | 0 | 0 | 0 | 0 | — | 0 | — | 0 | 0 | 0 | — | 0 | 0 | 0 | 0 | 0 | — | 0 | 0 | 0 | 0 | 0 | — | 0 | — |
| 16 | 4 | Pre | 0 | 0 | 5 | 0 | 0 | 0 | 0 | — | 5 | — | 0 | 0 | 0 | — | — | 0 | 0 | 0 | 0 | — | — | 0 | 0 | 0 | — | 2 | 2 | 2 |
|  | 4 | Post | 0 | 3 | 3 | 2 | 5 | 0 | 0 | — | 0 | — | 4 | 0 | 0 | — | 1 | 0 | 0 | 1 | 0 | — | 0 | 0 | 1 | 2 | 0 | — | 0 | 0 |
| 17 | 4 | Pre | 0 | 0 | 0 | 3 | 0 | 5 | 0 | — | 0 | — | 0 | 0 | 0 | — | 0 | 0 | 0 | 0 | 0 | 0 | — | 0 | 2 | 0 | 0 | — | 0 | — |
|  | 4 | Post | 2 | 0 | 3 | 3 | 0 | 0 | 0 | — | 0 | — | 2 | 0 | 0 | — | 5 | 0 | 0 | 0 | 0 | 0 | — | 0 | 0 | 2 | 2 | — | 0 | 0 |
| 20 | 4 | Pre | 0 | 0 | 0 | 0 | 0 | 0 | 0 | — | 0 | — | 0 | 0 | 0 | — | 2 | 4 | 5 | 2 | 2 | 4 | — | 9 | 9 | — | — | 9 | 5 | — |
| 26 | 0.5 | Pre | 9 | — | 3 | 8 | 0 | 0 | 9 | 9 | 9 | 4 | 9 | 6 | 4 | 9 | 0 | 5 | 0 | 2 | 0 | — | — | 5 | 8 | 9 | 9 | 9 | 5 | 0 |
|  | 4 | Post | 9 | 1 | 0 | 0 | 3 | 0 | — | — | 9 | 2 | 9 | 2 | 2 | — | 2 | 1 | — | 2 | 2 | 4 | — | 2 | 1 | 8 | — | — | 9 | 2 |
| 30 | 4 | Pre | 7 | 0 | 3 | 7 | 3 | 0 | 7 | — | 8 | 0 | 9 | 0 | 4 | — | 0 | 0 | — | 0 | 0 | — | — | 4 | 1 | — | 9 | 9 | 0 | 2 |
|  | 4 | Post | 0 | 0 | 1 | 2 | 2 | 1 | 0 | — | 0 | 5 | 6 | 0 | 0 | — | 2 | 2 | 0 | 1 | 1 | 0 | — | 0 | 1 | 3 | — | — | 0 | 0 |
| 33 | 3.16 | Pre | 0 | 0 | 0 | 0 | 3 | 2 | 0 | 5 | 3 | 3 | 0 | 0 | 0 | — | 2 | 5 | 2 | 0 | 0 | 2 | — | 0 | 3 | 0 | — | 5 | — | 1 | 3 |
|  | 3.16 | Post | 0 | 0 | 0 | 4 | 1 | 0 | 0 | 0 | 1 | 5 | 0 | 0 | 2 | — | 4 | 0 | 5 | 1 | 0 | 2 | — | 7 | 0 | — | — | 0 | 9 | 4 |
| 35 | 1 | Pre | 9 | — | 2 | 2 | 2 | 0 | 4 | 9 | 7 | 5 | 9 | 0 | 2 | — | 5 | 0 | 0 | 3 | 0 | 2 | — | 1 | 9 | — | — | 9 | 1 | 0 |
| 40 | 1 | Pre | 9 | — | 1 | 0 | 5 | 1 | 9 | 9 | 9 | 3 | 9 | 0 | 0 | — | 7 | 0 | 0 | 0 | 0 | 2 | — | 9 | 7 | — | — | 6 | 2 | 2 |
|  | 1 | Post | 9 | — | 0 | 3 | 0 | 1 | 6 | 9 | 9 | 5 | 9 | 2 | 2 | — | 0 | 0 | 5 | 0 | 1 | 2 | — | 3 | 3 | — | — | 0 | 0 | 0 |
| 44 | 0.25 | Pre | 4 | — | 2 | 4 | 3 | 0 | 2 | 0 | 9 | 5 | 9 | 0 | 2 | — | 0 | 0 | 0 | 0 | 0 | 2 | — | 0 | 8 | — | — | 9 | 0 | 0 |
|  | 0.25 | Post | 3 | — | 2 | 0 | 0 | 0 | 0 | 0 | 2 | 0 | 2 | 0 | 2 | — | 0 | 2 | 0 | 0 | 0 | 0 | — | 3 | 4 | — | — | 0 | 0 | 0 |
| 45 | 0.25 | Pre | 9 | — | 1 | 0 | 1 | 0 | 0 | 5 | 9 | 8 | 9 | 0 | 0 | 8 | 0 | 0 | 0 | 0 | 0 | 0 | — | 0 | 6 | — | — | 0 | 0 | 0 | 0 |
|  | 0.25 | Post | 6 | — | 2 | 0 | 3 | 0 | 0 | 0 | 6 | 0 | 8 | 0 | 0 | 0 | 0 | 0 | 0 | 0 | 0 | 0 | — | 0 | 3 | — | — | 9 | 0 | 9 | 0 |
| 48 | 0.25 | Pre | 0 | — | 1 | 0 | 1 | 0 | 0 | 0 | 0 | 0 | 0 | 0 | 0 | — | 0 | 0 | 0 | 0 | 0 | 0 | — | 0 | 0 | — | — | 0 | 0 | 0 | 0 |
| 52 | 0.25 | Pre | 0 | — | 0 | 2 | 2 | 0 | 0 | 0 | 0 | 0 | 0 | 0 | 0 | — | 0 | 2 | 0 | 0 | 0 | 0 | — | 0 | 0 | — | — | 0 | 0 | 0 | 0 |
| 56 | 1 | Pre | 0 | — | 4 | 1 | 0 | 2 | 2 | — | 5 | — | 2 | 0 | 0 | — | 2 | 5 | 3 | 2 | 2 | 0 | — | 5 | 3 | 0 | — | 5 | 0 | 2 | 2 |
| 61 | 4 | Post | 5 | 0 | 4 | 5 | 2 | 2 | 0 | 0 | 0 | — | 0 | 0 | 5 | — | 0 | 3 | 9 | 0 | 3 | — | — | 3 | 0 | 2 | — | 9 | 0 | 2 | 2 |
| 62 | 0.5 | Pre | 0 | 0 | 1 | 5 | 1 | 0 | 2 | 0 | 9 | — | 2 | 0 | 0 | 9 | 0 | 4 | 9 | 2 | 0 | 0 | — | 5 | 9 | — | 5 | 9 | 0 | 2 | 5 |
| 69 | 0.5 | Pre | 8 | 0 | 0 | 1 | 0 | 0 | 3 | 5 | 9 | — | 8 | 0 | 0 | 4 | 0 | 4 | 9 | 2 | 0 | 0 | — | 0 | 3 | — | 5 | 0 | 3 | 0 | 3 |
| 77 | 0.5 | Pre | 0 | 0 | 0 | 0 | 0 | 1 | 6 | 9 | 3 | — | 3 | 0 | 0 | 0 | 0 | 2 | 5 | 5 | 0 | 0 | — | 5 | 6 | — | — | 5 | 0 | 4 | 0 |
| 84 | 1 | Pre | 0 | 0 | 3 | 2 | 0 | 2 | 2 | 2 | 5 | — | 0 | 0 | 0 | — | 0 | 2 | 0 | 0 | 2 | 0 | — | 6 | 0 | — | — | 0 | 0 | 2 | 5 |
| 91 | 0.5 | Pre | 6 | 0 | 3 | 0 | 3 | 3 | 5 | 9 | 0 | — | 0 | 0 | 0 | — | 0 | 0 | 0 | 0 | 0 | 0 | — | 0 | 0 | — | — | 0 | 0 | 4 | 0 |
| 100 | 0.5 | Pre | 2 | 0 | 0 | 2 | 1 | 0 | 0 | 0 | 0 | — | 0 | 0 | 0 | — | 0 | 0 | 0 | 0 | 0 | 0 | — | 2 | 0 | — | — | 0 | 0 | 0 | 0 |
| 107 | 0.5 | Pre | 0 | 0 | 0 | 1 | 0 | 0 | 0 | — | 0 | — | 0 | 0 | 0 | — | 0 | 0 | 0 | 0 | 0 | 0 | — | 0 | 0 | — | — | 0 | 0 | 0 | 0 |
| 108 | 0.5 | Pre | 0 | 0 | 2 | 1 | 0 | 0 | 0 | — | 0 | — | 0 | 0 | 0 | — | 0 | 2 | 0 | 0 | 0 | 0 | — | 0 | 0 | — | — | 0 | 0 | 2 | 0 |
| 112 | 0.5 | Pre | 4 | 0 | 0 | 2 | 1 | 0 | 2 | — | 0 | — | 7 | 0 | 0 | — | 2 | 0 | 4 | 2 | 0 | 0 | — | 2 | 0 | 0 | — | 0 | 3 | 1 | 0 |
| 119 | 0.125 | Pre | 0 | 0 | 0 | 1 | 0 | 0 | 0 | — | 0 | — | 9 | 0 | 0 | — | 0 | 0 | 2 | 0 | 0 | 0 | — | 0 | 0 | 0 | — | 0 | 4 | 4 | 0 |
| 133 | 4 | Post | 2 | 0 | 0 | 0 | 0 | 0 | 2 | — | 0 | — | 0 | 0 | 0 | — | 0 | 0 | 0 | 0 | 0 | 0 | — | 0 | 0 | 0 | — | 2 | 6 | 0 | 0 |
| 134 | 4 | Pre | 2 | 0 | 0 | 5 | 2 | 0 | 0 | — | 0 | — | 0 | 0 | 0 | — | 0 | 0 | 0 | 0 | 0 | 0 | — | 0 | 0 | 0 | — | 3 | 0 | 0 | — |
| 138 | 4 | Pre | 9 | 0 | 0 | 9 | 0 | 0 | 3 | — | 9 | — | 9 | 0 | 0 | — | 5 | 2 | 0 | 2 | 0 | 0 | — | 5 | 9 | 0 | — | 0 | 4 | 9 | 0 |
| 146 | 4 | Post | 9 | 5 | 0 | 2 | 2 | 3 | 0 | — | 9 | 2 | 9 | 0 | 9 | — | 0 | 5 | 6 | 2 | 2 | 0 | — | 0 | 2 | 6 | — | — | 5 | 5 | 0 |
| 159 | 4 | Pre | 8 | 3 | 5 | 9 | 0 | 0 | 3 | — | 8 | 5 | 3 | 2 | 5 | — | 5 | 0 | 9 | 5 | 2 | 0 | — | 4 | 4 | — | 8 | — | 0 | 3 | 0 |
|  | 4 | Post | 8 | 0 | 0 | 2 | 3 | 2 | 0 | — | 7 | — | 9 | 4 | 4 | — | 4 | 5 | 5 | 2 | 2 | 0 | — | 6 | 9 | — | — | — | — | 9 | — |
| 166 | 3.8 | Pre | 4 | 3 | 0 | 0 | 0 | 0 | 0 | — | 9 | 0 | 9 | 0 | 0 | — | — | 0 | — | 0 | 0 | — | — | 0 | 0 | 4 | — | — | 3 | 3 | — |

TABLE XVI-continued

TEST PLANTS (see TABLE XVII)

| Compound No | Rate of Application kg/ha | Pre- or Post Emergence Application | BV | GH | GM | ZM | OS | TA | PA | MI | CA | GA | AR | BP | EH | PO | IH | AT | XT | AF | AM | LR | AE | SH | SV | DS | BL | PD | EC | CE |
|---|---|---|---|---|---|---|---|---|---|---|---|---|---|---|---|---|---|---|---|---|---|---|---|---|---|---|---|---|---|---|
| 171 | 0.5 | Pre | 9 | — | 3 | 2 | 2 | 0 | 9 | 9 | 9 | — | 9 | — | — | 9 | 7 | 5 | — | 0 | 9 | 9 | — | 9 | 9 | — | — | 9 | 9 | 9 |
| 174 | 0.5 | Pre | 9 | — | 0 | 0 | 0 | 0 | 5 | 9 | 9 | — | 9 | — | — | 9 | 3 | 3 | 2 | 3 | 3 | 0 | — | 2 | 9 | — | — | 9 | 0 | 0 |
| 197 | 1 | Pre | 9 | — | 0 | 0 | 2 | 0 | 5 | 9 | 9 | 4 | 9 | — | 3 | — | 0 | 0 | 2 | 0 | 0 | 0 | — | 8 | 9 | — | 6 | 9 | — | 2 |
| 206 | 1 | Pre | 9 | — | 2 | 2 | 2 | 2 | 0 | 8 | 9 | 4 | 9 | — | 0 | — | 3 | 5 | 2 | 4 | 4 | 3 | — | 9 | 9 | — | 9 | 9 | 5 | 3 |
| 211 | 1 | Pre | 1 | — | 0 | 3 | 9 | 0 | 5 | 9 | 2 | 3 | 7 | — | — | — | 2 | 0 | 0 | 2 | 3 | 4 | — | — | 6 | — | — | — | 0 | 0 |
| | 0.25 | Post | 0 | — | 2 | 0 | 0 | 0 | 0 | 1 | 9 | 0 | 4 | — | — | — | 0 | 0 | — | 0 | 0 | 0 | — | 2 | 0 | — | 0 | 4 | 9 | 4 |
| 216 | 1 | Pre | 9 | — | 0 | 0 | — | 0 | 5 | 9 | 9 | 3 | 5 | — | 3 | 0 | 4 | 3 | 4 | 0 | 0 | 0 | — | 9 | — | — | 2 | 5 | 9 | 0 |
| | 0.25 | Post | 4 | — | 3 | 0 | 0 | 0 | 0 | 1 | 6 | 0 | 9 | — | 0 | 3 | 0 | 0 | 0 | 0 | 0 | 0 | — | 0 | 2 | — | 3 | 2 | 0 | 0 |
| 220 | 1 | Pre | 0 | — | 0 | 2 | 0 | 0 | 2 | 2 | 8 | — | 5 | — | — | — | 4 | 5 | 3 | 3 | 5 | 0 | — | 0 | 0 | — | — | 5 | 0 | 4 |
| 221 | 1 | Pre | 3 | — | 0 | 0 | 0 | 0 | 5 | 4 | 5 | — | 0 | — | — | — | 6 | 3 | 2 | 0 | 2 | 0 | — | 3 | 0 | — | 2 | 2 | 0 | 0 |
| 227 | 0.235 | Pre | 5 | — | 1 | 2 | 2 | 0 | 9 | 9 | 9 | — | 9 | — | — | 3 | 3 | 3 | 0 | 2 | 5 | 2 | — | — | 0 | — | — | 5 | 5 | 0 |
| 231 | 0.5 | Pre | 5 | — | 9 | 0 | 0 | 0 | 9 | 8 | 9 | — | 9 | — | — | 6 | 2 | 2 | 3 | 0 | 2 | 3 | — | 3 | 2 | — | 3 | 0 | 0 | 0 |
| 233 | 4 | Pre | 0 | — | 0 | 0 | 2 | 0 | 0 | 2 | 5 | — | 5 | — | 0 | — | 5 | 3 | 3 | 4 | 2 | 0 | — | 3 | 4 | — | 9 | 6 | 3 | 0 |
| 241 | 0.5 | Pre | 4 | — | 4 | 4 | 0 | 0 | 0 | 0 | 0 | 0 | 0 | — | — | — | 3 | 2 | 2 | 2 | 2 | 2 | — | 3 | 4 | — | 0 | 4 | 3 | 2 |
| 281 | 0.5 | Pre | 3 | — | 2 | 0 | 1 | 0 | 0 | 0 | 9 | — | 5 | — | — | — | 3 | 2 | 0 | 0 | 2 | 3 | — | 3 | 5 | — | 6 | 9 | 3 | 4 |
| 282 | 1 | Pre | 4 | — | — | 0 | 0 | 0 | 2 | 2 | 8 | — | 2 | — | — | — | 3 | 3 | 3 | 3 | 5 | 0 | — | 5 | 3 | — | 0 | 9 | 3 | 5 |
| 285 | 1 | Pre | 0 | — | 5 | 3 | 0 | 0 | 0 | 0 | 2 | — | 0 | — | — | — | 2 | 2 | 3 | 0 | 2 | 0 | — | 6 | 9 | — | 9 | 9 | 3 | 0 |
| 301 | 0.5 | Pre | 2 | — | 3 | 2 | 0 | 0 | 5 | 9 | 9 | — | 2 | — | — | 9 | 0 | 0 | 0 | 0 | 2 | 0 | — | 3 | 3 | — | 0 | 4 | 3 | 5 |
| 307 | 0.5 | Pre | 4 | — | 3 | 0 | 0 | 0 | 0 | 0 | 0 | — | 0 | — | — | 9 | 0 | 0 | 0 | 0 | 2 | 0 | — | 3 | 9 | — | 9 | 9 | 5 | 0 |
| 316 | 1 | Pre | 0 | — | 0 | 2 | 0 | 0 | 0 | 0 | 2 | — | 0 | — | — | 9 | 0 | 0 | 0 | 0 | 2 | 2 | — | 0 | 0 | — | 9 | 9 | 0 | 0 |
| 318 | 0.5 | Pre | 0 | — | 5 | 3 | 3 | 0 | 0 | 0 | 0 | — | 0 | — | — | 9 | 0 | 0 | 0 | 3 | 2 | 2 | — | 0 | 0 | — | 9 | 9 | 9 | 0 |
| 321 | 0.5 | Pre | 9 | — | 0 | 2 | 0 | 0 | 0 | 9 | 9 | — | 9 | — | — | 0 | 0 | 2 | 0 | 0 | 2 | 2 | — | 3 | 9 | — | 9 | 9 | 9 | 0 |
| 326 | 1 | Pre | 9 | — | 5 | 0 | 2 | 0 | 0 | 0 | 9 | — | 9 | — | — | 9 | 0 | 3 | 0 | 3 | 3 | 2 | — | 2 | 9 | — | 9 | 4 | 0 | 0 |
| 328 | 0.5 | Pre | 8 | — | 0 | 0 | 0 | 0 | 8 | 9 | 9 | — | 0 | — | — | 9 | 0 | 4 | 0 | 0 | 2 | 1 | — | 4 | 0 | — | 0 | 2 | 9 | 4 |
| 331 | 0.5 | Pre | 2 | — | 0 | 0 | 0 | 0 | 0 | 0 | 0 | — | 0 | 2 | — | 0 | 4 | 3 | 0 | 2 | 3 | 0 | — | 0 | 0 | — | 6 | 0 | 0 | 5 |
| 336 | 0.5 | Pre | 2 | — | 0 | 0 | 0 | 0 | — | — | 5 | — | 0 | — | — | 5 | 3 | 0 | 0 | 0 | 2 | 0 | — | 3 | 2 | — | 9 | 4 | 6 | 0 |
| 337 | 0.5 | Pre | 6 | — | 3 | 0 | 0 | 0 | — | — | 1 | — | 2 | — | 0 | 5 | 2 | 4 | 0 | 0 | 3 | 5 | — | 9 | 3 | — | 9 | 0 | 0 | 5 |
| 339 | 0.5 | Pre | 9 | — | 2 | 0 | 6 | 0 | 0 | — | 3 | — | 0 | — | 4 | — | 5 | 6 | 0 | 0 | 4 | 3 | — | 9 | 9 | — | — | 0 | 0 | 0 |
| 340 | 0.5 | Pre | 9 | — | 1 | 0 | 2 | 0 | 6 | 9 | 9 | — | 9 | — | 3 | 9 | 3 | 2 | 0 | 0 | 3 | 3 | — | 9 | 9 | — | 9 | 9 | 9 | 0 |
| 344 | 5 | Pre | 0 | — | 0 | 0 | 5 | 0 | 9 | 0 | 9 | — | 9 | — | — | — | 7 | 0 | 0 | 0 | 0 | 0 | — | 9 | 9 | — | 9 | 8 | 7 | 6 |
| 359 | 0.25 | Pre | 9 | — | 2 | 1 | 2 | 0 | 9 | 9 | 9 | — | 9 | — | — | — | 0 | 2 | 0 | 0 | 0 | 5 | — | 9 | 0 | — | — | 9 | 0 | 3 |
| 360 | 0.25 | Pre | 0 | — | 2 | 0 | 3 | 0 | 0 | 0 | 6 | — | 0 | — | — | 5 | 8 | 2 | 0 | 0 | 0 | 3 | — | 3 | 0 | — | — | 0 | 0 | 4 |
| 361 | 0.5 | Pre | 9 | — | 2 | 0 | 0 | 0 | 4 | 0 | — | — | 3 | — | — | — | — | 0 | — | 0 | 0 | 0 | — | 0 | 0 | — | — | 0 | 0 | 5 |
| 369 | 1 | Pre | 7 | 4 | 0 | 0 | 0 | 0 | 2 | 0 | 0 | — | 0 | — | — | — | 0 | 0 | 0 | 0 | 0 | 0 | — | 0 | 2 | — | — | 0 | 2 | 0 |
| 383 | 1 | Post | 0 | — | 0 | 0 | 1 | 1 | 0 | 0 | 2 | 3 | 0 | — | 0 | 0 | 1 | 0 | 0 | 0 | 0 | 0 | — | 0 | 0 | — | — | 0 | 0 | 0 |
| 390 | 1 | Pre | 0 | — | 0 | 0 | 0 | 0 | 0 | 0 | 0 | 0 | 0 | — | — | — | 0 | 0 | 0 | 0 | 0 | 0 | — | 0 | 0 | — | — | 5 | 2 | 5 |
| 404 | 1 | Post | 0 | — | 0 | 0 | 0 | 0 | 0 | 0 | 0 | 1 | 0 | — | — | — | 2 | 0 | 0 | 0 | 0 | 0 | — | 0 | 2 | — | — | 2 | 0 | 0 |
| 448 | 0.5 | Pre | 2 | — | 5 | 1 | 0 | 0 | 4 | 5 | 3 | 0 | 3 | — | — | 0 | 6 | 5 | 2 | 1 | 0 | 2 | — | 1 | 2 | — | — | 5 | 2 | 0 |
| 508 | 0.5 | Pre | 4 | — | 4 | 0 | 2 | 0 | 2 | 2 | 9 | 2 | — | — | — | 5 | 2 | 0 | 4 | 0 | 0 | 4 | — | 2 | 0 | — | — | 2 | 0 | 3 |
| 561 | 0.5 | Pre | 9 | — | 0 | 0 | 3 | 0 | 0 | — | 9 | — | 3 | — | — | 9 | 7 | 7 | 0 | 0 | 0 | 4 | — | 4 | 6 | — | 7 | 9 | 5 | 0 |
| 667 | 0.5 | Pre | 5 | — | 3 | 3 | 1 | 3 | 4 | — | — | — | — | — | — | 3 | 6 | 8 | 3 | 0 | 0 | 0 | — | 0 | 8 | — | — | 6 | 0 | 0 |
| 700 | 1 | Pre | 0 | — | 0 | 0 | 2 | 0 | 2 | 0 | 6 | — | 0 | — | — | 0 | 0 | 6 | — | 0 | 0 | — | — | 0 | 0 | — | 0 | 0 | 0 | 0 |
| 66 | 0.46 | Pre | — | 2 | — | 2 | 2 | — | — | — | 9 | 9 | 9 | — | — | — | 3 | 2 | — | — | — | — | — | 3 | 6 | — | — | 7 | 4 | 5 |

TABLE XVI-continued

TEST PLANTS (see TABLE XVII)

| Compound No | Rate of Application kg/ha | Pre- or Post Emergence Application | BV | GH | GM | ZM | OS | TA | PA | MI | CA | GA | AR | BP | EH | PO | IH | AT | XT | AF | AM | LR | AE | SH | SV | DS | BL | PD | EC | CE |
|---|---|---|---|---|---|---|---|---|---|---|---|---|---|---|---|---|---|---|---|---|---|---|---|---|---|---|---|---|---|---|
| 122 | 1 | Pre | — | 0 | — | 3 | 0 | — | — | — | 9 | — | 9 | — | — | — | 3 | 0 | — | — | — | — | — | 3 | 9 | — | — | 7 | 8 | 2 |
| 248 | 1 | Pre | — | 2 | — | 1 | 1 | — | — | — | 9 | — | 9 | — | — | — | 0 | 2 | — | — | — | — | — | 4 | 9 | — | — | 9 | 9 | 3 |
| 248/249 (1:1) | 1 | Pre | — | 3 | — | 0 | 2 | — | — | — | 9 | — | 9 | — | — | — | 3 | 5 | — | — | — | — | — | 8 | 9 | — | — | 9 | 9 | 5 |
| 255 | 1 | Pre | — | 4 | — | 1 | 1 | — | — | — | 3 | — | 0 | — | — | — | 2 | 2 | — | — | — | — | — | 4 | 6 | — | — | 8 | 3 | 5 |
| 255/256 (1:1) | 1 | Pre | — | 0 | — | 6 | 5 | — | — | — | 9 | — | 9 | — | — | — | 3 | 5 | — | — | — | — | — | 8 | 9 | — | — | 9 | 9 | 3 |
| 260 | 1 | Pre | — | 3 | — | 0 | 0 | — | — | — | 9 | — | 9 | — | — | — | 5 | 5 | — | — | — | — | — | 5 | 5 | — | — | 5 | 6 | 4 |
| 262 | 1 | Pre | — | 1 | — | 0 | 2 | — | — | — | 9 | — | 9 | — | — | — | 0 | 1 | — | — | — | — | — | 0 | 5 | — | — | 2 | 2 | 2 |

TABLE XVII

Abbreviations used for Test Plants

| | |
|---|---|
| BV - | Sugar beet |
| GH - | Cotton |
| GM - | Soybean |
| ZM - | Maize |
| OS - | Rice |
| TA - | Winter wheat |
| PA - | *Polygonum aviculare* |
| CA - | *Chenopodium album* |
| GA - | *Galium aparine* |
| AR - | *Amaranthus retroflexus* |
| MI - | *Matricaria inodora* |
| BP - | *Bidens pilosa* |
| EH - | *Euphorbia heterophylla* |
| PO - | *Portulaca oleracea* |
| IH - | *Ipomoea hederacea* |
| AT - | *Abutilon theophrasti* |
| XT - | *Xanthium strumarium* |
| AF - | *Avena fatua* |
| AM - | *Alopecurus myosuroides* |
| LR - | *Lolium rigidum* |
| AE - | *Elymus repens* |
| SH - | *Sorghum halepense* |
| SV - | *Setaria viridis* |
| DS - | *Digitaria Sanguinalis* |
| BL - | *Brachiaria platyphylla* |
| PD - | *Panicum dichotomiflorum* |
| EC - | *Echinochloa crus-galli* |
| CE - | *Cyperus esculentus* |

CHEMICAL FORMULAE
(IN DESCRIPTION)

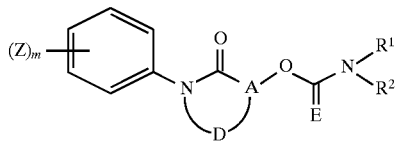 (I)

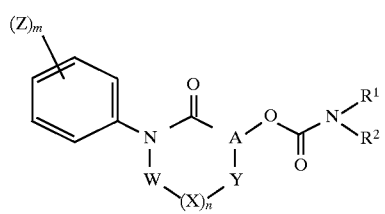 (II)

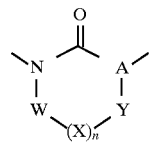 (i)

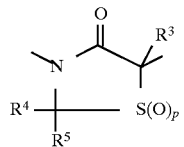 (a)

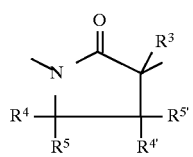 (b)

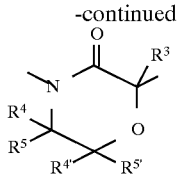 (c)

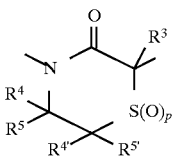 (d)

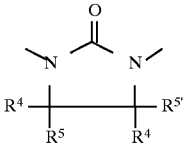 (e)

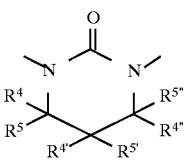 (f)

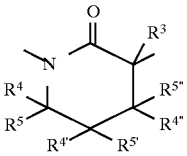 (g)

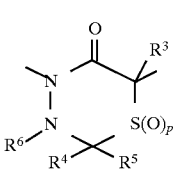 (h)

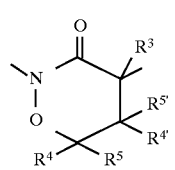 (i)

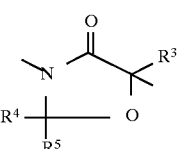 (j)

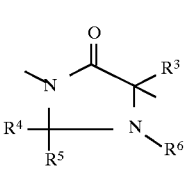 (k)

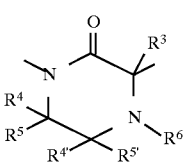 (l)

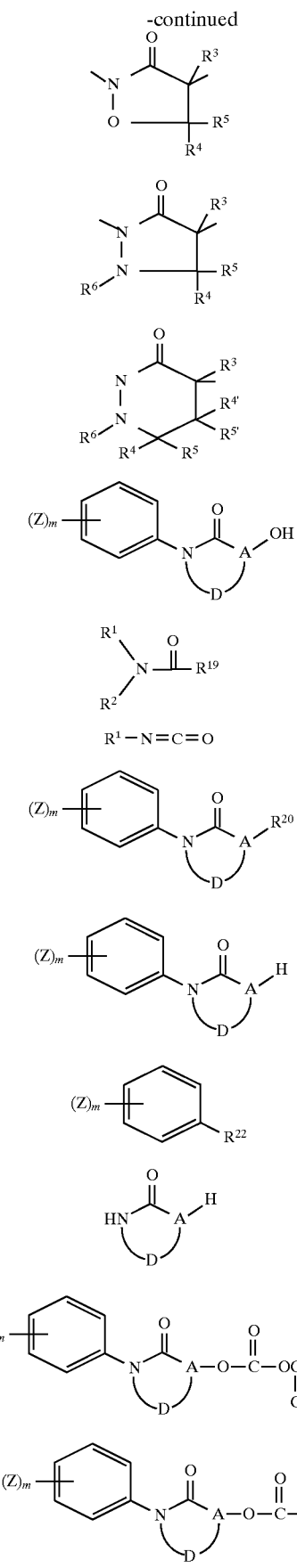
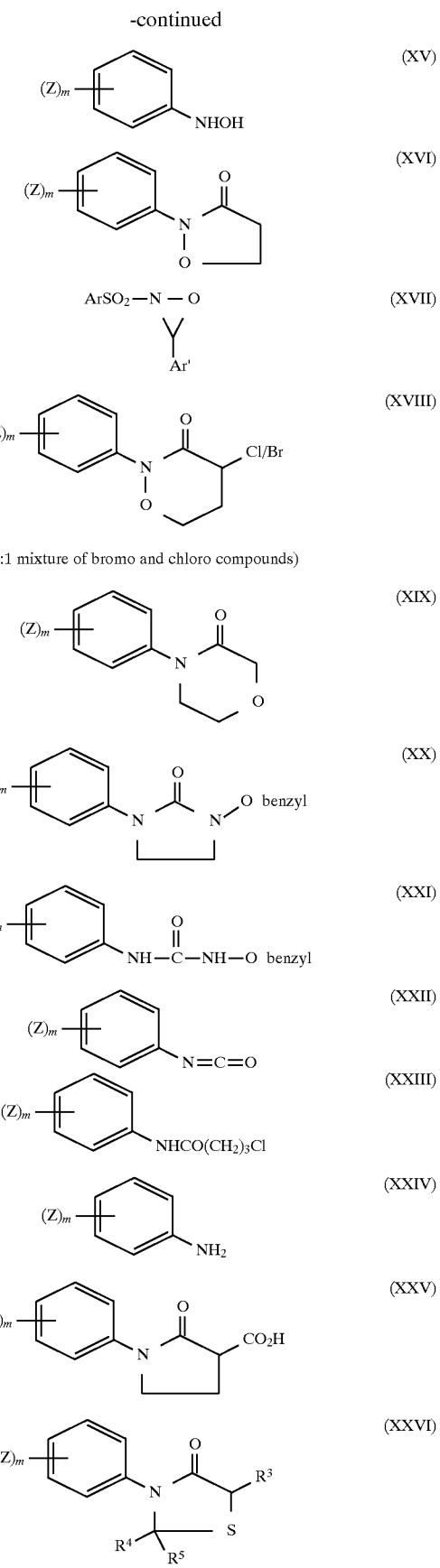

-continued (XXVII) (Z)ₘ—[phenyl]—N(R⁴R⁵C-S-)—C(=O)—CH(Cl)

(XXVIII) (Z)ₘ—[phenyl]—NHCH₂CH₂SCH₂CO₂C₂H₅

(XXIX) (Z)ₘ—[phenyl]—NH(CH₂)₂Br (XXX) (Z)ₘ—[phenyl]—NH(CH₂)₂OH (XXXI) cyclopropane-1,1-diyl bis(carbonyloxy ethyl ester)

(XXXII) (Z)ₘ—[phenyl]—N(R⁶)—N=... thiazine-like ring with S (XXXIII) (Z)ₘ—[phenyl]—N(HN-R⁶—R³⁰)—...—S ring (XXXIV) (Z)ₘ—[phenyl]—NH—NH₂

(XXXV) (Z)ₘ—[phenyl]—NH—C(=O)—CH₂—SH

We claim:

1. A compound of formula (I):

(I) (Z)ₘ—[phenyl]—N(D)—C(=O)—A—O—C(E)—N(R¹)(R²)

where E is oxygen or sulphur; A is $CR^3$ or N where $R^3$ is hydrogen; alkyl; alkenyl; alkynyl; cyclopropyl; cyclopropylmethyl; cyclobutyl; cyclopentyl; cyclohexyl; adamantyl or phenyl; D completes a 5 or 6-membered non-aromatic heterocyclic ring which optionally contains additional heteroatoms selected from oxygen, nitrogen or sulphur and which is unsubstituted or is substituted by a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; $R^1$ and $R^2$ are each independently hydrogen; a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, alkyl, alkenyl, alkynyl, cyclopropyl, cyclopropylmethyl, cyclobutyl, cyclopentyl, cyclohexyl, adamantyl or phenyl; or $R^1$ and $R^2$ together with the nitrogen atom to which they are attached, form a pyrrolidino, piperidino, thiomorpholino or morpholino ring each of which may be substituted by one or more methyl groups; or $R^1$ may also be a 3–6 membered cycloalkyl ring substituted by $CH_3$ or $C\equiv CH$ at the alpha position of the cycloalkyl ring; Z represents halogen; cyano; nitro; CHO; NHOH; $ONR^7R^{7''}$; $SF_5$; acylamino; $COOR^7$; $SO_2NR^8R^9$; $CONR^{10}R^{11}$; $OR^{12}$; $NR^{13}R^{14}$ or a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, $C_{1-10}$ alkyoxy, $C_{2-10}$ alkenyloxy, $C_{2-10}$ alkynyloxy, cyclopropyloxy, cyclopropylmethyloxy, cyclobutyloxy, cyclopentyloxy, cyclohexyloxy, adamantyloxy, phenoxy, $C_{1-10}$ alkylthio, $C_{2-10}$ alkenylthio, $C_{2-10}$ alkynylthio, cyclopropylthio, cyclopropylmethylthio, cyclobutylthio, cyclopentylthio, cyclohexylthio, adamantylthio, phenylthio, $C_{1-10}$ alkylsulphinyl, $C_{2-10}$ alkenylsulphinyl, $C_{2-10}$ alkynylsulphinyl, cyclopropylsulphinyl, cyclopropylmethylsulphinyl, cyclobutylsulphinyl, cyclopentylsulphinyl, cyclohexylsulphinyl, adamantylsulphinyl, phenylsulphinyl, $C_{1-10}$ alkylsulphonyl, $C_{2-10}$ alkenylsulphonyl, $C_{2-10}$ alkynylsulphonyl, cyclopropylsulphonyl, cyclopropylmethylsulphonyl, cyclobutylsulphonyl, cyclopentylsulphonyl, cyclohexylsulphonyl, adamantylsulphonyl, phenylsulphonyl, CO $C_{1-10}$ alkyl, CO $C_{2-10}$ alkenyl, CO $C_{2-10}$ alkynyl, CO cyclopropyl, CO cyclopropylmethyl, CO cyclobutyl, CO cyclopentyl, CO cyclohexyl, CO adamantyl, COphenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, alkenyl, alkynyl, cyclopropyl, cyclopropylmethyl, cyclobutyl, cyclopentyl, cyclohexyl, adamantyl or phenyl; where $R^7$, $R^{7'}$, $R^{7''}$, $R^8$, $R^9$, $R^{10}$ and $R^{11}$ are independently H or $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; $R^{12}$ is hydrogen; $SO_2$ $C_{1-10}$ alkyl; $SO_2$ $C_{2-10}$ alkenyl; $SO_2$ $C_{2-10}$ alkynyl; $SO_2$ cyclopropyl; $SO_2$ cyclopropylmethyl; $SO_2$ cyclobutyl; $SO_2$ cyclopentyl; $SO_2$ cyclohexyl; $SO_2$ adamantyl; $SO_2$ phenyl or $COR^{15}$; $R^{13}$ and $R^{14}$ are independently $C_{1-10}$ alkyl; $C_{2-10}$ alkenyl; $C_{2-10}$ alkynyl; cyclopropyl; cyclopropylmethyl; cyclobutyl; cyclopentyl; cyclohexyl; adamantyl; phenyl; $C_{1-10}$ alkyoxy; $C_{2-10}$ alkenyloxy; $C_{2-10}$ alkynyloxy; cyclopropyloxy; cyclopropylmethyloxy; cyclobutyloxy; cyclopentyloxy; cyclohexyloxy; adamantyloxy; phenoxy or a group $R^{12}$; $R^{15}$ is $OR^{16}$; $NR^{17}R^{18}$; hydrogen; $C_{1-10}$ alkyl; $C_{2-10}$ alkenyl; $C_{2-10}$ alkynyl; cyclopropyl; cyclopropylmethyl; cyclobutyl; cyclopentyl; cyclohexyl; adamantyl or phenyl; $R^{16}$ is $C_{1-10}$ alkyl; $C_{2-10}$ alkenyl; $C_{2-10}$ alkynyl; cyclopropyl; cyclopropylmethyl; cyclobutyl; cyclopentyl; cyclohexyl; adamantyl or phenyl; $R^{17}$ and $R^{18}$ are independently hydrogen; $C_{1-10}$ alkyl; $C_{2-10}$ alkenyl; $C_{2-10}$ alkynyl; cyclopropyl; cyclopropylmethyl; cyclobutyl; cyclopentyl; cyclohexyl; adamantyl or phenyl provided that when there are two or more substituents Z, they may be the same or different; and m is 0 or an integer from 1 to 5.

2. A compound according to claim 1 in which the compounds are of formula (II):

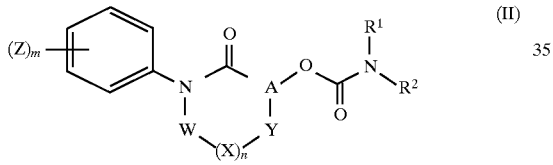
(II)

wherein A, E, $R^1$, $R^2$, Z and m, are as defined in relation to formula (I) in claim 1 and W, X and Y are independently selected from $CR^4R^5$; $NR^6$; O and $S(O)_p$ where p is 0, 1 or 2; $R^4$, $R^5$ and $R^7$ are independently selected from hydrogen or a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; or $R^4$ and $R^5$ together with the carbon atom to which they are attached may form a carbocyclic ring; and n is 0 or 1 provided that no more than two of A, W, X and Y comprise heteroatoms in the ring; and when more than one of W, X or Y is $CR^4R^5$, $R^4$ and $R^5$ may each be the same or different; and when more than one of W, X or Y is $NR^6$, $R^6$ may each be the same or different.

3. A compound according to claim 2 wherein the ring system

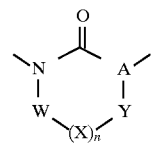
(i)

is selected from any one of ring systems (a)–(o)

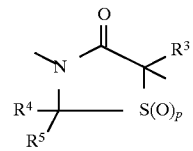
(a)

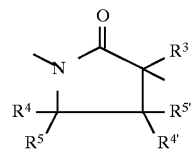
(b)

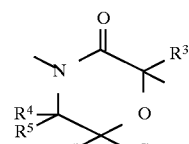
(c)

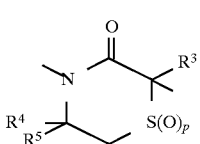
(d)

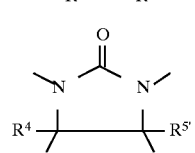
(e)

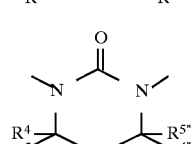
(f)

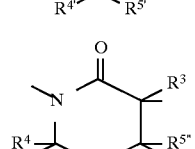
(g)

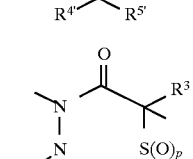
(h)

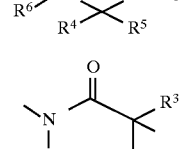
(i)

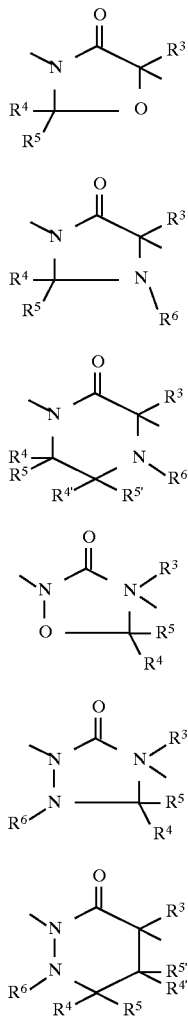

(j)

(k)

(l)

(m)

(n)

(o)

in which R³ is as defined in claim 1; R⁴, R⁵ and R⁶ are independently selected from hydrogen or a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; or R⁴ and R⁵ together with the carbon atom to which they are attached may form a carbocyclic ring; R⁴ and R⁵ may each be the same or different and R⁴', R⁴", R⁵' and R⁵" are as defined for R⁴ and R⁵ respectively.

4. A compound according to claim 3 in which the ring system

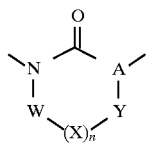

(i)

is a thiazolidine of sub-fomula (a) or a pyrrolidine of sub-formula (b) where R³, R⁴, R⁴', R⁵ and R⁵' are as defined in claim 3.

5. A compound according to claim 1 in which Z is $CF_3$; $OCF_3$; $OCHF_2$; $CHF_2$; OMe; F; Cl; Br; I; $NH_2$; $NO_2$; CN; $C_{1-4}$ alkyl; $C_{1-4}$ alkoxy, CO $C_{1-4}$ alkyl; NHCO $C_{1-4}$ alkyl; $SO_2$ $C_{1-4}$ alkyl; $OCF_2CHF_2$; $CF_2CF_3$; $OCF_2CHF_2$ or $SO_2NR^8R^9$ where R⁸ and R⁹ are as defined in relation to formula (I) in claim 1 and m is 1, 2 or 3.

6. A compound according to claim 1 wherein R¹ is iso-propyl, sec-butyl, t-butyl, $C(CH_3)_2$ C≡CH or a 3–6 membered cycloalkyl ring optionally substituted by $CH_3$ or C≡CH at the alpha position of the cycloalkyl ring.

7. A compound according to claim 1 wherein R² is hydrogen or $C_{1-4}$ alkyl.

8. A compound according to claim 3 wherein R⁴, R⁴', R⁴", R⁵, R⁵' and R⁵" are independently hydrogen or $C_{1-4}$ alkyl.

9. A compound according to claim 3 wherein R⁶ is $C_{1-4}$ alkyl.

10. A compound according to claim 1 wherein R³ is hydrogen.

11. A compound according to claim 1 wherein D completes a thiazolidine ring of sub-formula (a)

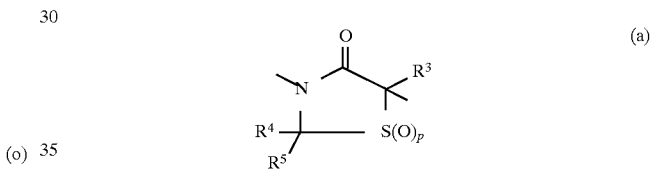

(a)

E is oxygen, R³ is hydrogen; R¹ and R² are each independently hydrogen or a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; or R¹ and R² together with the nitrogen atom to which they are attached, form a pyrrolidino, piperidino, thiomorpholino or morpholino ring each of which may be substituted by one or more methyl groups; or R¹ may also be a 3–6 membered cycloalkyl ring substituted by $CH_3$ or C≡CH at the alpha position of the cycloalkyl ring; m is 0 or an integer from 1 to 5; R⁴ and R⁵ are independently selected from hydrogen or a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; or $R^4$ and $R^5$ together with the carbon atom to which they are attached may form a carbocyclic ring; p is 0, 1 or 2; and Z is a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, $C_{1-10}$ alkyoxy, $C_{2-10}$ alkenyloxy, $C_{2-10}$ alkynyloxy, cyclopropyloxy, cyclopropylmethyloxy, cyclobutyloxy, cyclopentyloxy, cyclohexyloxy, adamantyloxy, phenoxy, $C_{1-10}$ alkylthio, $C_{2-10}$ alkenylthio, $C_{2-10}$ alkynylthio, cyclopropylthio, cyclopropylmethylthio, cyclobutylthio, cyclopentylthio, cyclohexylthio, adamantylthio, phenylthio, $C_{1-10}$ alkylsulphinyl, $C_{2-10}$ alkenylsulphinyl, $C_{2-4}$ alkynylsulphinyl, cyclopropylsulphinyl, cyclopropylmethylsulphinyl, cyclobutylsulphinyl, cyclopentylsulphinyl, cyclohexylsulphinyl, adamantylsulphinyl, phenylsulphinyl, $C_{1-10}$ alkylsulphonyl, $C_{2-10}$ alkenylsulphonyl, $C_{2-10}$ alkynylsulphonyl, cyclopropylsulphonyl, cyclopropylmethylsulphonyl, cyclobutylsulphonyl, cyclopentylsulphonyl, cyclohexylsulphonyl, adamantylsulphonyl and phenylsulphonyl, CO $C_{1-10}$ alkyl, CO $C_{2-10}$ alkenyl, CO $C_{2-10}$ alkynyl, CO cyclopropyl, CO cyclopropylmethyl, CO cyclobutyl, CO cyclopentyl, CO cyclohexyl, CO adamantyl or CO phenyl group, each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen, $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; halogen; cyano; nitro; acyl; amino or acylamino provided that when there are two or more substituents Z, they may be the same or different.

12. A compound of formula (III)

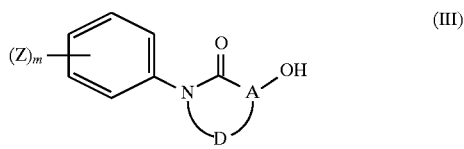

wherein the ring

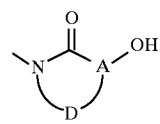

is a group of sub-formula (a')

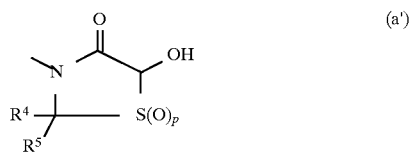

where $R^4$ and $R^5$ are independently selected from hydrogen or a $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl, phenyl, pyridyl, pyrimidyl, triazinyl, thienyl, furyl or thiazolyl group each of which may be substituted by halogen, cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, alkoxy carbonyl wherein the alkoxy group may have from 1 to 6 or more carbon atoms, aryl such as phenyl, carboxy or carboxyamide in which the groups attached to the N atom may be hydrogen $C_{1-10}$ alkyl, $C_{2-10}$ alkenyl, $C_{2-10}$ alkynyl, cyclopropyl, cyclopropylmethyl, cyclobutyl, cyclopentyl, cyclohexyl, adamantyl or phenyl; or $R^4$ and $R^5$ together with the carbon atom to which they are attached may form a carbocyclic ring; $R^4$ and $R^5$ may each be the same or different and p is 0, 1 or 2.

13. A process for preparing compounds of formula (I) as defined in claim 1 by reacting compounds of formula (III):

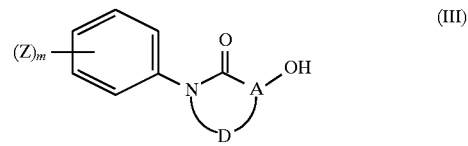

wherein Z, m, A and D are as defined in relation to formula (I) with a compound of formula (IV)

in which $R^1$ and $R^2$ are as defined in relation to formula (I) in claim 1 and $R^{19}$ is a leaving group; or a compound of formula (V)

$$R^1-N=C=O \quad \text{(V)}$$

in which $R^1$ is as defined in relation to formula (I) in claim 1.

14. A herbicidal composition comprising a compound of formula (I) according to claim 1 in combination with a herbicidal carrier or diluent.

15. A process for severely damaging or killing unwanted plants which process comprises applying to the plants, or to the growth medium of the plants, a herbicidally effective amount of a compound of formula (I) as defined in claim 1.

16. A compound according to claim 3 wherein the ring system

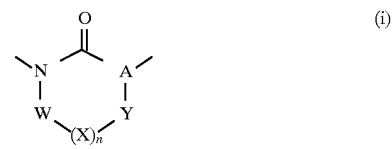

is selected from any one of ring systems (a) (b) or (j).

* * * * *